(12) United States Patent
Kim et al.

(10) Patent No.: US 10,797,245 B2
(45) Date of Patent: Oct. 6, 2020

(54) COMPOUND FOR ORGANIC OPTOELECTRONIC ELEMENT, ORGANIC OPTOELECTRONIC ELEMENT, AND DISPLAY DEVICE

(71) Applicant: SAMSUNG SDI CO., LTD., Yongin-si, Gyeonggi-do (KR)

(72) Inventors: Hyung Sun Kim, Suwon-si (KR); Byungku Kim, Suwon-si (KR); Youngkwon Kim, Suwon-si (KR); Younhwan Kim, Suwon-si (KR); Hun Kim, Suwon-si (KR); Eun Sun Yu, Suwon-si (KR); Sung-Hyun Jung, Suwon-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 506 days.

(21) Appl. No.: 15/517,622

(22) PCT Filed: Nov. 20, 2015

(86) PCT No.: PCT/KR2015/012551
§ 371 (c)(1),
(2) Date: Apr. 7, 2017

(87) PCT Pub. No.: WO2016/171358
PCT Pub. Date: Oct. 27, 2016

(65) Prior Publication Data
US 2017/0309830 A1 Oct. 26, 2017

(30) Foreign Application Priority Data
Apr. 24, 2015 (KR) .................... 10-2015-005 8117

(51) Int. Cl.
| | | |
|---|---|---|
| H01L 51/54 | (2006.01) | |
| C09K 11/06 | (2006.01) | |
| H01L 51/00 | (2006.01) | |
| H01L 51/50 | (2006.01) | |
| H05B 33/20 | (2006.01) | |
| C07D 233/58 | (2006.01) | |
| C07D 235/18 | (2006.01) | |
| C07D 239/26 | (2006.01) | |
| C07D 239/70 | (2006.01) | |
| C07D 239/74 | (2006.01) | |
| C07D 249/08 | (2006.01) | |

(Continued)

(52) U.S. Cl.
CPC ........ *H01L 51/0067* (2013.01); *C07D 233/58* (2013.01); *C07D 235/18* (2013.01); *C07D 239/26* (2013.01); *C07D 239/70* (2013.01); *C07D 239/74* (2013.01); *C07D 249/08* (2013.01); *C07D 251/24* (2013.01); *C07D 271/107* (2013.01); *C07D 285/12* (2013.01); *C07D 401/10* (2013.01); *C07D 401/14* (2013.01); *C09K 11/025* (2013.01); *C09K 11/06* (2013.01); *H01L 51/0069* (2013.01); *H01L 51/0072* (2013.01); *H01L 51/50* (2013.01); *H05B 33/20* (2013.01); *C09K 2211/1007* (2013.01); *C09K 2211/1029* (2013.01); *C09K 2211/185* (2013.01); *H01L 51/007* (2013.01); *H01L 51/0054* (2013.01); *H01L 51/0073* (2013.01); *H01L 51/0077* (2013.01); *H01L 51/0085* (2013.01); *H01L 51/5016* (2013.01); *H01L 51/5072* (2013.01); *H01L 51/5206* (2013.01); *H01L 51/5221* (2013.01)

(58) Field of Classification Search
CPC .. C07D 239/26; C07D 239/70; C07D 239/74; C07D 233/58; C07D 235/18; C07D 249/09; C07D 251/24; C07D 271/107; C07D 285/12; C07D 401/00; C07D 401/10; C07D 401/14; H05B 33/20; C09K 11/025; C09K 11/06; C09K 2211/1029; C09K 2211/00; C09K 2211/10; C09K 2211/1007; C09K 2211/185; H01L 51/0032; H01L 51/005; H01L 51/0054; H01L 51/007; H01L 51/0077; H01L 51/0073; H01L 51/0074; H01L 51/0085; H01L 51/5221; H01L 51/50; H01L 51/5012; H01L 51/5016; H01L 51/0072; H01L 51/0069; H01L 51/0067
USPC ..................... 428/690, 691, 917, 411.4, 336; 427/500–512; 313/500–512; 257/40, 257/88–104, E51.001–E51.052; 252/301.16–301.35
See application file for complete search history.

(56) References Cited

U.S. PATENT DOCUMENTS

| | | | |
|---|---|---|---|
| 7,232,617 B2 | 6/2007 | Lee et al. | |
| 2003/0039858 A1 | 2/2003 | Igarashi et al. | |

(Continued)

FOREIGN PATENT DOCUMENTS

| | | | |
|---|---|---|---|
| CN | 104277824 A | 1/2015 | |
| CN | 104498025 A | 4/2015 | |

(Continued)

OTHER PUBLICATIONS

Machine translation of WO2009-054253. (Year: 2009).*

(Continued)

*Primary Examiner* — Andrew K Bohaty
(74) *Attorney, Agent, or Firm* — Lee IP Law, PC

(57) ABSTRACT

The present invention relates to a compound for an organic optoelectronic element, represented by chemical formula I, an organic optoelectronic element employing the same, and a display device. The details of chemical formula I above are defined as in the specification.

18 Claims, 2 Drawing Sheets

(51) Int. Cl.
  C07D 251/24    (2006.01)
  C07D 271/107   (2006.01)
  C07D 285/12    (2006.01)
  C07D 401/10    (2006.01)
  C07D 401/14    (2006.01)
  C09K 11/02     (2006.01)
  H01L 51/52     (2006.01)

(56) References Cited

U.S. PATENT DOCUMENTS

| | | | |
|---|---|---|---|
| 2011/0253991 A1 | | 10/2011 | Oyamada et al. |
| 2013/0234119 A1* | | 9/2013 | Mizuki ............... H01L 51/0072 257/40 |
| 2015/0001488 A1 | | 1/2015 | Min et al. |

FOREIGN PATENT DOCUMENTS

| | | | | |
|---|---|---|---|---|
| JP | 2003-027048 | A | | 1/2003 |
| JP | 2004-244400 | A | | 9/2004 |
| JP | 2005068078 | A | * | 3/2005 |
| JP | 2005-268022 | A | | 9/2005 |
| JP | 2010-134121 | A | | 6/2010 |
| JP | 2011-049512 | A | | 3/2011 |
| KR | 10-2012-0140603 | | | 12/2012 |
| KR | 10-2013-0127994 | A | | 11/2013 |
| KR | 10-2014-0064892 | A | | 5/2014 |
| KR | 10-2014-0120975 | A | | 10/2014 |
| KR | 10-2015-0003658 | A | | 1/2015 |
| KR | 10-2015-0042650 | A | | 4/2015 |
| KR | 10-2015-0088712 | A | | 8/2015 |
| KR | 10-2015-0090836 | A | | 8/2015 |
| WO | WO 2004/077885 | A2 | | 9/2004 |
| WO | WO 2005/124890 | A1 | | 12/2005 |
| WO | WO 2009/054253 | A1 | | 4/2009 |
| WO | WO 2012/137958 | A1 | | 10/2012 |
| WO | WO 2014/185589 | A1 | | 11/2014 |

OTHER PUBLICATIONS

Machine translation of JP2005-068078. (Year: 2005).*
Office Action/Search Report dated Apr. 25, 2017, of the corresponding Taiwanese Patent Application No. 105112565.
Synthesis and electroluminescence property of new hexaphenylbenzene derivatives including amine group for blue emitters, Shin et al., Nanoscale Research Letters, 2013.
Chinese Office Action dated Jan. 11, 2019.
Peter Bergmann et al: "Zur Synthese gemischter Hexa-hetaryl-aryl-benzole und ahnlicher Verbindungen", Chemische Berichte, vol. 100, No. 3, Mar. 1, 1967 (Mar. 1, 1967), pp. 828-835, XP055496543.
Frances A. Murphy et al: "Superaromatic Terpyridines: Hexa-peri-hexabenzocoronenes with Tridentate Functionality", Journal of Organic Chemistry, vol. 75, No. 6, Mar. 19, 2010 (Mar. 19, 2010), pp. 1862-1870, XP055496651.
N. N. Smirnova et al: "Thermodynamics of hard poly(phenyleneepyridyl) dendrimers", Russian Chemical Bulletin International Edition, Oct. 1, 2013 (Oct. 1, 2013), pp. 2258-2262, XP055496516, Retrieved from the Internet: URL:https://link.springer.com/content/pdf/10.1007/s11172-013-0326-4.pdf [retrieved on Aug. 1, 2018].
Zhikun Zheng et al: "Square-Micrometer-Sized, Free-Standing Organometallic Sheets and Their Square-Centimeter-Sized Multilayers on Solid Substrates", Macromolecular Rapid Communications, vol. 34, No. 21, Nov. 1, 2013 (Nov. 1, 2013), pp. 1670-1680, XP055496668.
Extended European Search Report dated Aug. 14, 2018, of the corresponding European Patent Application No. 15890024.1.

* cited by examiner

[Fig. 1]
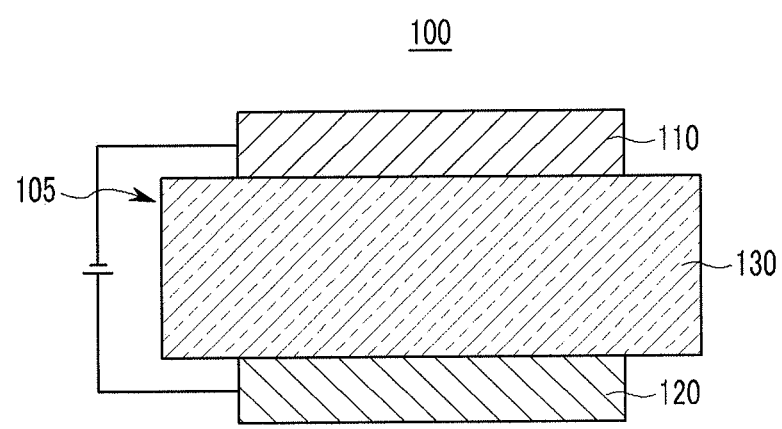
[Fig. 2]
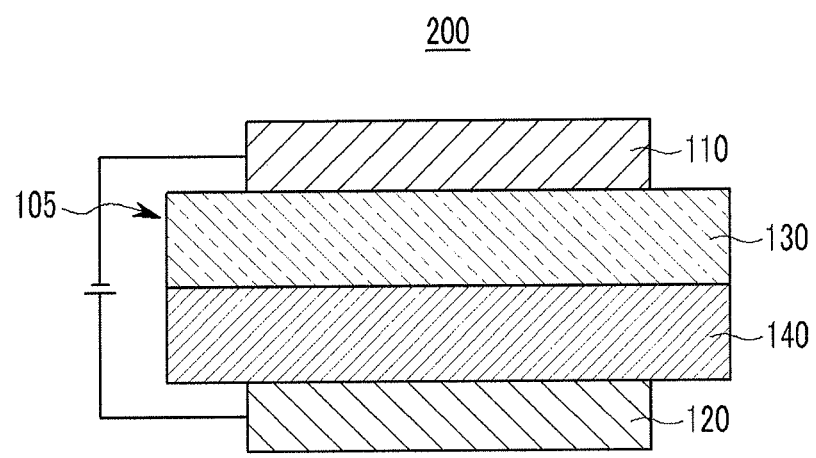

[Fig. 3]
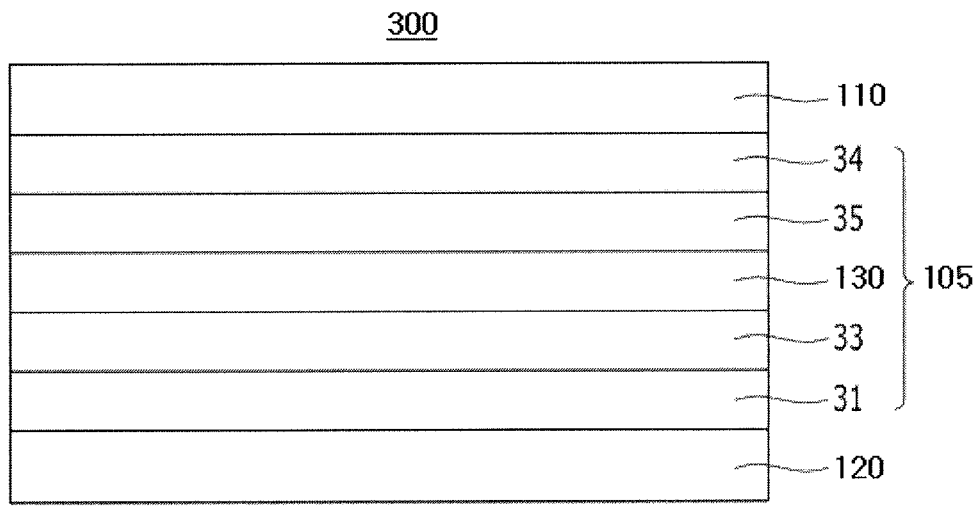
[Fig. 4]
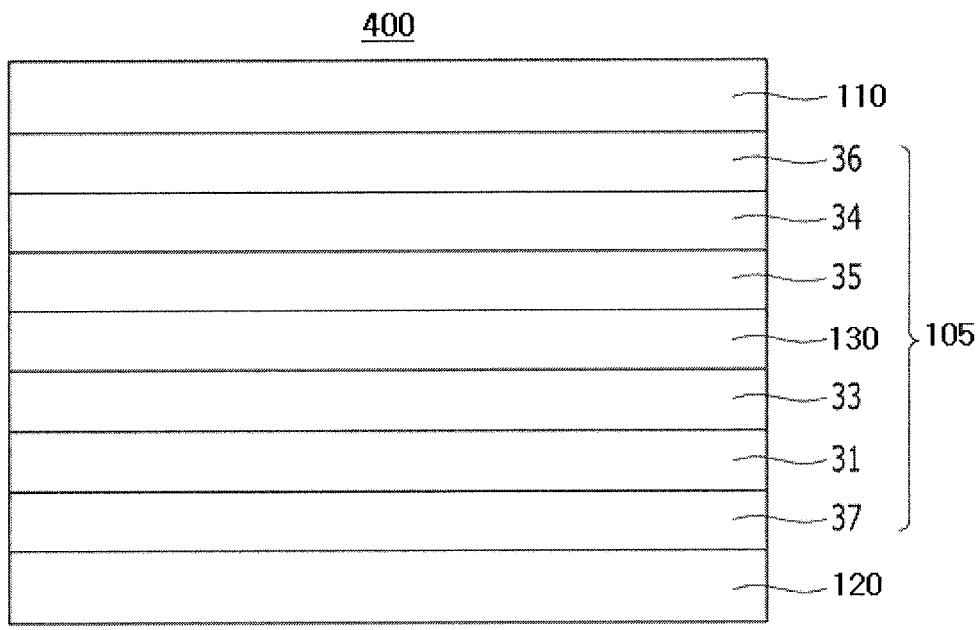

COMPOUND FOR ORGANIC OPTOELECTRONIC ELEMENT, ORGANIC OPTOELECTRONIC ELEMENT, AND DISPLAY DEVICE

CROSS REFERENCE TO RELATED APPLICATIONS

This is the U.S. national phase application based on PCT Application No. PCT/KR2015/012551, filed Nov. 20, 2015, which is based on Korean Patent Application No. 10-2015-0058117, filed Apr. 24, 2015, the entire contents of all of which are hereby incorporated by reference.

TECHNICAL FIELD

A compound for an organic optoelectric device, an organic optoelectric device, and a display device are disclosed.

BACKGROUND ART

An organic optoelectric device is a device that converts electrical energy into photoenergy, and vice versa.

An organic optoelectric device may be classified as follows in accordance with its driving principles. One is a photoelectric device where excitons generated by photoenergy are separated into electrons and holes and the electrons and holes are transferred to different electrodes respectively and electrical energy is generated, and the other is a light emitting device to generate photoenergy from electrical energy by supplying a voltage or a current to electrodes.

Examples of the organic optoelectric device include an organic photoelectric device, an organic light emitting diode, an organic solar cell, and an organic photo-conductor drum, and the like.

Among them, the organic light emitting diode (OLED) has recently drawn attention due to an increase in demand for flat panel displays. The organic light emitting diode converts electrical energy into light by applying current to an organic light emitting material, and has a structure in which an organic layer is interposed between an anode and a cathode. Herein, the organic layer may include an emission layer and optionally an auxiliary layer, and the auxiliary layer may include at least one layer selected from, for example a hole injection layer, a hole transport layer, an electron blocking layer, an electron transport layer, an electron injection layer, and a hole blocking layer in order to improve efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

An embodiment provides a compound for an organic optoelectric device having high efficiency and a long lifespan.

Another embodiment provides a display device including the compound for an organic optoelectric device.

Yet another embodiment provides a display device including the organic optoelectric device.

Technical Solution

According to an embodiment, a compound for an organic optoelectric device represented by Chemical Formula I is provided

[Chemical Formula I]

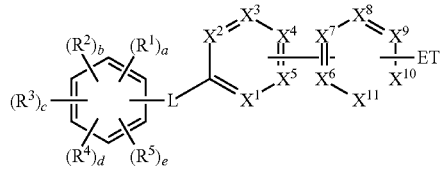

In Chemical Formula I, $X^1$ to $X^{11}$ are independently, N, C, or $CR^a$, $R^a$ is independently, hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heterocyclic group, a substituted or unsubstituted C6 to C30 arylamine group, a substituted or unsubstituted C1 to C30 alkoxy group, a substituted or unsubstituted C3 to C40 silyl group, a substituted or unsubstituted C3 to C40 silyloxy group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof, $R^1$ to $R^5$ are independently a substituted or unsubstituted C6 to C30 aryl group, a substituted or unsubstituted C2 to C30 heteroaryl group, or a combination thereof, and $R^1$ to $R^5$ are independently present or adjacent groups of $R^1$ to $R^5$ are linked to provide a ring, a to e are independently an integer of 0 or 1, $4 \leq a+b+c+d+e \leq 5$, L is a single bond, a substituted or unsubstituted C6 to C30 arylene group, a substituted or unsubstituted C2 to C30 heteroarylene group, or a combination thereof, and ET is a substituted or unsubstituted heteroaryl group including at least one N except a carbazolyl group, wherein "substituted" refers to that at least one hydrogen is replaced by deuterium, a halogen, a hydroxy group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

According to another embodiment, an organic optoelectric device includes an anode and a cathode facing each other and at least one organic layer between the anode and the cathode, wherein the organic layer includes the compound for an organic optoelectric device.

According to yet another embodiment, a display device including the organic optoelectric device is provided.

Advantageous Effects

An organic optoelectric device having high efficiency long life-span may be realized.

DESCRIPTION OF THE DRAWINGS

FIG. 1 is a cross-sectional view showing an organic light emitting diode according to an embodiment.

FIG. 2 is a cross-sectional view specifically showing an organic layer of an organic light emitting diode according to an embodiment.

FIGS. 3 and 4 are cross-sectional views specifically showing a part of an organic layer of an organic light emitting diode according to an embodiment.

BEST MODE

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to one substituted with a deuterium, a halogen, a hydroxy group, an amino group, a C1 to C30 amine group, a nitro group, a C1 to C40 silyl group, a C1 to C30 alkyl group, a C1 to C10 alkylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group such as a trifluoromethyl group, or a cyano group, instead of at least one hydrogen of a substituent or a compound.

In addition, two adjacent substituents of the substituted halogen, a hydroxy group, amino group, C1 to C30 amine group, nitro group, C1 to C40 silyl group, C1 to C30 alkyl group, C1 to C10 alkylsilyl group, C3 to C30 cycloalkyl group, C2 to C30 heterocycloalkyl group, C6 to C30 aryl group, C2 to C30 heteroaryl group, C1 to C20 alkoxy group, fluoro group, C1 to C10 trifluoroalkyl group such as trifluoromethyl group, or cyano group may be fused with each other to form a ring. For example, the substituted C6 to C30 aryl group may be fused with another adjacent substituted C6 to C30 aryl group to form a substituted or unsubstituted fluorene ring.

In the present specification, when specific definition is not otherwise provided, the term "hetero" refers to one including 1 to 3 hetero atoms selected from N, O, S, P, and Si, and remaining carbons in one compound or substituent.

In the present specification, when a definition is not otherwise provided, an "alkyl group" may refer to an aliphatic hydrocarbon group. The alkyl group may refer to "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group includes 1 to 4 carbons in alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl-group, a butyl group, an isobutyl group, a t-butyl group, a pentyl group, a hexyl group, a cyclopropyl group, a cyclobutyl group, a cyclopentyl group, a cyclohexyl group, and the like.

In the present specification "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one hetero atom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, a "heteroaryl group" may refer to aryl group including at least one hetero atom selected from N, O, S, P, and Si instead of carbon (C). Two or more heteroaryl groups are linked by a sigma bond directly, or when the C2 to C60 heteroaryl group includes two or more rings, the two or more rings may be fused. When the heteroaryl group is a fused ring, each ring may include 1 to 3 hetero atoms.

Specific examples of the heteroaryl group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridinyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or a combination thereof, but are not limited thereto.

In the present specification, the single bond refers to a direct bond not by carbon or a hetero atom except carbon, and specifically the meaning that L is a single bond means that a substituent linked to L directly bonds with a central core. That is, in the present specification, the single bond does not refer to methylene that is bonded via carbon.

In the specification, hole characteristics refer to an ability to donate an electron to form a hole when an electric field is applied and that a hole formed in the anode may be easily injected into the emission layer and transported in the emission layer due to conductive characteristics according to a highest occupied molecular orbital (HOMO) level.

In addition, electron characteristics refer to an ability to accept an electron when an electric field is applied and that electron formed in the cathode may be easily injected into the emission layer and transported in the emission layer due to conductive characteristics according to a lowest unoccupied molecular orbital (LUMO) level.

Hereinafter, a compound for an organic optoelectric device according to an embodiment is described.

A compound for an organic optoelectric device according to an embodiment is represented by Chemical Formula I.

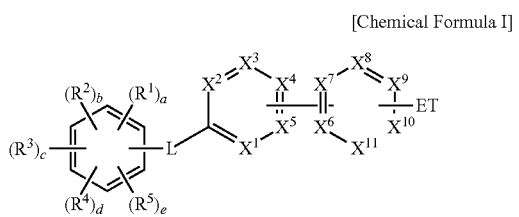

[Chemical Formula I]

In Chemical Formula I, $X^1$ to $X^{11}$ are independently, N, C, or $CR^a$, $R^a$ is independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heterocyclic group, a substituted or unsubstituted C6 to C30 arylamine group, a substituted or unsubstituted C1 to C30 alkoxy group, a substituted or unsubstituted C3 to C40 silyl group, a substituted or unsubstituted C3 to C40 silyloxy group, a substituted or unsubstituted C1 to C30 alkylthio group, a substituted or unsubstituted C6 to C30 arylthio group, halogen, a halogen-containing group, a cyano group, a hydroxyl group, an amino group, a nitro group, or a combination thereof, $R^1$ to $R^5$ are independently a substituted or unsubstituted C6 to C30 aryl group, a substituted or unsubstituted C2 to C30 heteroaryl group, or a combination thereof, $R^1$ to $R^5$ are independently present, or adjacent groups of $R^1$ to $R^5$ are linked to provide a ring, a to e are independently an integer of 0 or 1, $4 \leq a+b+c+d+e \leq 5$, L is a single bond, a substituted or unsubstituted C6 to C30 arylene group, a substituted or unsubstituted C2 to C30 heteroarylene group, or a combination thereof, and ET is a substituted or unsubstituted heteroaryl group including at least one N except a carbazolyl group, "substituted" refers to that at least one hydrogen is replaced by deuterium, a halogen, a hydroxy group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

In one example of the present invention, $R^1$ to $R^5$ of Chemical Formula I may independently be a substituted or unsubstituted phenyl group, a substituted or unsubstituted naphthyl group, a substituted or unsubstituted pyridinyl group, or a substituted or unsubstituted pyrimidinyl group. For specific examples, $R^1$ to $R^5$ of Chemical Formula I may independently be a substituted or unsubstituted phenyl group, or a substituted or unsubstituted naphthyl group.

In one example of the present invention, $X^1$ to $X^{11}$ of Chemical Formula I may independently be C, or $CR^a$, wherein $R^a$ is hydrogen, deuterium, a substituted or unsubstituted C1 to C30 alkyl group, a substituted or unsubstituted C6 to C30 aryl group, a substituted or unsubstituted C2 to C30 heteroaryl group. For specific examples, $X^1$ to $X^{11}$ of Chemical Formula I may independently be C or $CR^a$, wherein $R^a$ is hydrogen, or a substituted or unsubstituted C6 to C30 aryl group.

In one example of the present invention, the ET group of Chemical Formula I may be a substituted or unsubstituted pyrimidinyl group, a substituted or unsubstituted triazinyl group, a substituted or unsubstituted benzimidazolyl group, a substituted or unsubstituted imidazolyl group, a substituted or unsubstituted triazolyl group, a substituted or unsubstituted oxadiazolyl group, a substituted or unsubstituted thiadiazolyl group, a substituted or unsubstituted benzimidazolyl group, a substituted or unsubstituted quinazolinyl group, or a substituted or unsubstituted phenanthrolinyl group. For specific examples, the ET group of Chemical Formula I may be a substituted or unsubstituted triazinyl group, or a substituted or unsubstituted benzimidazolyl group.

The compound for an organic optoelectric device of Chemical Formula I consists of a moiety having a bulky aromatic group substituted with four or more substituents and a moiety having a nitrogen-containing heteroaryl group. The nitrogen-containing heteroaryl group facilitates injection or transport of electrons in a device, and the bulky aromatic group helps injection or transport of holes or increases a glass transition temperature of the compound, and thus luminance efficiency may be increased due to suppression of an intermolecular interaction, and the compound may have a low deposition temperature relative to the molecular weight.

Accordingly, when the compound for an organic optoelectric device represented by Chemical Formula I forms a film, the compound may facilitate injection and transport of electrons in the device due to excellent packing of the nitrogen-containing heteroaryl group having a relatively flat structure compared with the bulky aromatic group. Therefore, when the compound for an organic optoelectric device represented by Chemical Formula I is particularly used to form an electron injection auxiliary layer, the compound may decrease a driving voltage of the device due to excellent electron transport characteristics and increase luminous efficiency due to rapid injection of electrons into an emission layer. On the other hand, when the compound is mixed with a material having excellent hole injection and transport characteristics to form the emission layer, the compound may also decrease a driving voltage due to excellent electron transport capability and obtain excellent luminance efficiency due to an intermolecular interaction by the moiety having the bulky aromatic group. In addition, excellent electron injection and transport characteristics of the compound for an organic optoelectric device represented by Chemical Formula I may not be much changed, even though a large nitrogen-containing substituent having electron transport characteristics is introduced in addition to the moiety having the bulky aromatic group, and in addition, the compound may still maintain excellent electron injection and transport characteristics even when used to from an electron injection auxiliary layer or to form an emission layer as a mixture with with a compound having excellent hole characteristics.

The compound for an organic optoelectric device represented by Chemical Formula I includes at least five substituted or unsubstituted C6 to C30 aryl groups in addition to a phenyl group in the center in a region where holes are easy to be accepted and thus may have a molecular weight of greater than or equal to 750.

On the other hand, in compounds having a molecular weight of greater than or equal to 750, such as a linear structure may increase a deposition temperature of the compounds and thus have an influence on their heat-resisting stability during a process of manufacturing a device, but the compounds for an organic optoelectric device represented by Chemical Formula I according to the present invention may have a low deposition temperature relative to a molecular weight by introducing a bulky substituent into the end and thus excellent heat-resisting stability even it has a molecular weight of greater than or equal to 750.

The compound for an organic optoelectric device represented by Chemical Formula I may include a linking group between L and ET is linked in a meta, para, or ortho, and may be represented by one of, for example Chemical Formulae I-1 to I-3.

[Chemical Formula I-1]

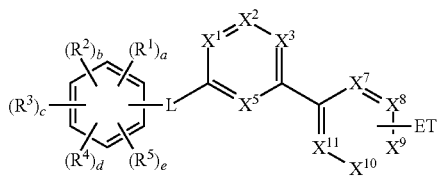

[Chemical Formula I-2]

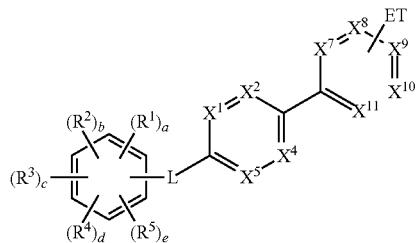

[Chemical Formula I-3]

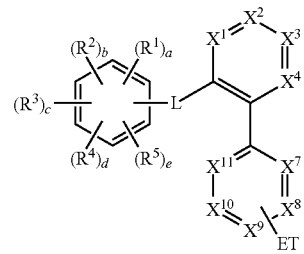

In Chemical Formulae I-1 to I-3, $X^1$ to $X^{11}$, $R^1$ to $R^5$, a to e, L and ET are the same as described above.

Specifically, the compound for an organic optoelectric device represented by Chemical Formula I-1 may be represented by one of, for example Chemical Formulae I-1a to I-1f according to positions of the ET group and the number of the substituents of the aromatic group.

[Chemical Formula I-1a]

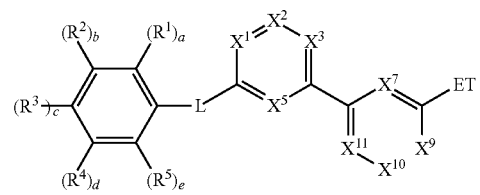

[Chemical Formula I-1b]

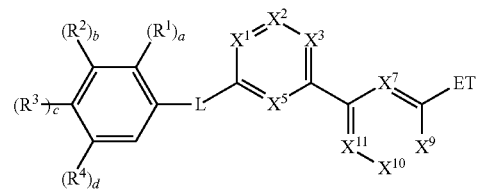

[Chemical Formula I-1c]

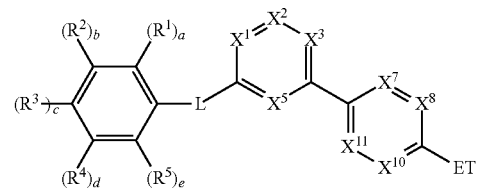

[Chemical Formula I-1d]

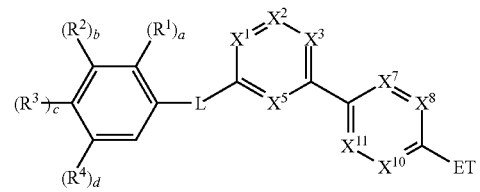

[Chemical Formula I-1e]

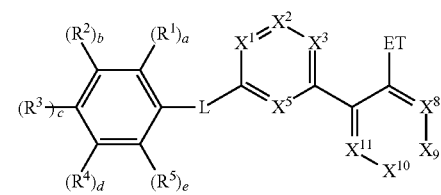

[Chemical Formula I-1f]

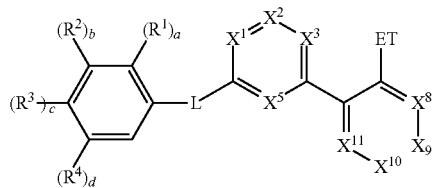

In addition, the compound for an organic optoelectric device represented by Chemical Formula I-2 may be represented by one of, for example Chemical Formulae I-2a to I-2f according to positions of the ET group and the number of the substituents of the aromatic group.

[Chemical Formula I-2a]

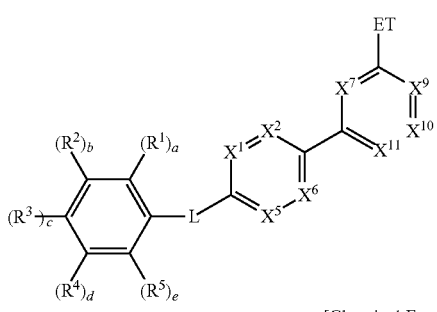

[Chemical Formula I-2b]

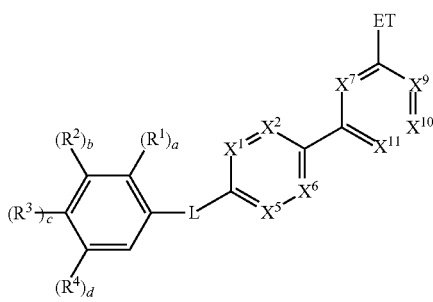

[Chemical Formula I-2c]

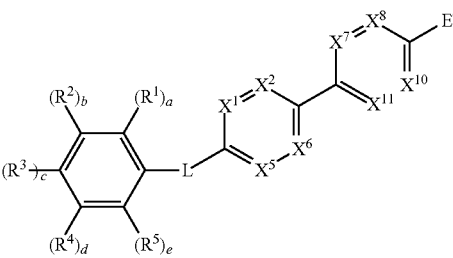

[Chemical Formula I-2d]

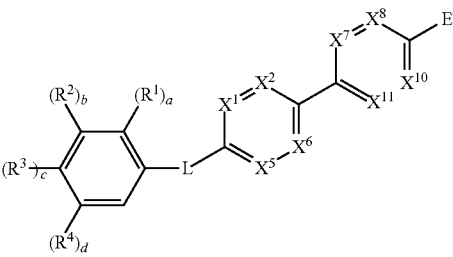

[Chemical Formula I-2e]

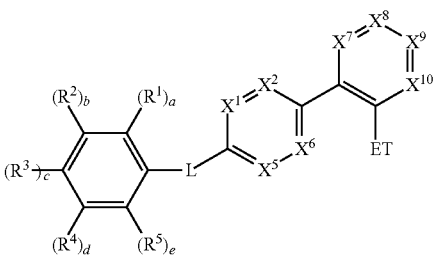

[Chemical Formula I-2f]

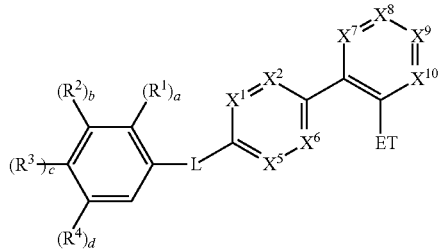

In addition, the compound for an organic optoelectric device represented by Chemical Formula I-3 may be represented by one of, for example Chemical Formulae I-3a to I-3f according to positions of the ET group and the number of the substituents of the aromatic group.

[Chemical Formula I-3a]

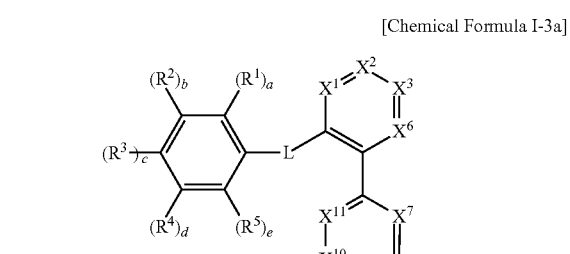

[Chemical Formula I-3b]

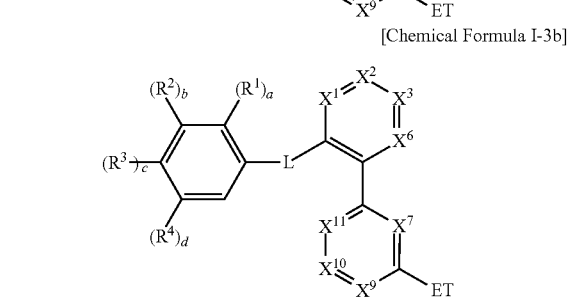

[Chemical Formula I-3c]

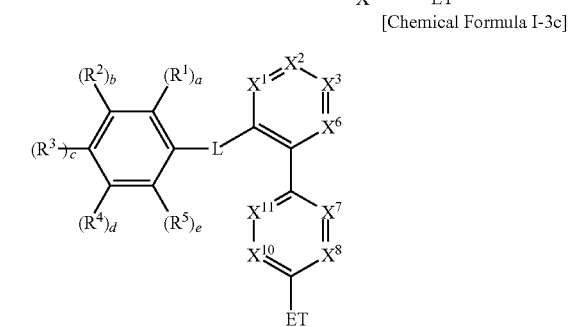

[Chemical Formula I-3d]

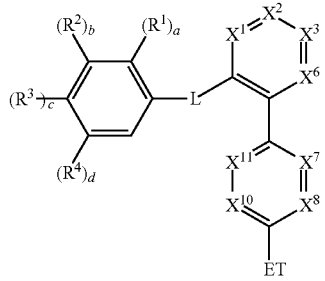

[Chemical Formula I-3e]

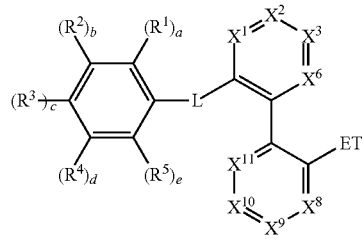

[Chemical Formula I-3f]

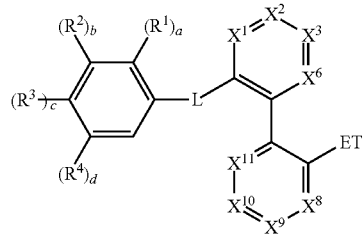

In Chemical Formulae I-1a to I-1f, I-2a to I-2f and I-3a to I-3f, $X^1$ to $X^{11}$, $R^1$ to $R^5$, L, and ET are the same as described in Chemical Formula I, and a to e are integers of 1.

In one example of the present invention, the Chemical Formulae I-1a to I-1f are preferable.

In addition, in one example of the present invention, in Chemical Formulae I-1a to I-1f, I-2a to I-2f, and I-3a to I-3f, $R^1$ to $R^5$ may independently be a substituted or unsubstituted phenyl group, a substituted or unsubstituted naphthyl group, a substituted or unsubstituted pyridinyl group, or a substituted or unsubstituted pyrimidinyl group, and a to e are integers of 1. Preferably, $R^1$ to $R^5$ may independently be a substituted or unsubstituted phenyl group, a substituted or unsubstituted naphthyl group, a substituted or unsubstituted pyridinyl group, and a to e are integers of 1. More preferably, $R^1$ to $R^5$ may independently be a substituted or unsubstituted phenyl group, and a to e are integers of 1.

According to an embodiment of the present invention, the ET may be selected from a 5-membered heteroaryl group and 6-membered heteroaryl group.

Specifically, the ET may be a substituted or unsubstituted imidazolyl group, a substituted or unsubstituted pyrazolyl group, a substituted or unsubstituted thiazolyl group, a substituted or unsubstituted isothiazolyl group, a substituted or unsubstituted oxazolyl group, a substituted or unsubstituted isoxazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted triazinyl group, a substituted or unsubstituted indazolyl group, a substituted or unsubstituted purinyl group, a substituted or unsubstituted quinolinyl group, a substituted or unsubstituted isoquinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzimidazolyl group, a substituted or unsubstituted isobenzothiazolyl group, a substituted or unsubstituted benzoxazolyl group, a substituted or unsubstituted benzothiazolyl group, a substituted or unsubstituted benzoquinazolinyl group, a substituted or unsubstituted isobenzooxazolyl group, a substituted or unsubstituted triazolyl group, a substituted or unsubstituted tetrazolyl group, a substituted or unsubstituted oxadiazolyl group, a substituted or unsubstituted thiadiazolyl group, a substituted or unsubstituted imidazopyridinyl group, a substituted or unsubstituted imidazopyrimidinyl group, or a combination thereof, and may be, for example a substituted or unsubstituted groups of Group I.

[Group I]

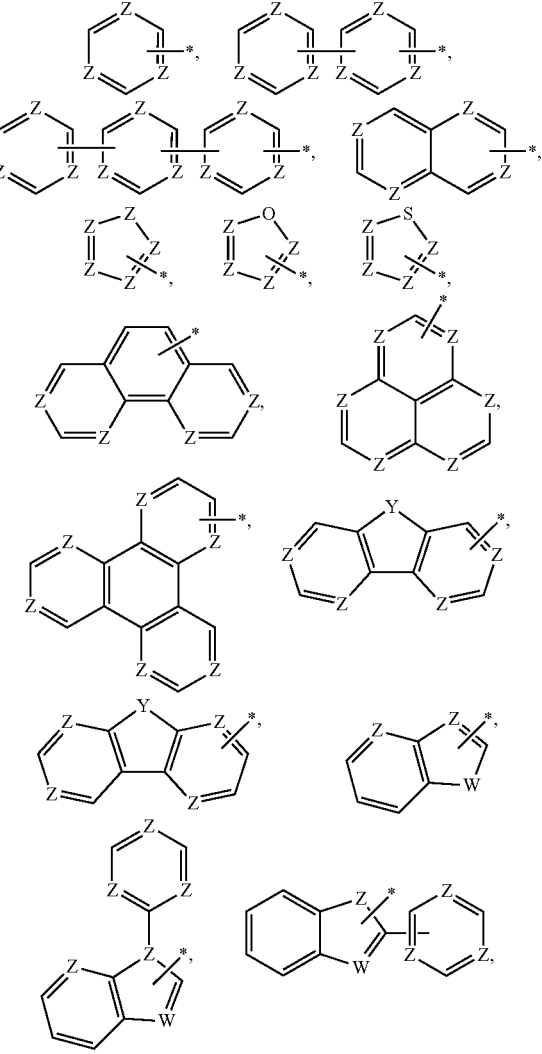

-continued

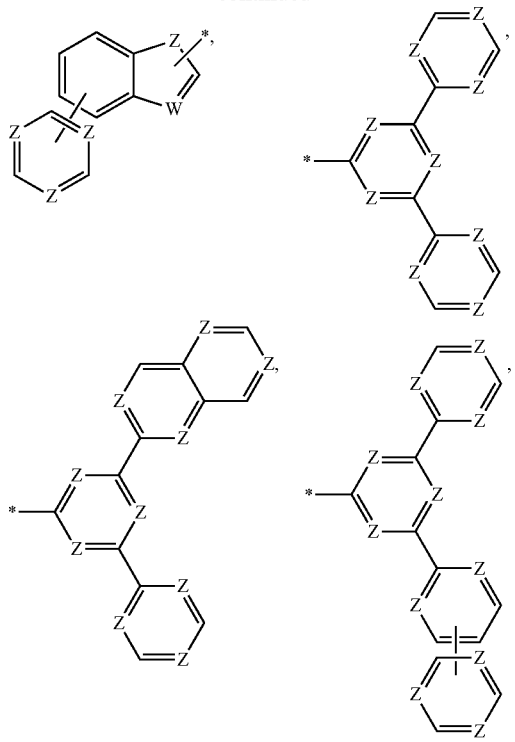

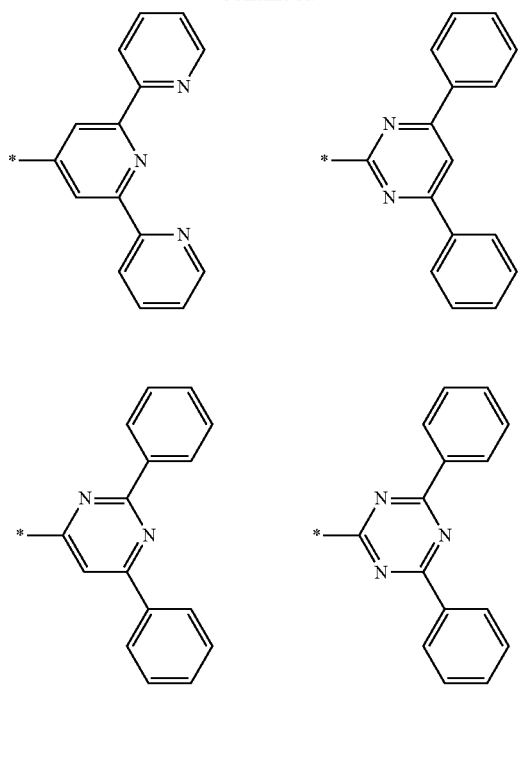

In Group I,

Z is independently N or CR$^b$, wherein at least one of Z is N, and

W and Y are independently N, O, S, SO, SO$_2$, CR$^c$, CR$^d$R$^e$, SiR$^f$, or SiR$^g$R$^h$, wherein R$^b$ to R$^h$ are independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C2 to C30 heteroaryl group, or a combination thereof, and \* indicates bonding sites with neighboring atoms, and is positioned at one of element of the functional group.

More specifically, the ET may be a group that is further substituted with a substituted or unsubstituted phenyl group and may be one of substituted or unsubstituted functional groups of Group I-1.

[Group I-1]

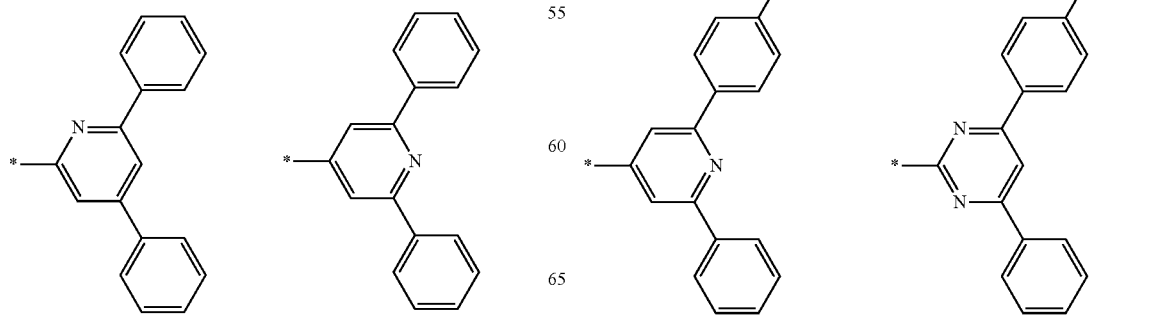

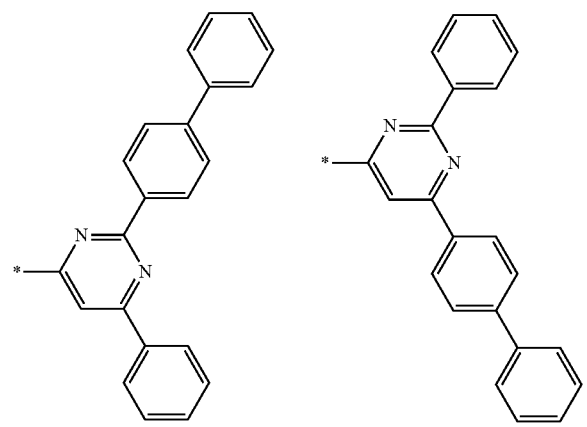
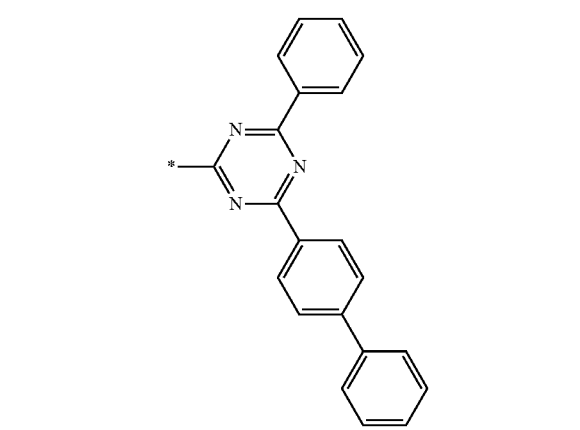
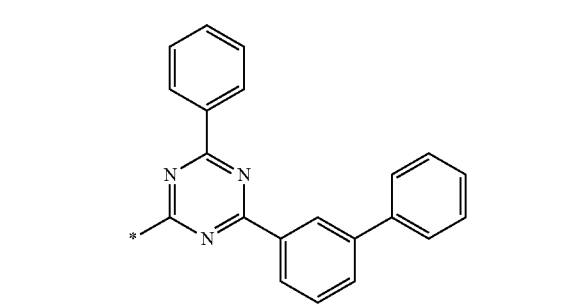
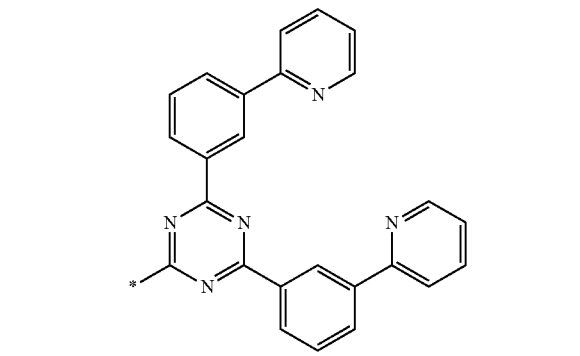
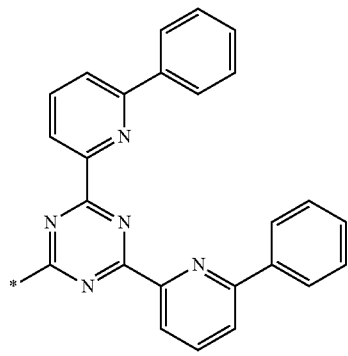
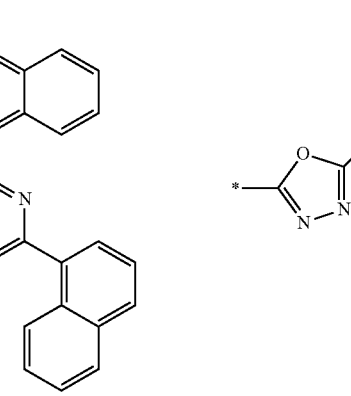

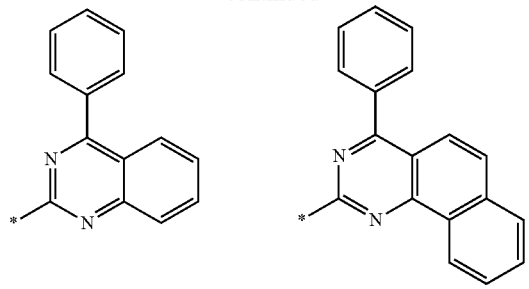

In Group I-1, * indicates bonding sites with neighboring atoms.

In addition, according to an embodiment of the present invention, the L may be a single bond, a phenylene group, a biphenylene group, a terphenylene group, a quarterphenylene group, a pentalenylene group, an indenylene group, a naphthylene group, a phenalenylene group, a phenanthrenylene group, an anthracenylene group, a fluoranthrenylene group, a triphenylenylene group, a pyrenylene group, a chrysenylene group, a pyrrolylene group, an imidazolylene group, a pyrazolylene group, a pyridinylene group, a pyrazinylene group, a pyrimidinylene group, a triazinylene group, a pyridazinylene group, a quinolinylene group, an isoquinolinylene group, an oxazolylene group, a triazolylene group a tetrazolylene group, an oxadiazolylene group, or a combination thereof.

Specifically, it may be selected from substituted or unsubstituted groups of Group II.

[Group II]

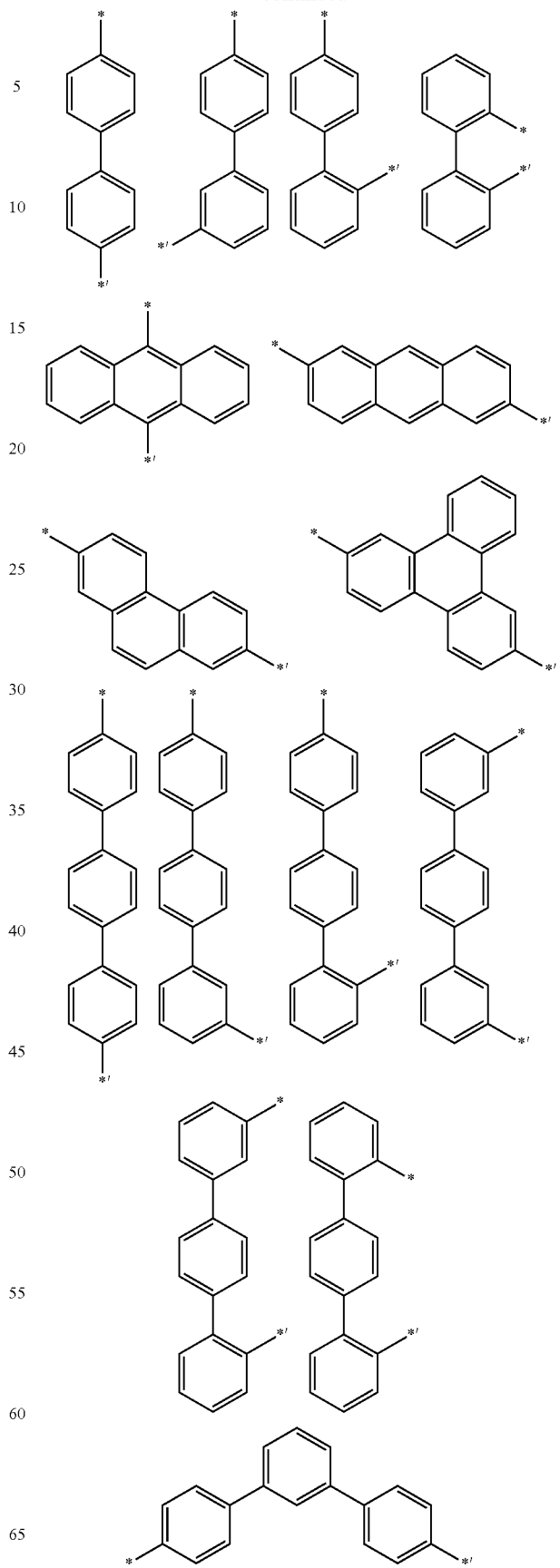

-continued
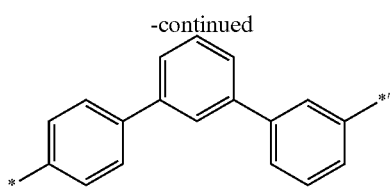
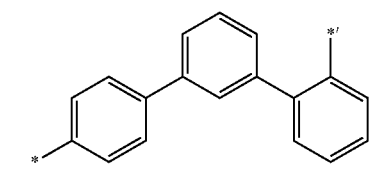
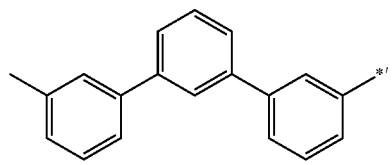
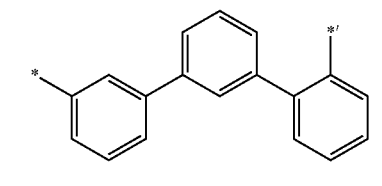
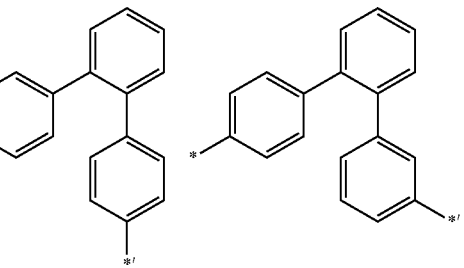
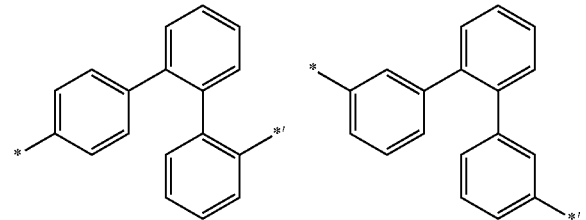
* and *' indicate bonding sites with neighboring atoms.
The compound for an organic optoelectric device represented by Chemical Formula I may be, for example one of compounds of Group 1, but is not limited thereto.
[Group 1]
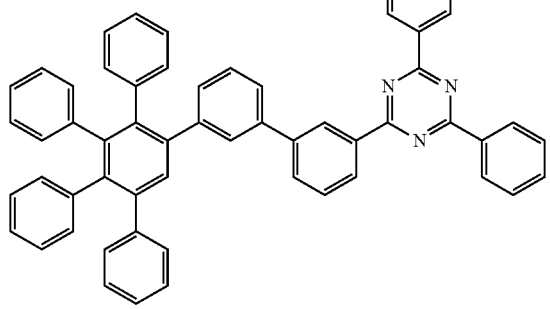
[1]
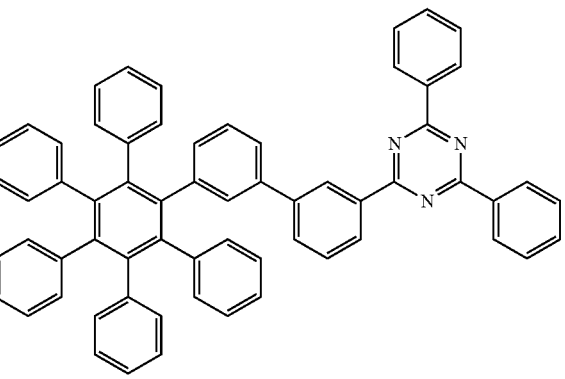
[2]
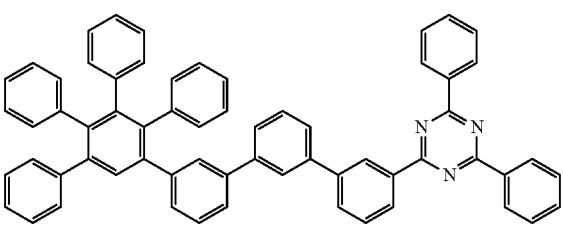
[3]
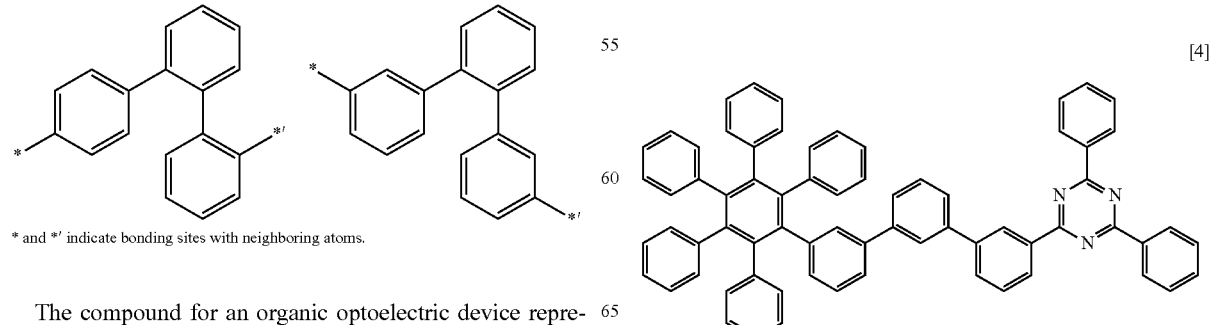
[4]

[5]
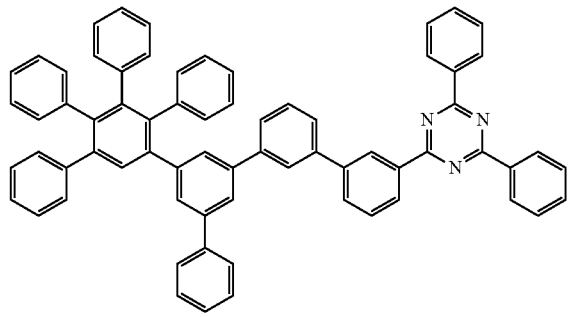
[6]
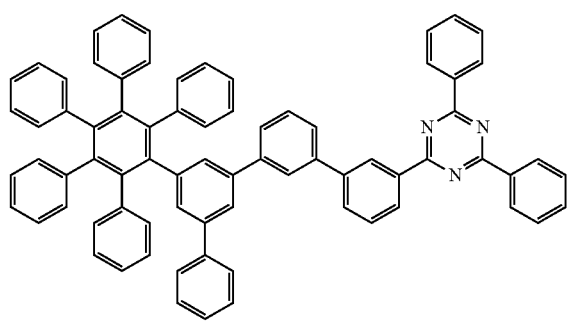
[7]
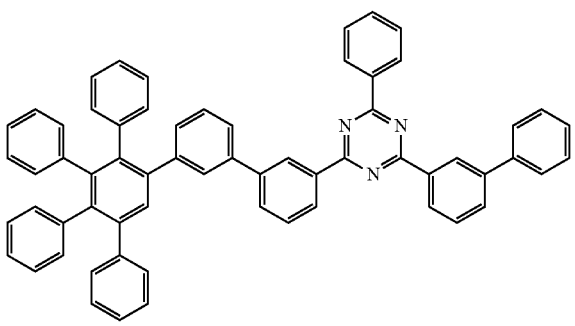
[8]
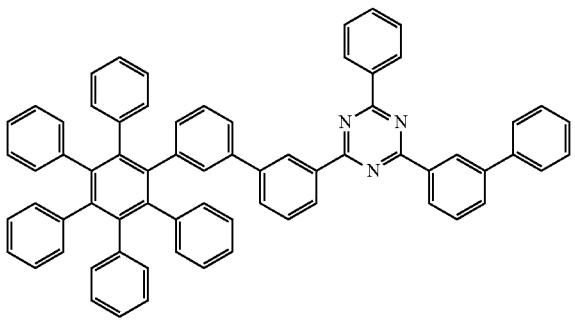
[9]
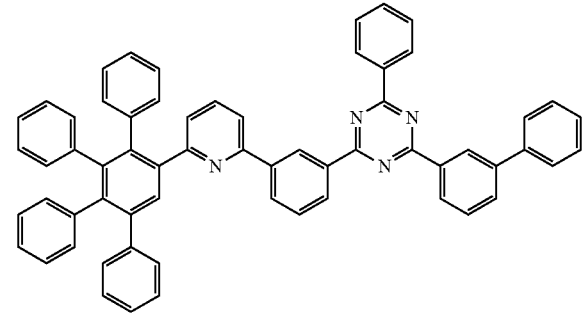
[10]
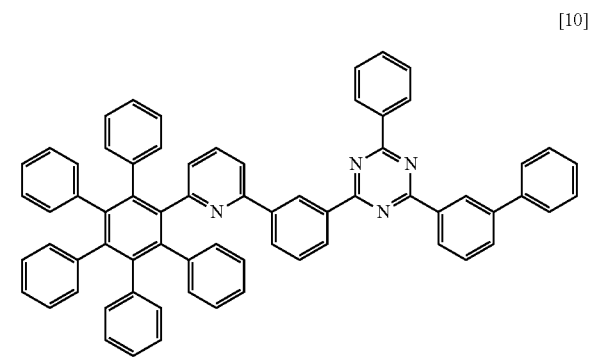
[11]
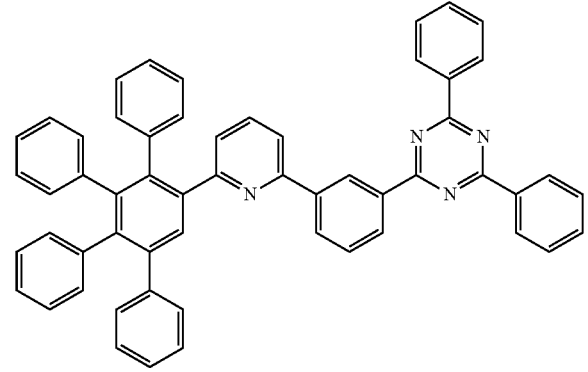
[12]
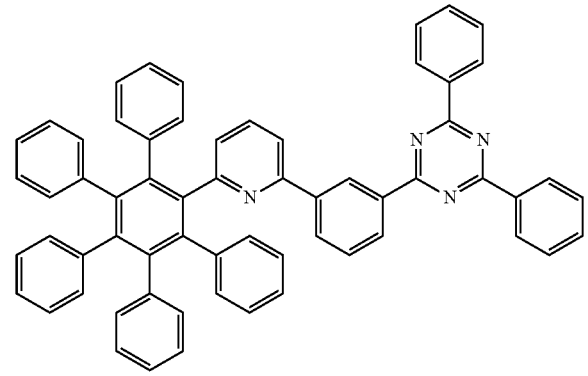

-continued
[13]
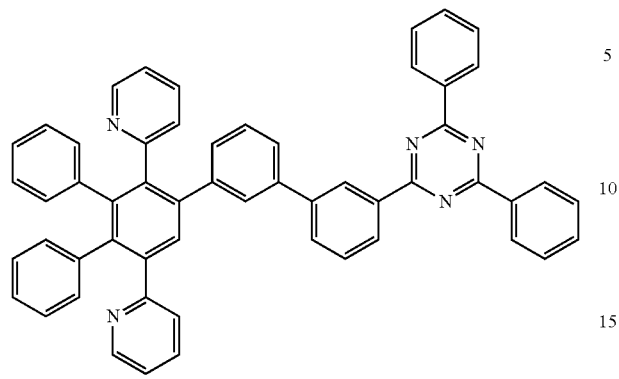
[14]
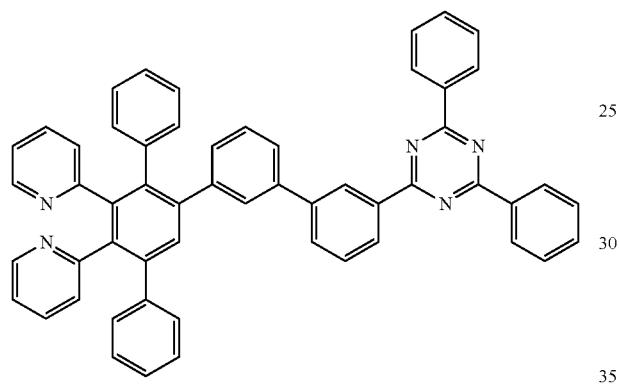
[15]
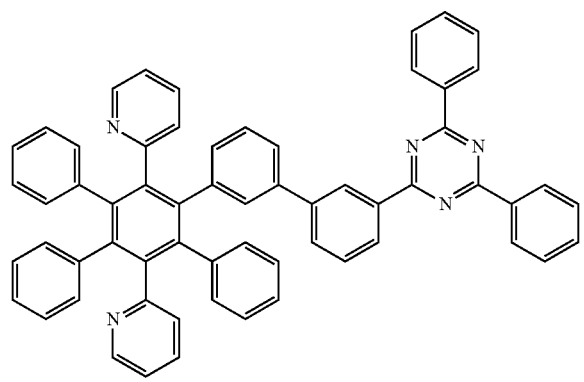
[16]
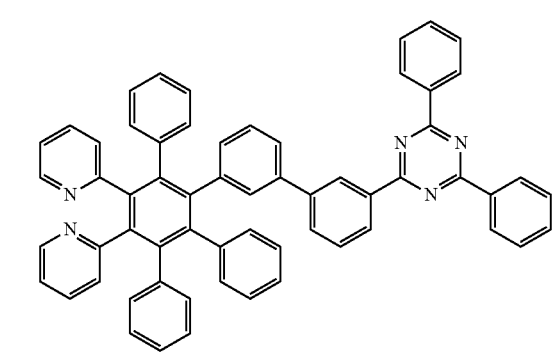
-continued
[17]
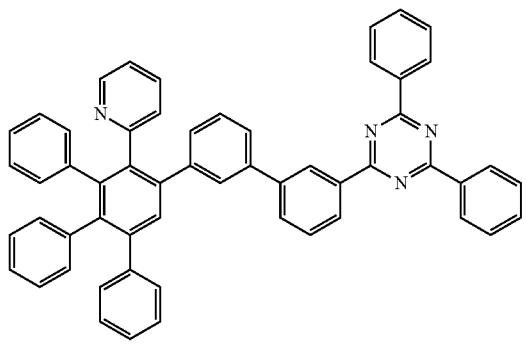
[18]
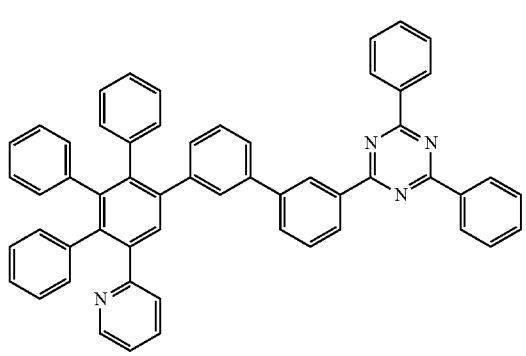
[19]
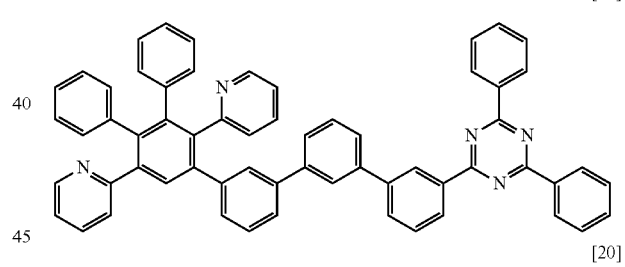
[20]
[21]
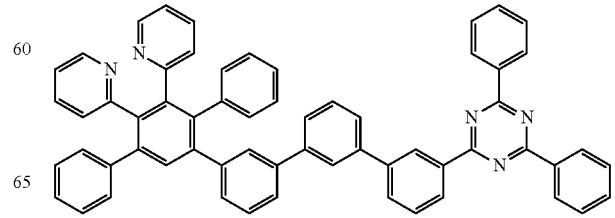

[22]
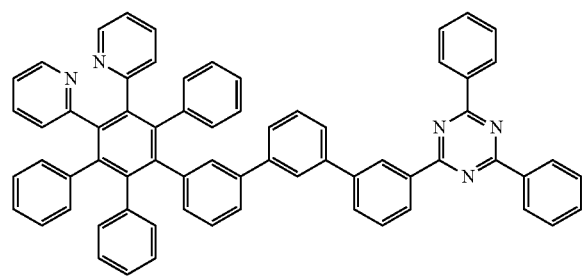
[23]
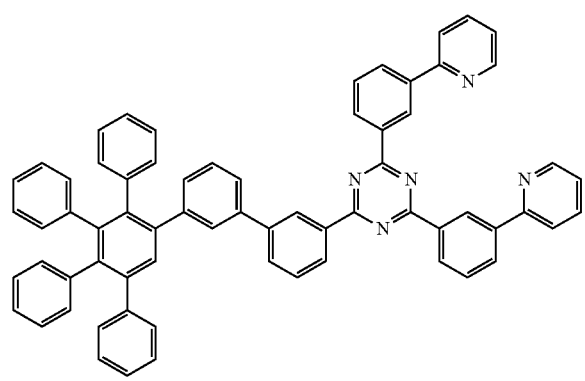
[24]
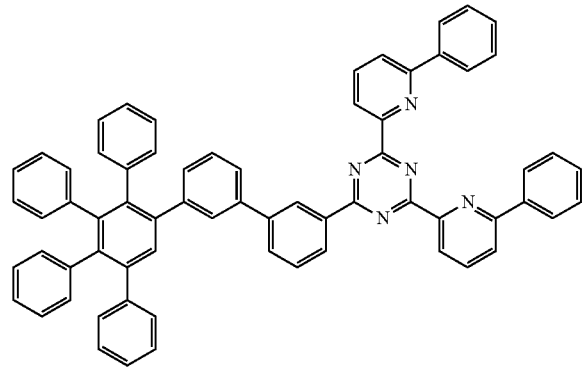
[25]
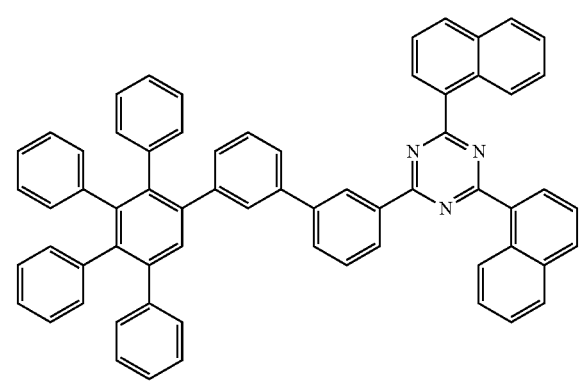
[26]
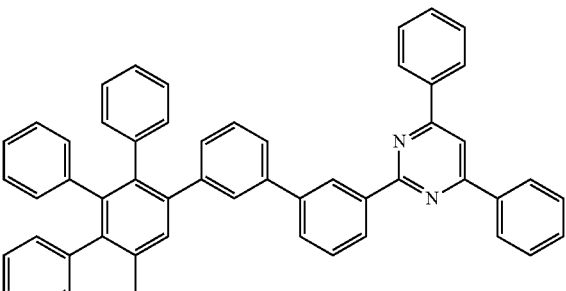
[27]
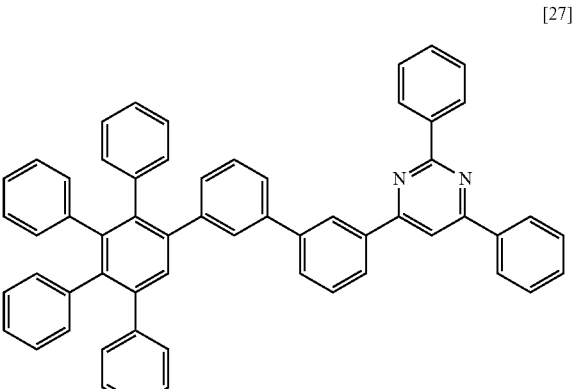
[28]
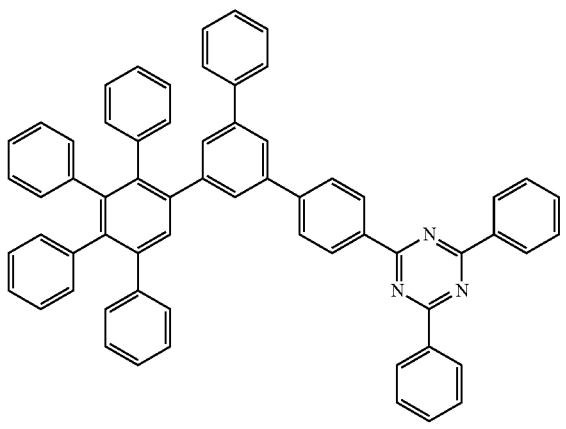
[29]
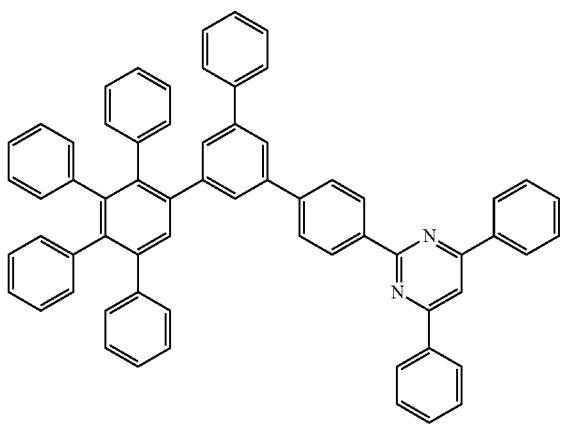

[30]
[31]
[32]
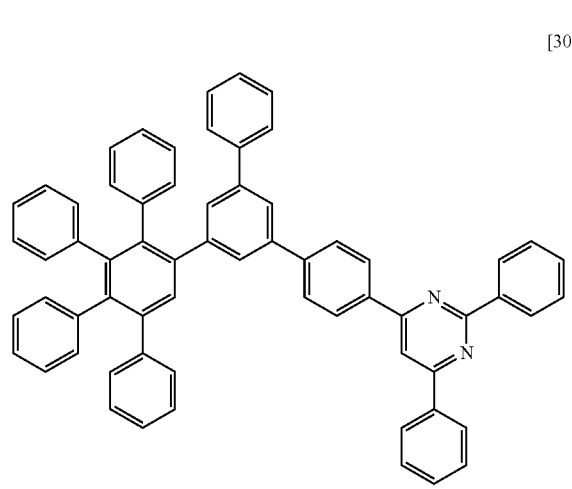
[33]
[34]
[35]
[36]
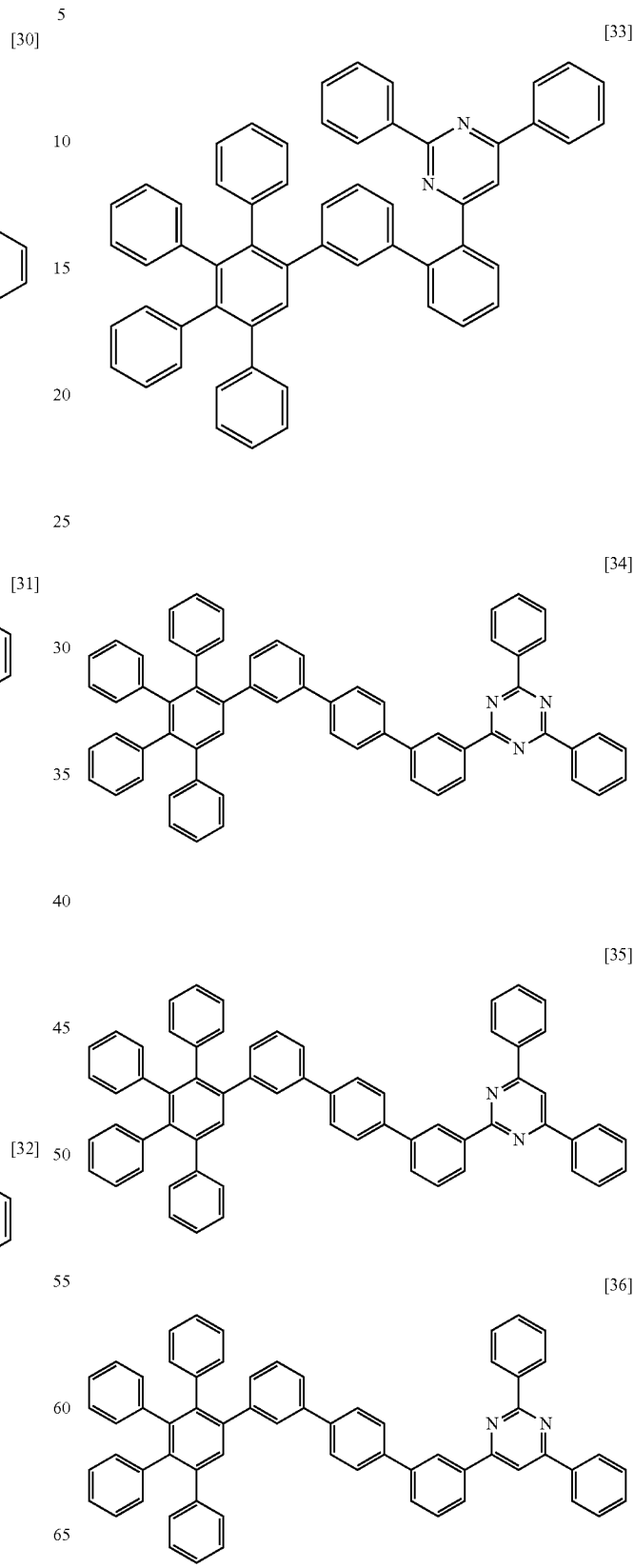

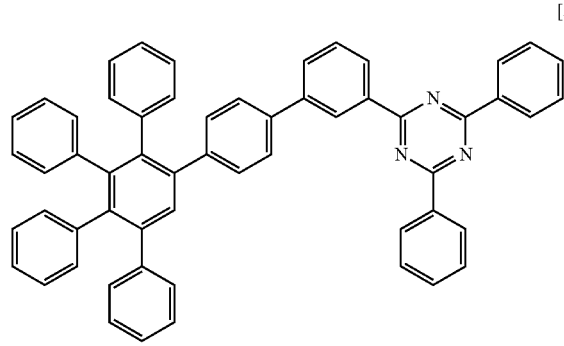
[37]
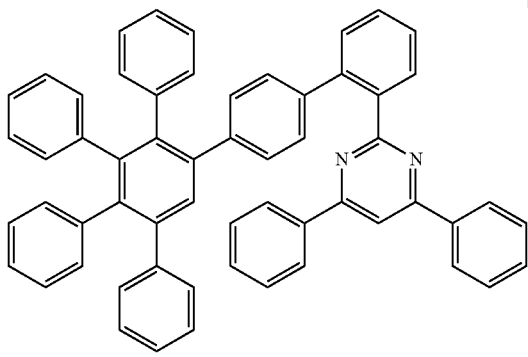
[41]
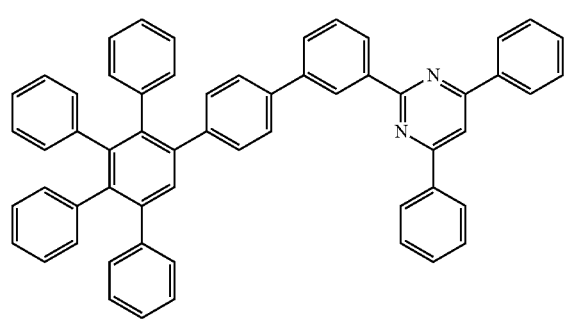
[38]
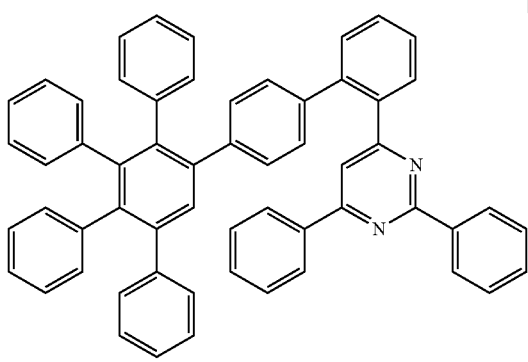
[42]
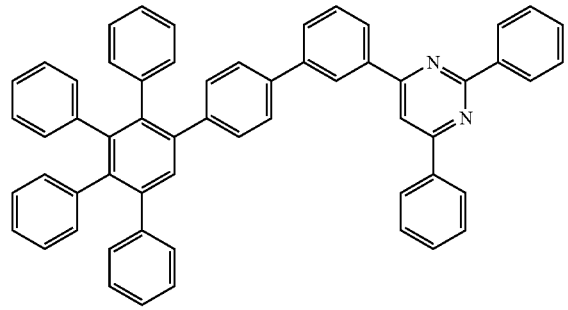
[39]
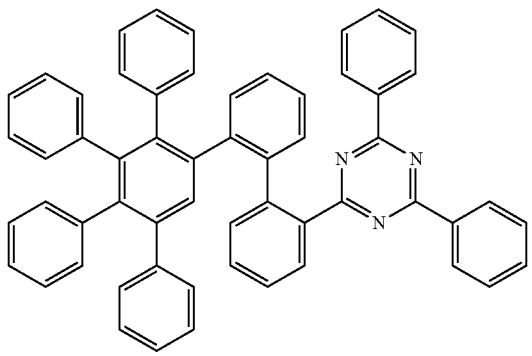
[43]
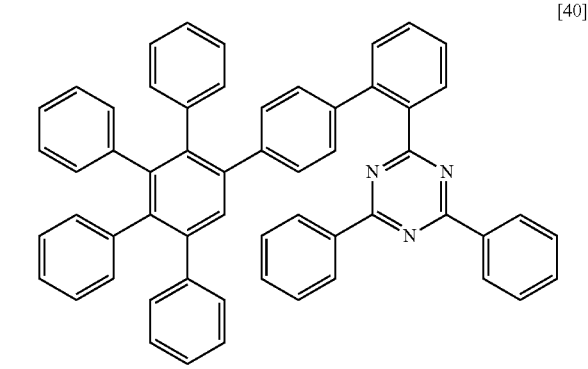
[40]
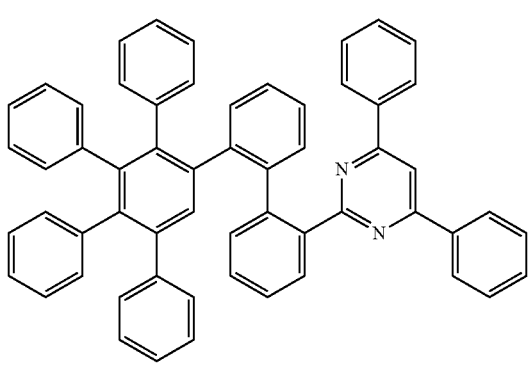
[44]

[45] 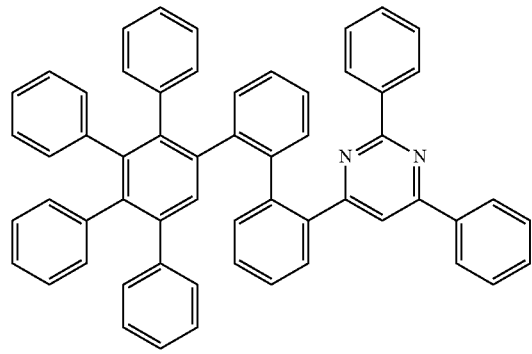
[46] 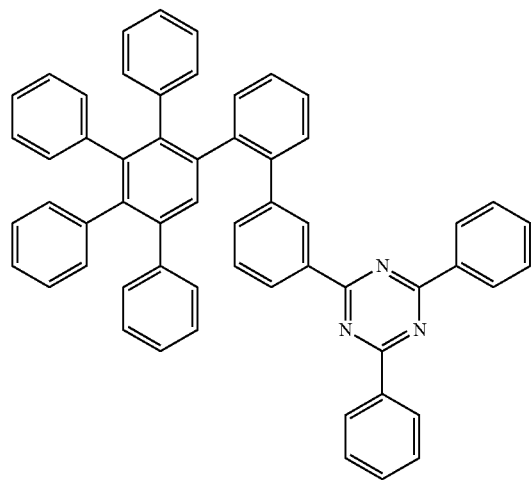
[47] 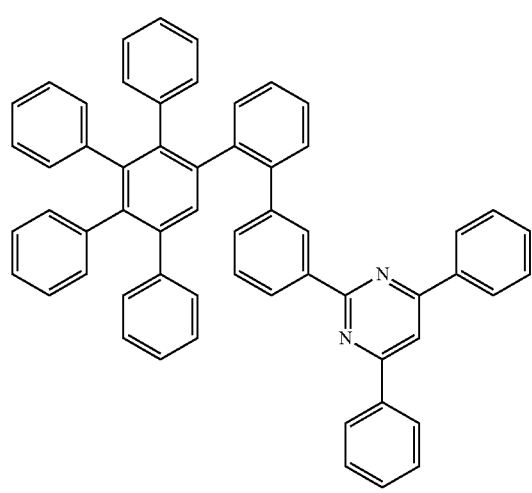
[48] 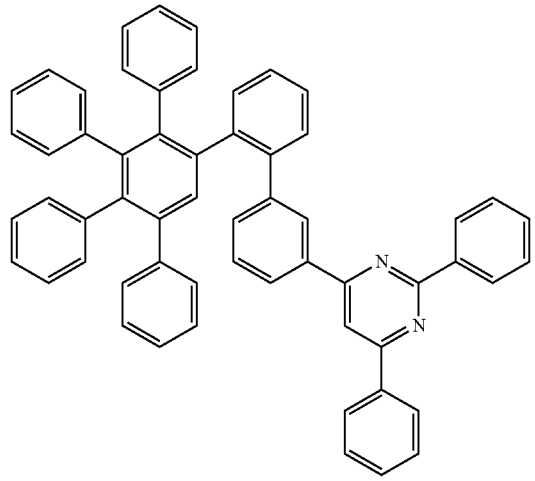
[49] 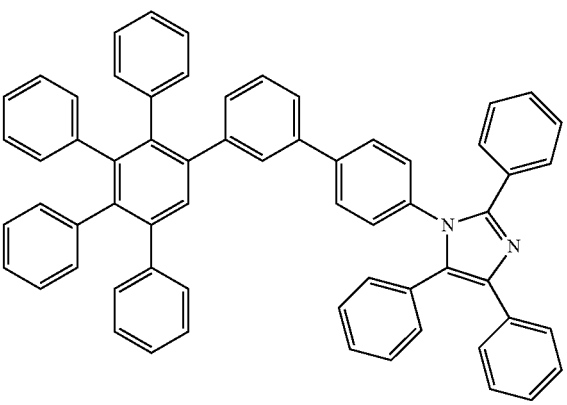
[50] 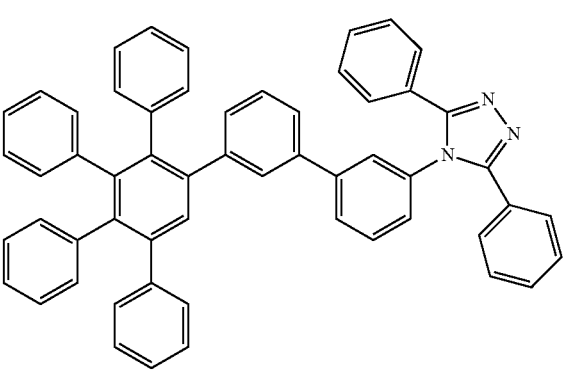
[51] 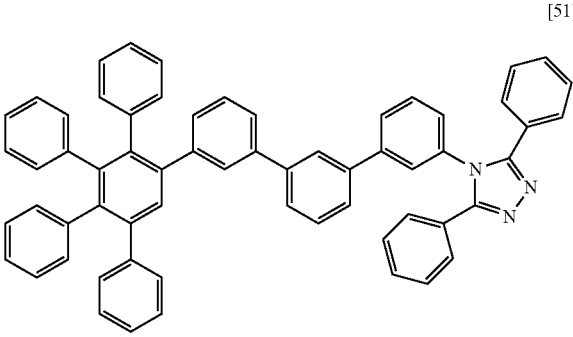

-continued
[52]
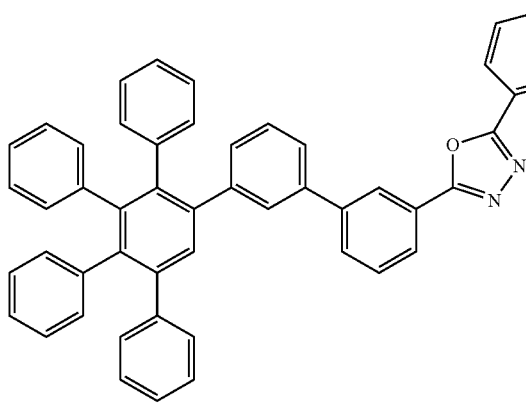
[53]
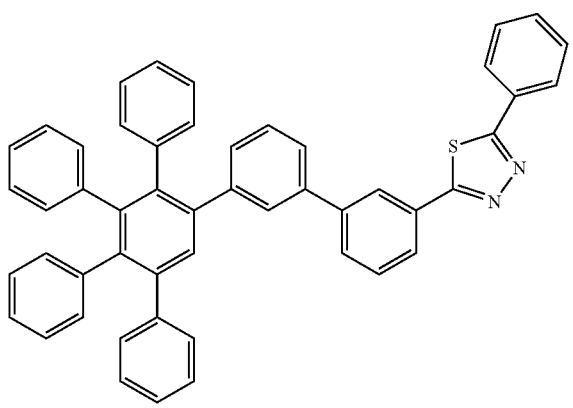
[54]
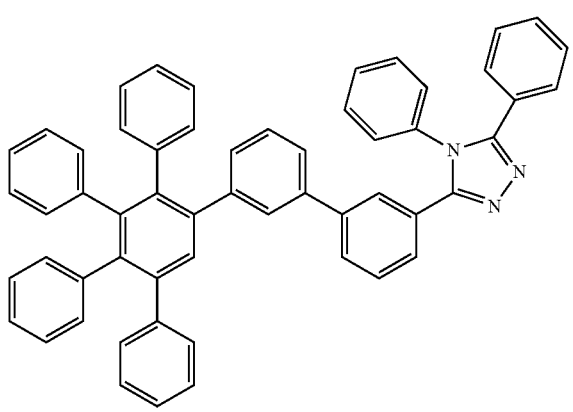
[55]
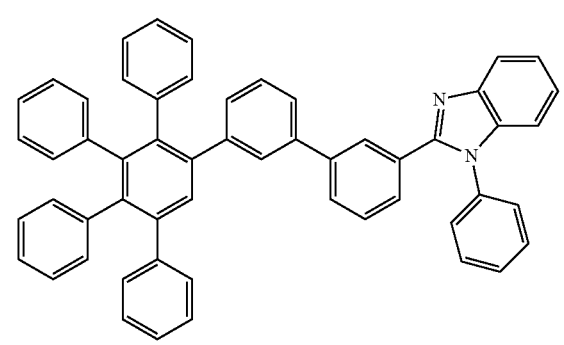
-continued
[56]
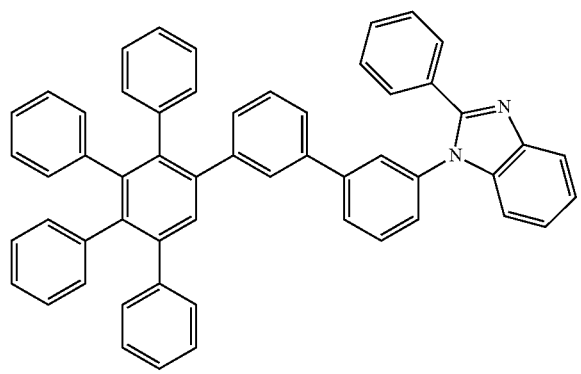
[57]
[58]
[59]

-continued

[60]

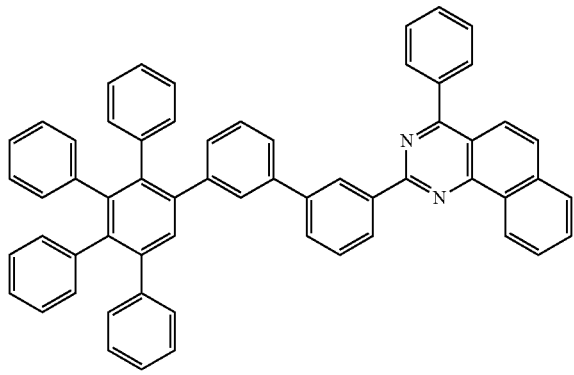

One or more of the compound for an organic optoelectric device may be used.

Hereinafter, an organic optoelectric device according to another embodiment is described.

An organic optoelectric device according to another embodiment includes an anode and a cathode facing each other and at least one organic layer between the anode and the cathode and the organic layer includes the compound for an organic optoelectric device.

The compound for an organic optoelectric device represented by Chemical Formula I may be appropriate for an organic layer of an organic optoelectric device, for example, a host of an emission layer or an electron transport auxiliary layer of the organic layer.

The organic optoelectric device may realize a low driving voltage, high efficiency, high luminance and long life-span by including the organic layer including the compound for an organic optoelectric device.

FIGS. 1 to 4 are schematic cross-sectional views of organic light emitting diodes 100, 200, 300, and 400 according to an embodiment of the present invention. Hereinafter, referring to FIG. 1, a structure of an organic light emitting diode according to an embodiment of the present invention and a method of manufacturing the same are as follows. The organic light emitting diode 100 has a structure where a cathode 110, an emission layer 130, and an anode 120 that are sequentially stacked.

A substrate may be further disposed under the cathode 110 or on the anode 120. The substrate may be a substrate that used in a general organic light emitting diode and may be a glass substrate or a transparent plastic substrate with strong mechanical strength, thermal stability, transparency, surface smoothness, ease of handling, and water resistance.

The anode 120 may be formed by depositing or sputtering an anode material on a substrate. The anode material may be selected from materials having a high work function that makes hole injection easy. The anode 120 may be a reflective electrode, a transflective electrode, or a transmissive electrode. The anode material may use indium tin oxide (ITO), indium zinc oxide (IZO), tin oxide (SnO$_2$), zinc oxide (ZnO), and the like. Or, it may be a metal such as magnesium (Mg), aluminum (Al), aluminum-lithium (Al—Li), calcium (Ca), magnesium-indium (Mg—In), or magnesium-silver (Mg—Ag).

The anode 120 may have a monolayer or a multi-layer structure of two or more layers.

An organic layer 105 is disposed on the anode 120.

The organic layer 105 may include a hole transport region; an emission layer; and an electron transport region. For example, referring to FIG. 2, an organic light emitting diode according to an embodiment of the present invention is described.

The organic layer 105 further includes a hole auxiliary layer 140 between the anode 120 and the emission layer 130.

Referring to FIG. 3, the hole transport region may include at least two layered hole auxiliary layer, and in this case, a hole auxiliary layer contacting the emission layer is defined as a hole transport auxiliary layer 33 and a hole auxiliary layer contacting an anode is defined as a hole transport layer 31.

The hole transport region may include at least one of a hole injection layer, a hole transport layer, an electron blocking layer, and a buffer layer.

The hole transport region may include only hole injection layer or only hole transport layer. Or, the hole transport region may have a structure where a hole injection layer 37/hole transport layer 31 or hole injection layer 37/hole transport layer 31/electron blocking layer is sequentially stacked from the anode 120.

For example, the hole injection layer 37 and the electron injection layer 36 are additionally included and as shown in FIG. 4, anode 120/hole injection layer 37/hole transport layer 31/hole transport auxiliary layer 33/emission layer 130/electron transport auxiliary layer 35/electron transport layer 34/electron injection layer 36/cathode 110 are sequentially stacked.

The hole injection layer 37 may improve interface properties between ITO as an anode and an organic material used for the hole transport layer 31, and is applied on a non-planarized ITO and thus planarizes the surface of the ITO. For example, the hole injection layer 37 may include a material having a median value, particularly desirable conductivity between a work function of ITO and HOMO of the hole transport layer 31, in order to adjust a difference a work function of ITO as an anode and HOMO of the hole transport layer 31. In connection with the present disclosure, the hole injection layer 37 may include N4,N4'-diphenyl-N4,N4'-bis (9-phenyl-9H-carbazol-3-yl)biphenyl-4,4'-diamine), but is not limited thereto. In addition, the hole injection layer 37 may further include a conventional material, for example, copper phthlalocyanine (CuPc), aromatic amines such as N,N'-dinaphthyl-N,N'-phenyl-(1,1'-biphenyl)-4,4'-diamine, NPD), 4,4',4''-tris[methylphenyl(phenyl)amino] triphenyl amine (m-MTDATA), 4,4',4''-tris[1-naphthyl(phenyl) amino] triphenyl amine (1-TNATA), 4,4',4''-tris[2-naphthyl (phenyl)amino]triphenyl amine (2-TNATA), 1,3,5-tris[N-(4-diphenylaminophenyl)phenylamino] benzene (p-DPA-TDAB), and the like, compounds such as 4,4'-bis[N-[4-{N, N-bis(3-methylphenyl)amino}phenyl]-N-phenylamino] biphenyl (DNTPD), hexaazatriphenylene-hexacarbonitrile (HAT-CN), and the like, a polythiophene derivative such as poly(3,4-ethylenedioxythiophene)-poly(styrnesulfonate) (PEDOT) as a conductive polymer. The hole injection layer 37 may be, for example coated on ITO as an anode in a thickness of 10 to 300 Å.

When the hole transport region includes a hole injection layer 37, the hole injection layer may be formed on the anode 120 by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-8}$ torr to about $10^{-3}$ torr, and a deposition rate of about 0.01 to about 100 Å/sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

Conditions for forming the hole transport layer and the electron blocking layer may be defined based on the above-described formation conditions for the hole injection layer.

The hole transport region may include, for example, at least one of m-MTDATA, TDATA, 2-TNATA, NPB, β-NPB, TPD, Spiro-TPD, Spiro-NPB, α-NPB, TAPC, HMTPD, TCTA (4,4',4''-tris(N-carbazolyl)triphenylamine), Pani/DBSA (polyaniline/dodecylbenzenesulfonic acid), PEDOT/PSS (poly(3,4-ethylenedioxythiophene)/poly(4-styrenesulfonate)), Pani/CSA (polyaniline/Camphor sulfonic acid), PANI/PSS (polyaniline)/poly(4-styrenesulfonate)), a compound represented by Chemical Formula 201, a compound represented by Chemical Formula 202:

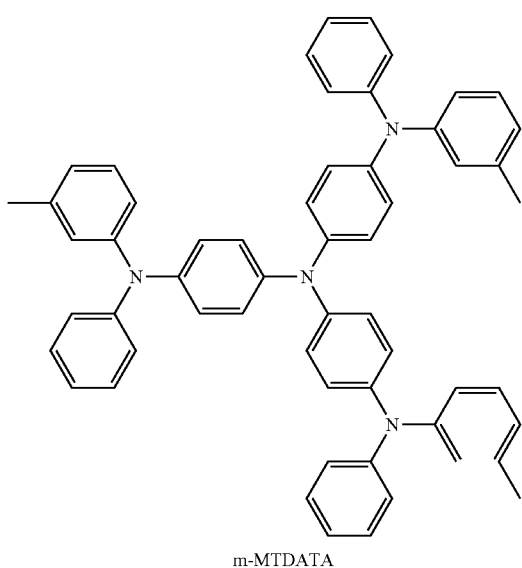

m-MTDATA

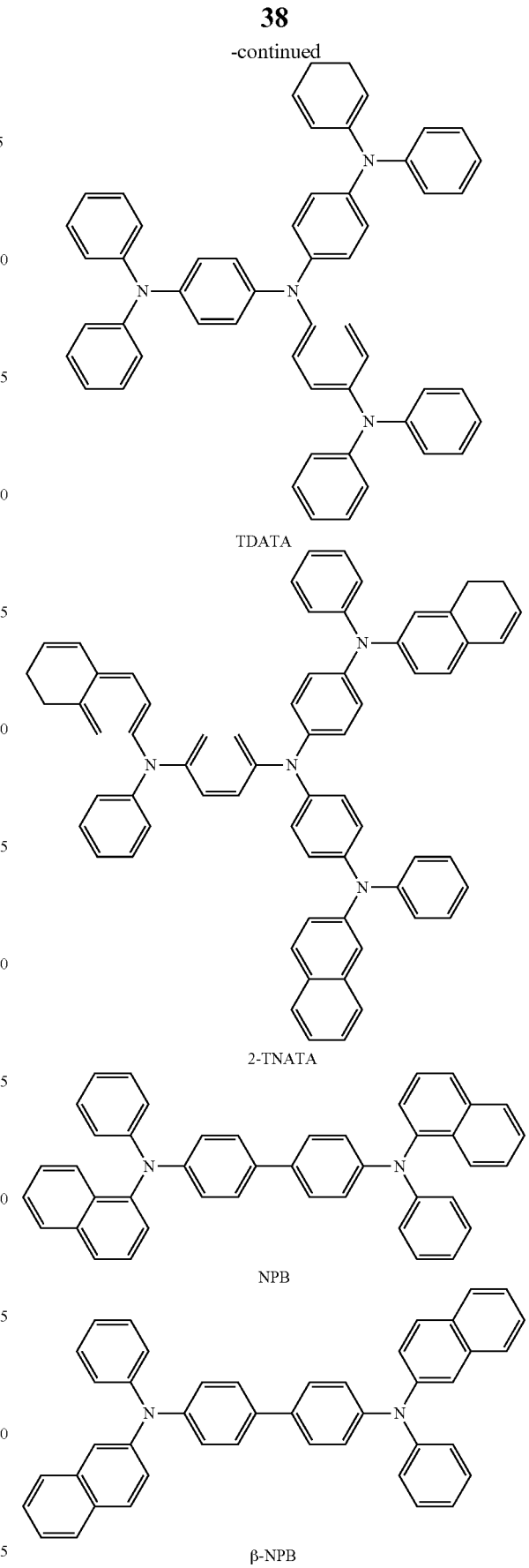

TDATA

2-TNATA

NPB

β-NPB

-continued

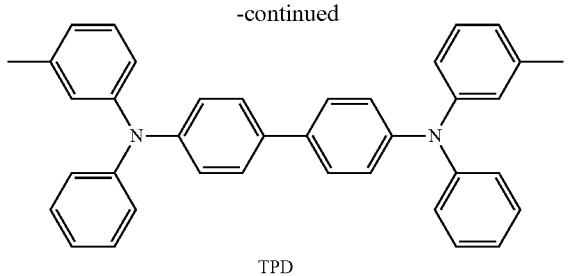

TPD

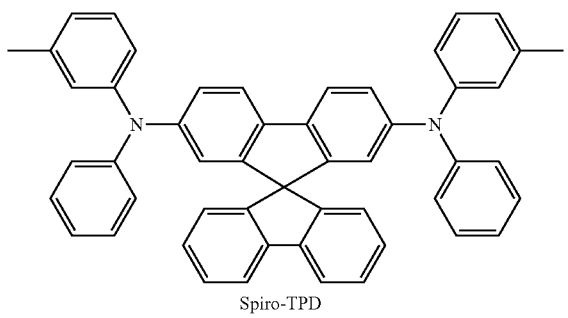

Spiro-TPD

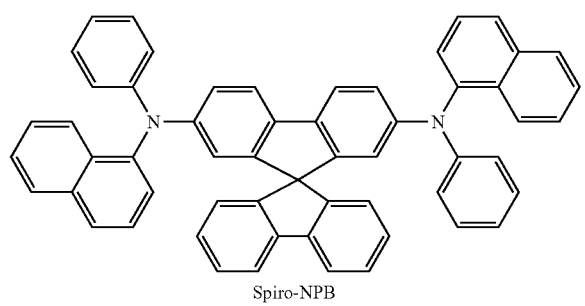

Spiro-NPB

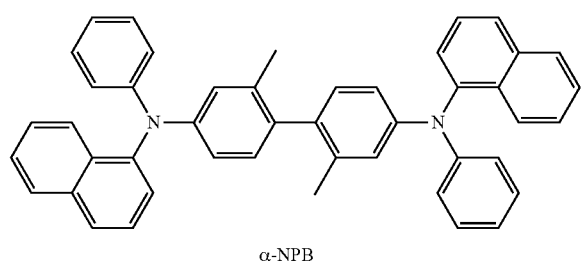

α-NPB

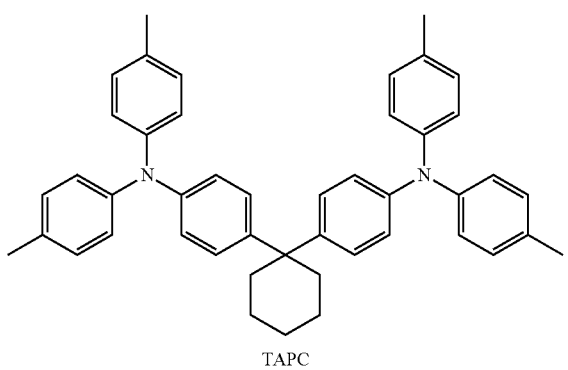

TAPC

-continued

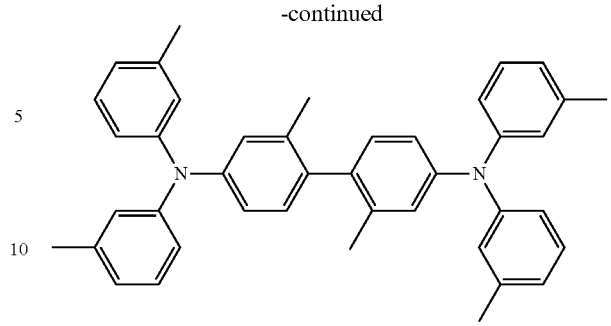

HMTPD

<Chemical Formula201>

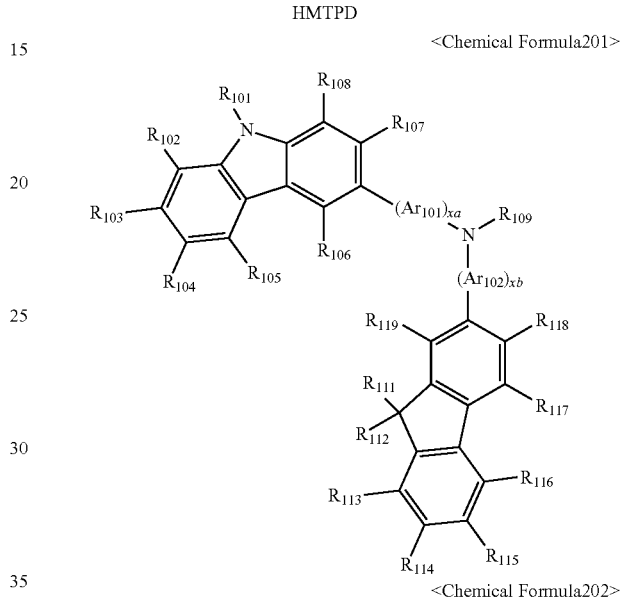

<Chemical Formula202>

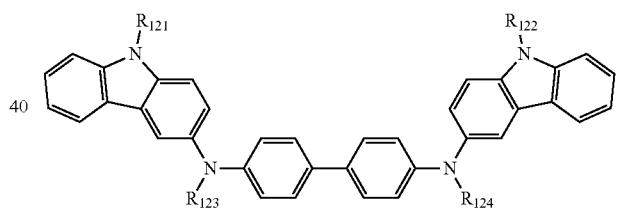

In Chemical Formula 201, $Ar_{101}$ and $Ar_{102}$ are independently a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, and a pentacenylene group; or a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, or a pentacenylene group substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero condensed polycyclic group.

In Chemical Formula 201, the xa and xb may independently be an integer of 0 to 5, or 0, 1 or 2. For example, the xa may be 1 and xb may be 0, but are not limited thereto.

In Chemical Formulae 201 and 202, the $R_{101}$ to $R_{108}$, $R_{111}$ to $R_{119}$ and $R_{121}$ to $R_{124}$ are independently a hydrogen, a deuterium, —F, —Cl, —Br, —I, a hydroxyl group, a cyano group, a nitro group, an amino group, amidino group, hydrazine group, hydrazone group, a carboxylic acid or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, etc.), or a $C_1$-$C_{10}$ alkoxy group (for example, a methoxy group, an ethoxy group, a propoxy group, a butoxy group, a pentoxy group, etc.);

a $C_1$-$C_{10}$ alkyl group and a $C_1$-$C_{10}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, or a pyrenyl group; or a phenyl group, a naphthyl group, an anthracenyl group, a fluorenyl group, and a pyrenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but is not limited thereto.

In Chemical Formula 201, $R_{109}$ may be a phenyl group, a naphthyl group, an anthracenyl group, or a pyridinyl group; or a phenyl group, a naphthyl group, an anthracenyl group, and a pyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, or a pyridinyl group.

According to an embodiment, the compound represented by Chemical Formula 201 may be represented by Formula 201A, but is not limited thereto:

<Chemical Formula 201A>

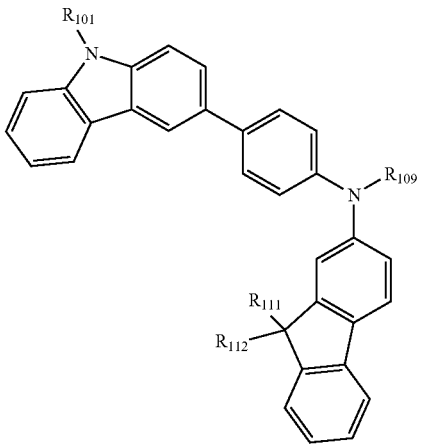

In Chemical Formula 201A, $R_{101}$, $R_{111}$, $R_{112}$, and $R_{109}$ may be the same as those defined above.

For example, the compound represented by Chemical Formula 201 and the compound represented by Chemical Formula 202 may include Compounds HT1 to HT20 below, but are not limited thereto:

HT1

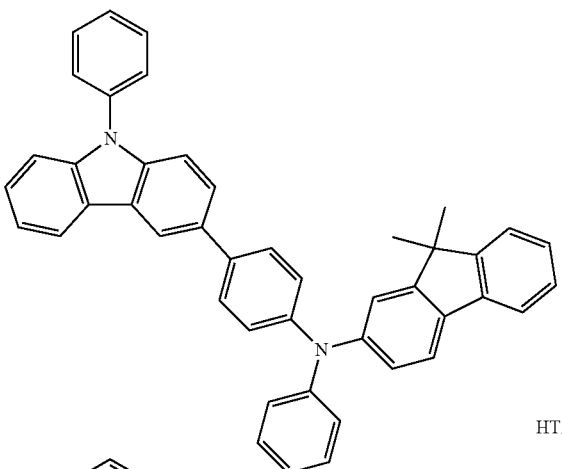

HT2

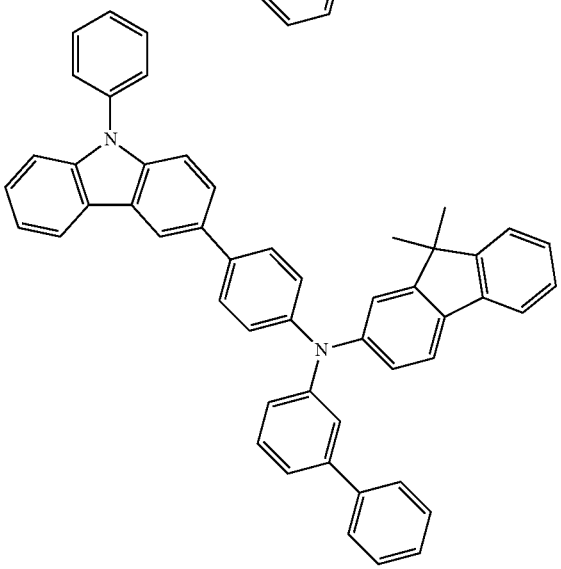

HT3
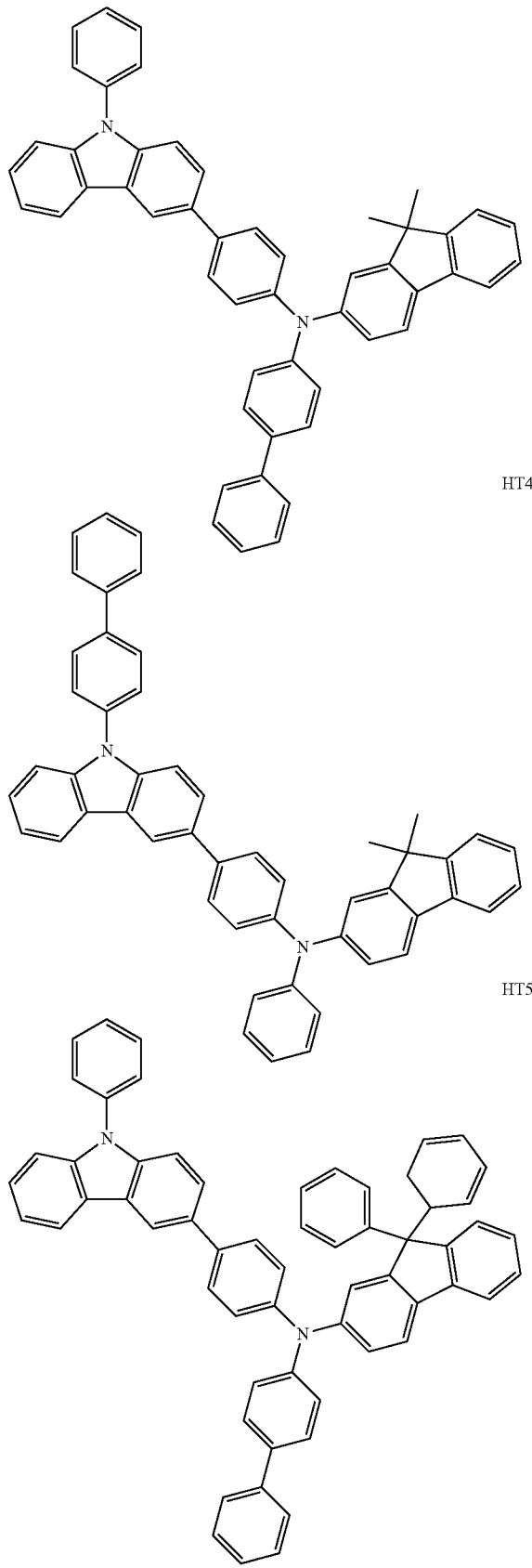
HT4
HT5
HT6
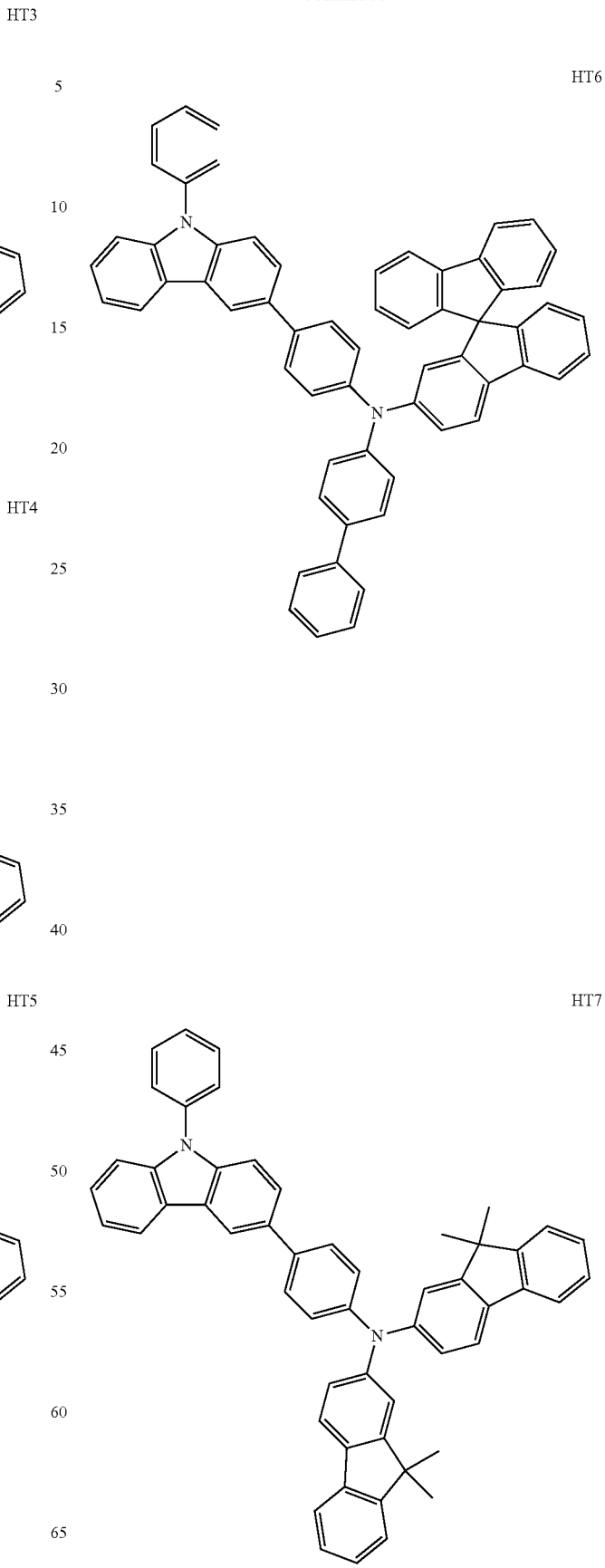
HT7

HT8
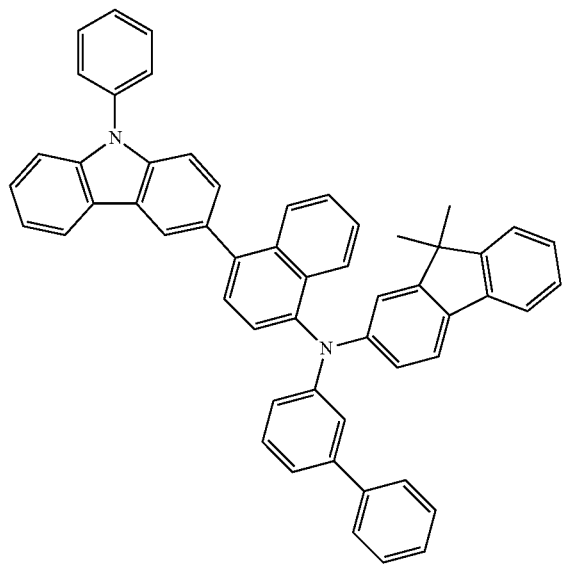
HT9
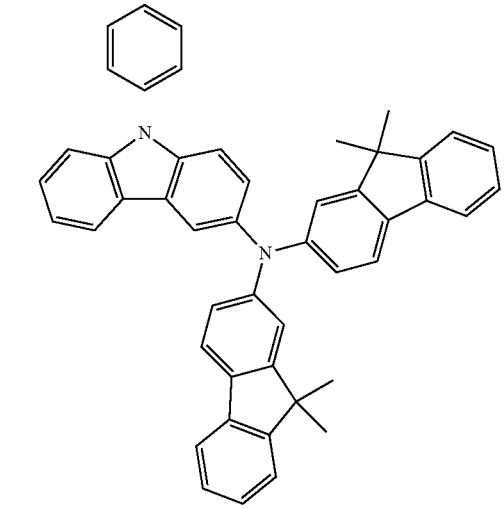
HT10
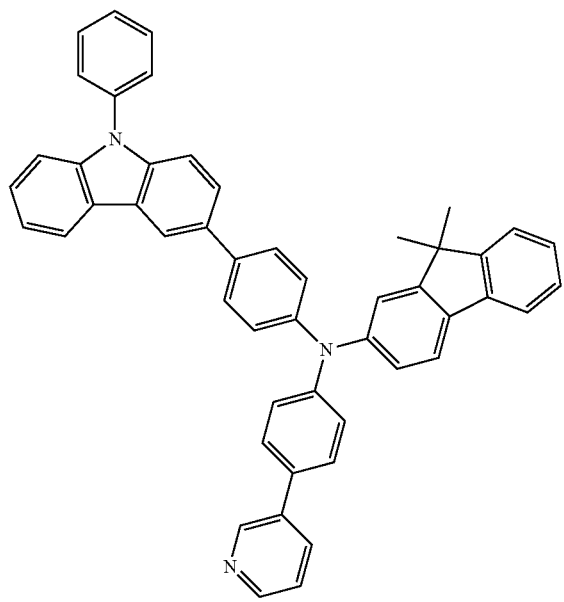
HT11
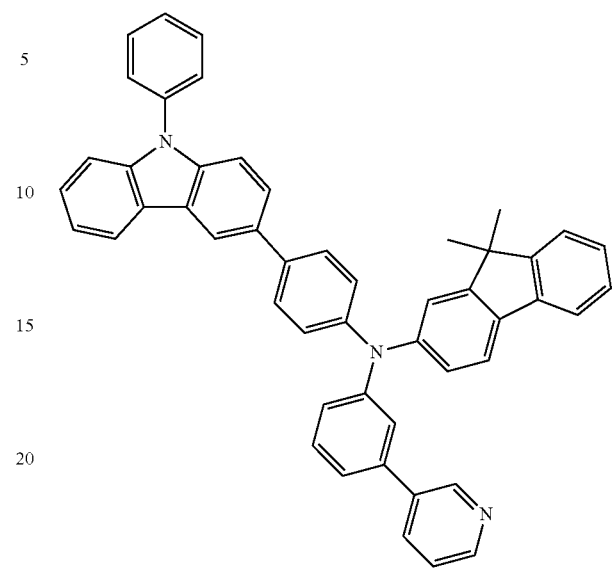
HT12
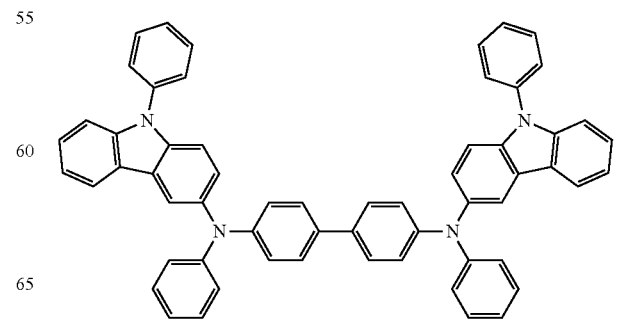
HT13

HT14

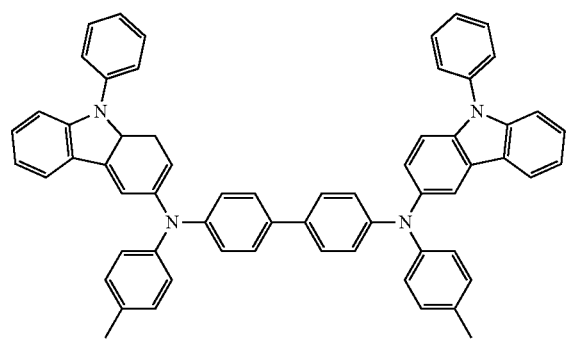

HT18

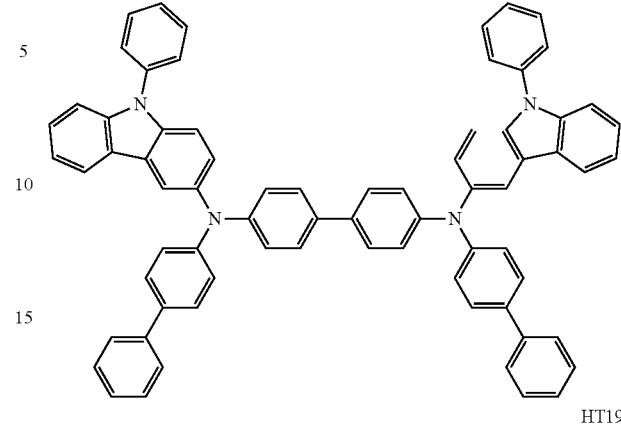

HT15

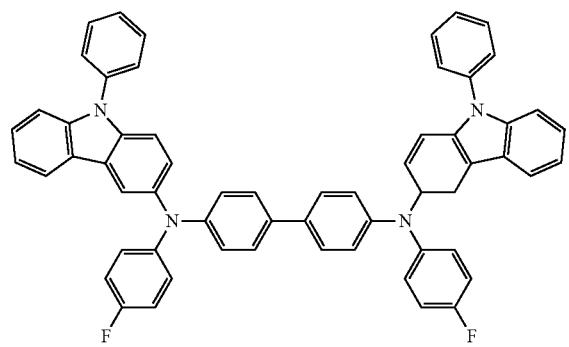

HT19

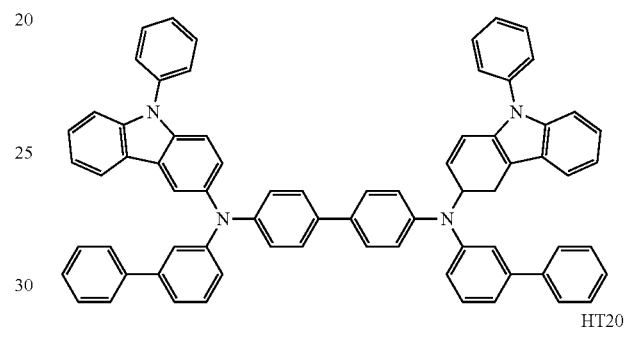

HT16

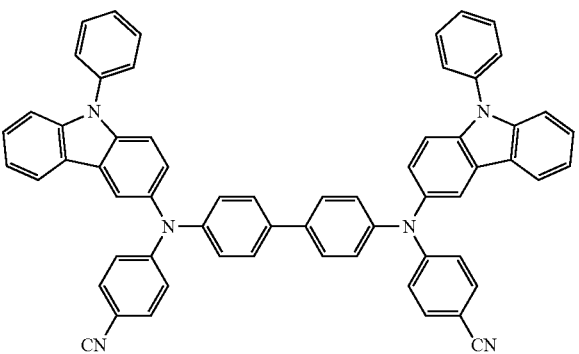

HT20

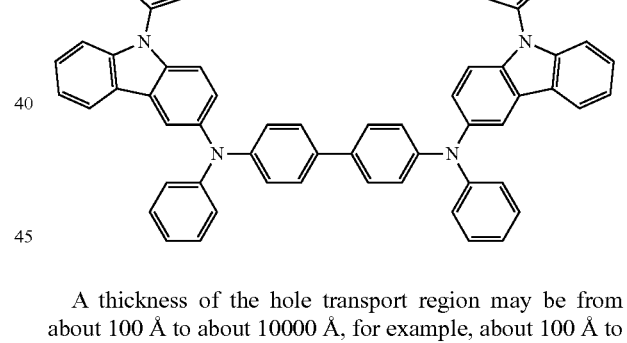

HT17

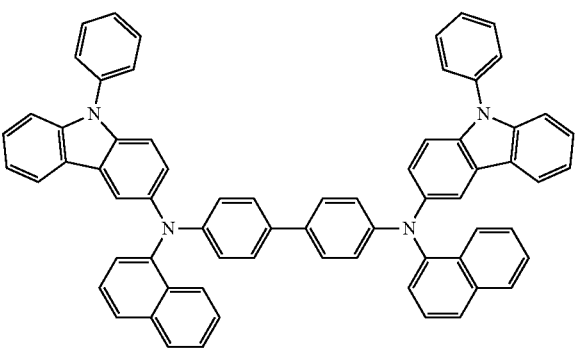

A thickness of the hole transport region may be from about 100 Å to about 10000 Å, for example, about 100 Å to about 1000 Å. When the hole transport region includes the hole injection layer and the hole transport layer, a thickness of the hole injection layer may be from about 100 Å to about 10,000 Å, for example about 100 Å to about 1000 Å and a thickness of the hole transport layer may be from about 50 Å to about 2,000 Å, for example about 100 Å to about 1500 Å. When the thicknesses of the hole transport region, the HIL, and the HTL are within these ranges, satisfactory hole transport characteristics may be obtained without a substantial increase in driving voltage.

The hole transport region may further include a charge-generating material to improve conductivity, in addition to the materials as described above. The charge-generating material may be homogeneously or non-homogeneously dispersed in the hole transport region.

The charge-generating material may be, for example, a p-dopant. The p-dopant may be one of a quinine derivative, a metal oxide, and a cyano group-containing compound, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as compound HT-D1 below.

<Compound HT-D1>

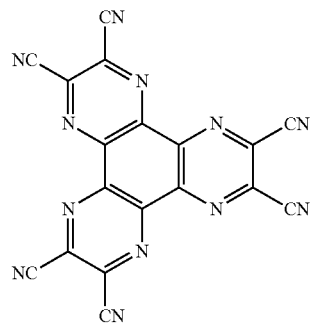

<F4-TCNQ>

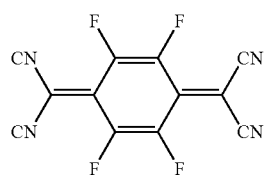

The hole transport region may further include a buffer layer.

The buffer layer may compensate for an optical resonance distance of light according to a wavelength of the light emitted from the EML, and thus may increase efficiency.

The emission layer (EML) may be formed on the hole transport region by using vacuum deposition, spin coating, casting, LB method, or the like. When the emission layer is formed using vacuum deposition or spin coating, the conditions for deposition and coating may be similar to those for the formation of the hole injection layer, though the conditions for the deposition and coating may vary depending on the material that is used to form the emission layer.

The emission layer may include a host and a dopant. The host may include at least one of the compound represented by Chemical Formula I for an organic optoelectric device. For example, the host may include a first host and a second host, and the first host and the second host may be different.

An organic light emitting diode according to an embodiment of the present invention includes the compound for an organic optoelectric device represented by Chemical Formula I alone, or the compound for an organic optoelectric device represented by Chemical Formula I as a first host, and at least one of a compound represented by Chemical Formula II, and a compound consisting of a combination of a moiety represented by Chemical Formula III and a moiety represented by Chemical Formula IV as a second host.

[Chemical Formula II]

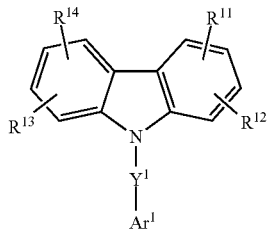

In Chemical Formula II, $Y^1$ is a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, $Ar^1$ is a substituted or unsubstituted C6 to C30 aryl group, a substituted or unsubstituted C2 to C30 heterocyclic group, or a combination thereof, $R^{11}$ to $R^{14}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, and at least one of $R^{11}$ to $R^{14}$ and $Ar^1$ includes a substituted or unsubstituted triphenylene group or a substituted or unsubstituted carbazole group,

[Chemical Formula III]

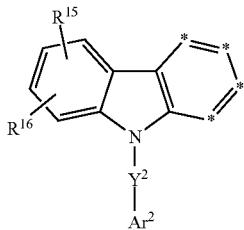

[Chemical Formula IV]

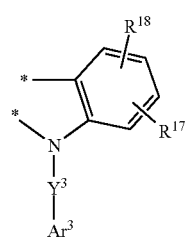

In Chemical Formulae III and IV, $Y^2$ and $Y^3$ are independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, $Ar^2$ and $Ar^3$ are independently a substituted or unsubstituted C6 to C30 aryl group, a substituted or unsubstituted C2 to C30 heterocyclic group, or a combination thereof, $R^{15}$ to $R^{18}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, adjacent two *'s of Chemical Formula III are combined with two *'s of Chemical Formula IV to form a fused ring and * that does not form the fused ring of Chemical Formula III is independently $CR^i$, and $R^i$ is hydrogen, deuterium, a substituted or unsubstituted C1 to C10 alkyl group, a substituted or unsubstituted C6 to C12 aryl group, a substituted or unsubstituted C2 to C12 heterocyclic group or a combination thereof.

The compound represented by Chemical Formula II and the compound consisting of a combination of the moiety represented by Chemical Formula III and the moiety represented by Chemical Formula IV is a bipolar or unipolar compound having relatively stronger hole characteristics relative to the compound represented by Chemical Formula I, and thus forms a composition with the compound represented by Chemical Formula I having strong electron transport characteristics to increase charge mobility and stability and thereby to improve luminance efficiency, a driving characteristics, and life-span characteristics. The composition may be used in an electron transport auxiliary layer as well as an emission layer, and the compound represented by Chemical Formula I may be used alone in the electron transport auxiliary layer.

The compound represented by Chemical Formula II may be, for example represented by at least one of Chemical Formulae II-1 to II-3.

[Chemical Formula II-1]

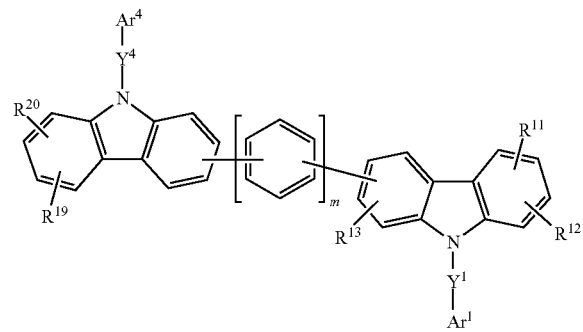

[Chemical Formula II-2]

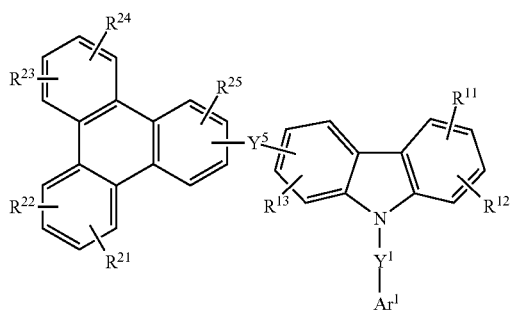

[Chemical Formula II-3]

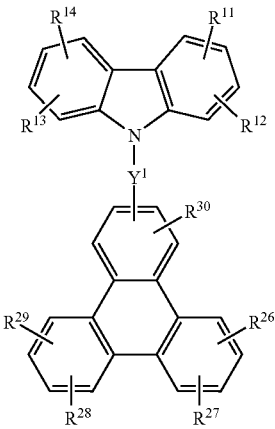

In Chemical Formulae II-1 to II-3, $Y^1$ is the same as described above, and $Y^4$ and $Y^5$ are the same as defined in $Y^1$.

$Ar^1$ is the same as described above, and $Ar^4$ is the same as defined in $Ar^1$.

$R^{11}$ to $R^{14}$ are the same as described above, and $R^{19}$ to $R^{30}$ are the same as defined in $R^{11}$ to $R^{14}$.

m is one of integers of 0 to 4.

Herein, "substituted" refers to that at least one hydrogen is replaced by deuterium, a halogen, a hydroxy group, an amino group, a C1 to C30 amine group, a nitro group, a C1 to C40 silyl group, a C1 to C30 alkyl group, a C3 to C30 cycloalkyl group, a C2 to C30 heterocycloalkyl group, a C6 to C30 aryl group, a C2 to C30 heterocyclic group, a C1 to C20 alkoxy group, a fluoro group, C1 to C10 trifluoroalkyl group, or a cyano group.

$Ar^1$ and $Ar^4$ of Chemical Formulae II-1 to II-3 are substituents having hole or electron characteristics, and may be, for example a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted carbazolyl group, a substituted or unsubstituted benzofuranyl group, a substituted or unsubstituted benzothiophenyl group, a substituted or unsubstituted fluorenyl group, a substituted or unsubstituted dibenzothiophenyl group, a substituted or unsubstituted dibenzofuranyl group, a substituted or unsubstituted pyridinyl group, or a combination thereof.

Specifically, Chemical Formula II-1 may be one of structures of Group 2, and the *—$Y^1$—$Ar^1$, and *—$Y^4$—$Ar^4$ may be one of substituents of Group 3.

[Group 2]

C-1

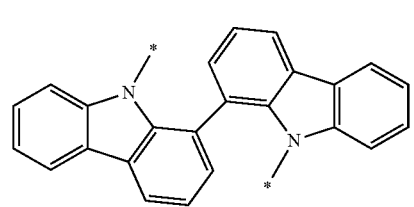

C-2
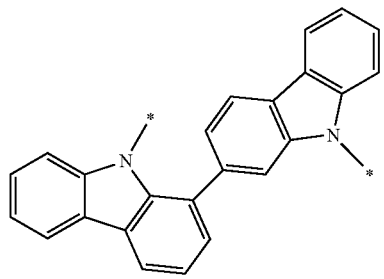
C-3
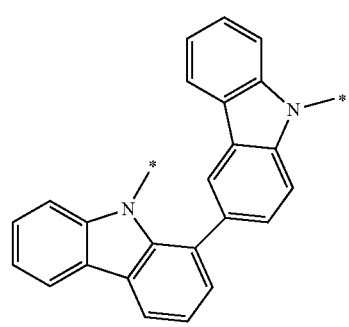
C-4
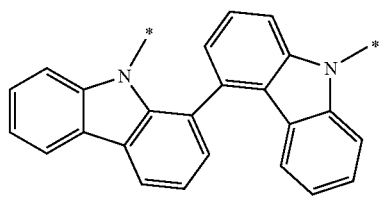
C-5
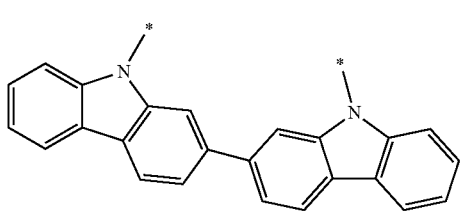
C-6
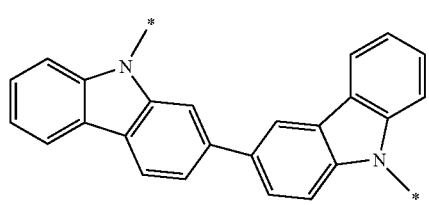
C-7
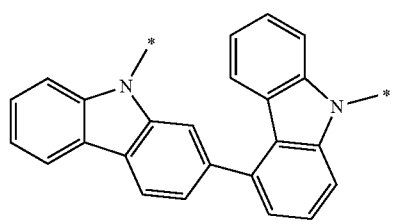
C-8
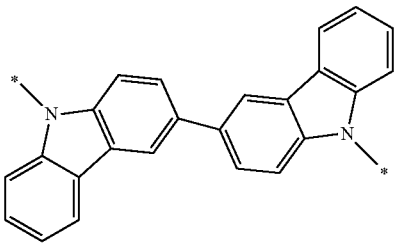
C-9
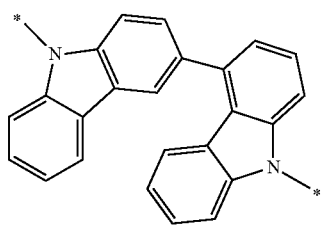
C-10
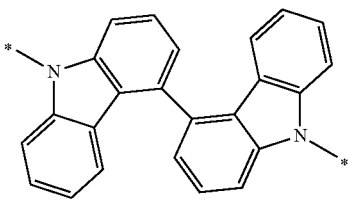
c-11
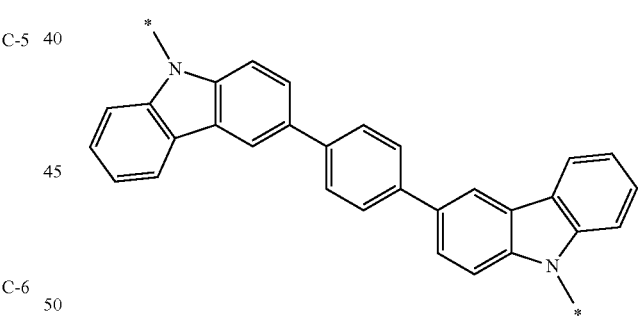
c-12
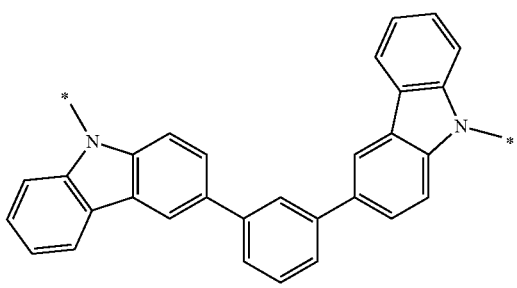

c-13
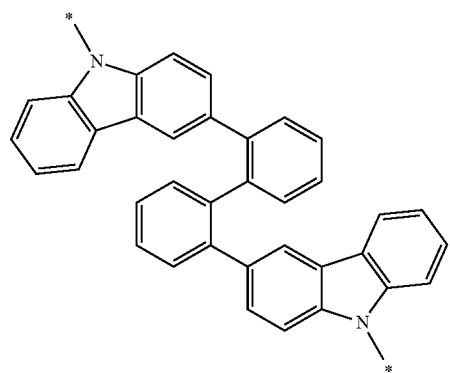
c-14
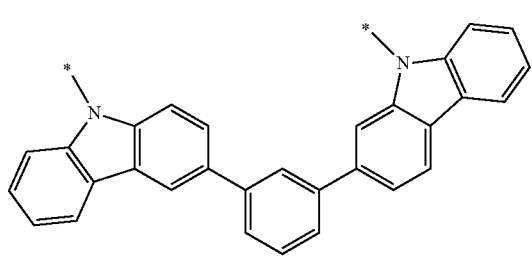
c-15
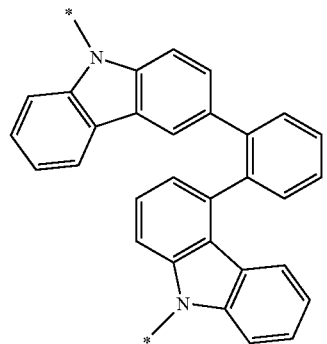
[Group 3]
B-1
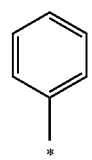
B-2
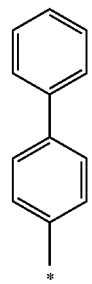
B-3
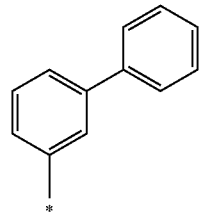
B-4
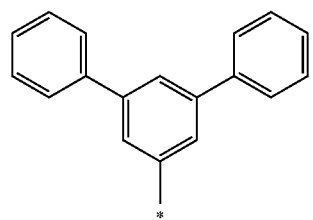
B-5
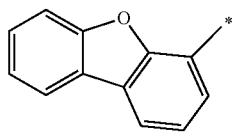
B-6
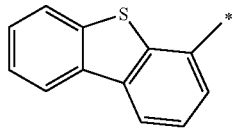
B-7
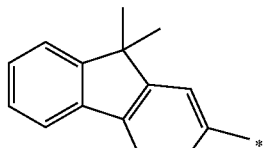
B-8
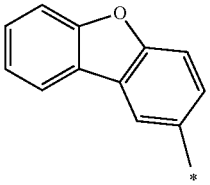
B-9
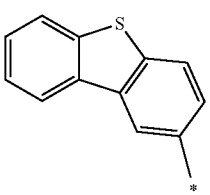
B-10
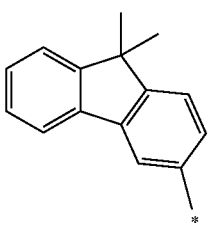

B-11 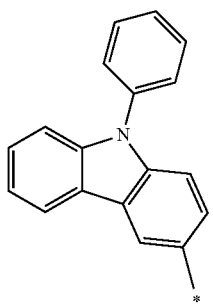
B-12 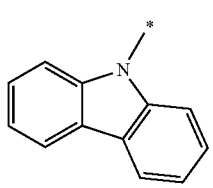
B-13 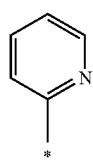
B-14 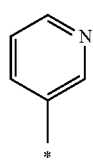
B-15 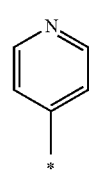
B-16 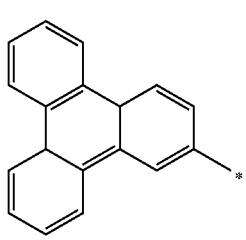
B-17 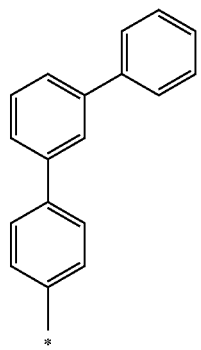
B-18 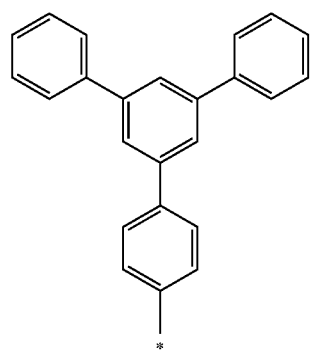
B-19 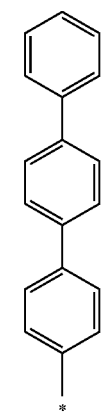
B-20 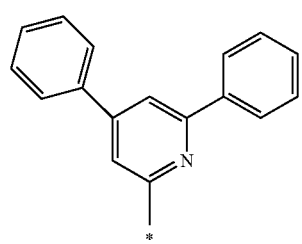
In Groups 2 and 3, * is a linking point
The compound represented by Chemical Formula II may be, for example compounds of Group B to Group D, but is not limited thereto.

[Group B]
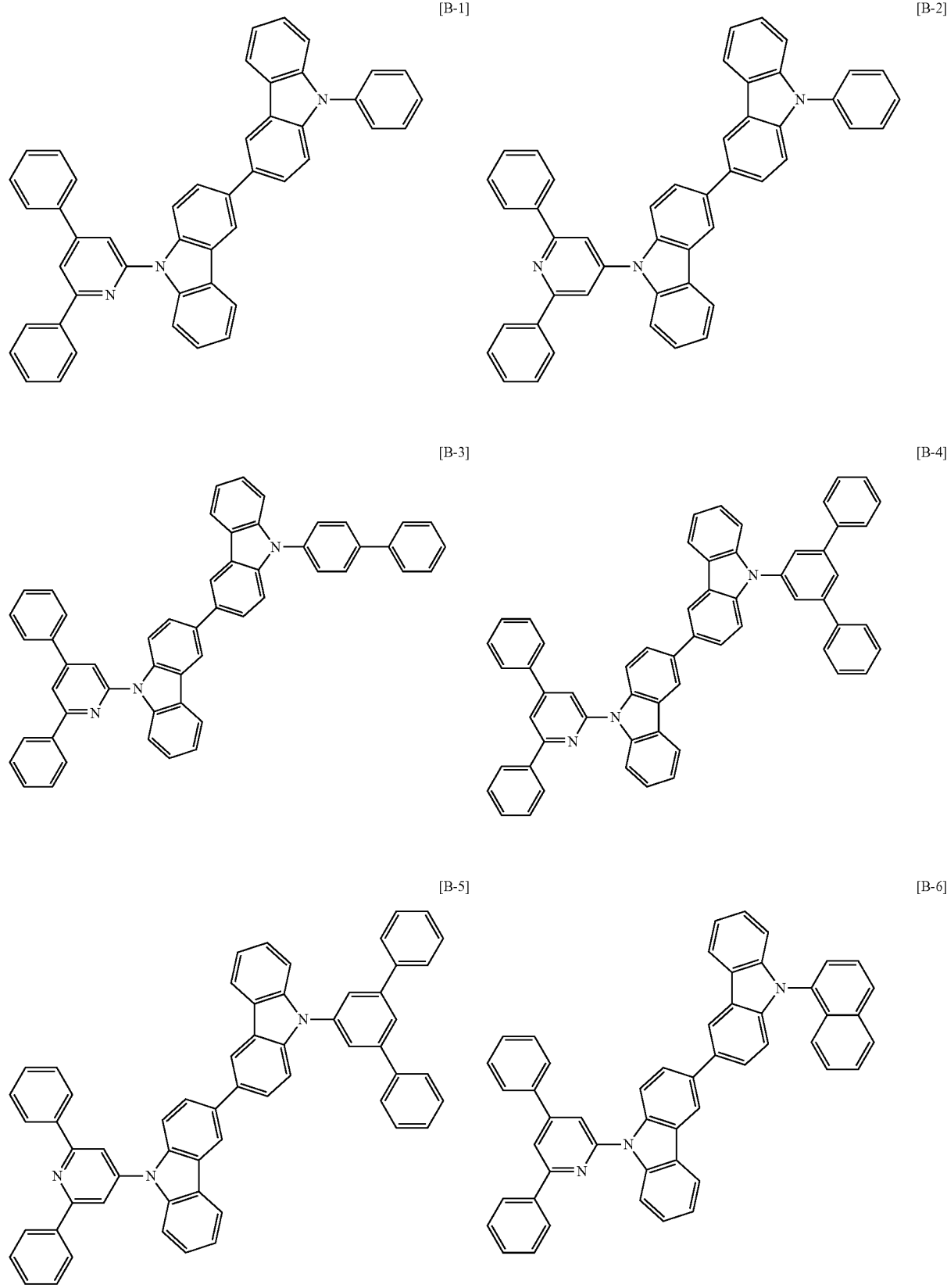

[B-7]
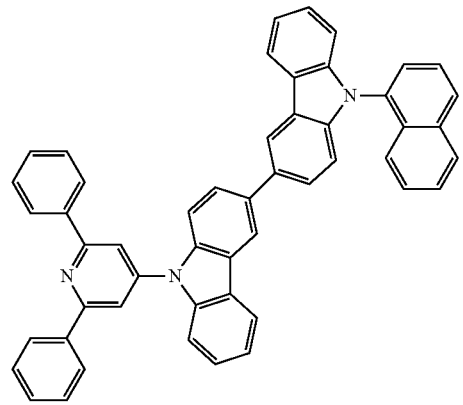
[B-8]
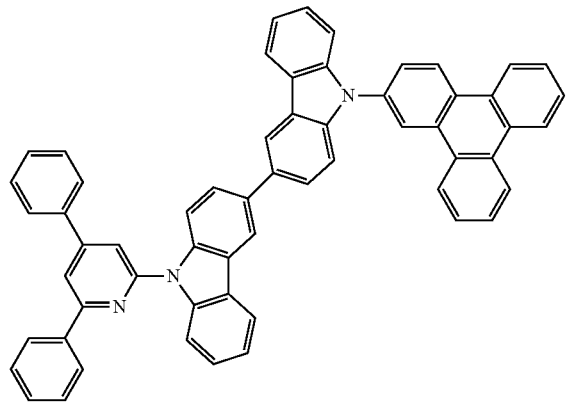
[B-9]
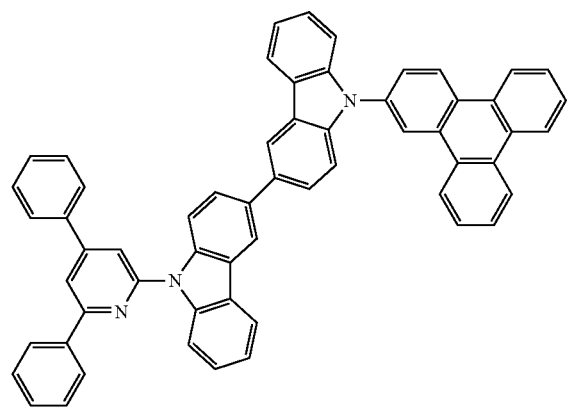
[B-10]
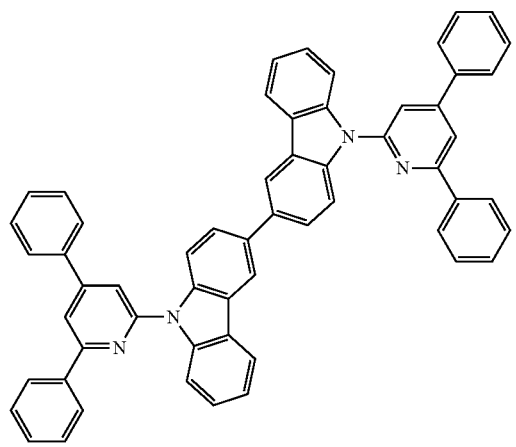
[B-11]
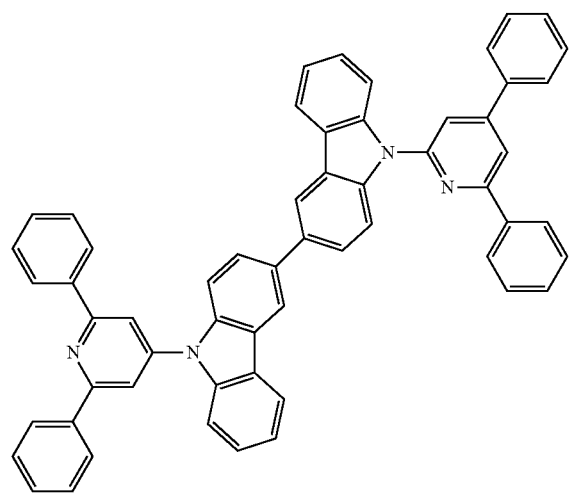
[B-12]
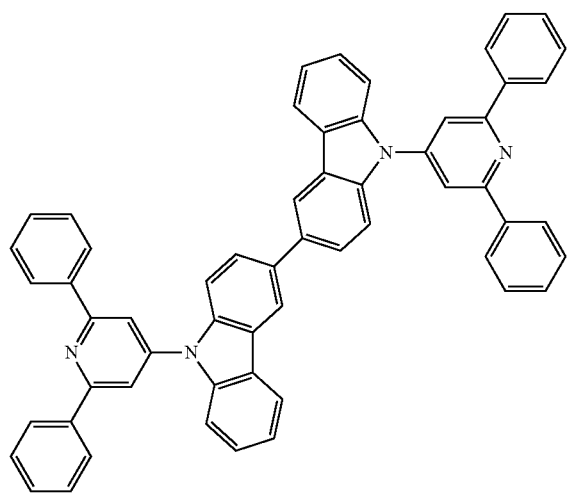

-continued
[B-13]
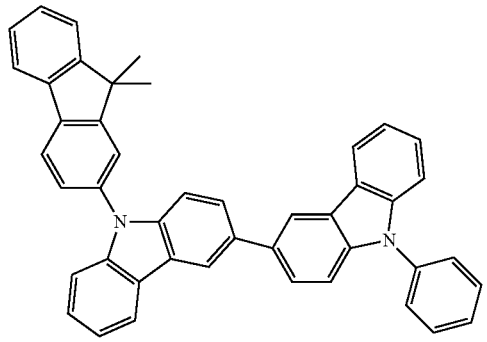
[B-14]
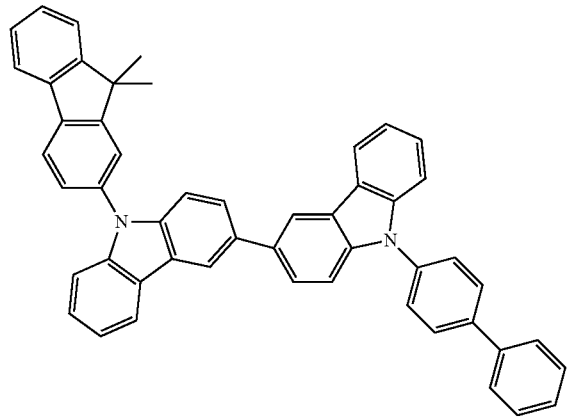
[B-15]
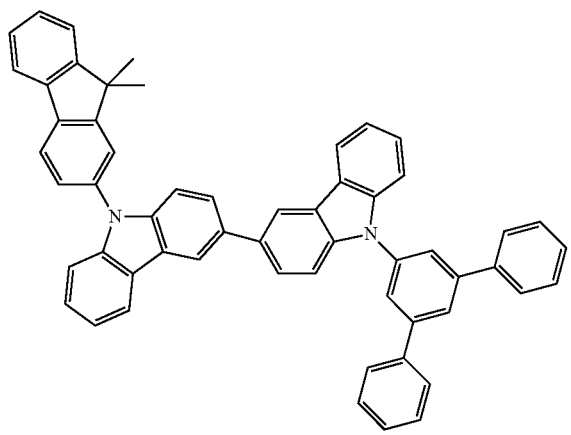
[B-16]
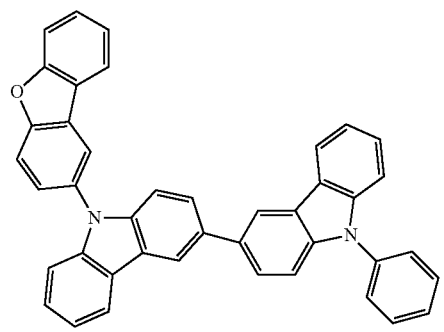
[B-17]
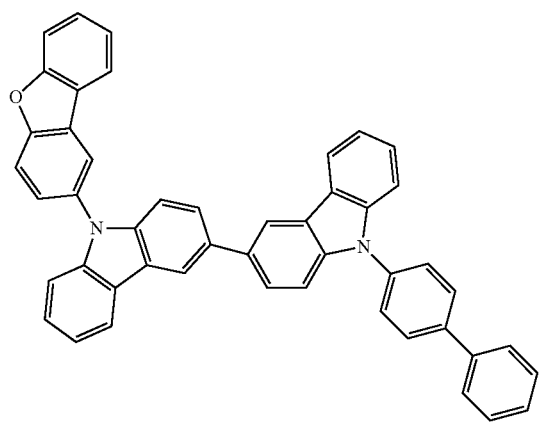
[B-18]
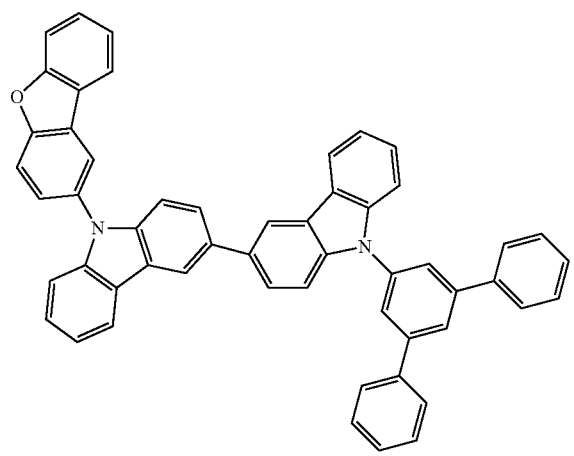

-continued
[B-19]
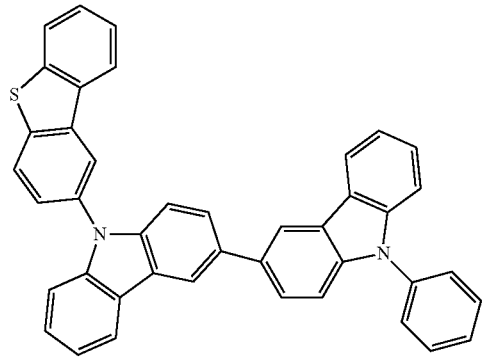
[B-20]
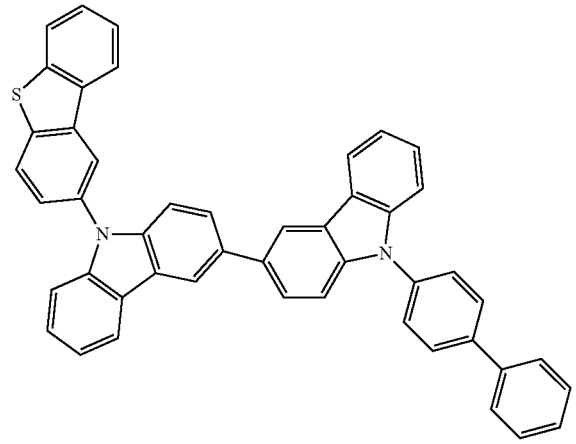
[B-21]
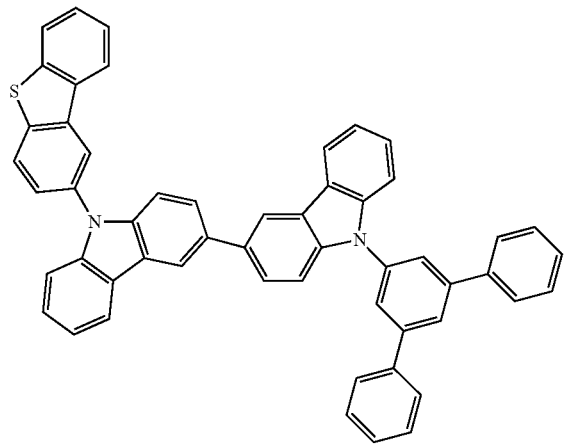
[B-22]
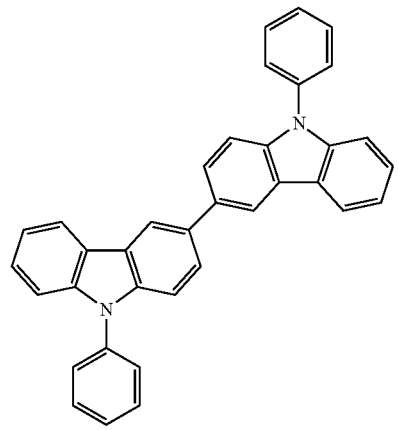
[B-23]
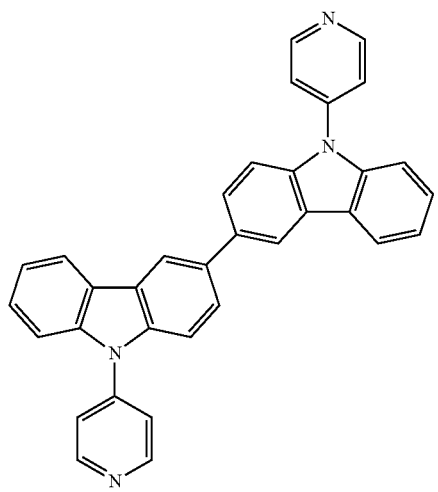
[B-24]
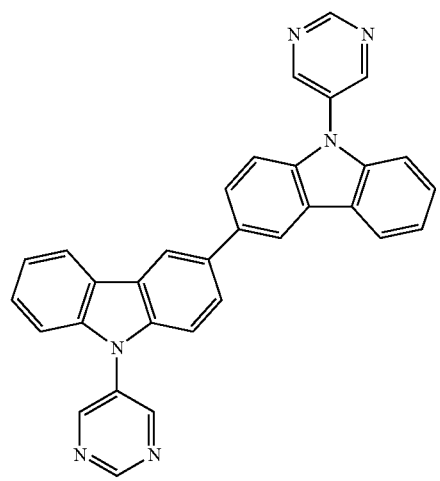

-continued
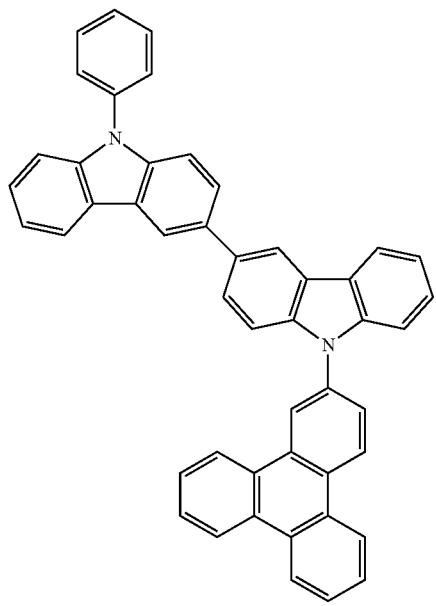
[B-25]
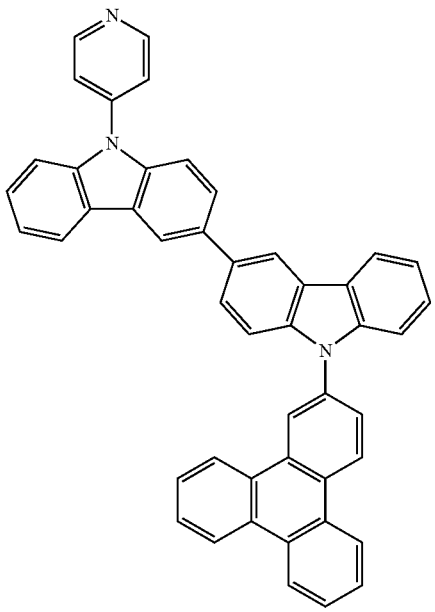
[B-26]
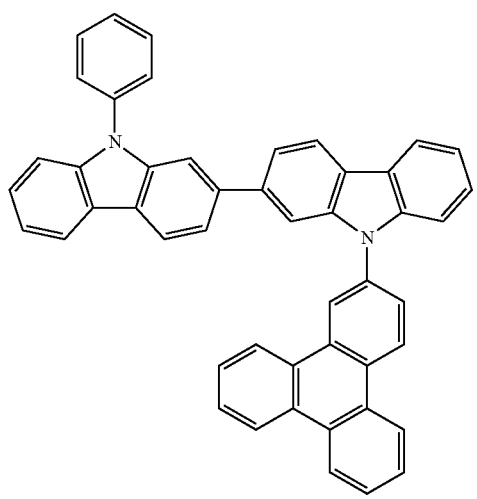
[B-27]
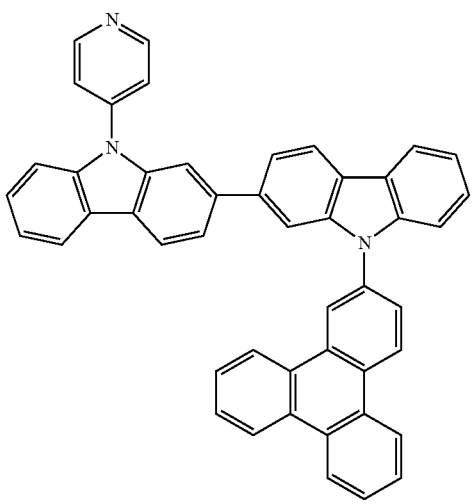
[B-28]
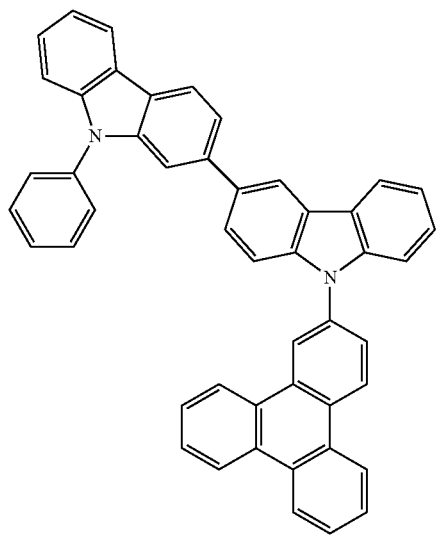
[B-29]
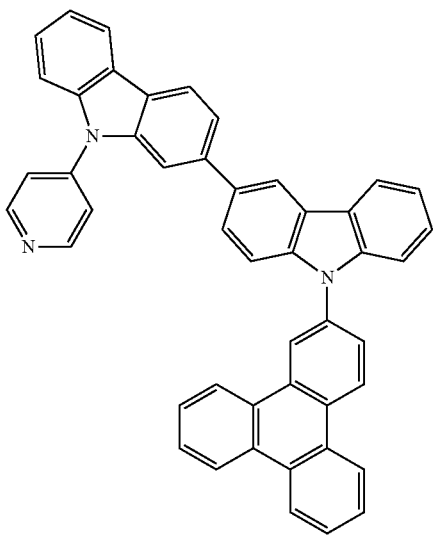
[B-30]

-continued
[B-31] 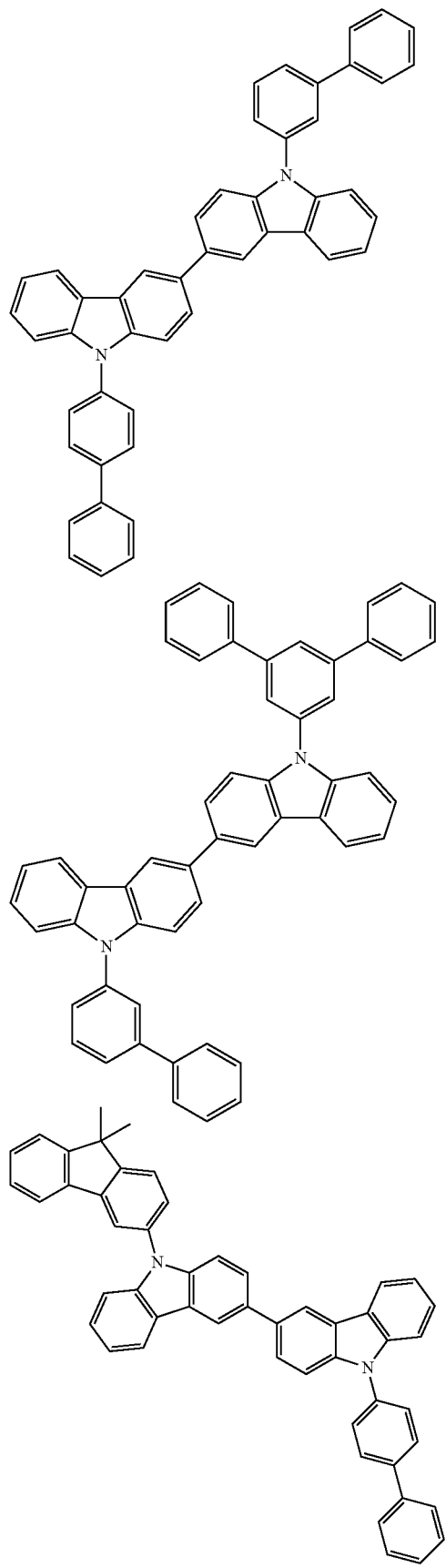 [B-32]
[B-33] [B-34] 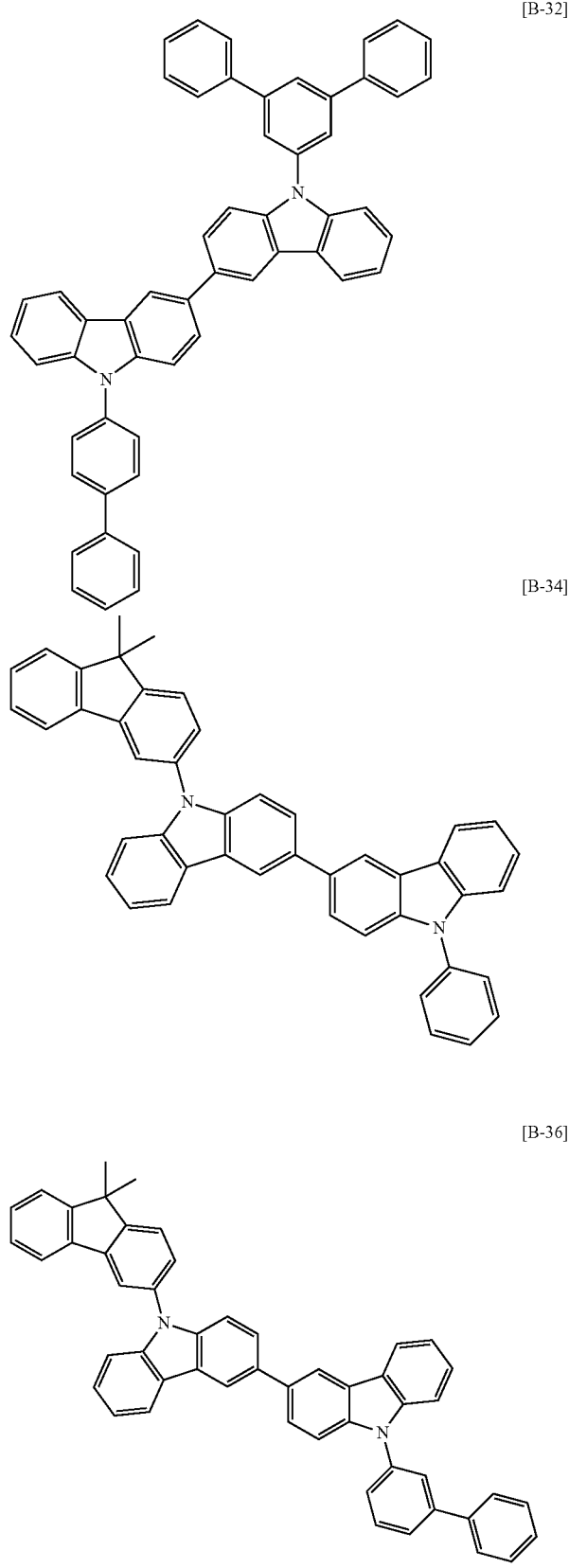
[B-35] [B-36]

-continued
[B-37]
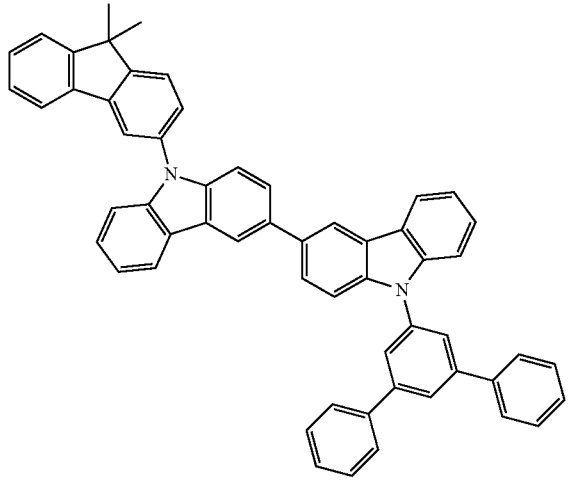
[B-38]
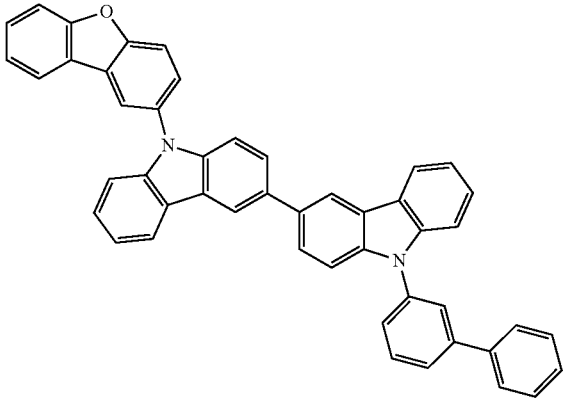
[B-39]
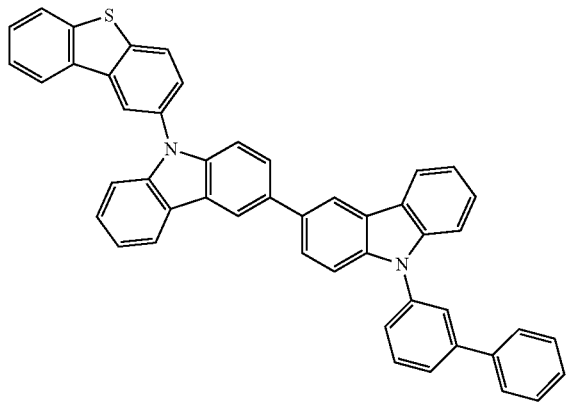
[B-40]
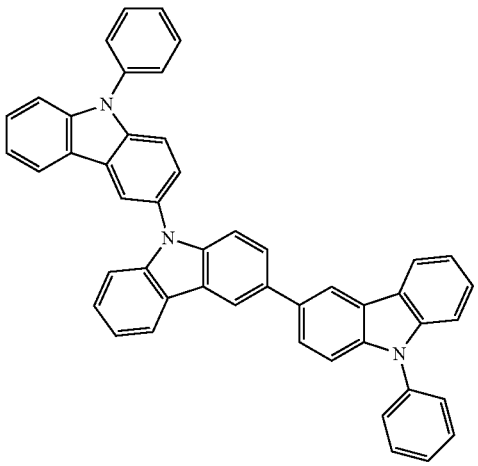
[B-41]
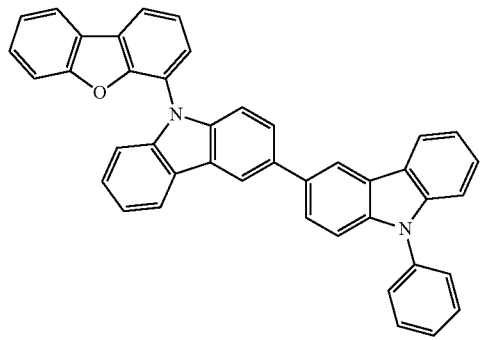
[B-42]
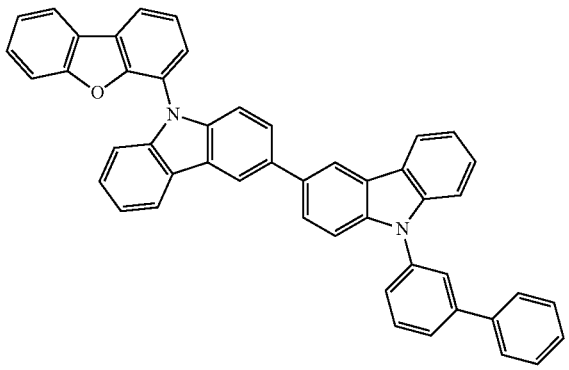

-continued
[B-43]
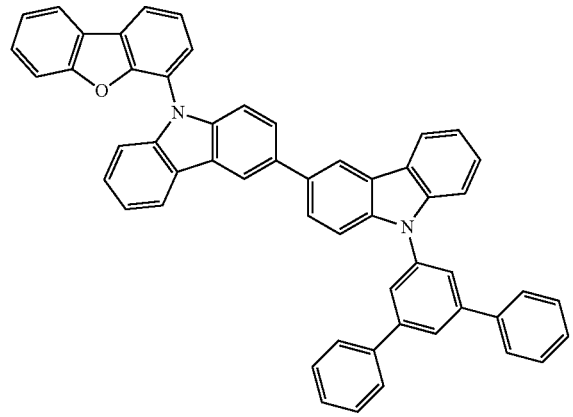
[B-44]
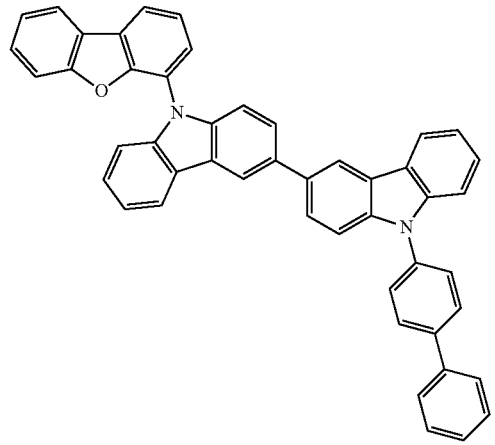
[B-45]
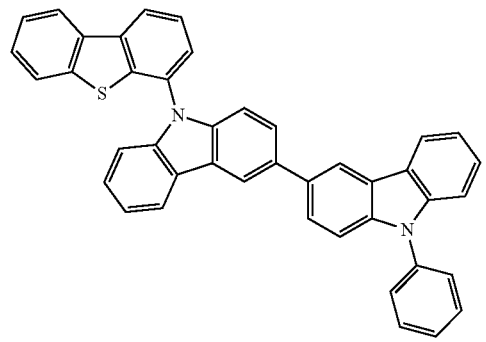
[B-46]
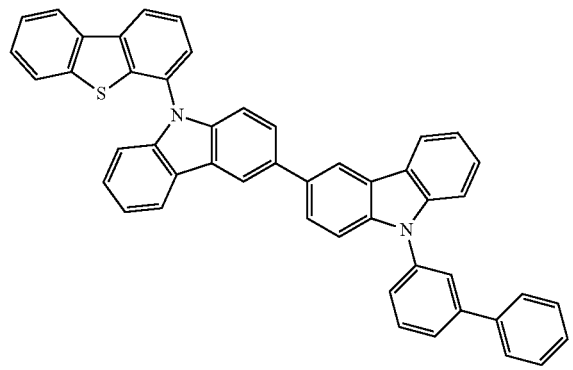
[B-47]
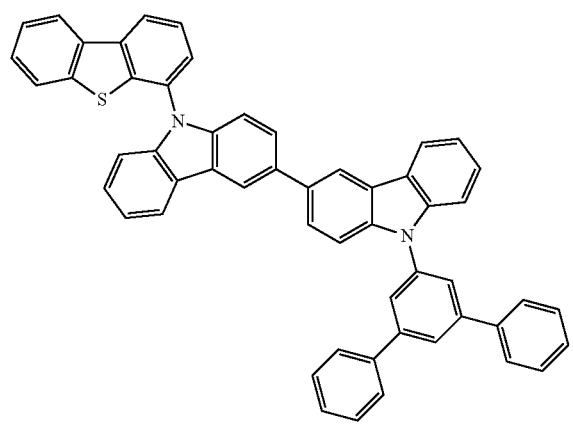
[B-48]
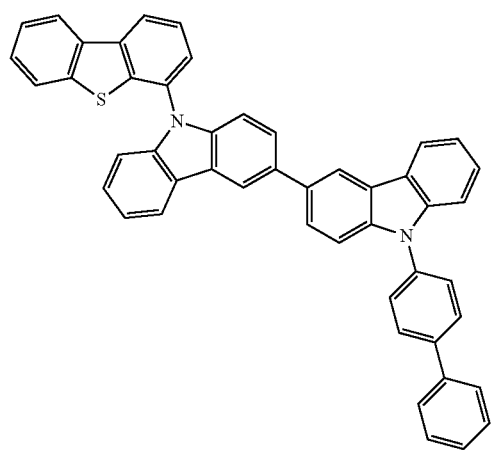

-continued
[B-49]
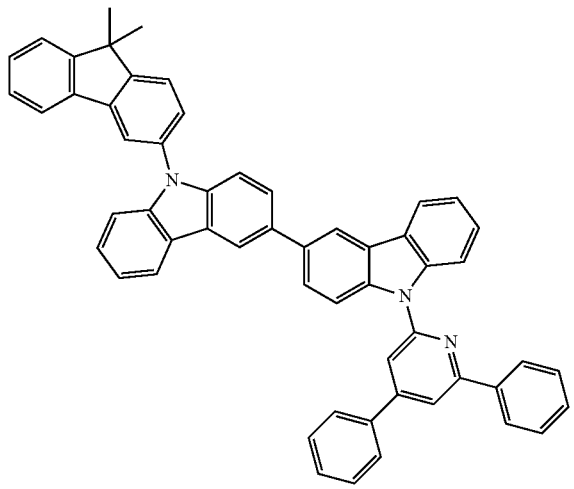
[B-50]
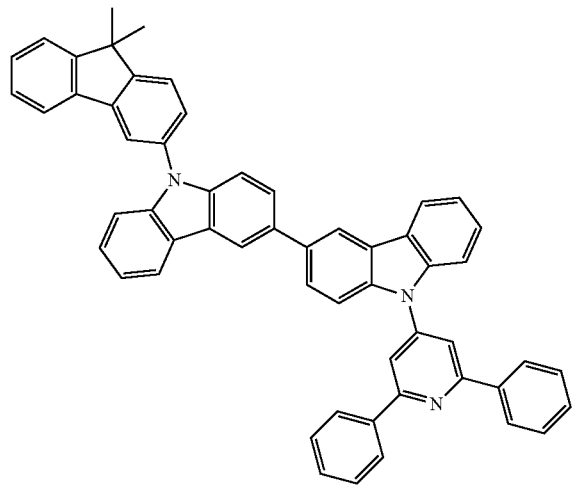
[B-51]
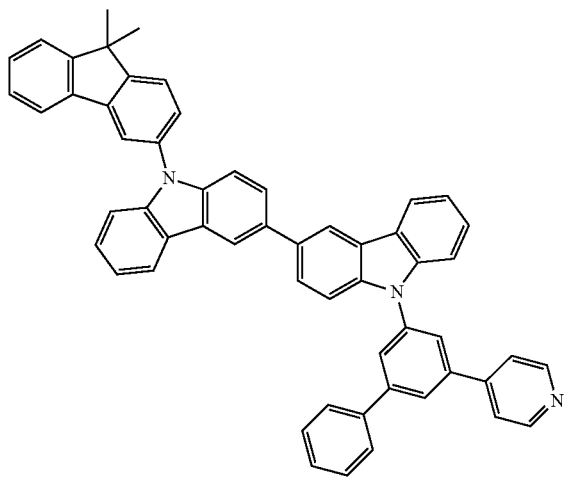
[B-52]
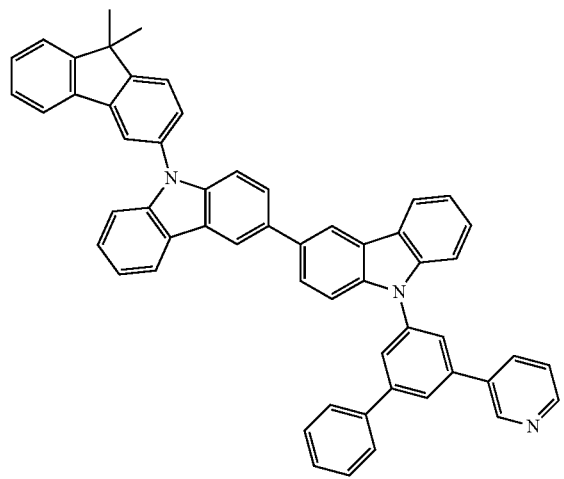
[B-53]
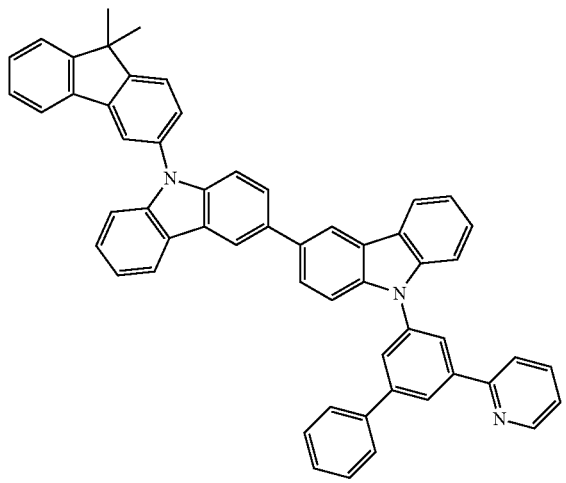
[B-54]
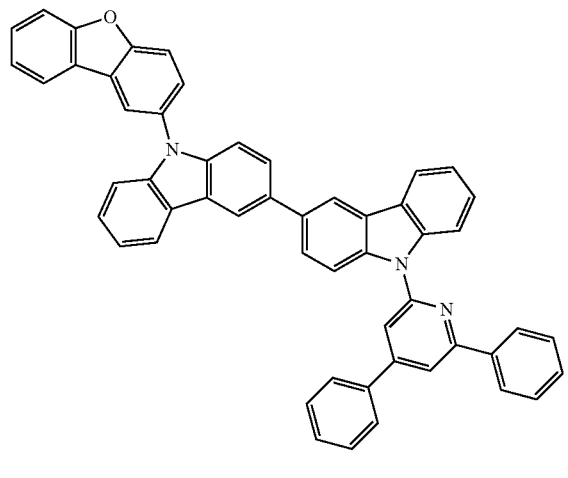

-continued
[B-55]
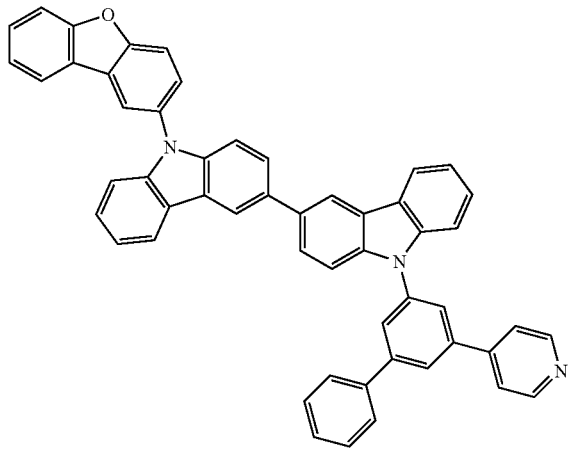
[B-56]
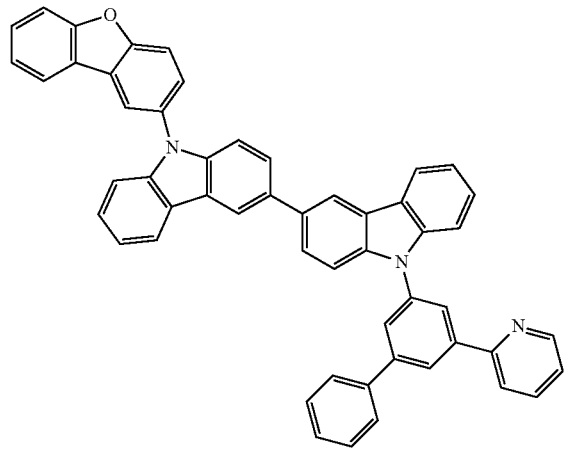
[B-57]
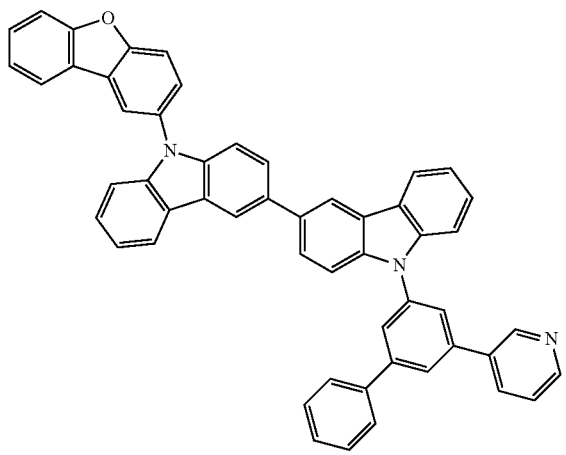
[B-58]
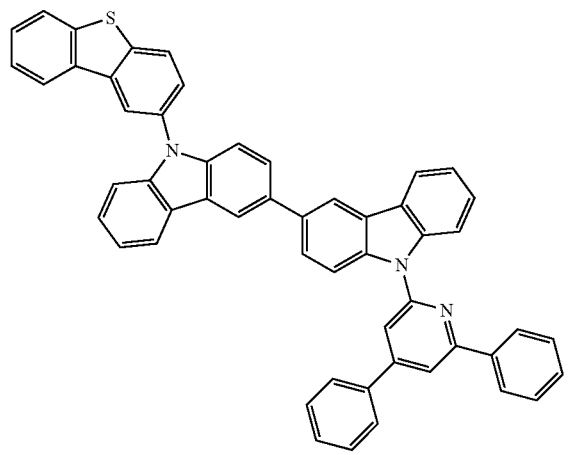
[B-59]
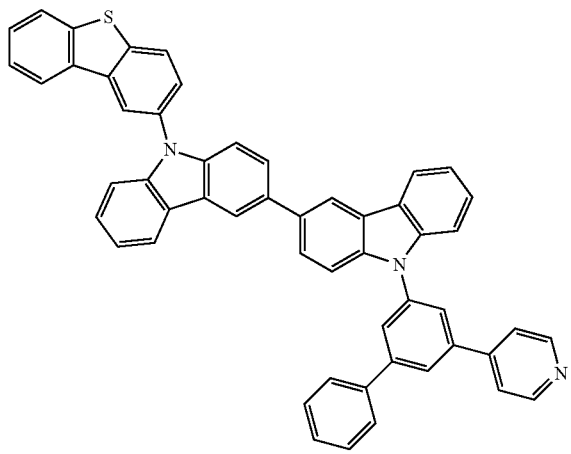
[B-60]
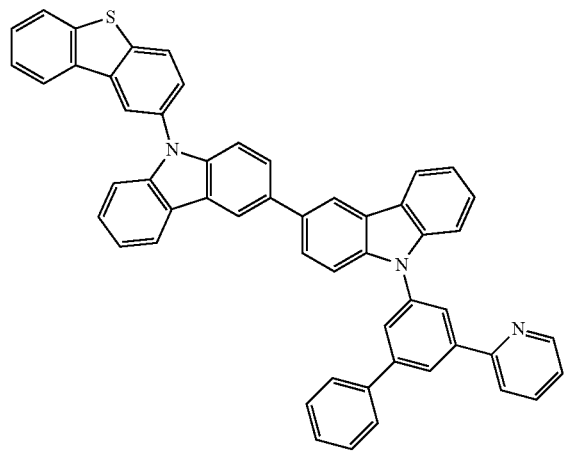

-continued
[B-61]
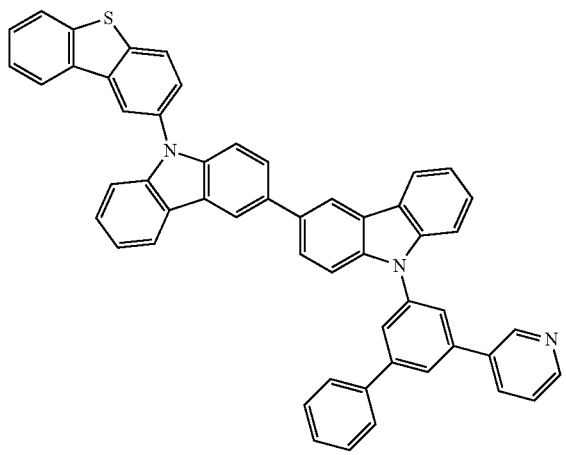
[B-62]
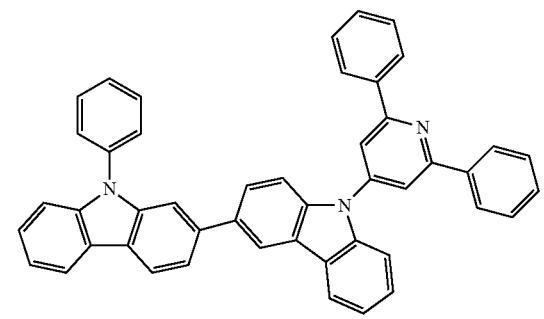
[B-63]
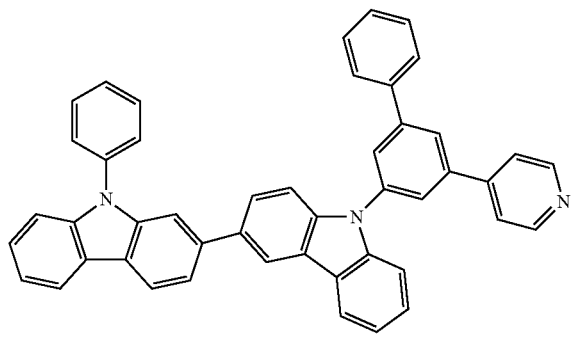
[B-64]
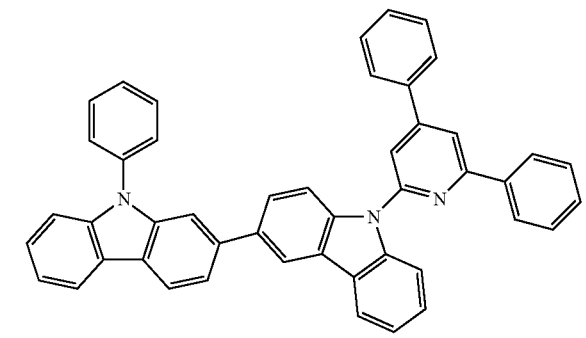
[B-65]
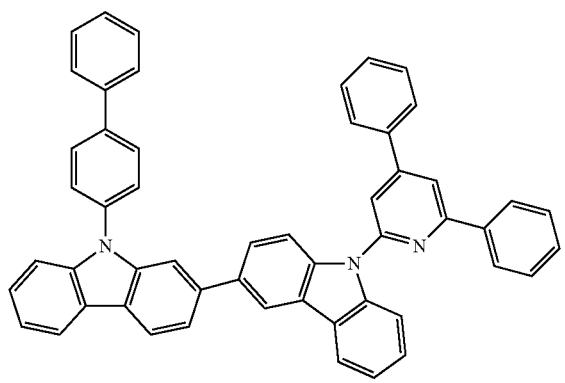
[B-66]
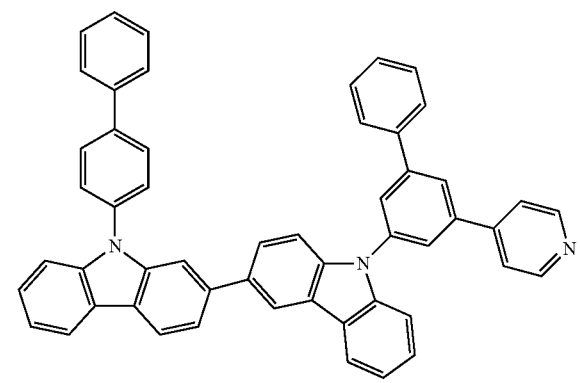
[B-67]
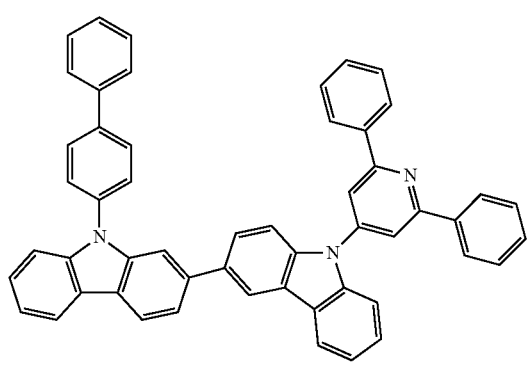
[B-68]
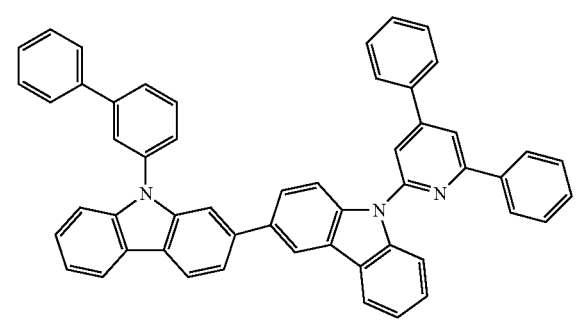

[B-69]
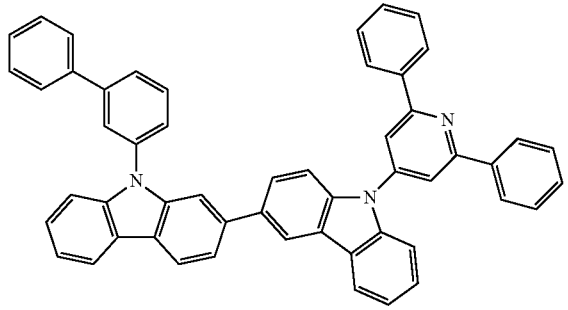
[B-70]
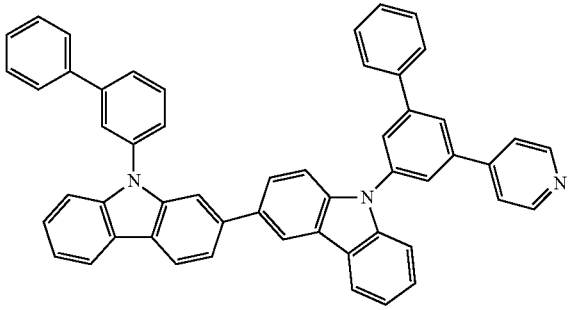
[B-71]
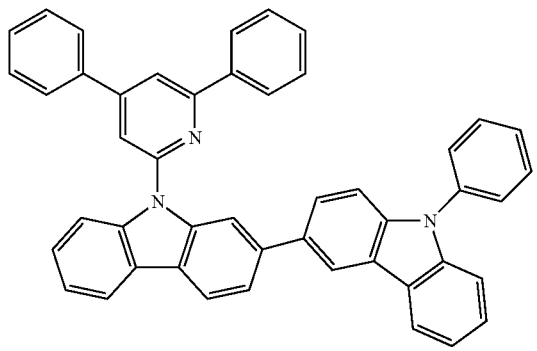
[B-72]
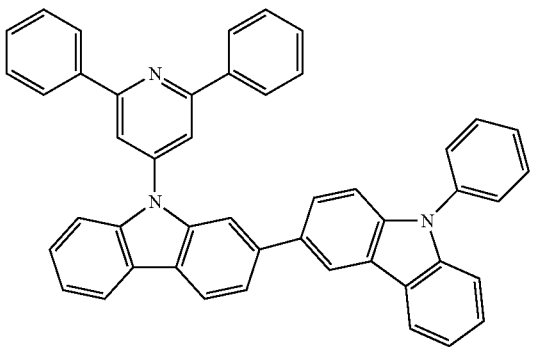
[B-73]
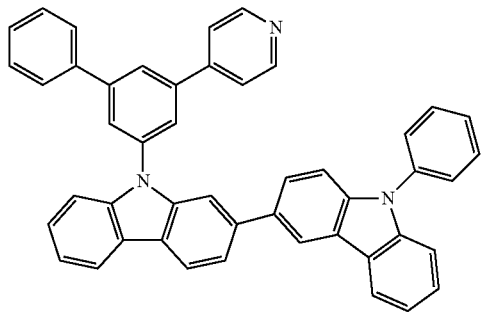
[B-74]
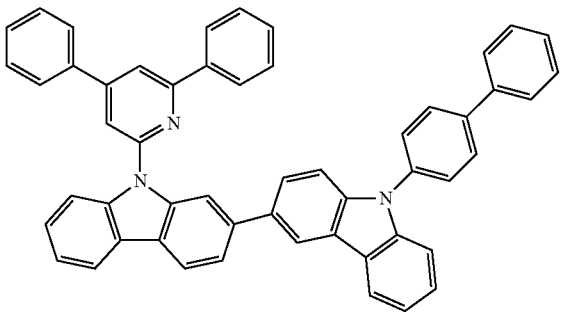
[B-75]
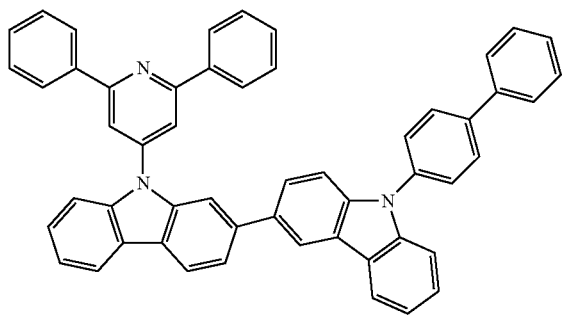
[B-76]
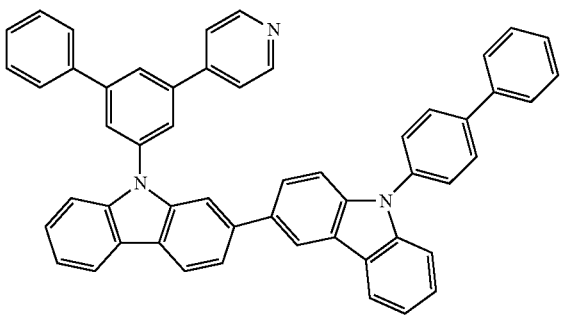

-continued
[B-77]
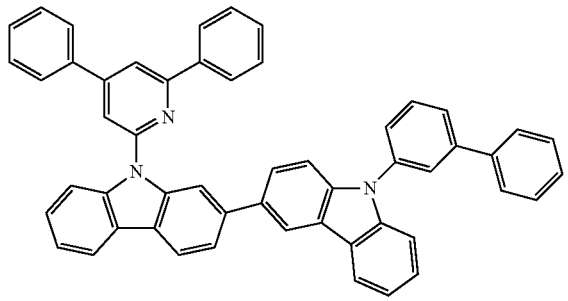
[B-78]
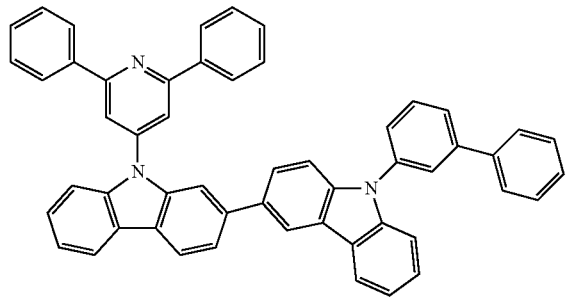
[B-79]
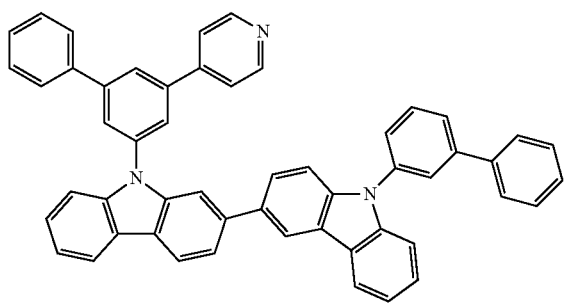
[B-80]
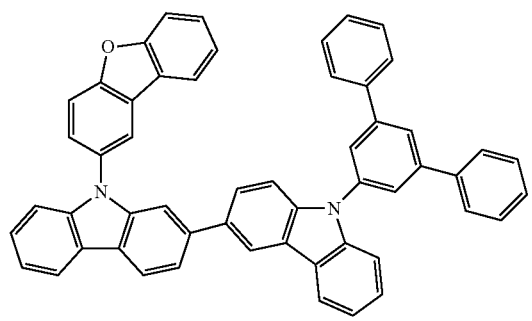
[B-81]
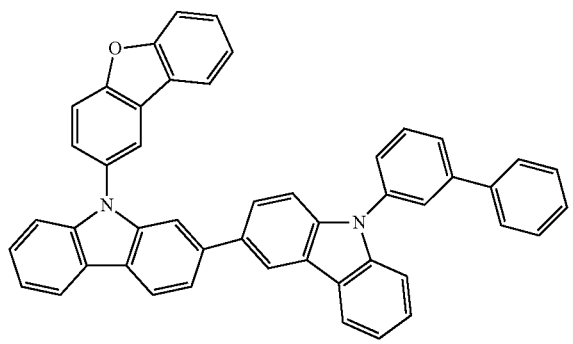
[B-82]
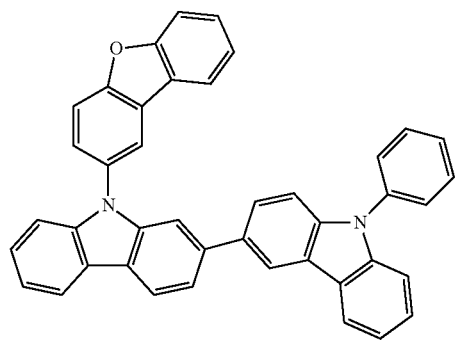
[B-83]
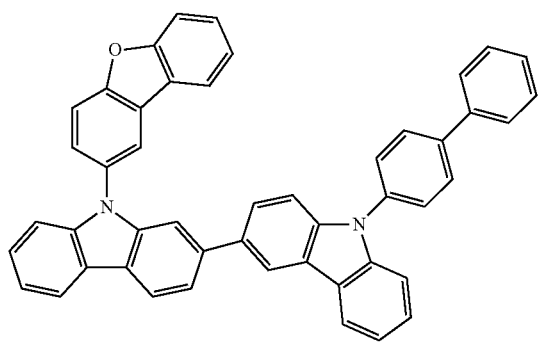
[B-84]
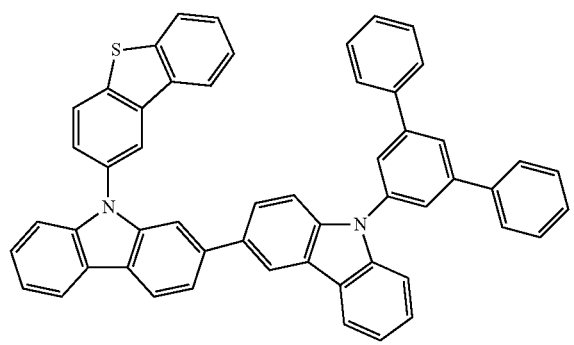

-continued
[B-85]
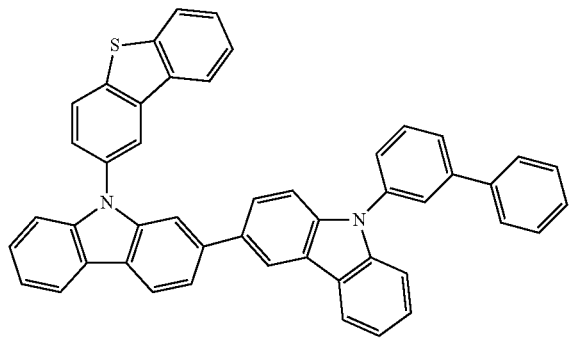
[B-86]
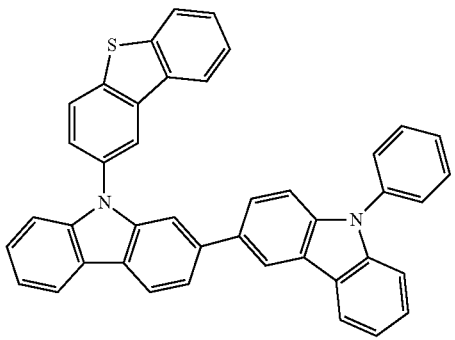
[B-87]
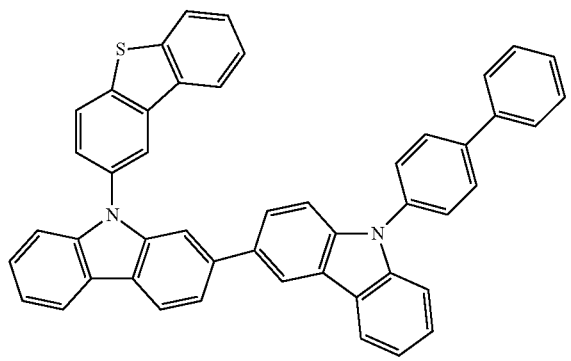
[B-88]
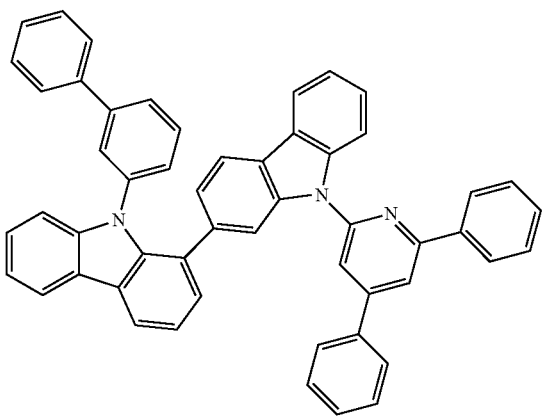
[B-89]
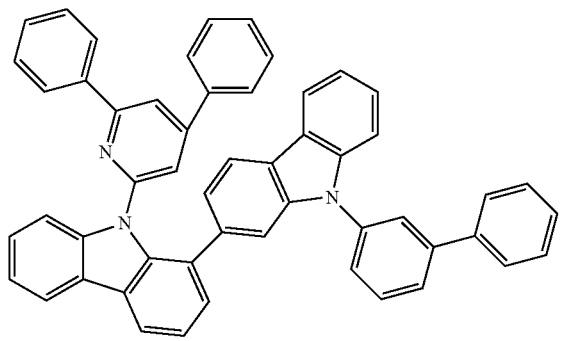
[B-90]
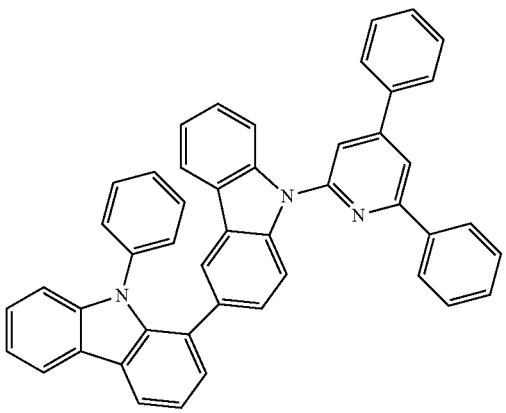
[B-91]
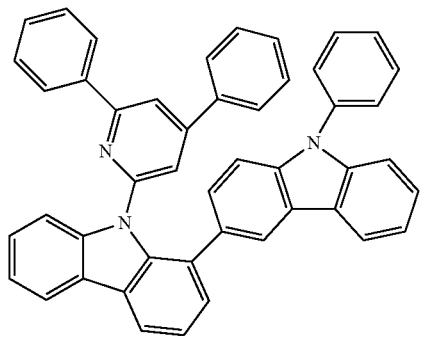
[B-92]
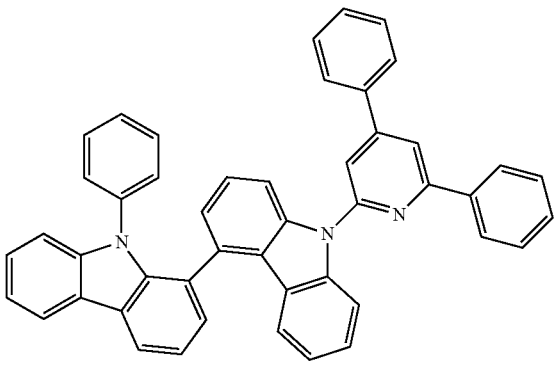

-continued
[B-93]
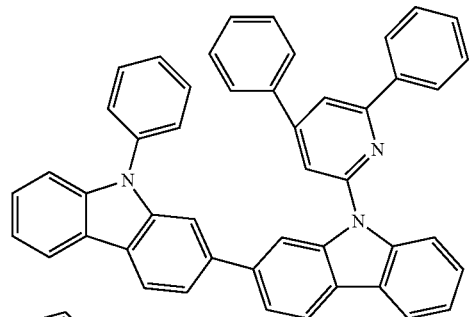
[B-94]
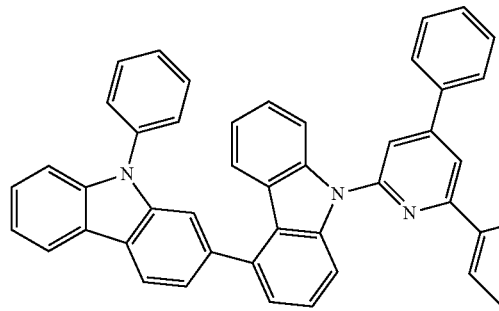
[B-95]
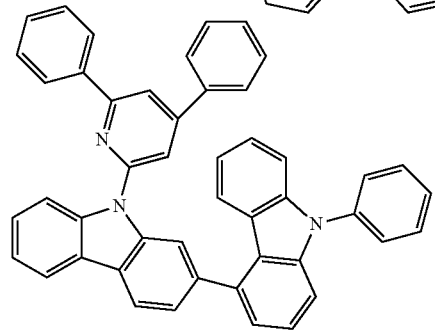
[B-96]
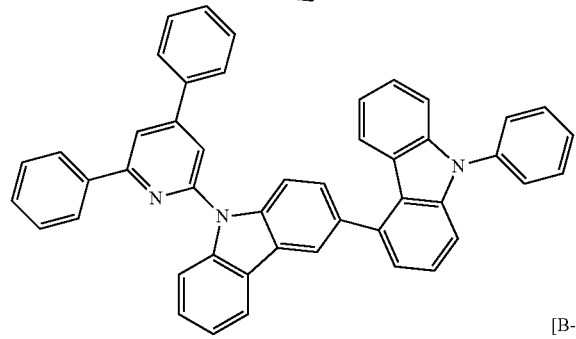
[B-97]
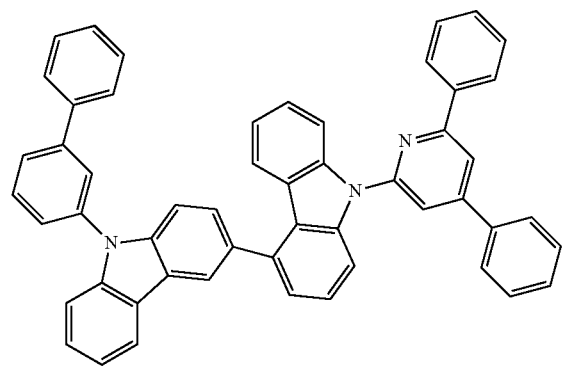
[B-98]
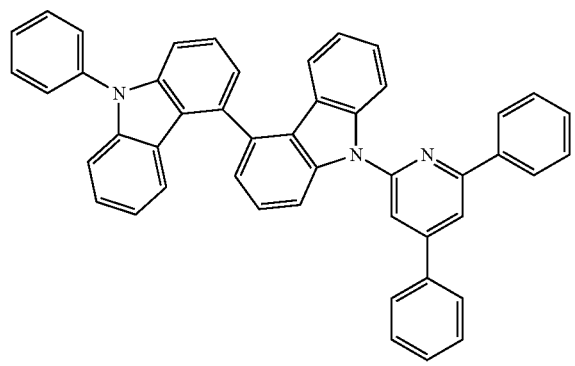
[B-99]
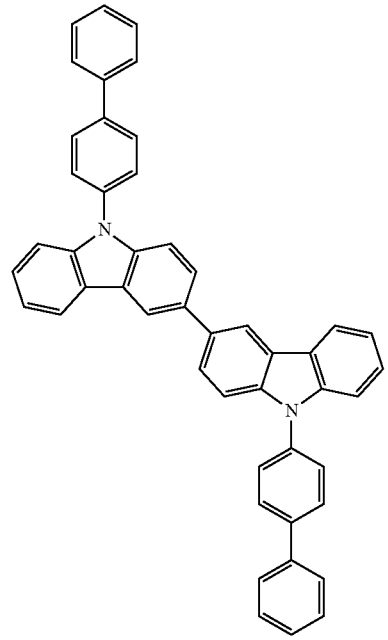
[B-100]
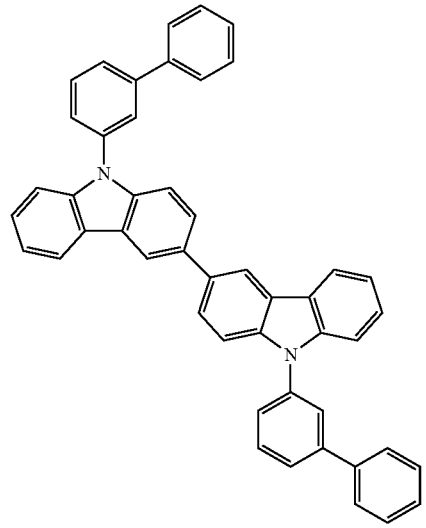

-continued
[B-101]
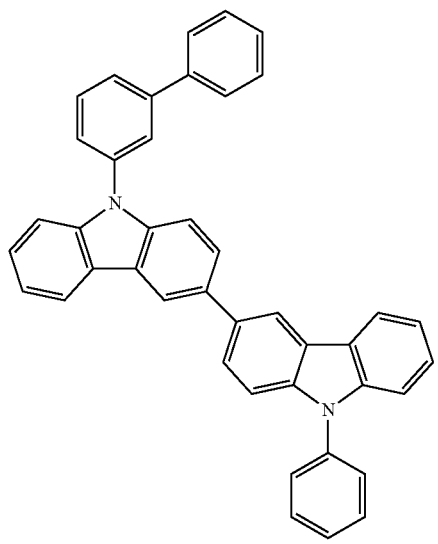
[B-102]
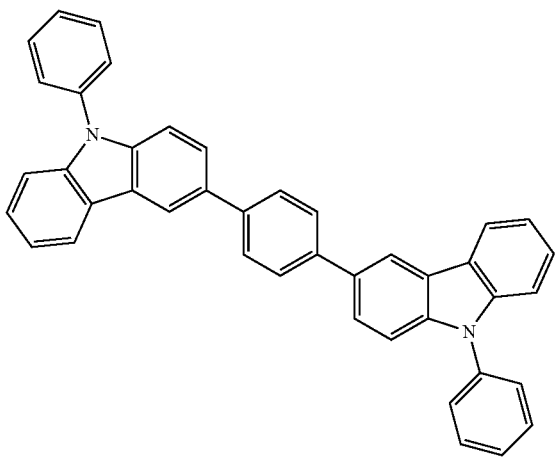
[B-103]
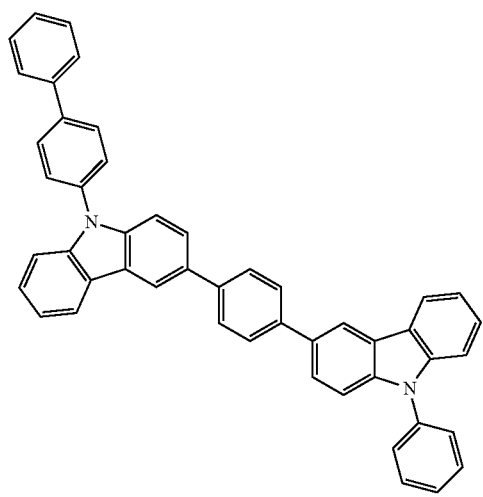
[B-104]
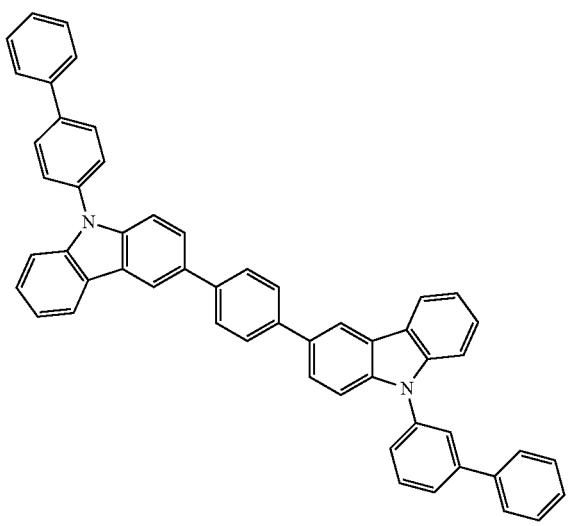
[B-105]
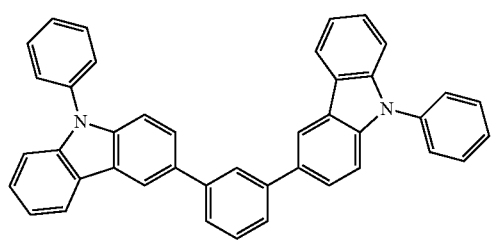
[B-106]
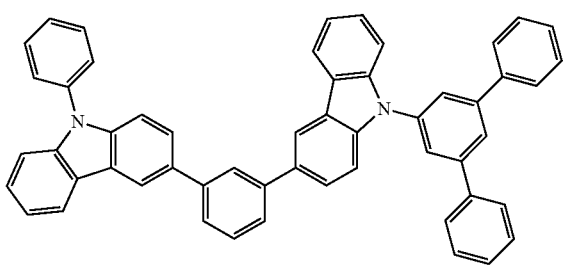

-continued
[B-107]
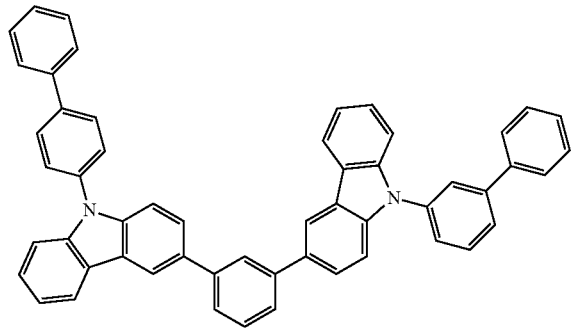
[B-108]
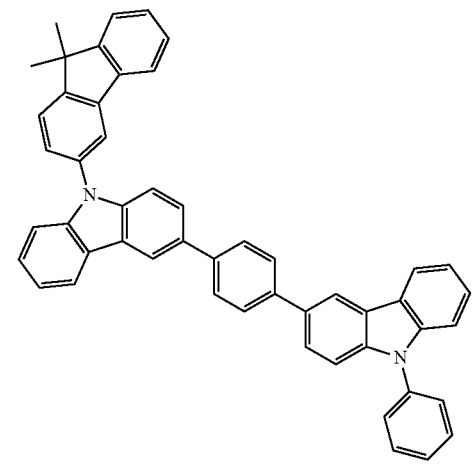
[B-109]
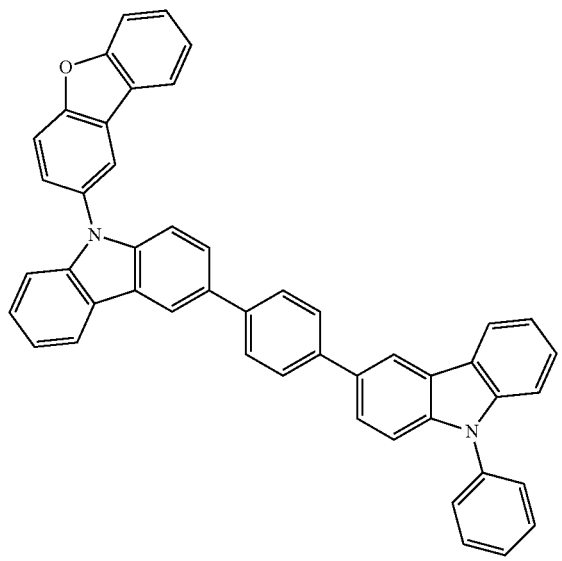
[B-110]
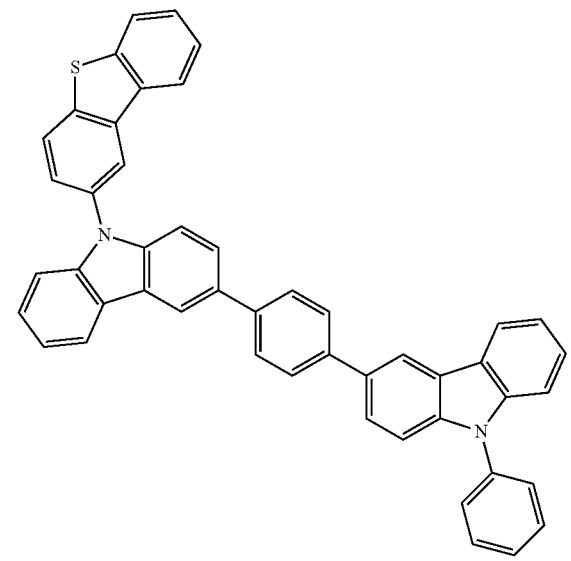
[B-111]
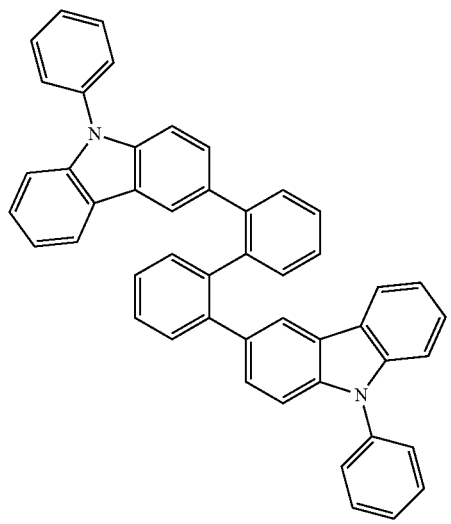
[B-112]
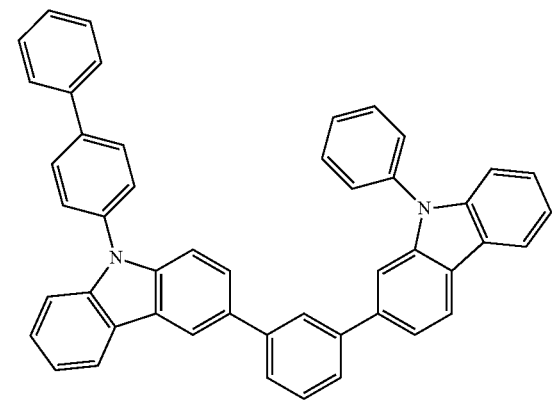

-continued
[B-113]
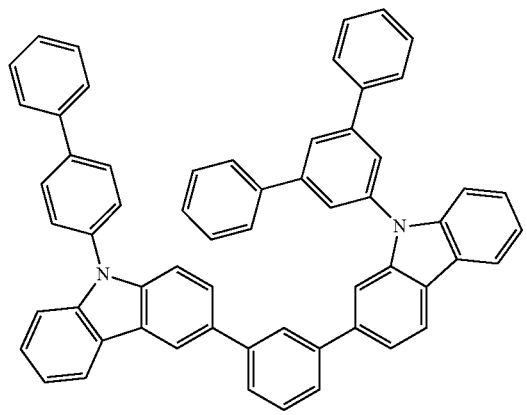
[B-114]
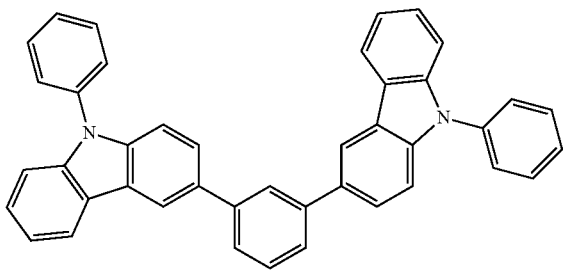
[B-115]
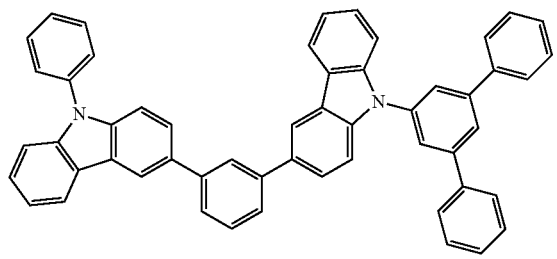
[B-116]
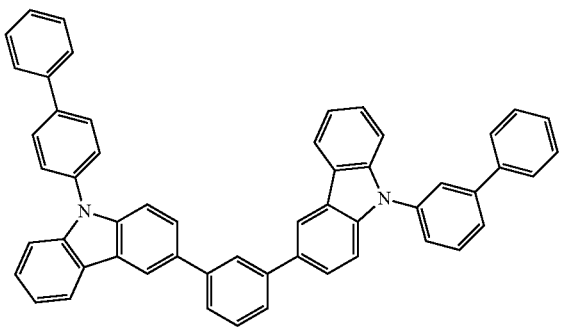
[B-117]
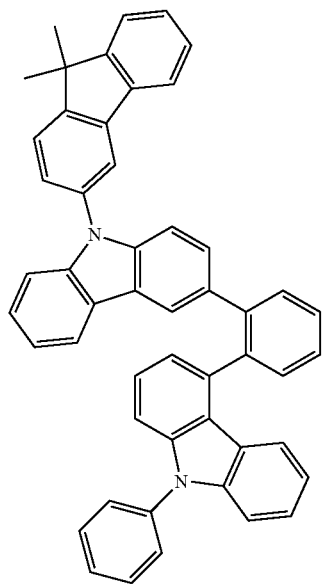
[B-118]
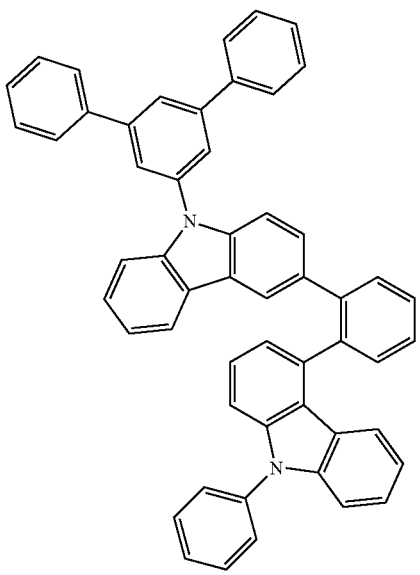

-continued
[B-119]
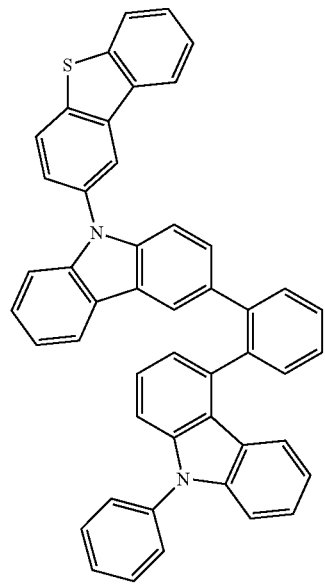
[B-120]
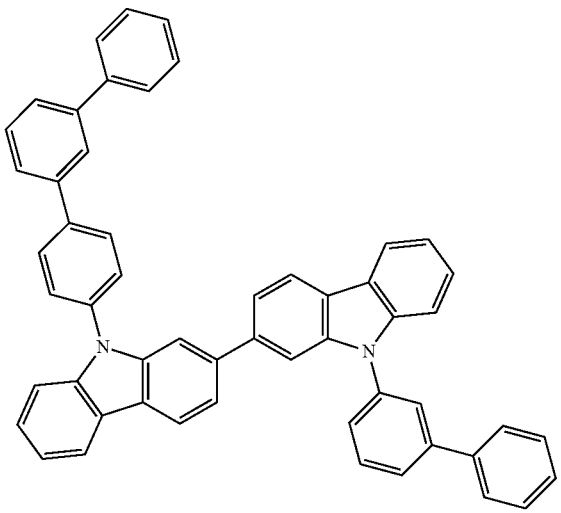
[B-121]
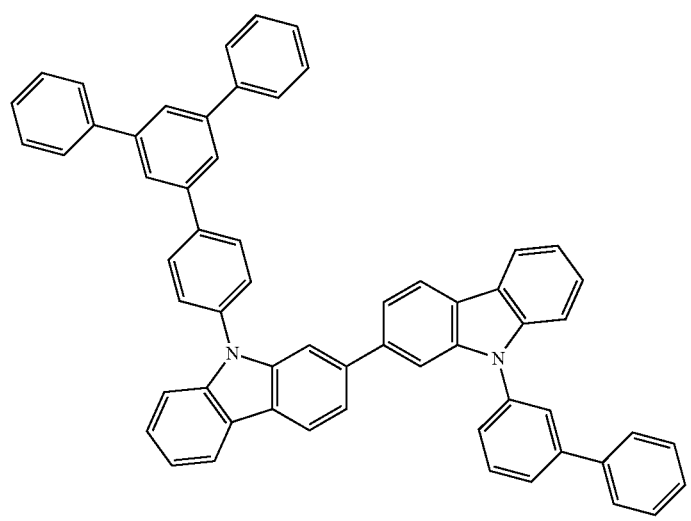
[B-122]
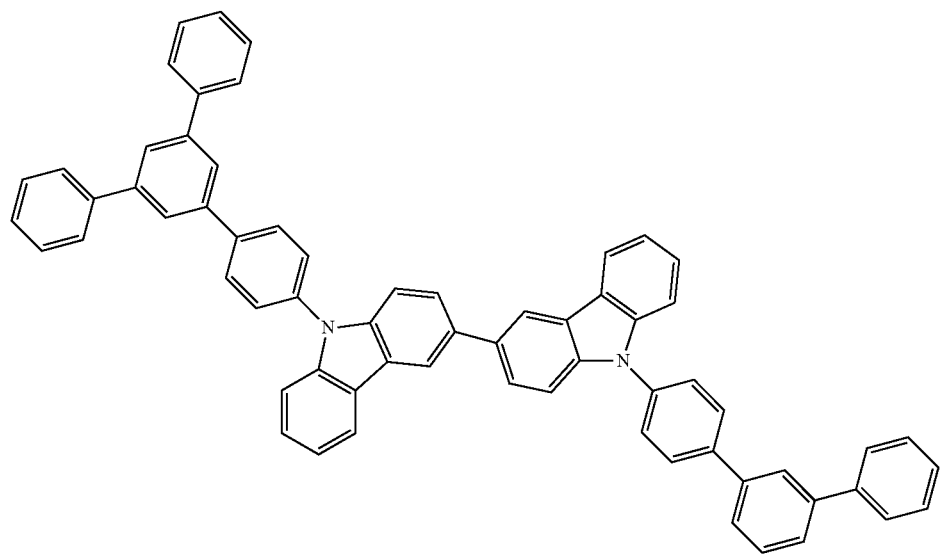

-continued
[B-123]
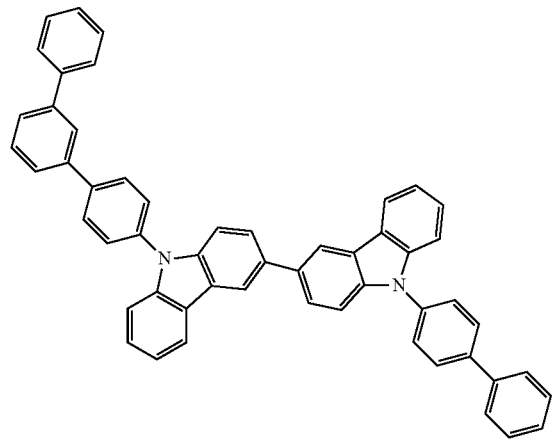
[B-124]
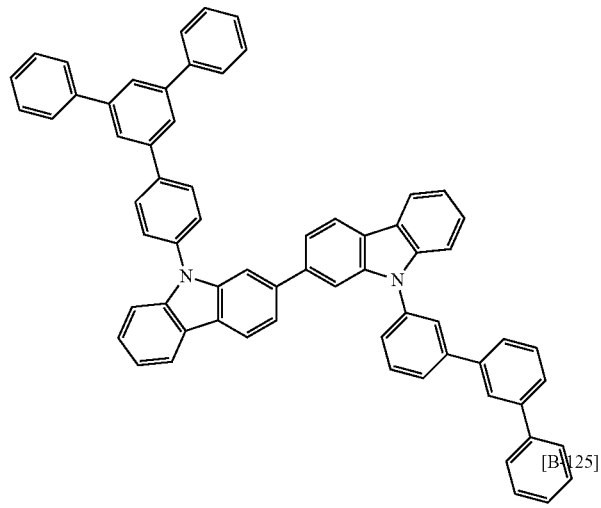
[B-125]
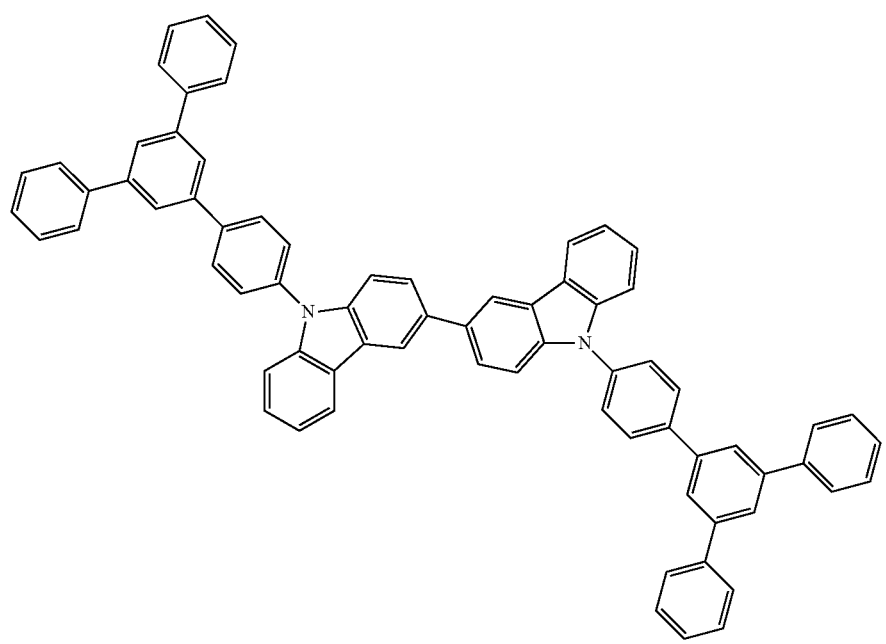
[B-126]
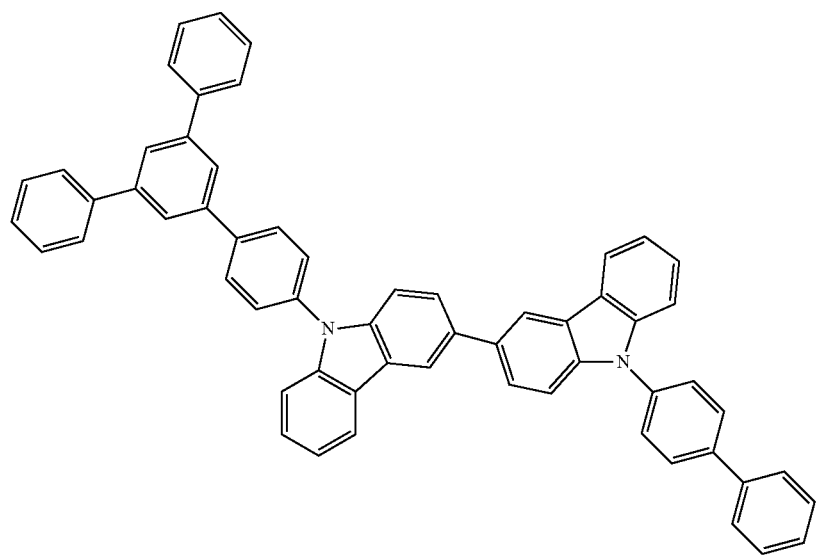

[B-127]
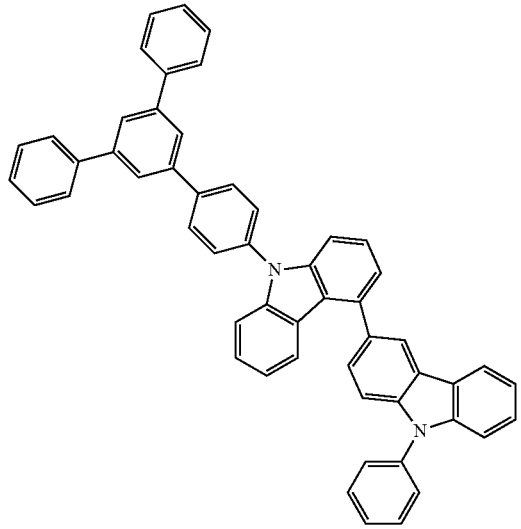
[B-128]
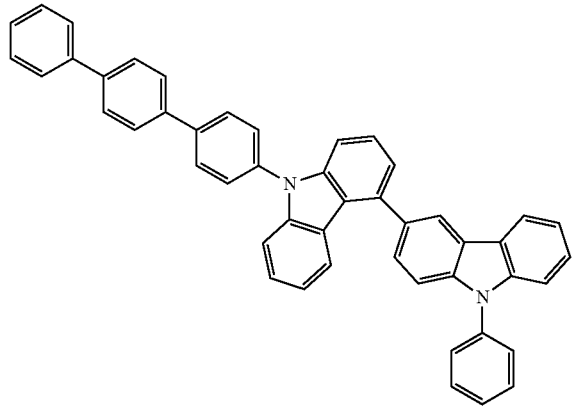
[B-129]
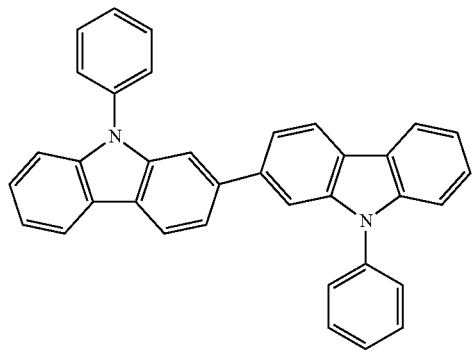
[B-130]
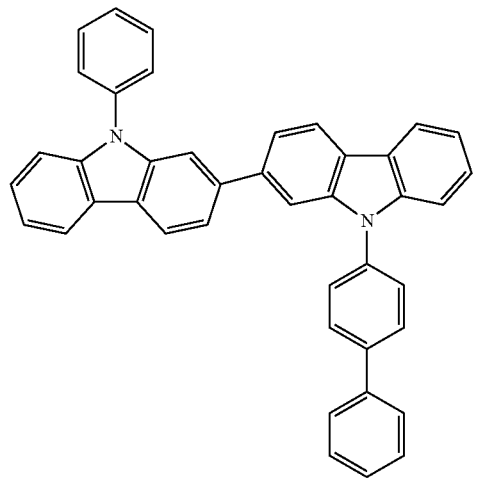
[B-131]
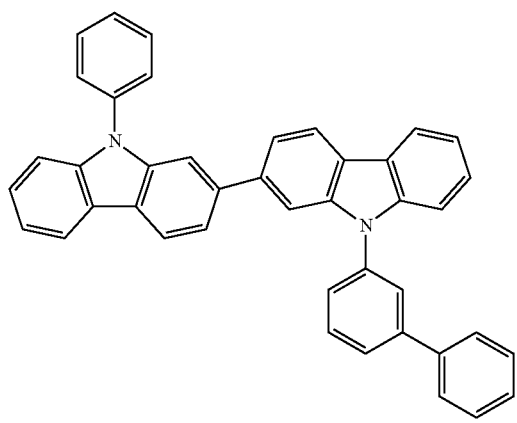
[B-131]
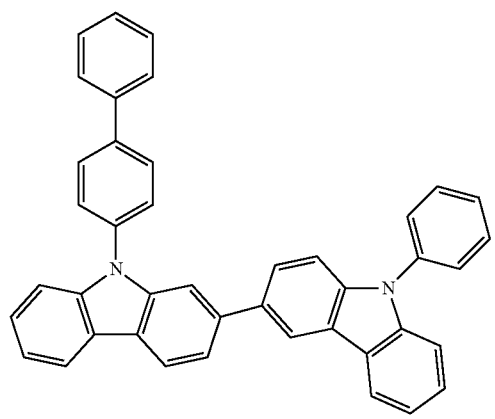

-continued
[B-133]
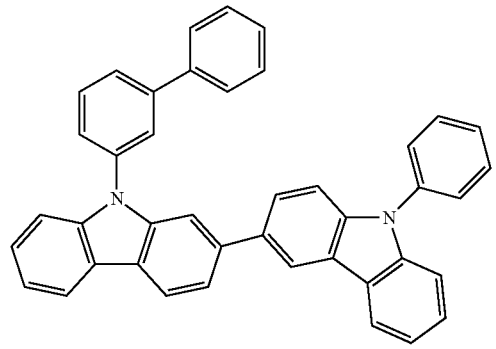
[B-134]
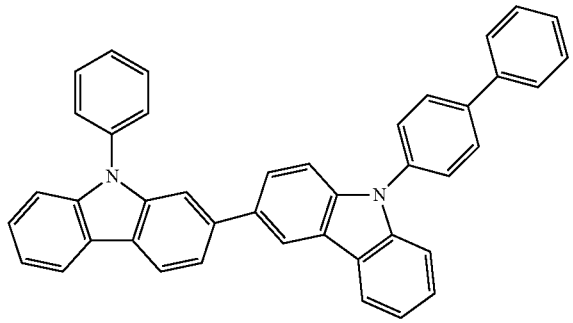
[B-135]
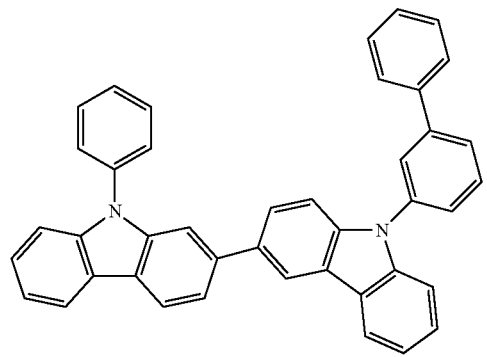
[B-136]
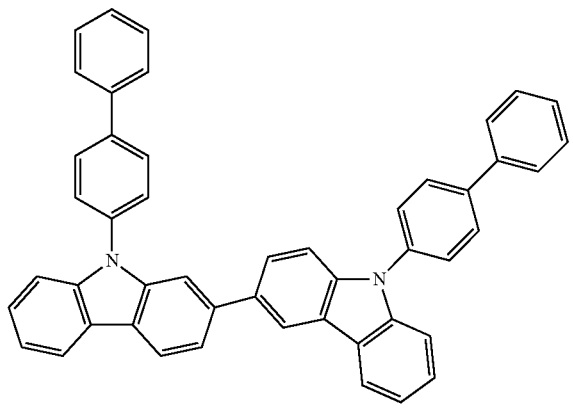
[B-137]
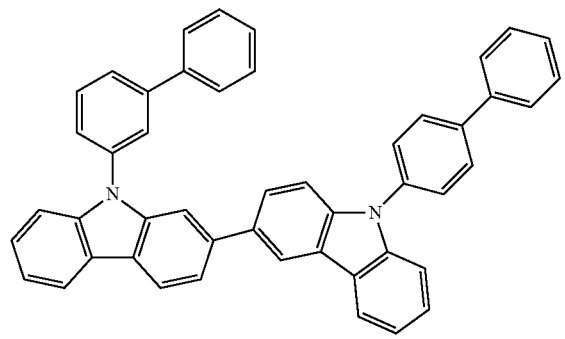
[B-138]
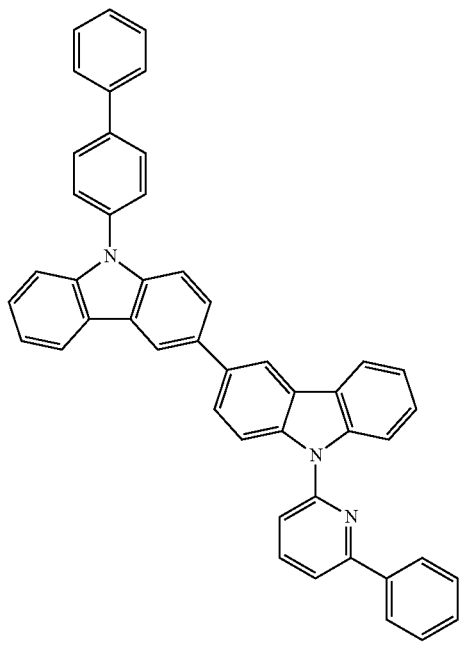

-continued
[B-139]
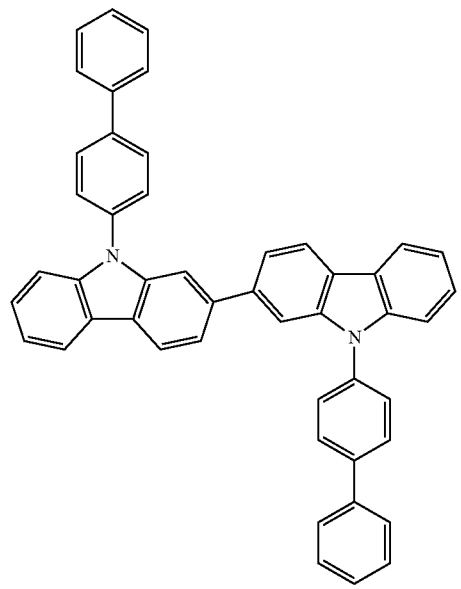
[B-140]
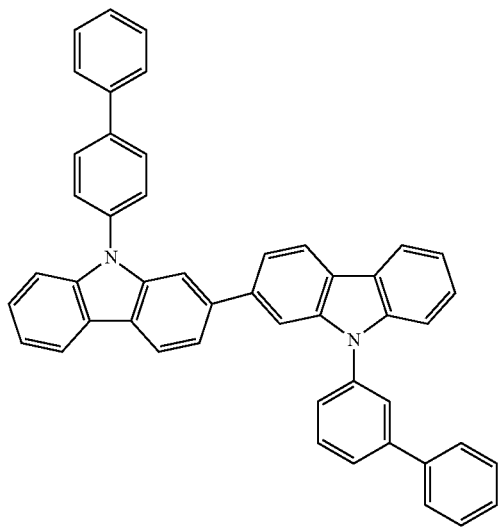
[B-141]
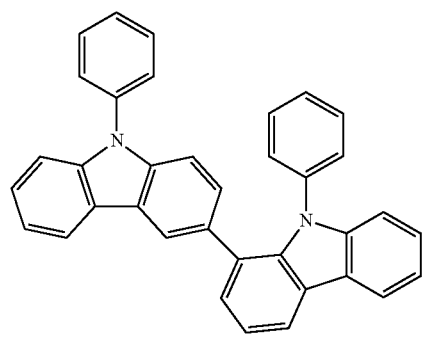
[B-142]
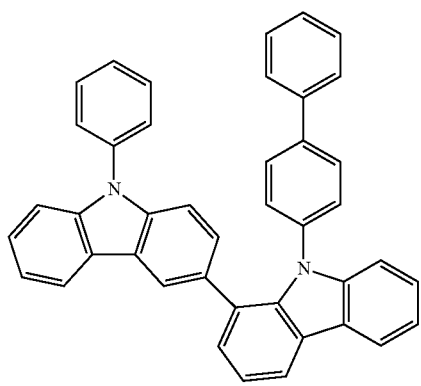
[B-143]
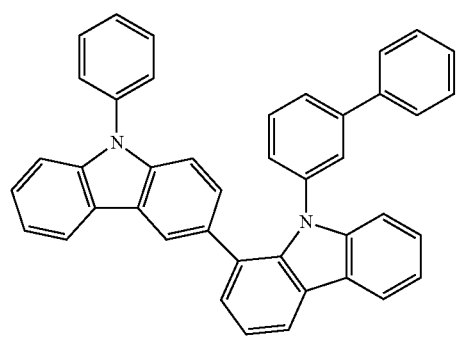
[B-144]
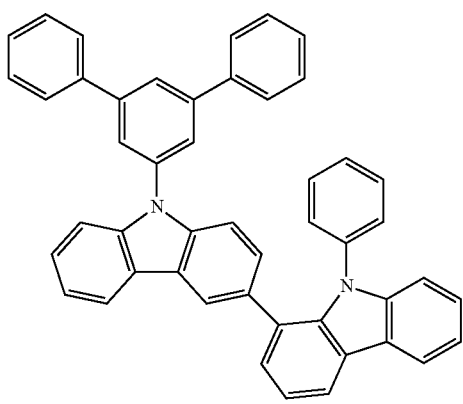

-continued
[B-145]
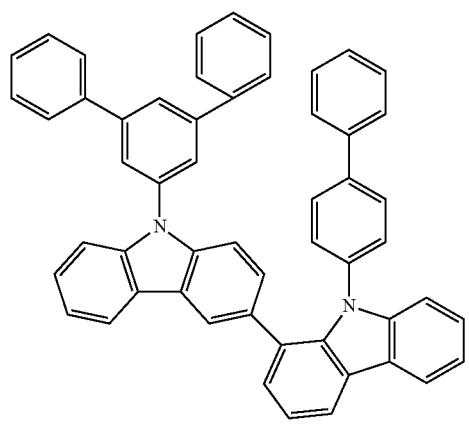
[B-146]
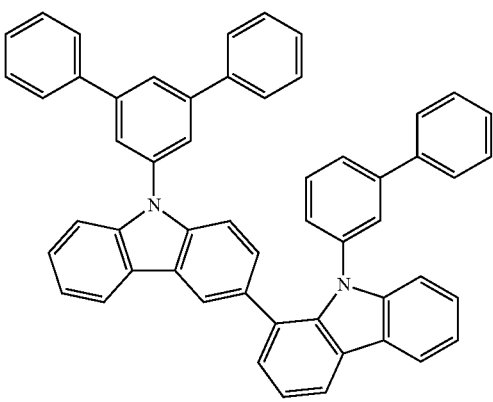
[B-147]
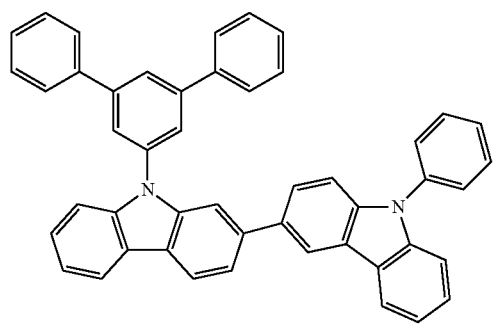
[B-148]
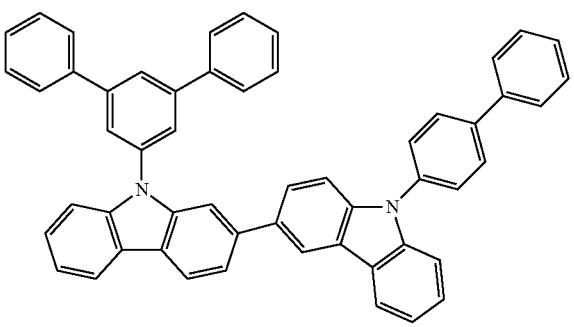
[B-149]
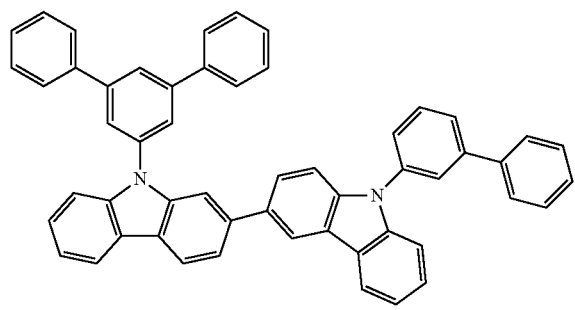
[B-150]
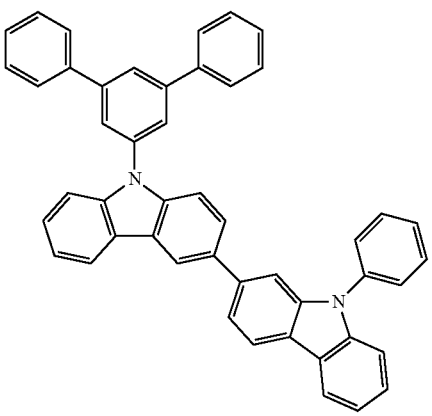
[B-151]
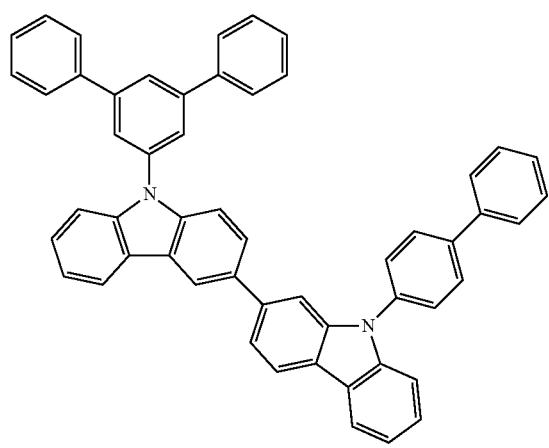
[B-152]
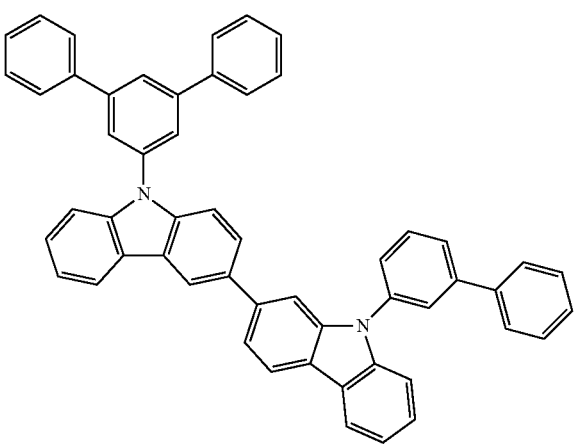

-continued
[B-153]
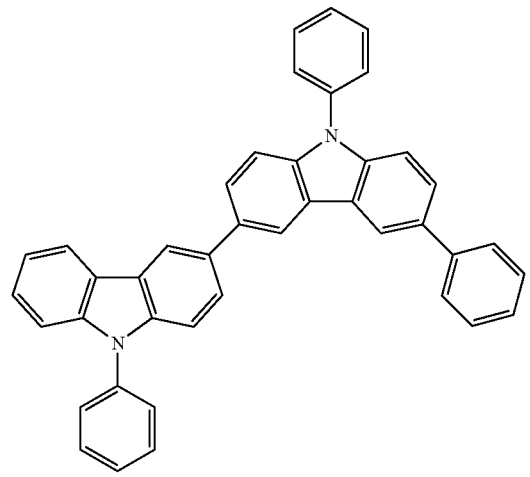
[B-154]
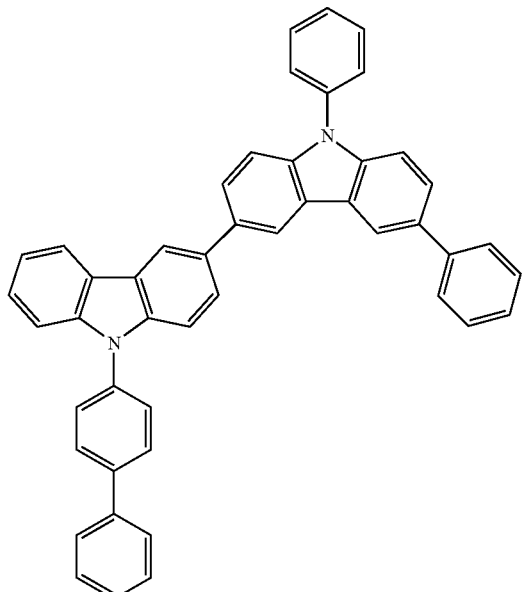
[B-155]
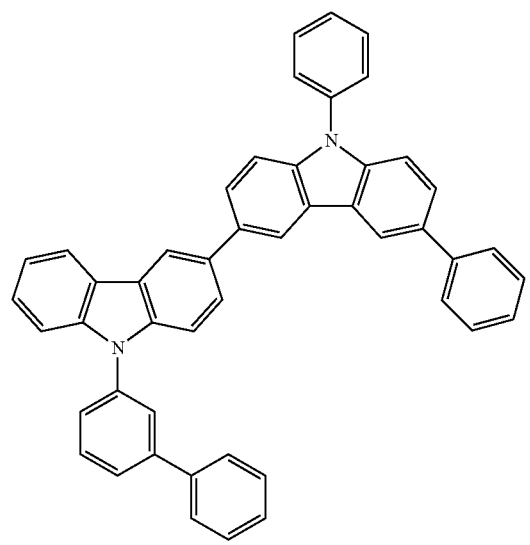
[B-156]
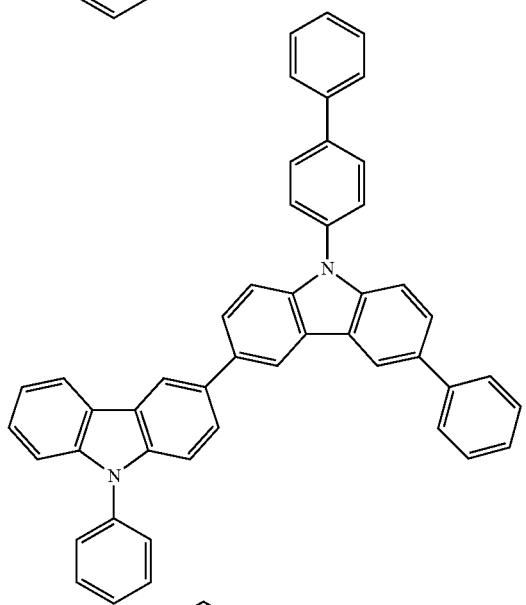
[B-157]
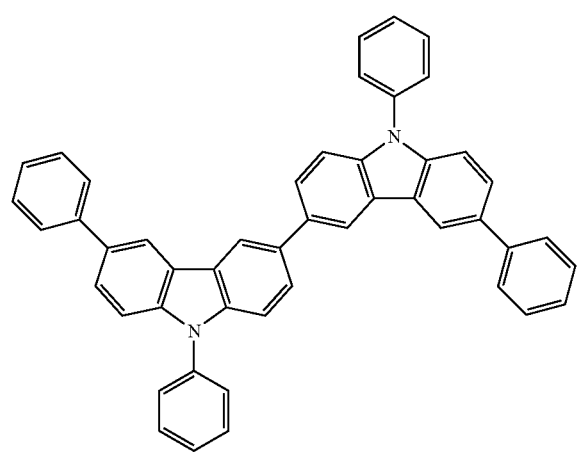
[B-158]
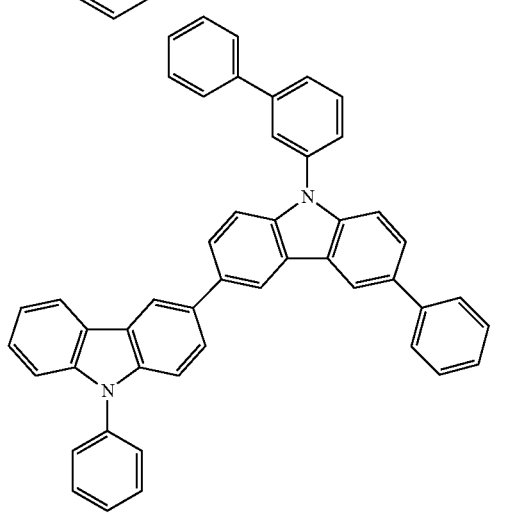

[B-159]
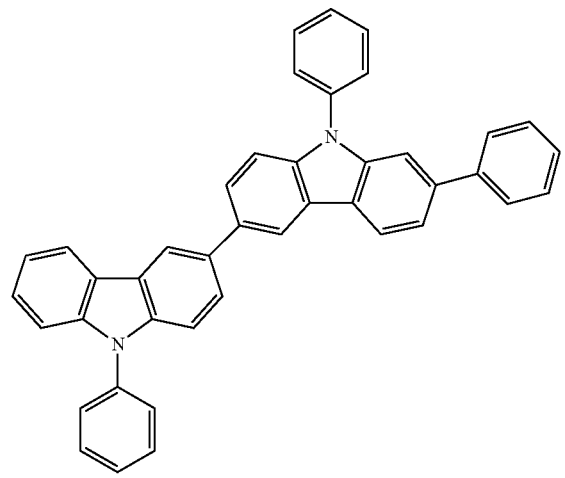
[B-160]
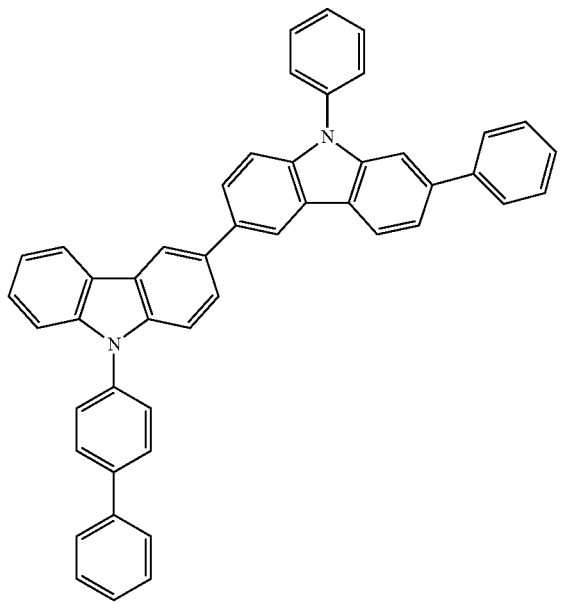
[B-161]
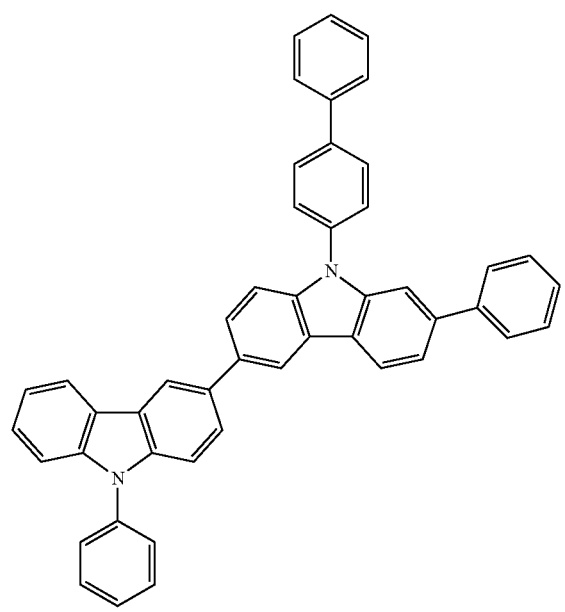
[B-162]
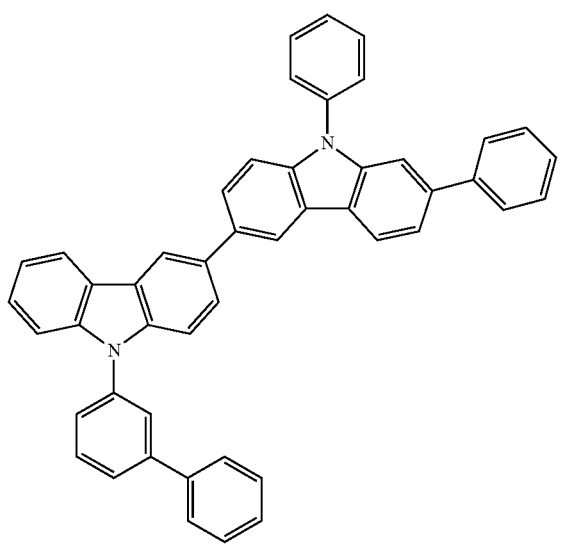

[B-163]
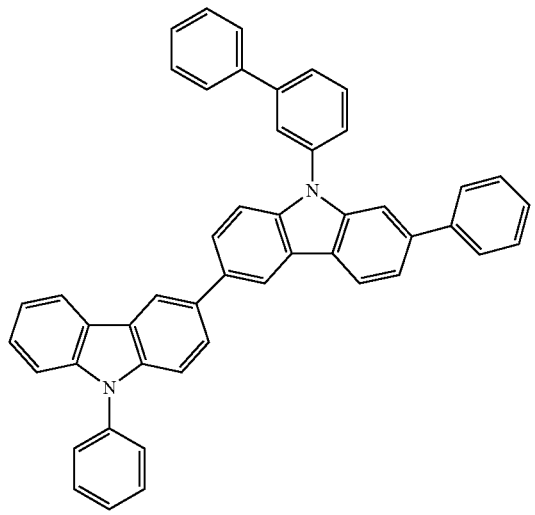
[B-164]
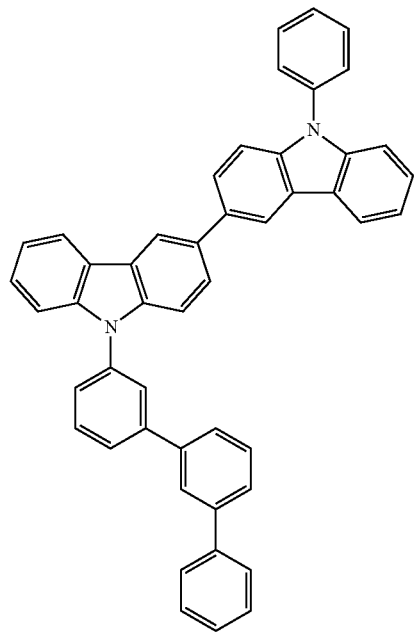
[B-165]
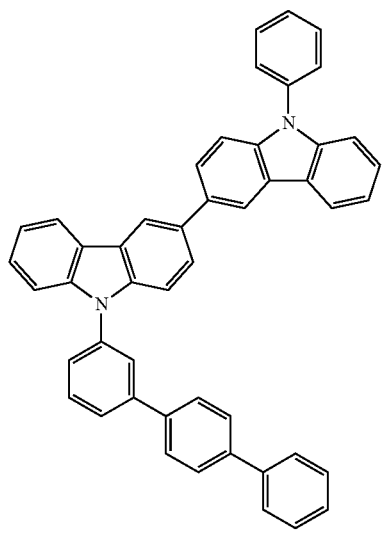
[B-166]
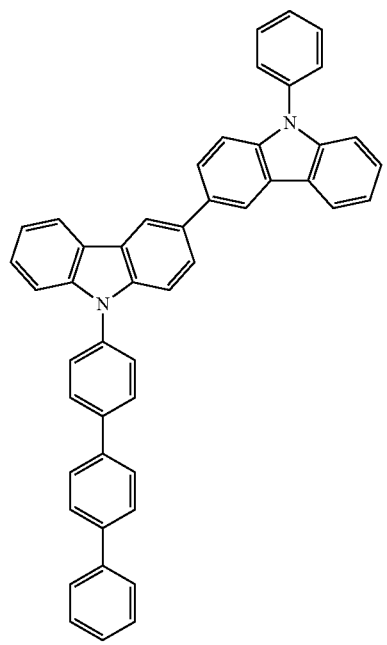

-continued
[C group]
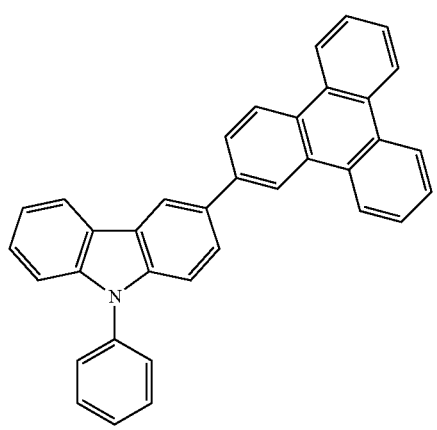
[C-1]
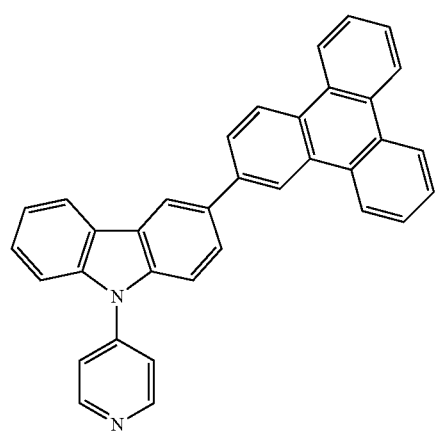
[C-2]
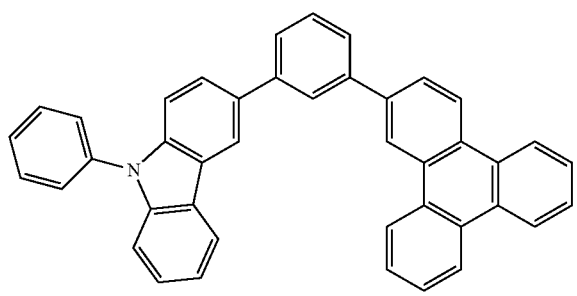
[C-3]
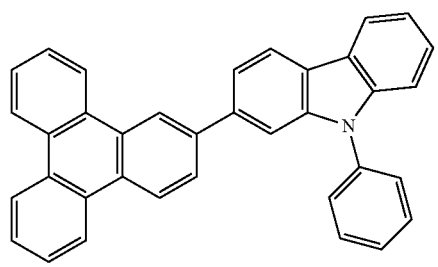
[C-4]
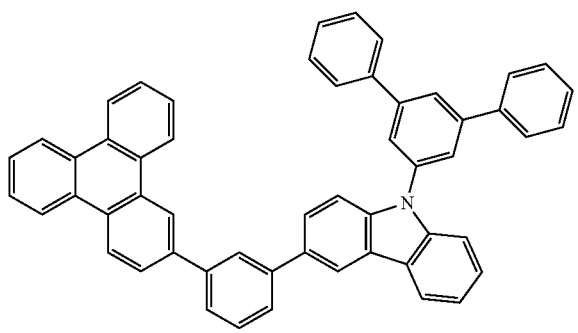
[C-5]
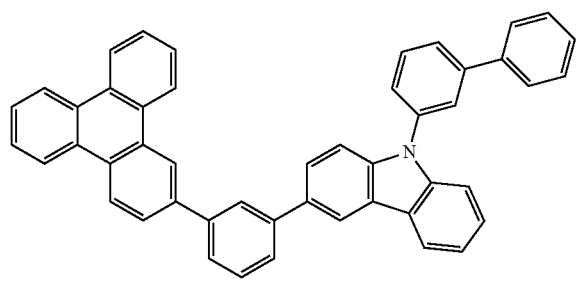
[C-6]
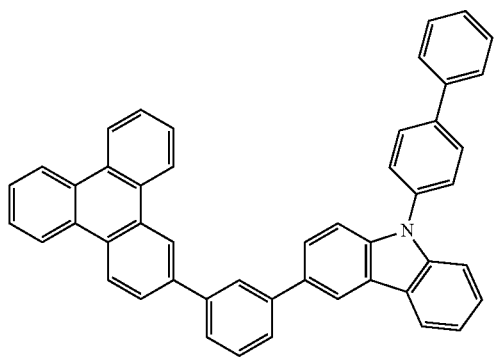
[C-7]
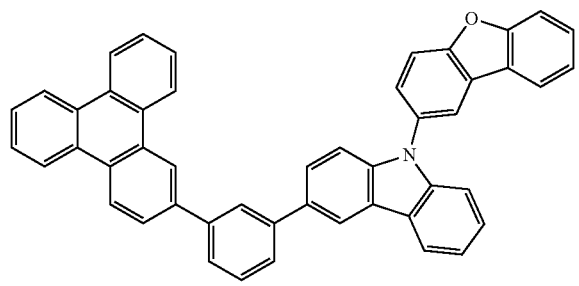
[C-8]

-continued
[C-9]
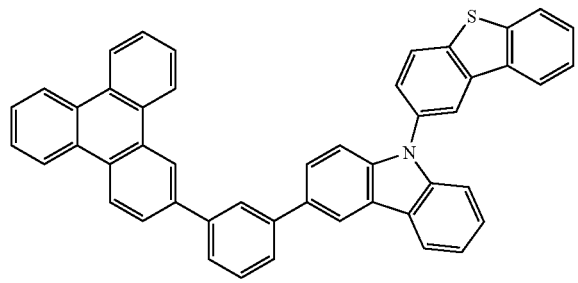
[C-10]
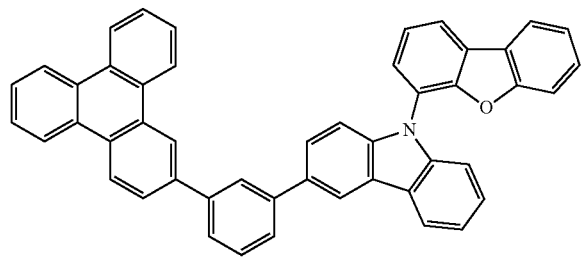
[C-11]
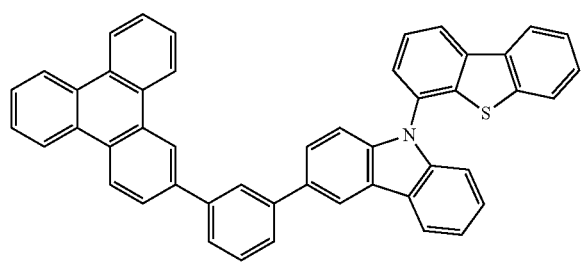
[C-12]
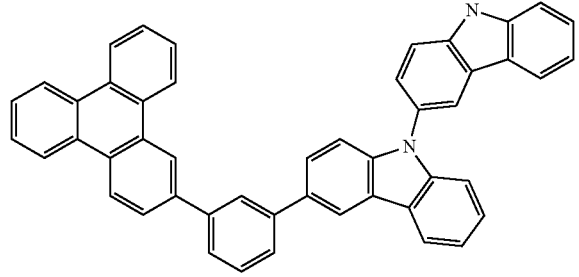
[C-13]
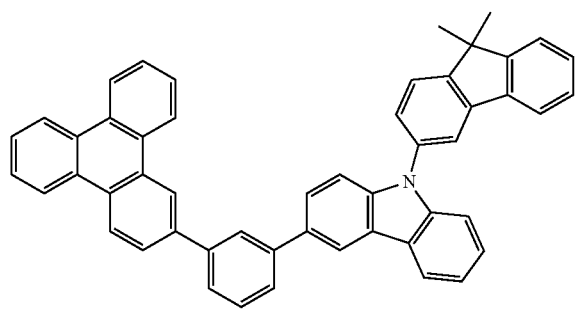
[C-14]
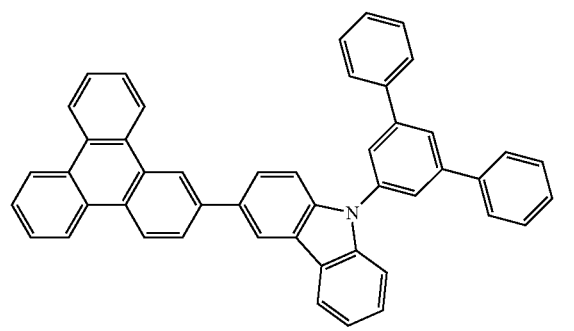
[C-15]
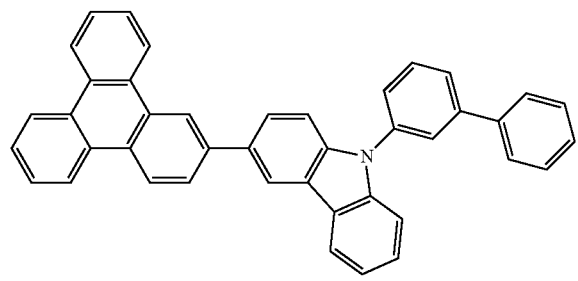
[C-16]
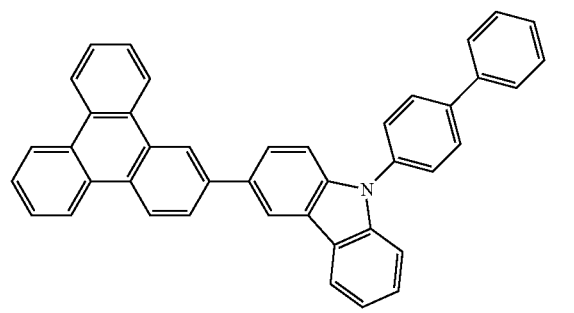

-continued
[C-17]
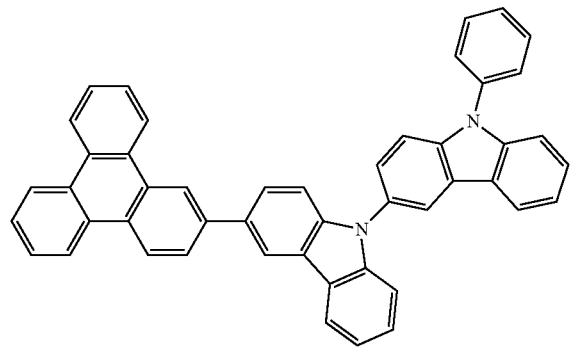
[C-18]
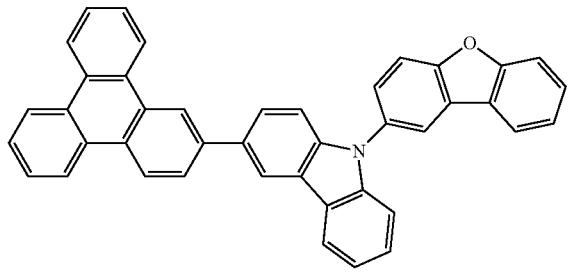
[C-19]
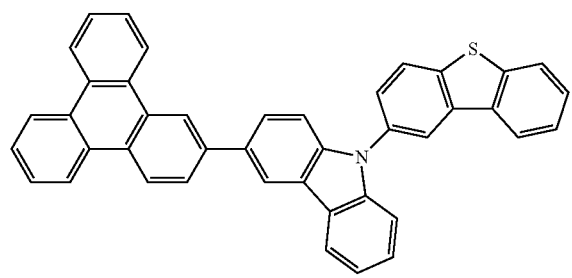
[C-20]
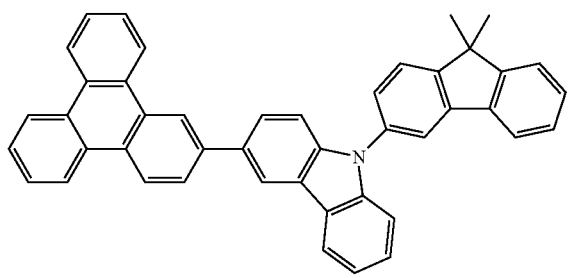
[C-21]
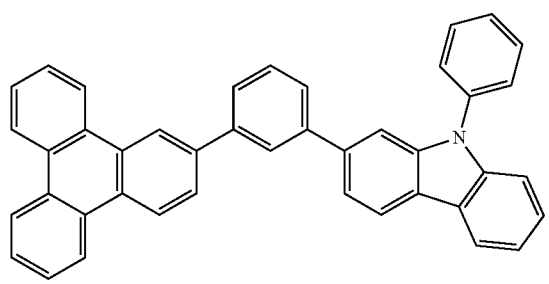
[C-22]
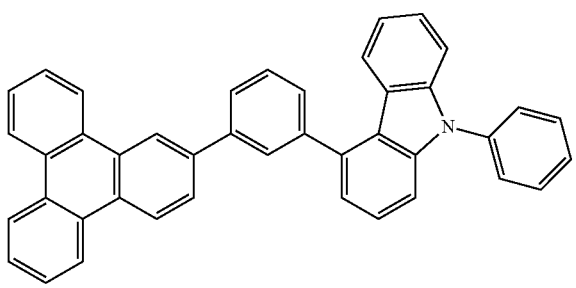
[C-23]
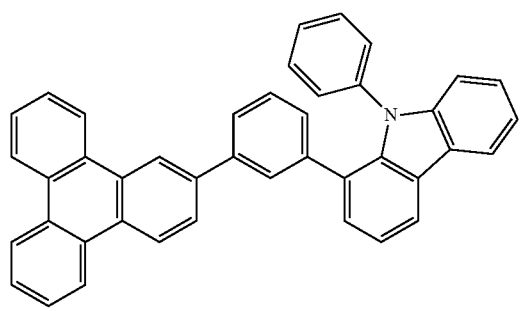
[C-24]
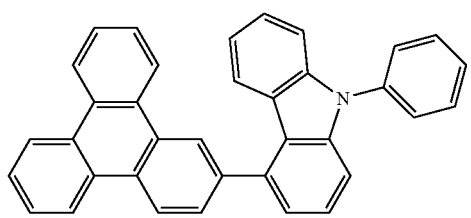

[D group]
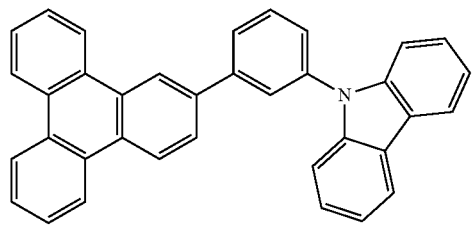
[D-1]
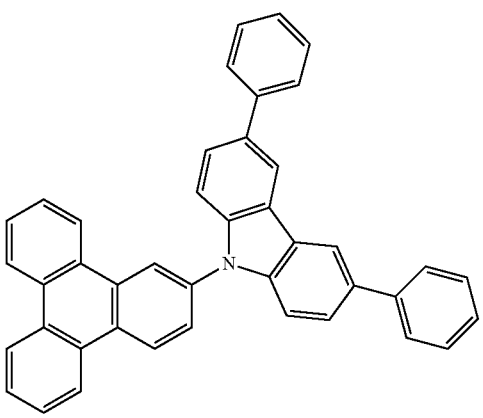
[D-2]
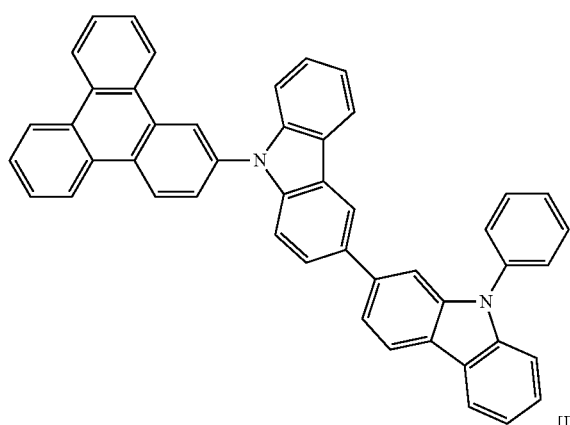
[D-3]
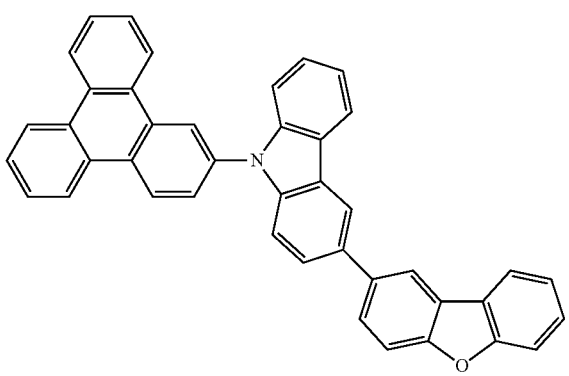
[D-4]
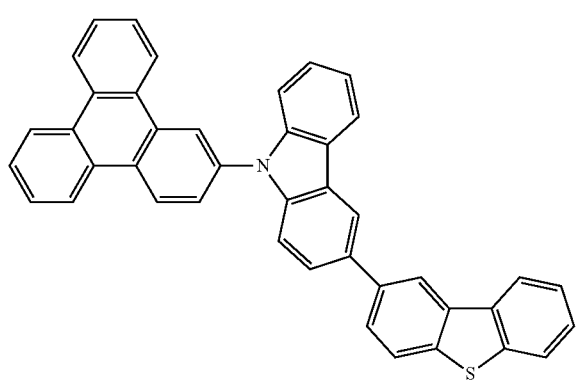
[D-5]
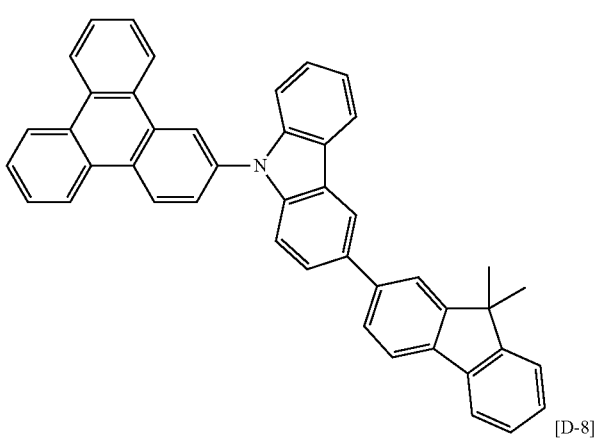
[D-6]
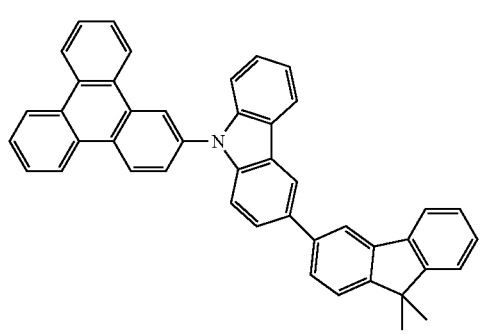
[D-7]
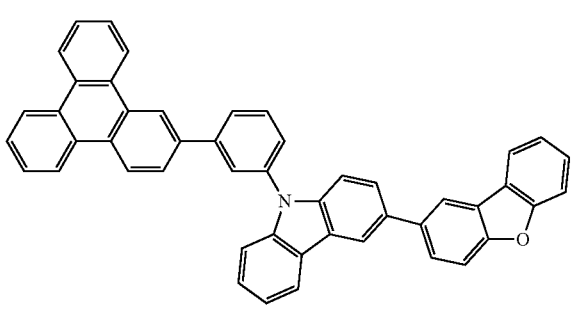
[D-8]

-continued
[D-9]
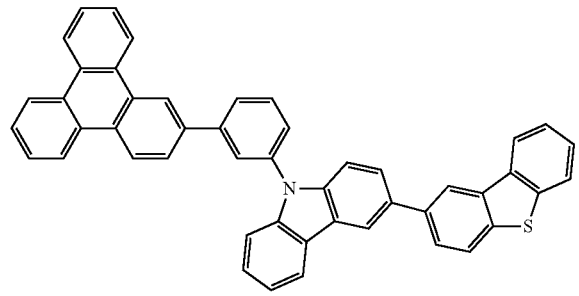
[D-10]
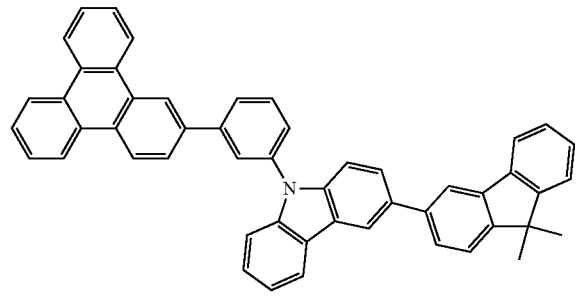
[D-11]
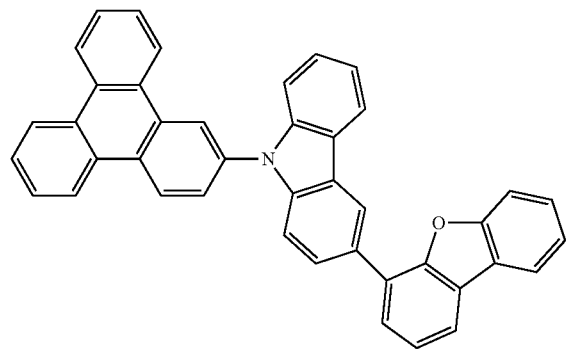
[D-12]
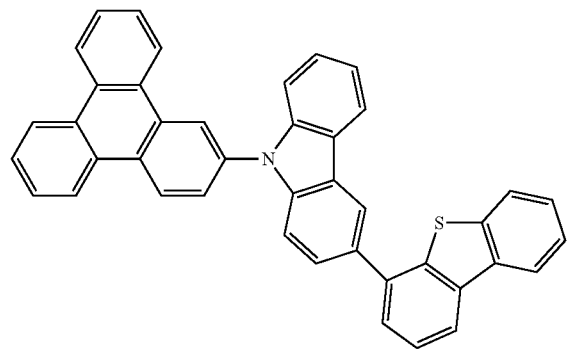
[D-13]
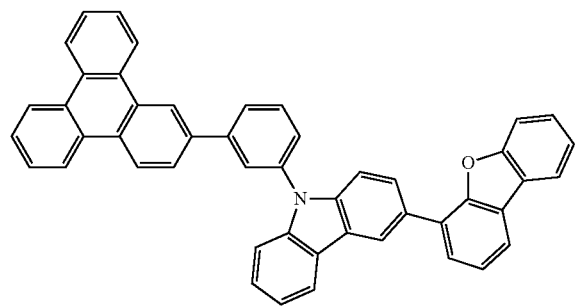
[D-14]
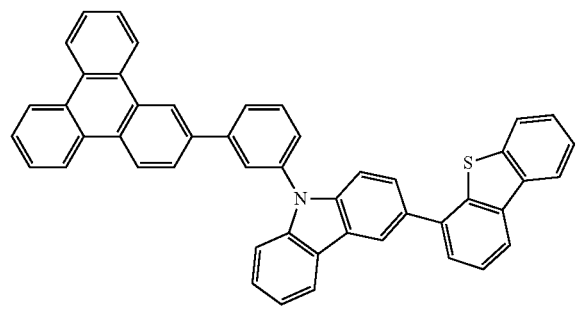
[D-15]
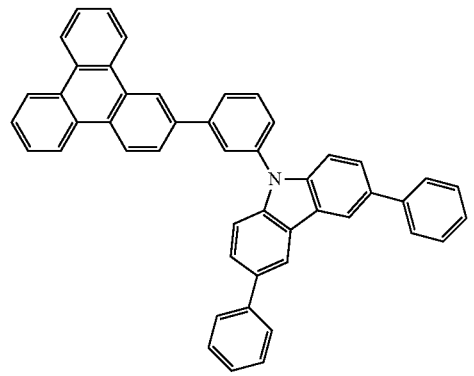
[D-16]
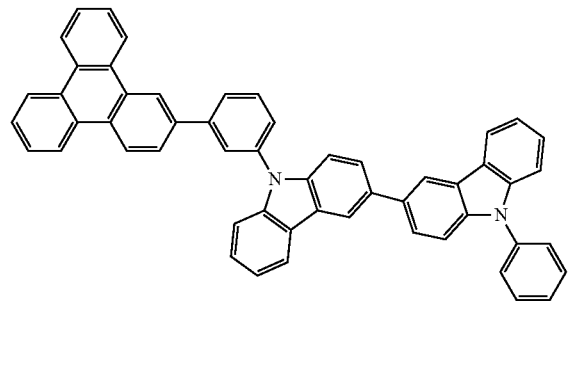

[D-17]
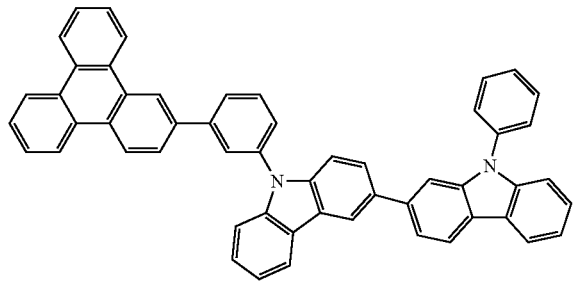
[D-18]
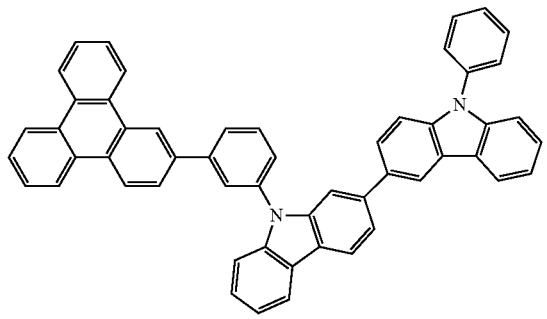
[D-19]
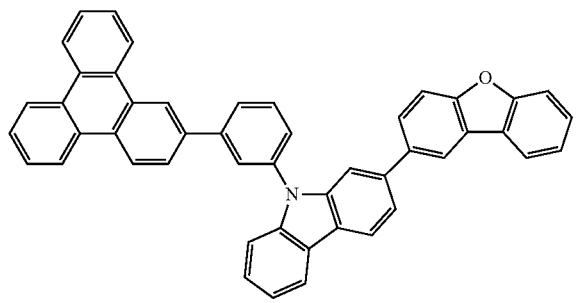
[D-20]
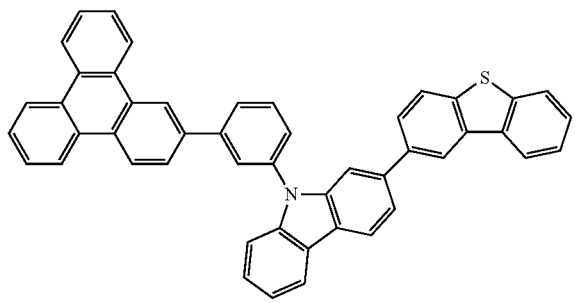
In addition, the compound consisting of a combination of the moiety represented by Chemical Formula III and the moiety represented by Chemical Formula IV may be, for example represented by at least one of Chemical Formulae III-1 to III-5, but is not limited thereto.
[Chemical Formula III-1]
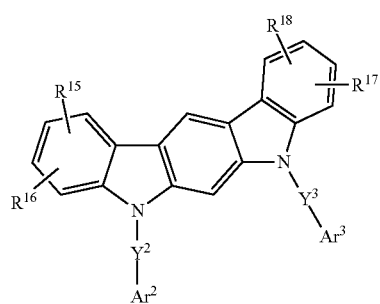
[Chemical Formula III-2]
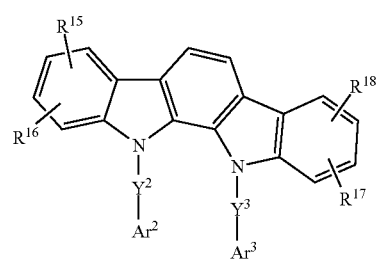
[Chemical Formula III-3]
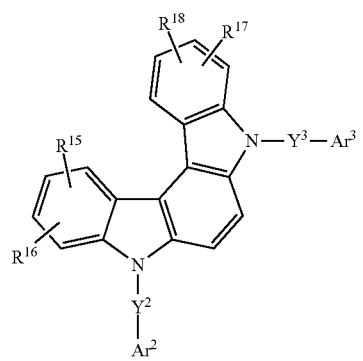
[Chemical Formula III-4]
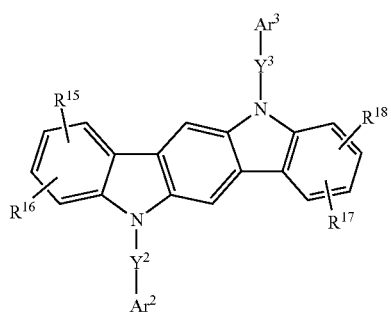

[Chemical Formula III-5]

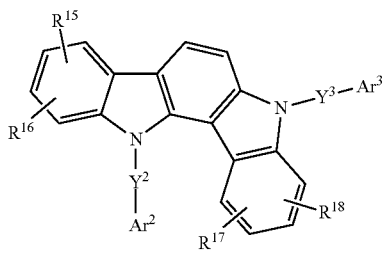

In Chemical Formulae III-1 to III-5, $Y^2$, $Y^3$, $Ar^2$, $Ar^3$, and $R^{15}$ to $R^{18}$ are the same as described above, Herein, "substituted" refers to that at least one hydrogen is replaced by deuterium, a halogen, a hydroxy group, an amino group, a C1 to C30 amine group, a nitro group, a C1 to C40 silyl group, a C1 to C30 alkyl group, a C3 to C30 cycloalkyl group, a C2 to C30 heterocycloalkyl group, a C6 to C30 aryl group, a C2 to C30 heterocyclic group, a C1 to C20 alkoxy group, a fluoro group, C1 to C10 trifluoroalkyl group, or a cyano group.

The compound consisting of a combination of the moiety represented by Chemical Formula III and the moiety represented by Chemical Formula IV may be compounds of Group E, but is not limited thereto.

[Group E]

[E-1]

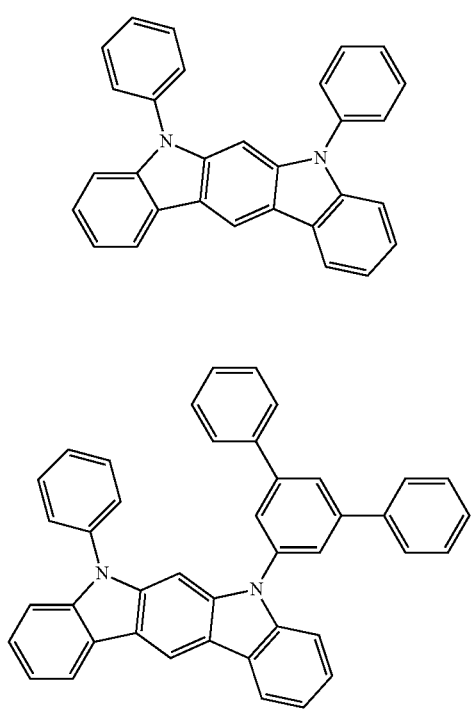

[E-2]

[E-3]

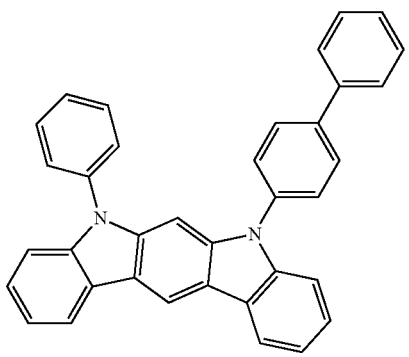

[E-4]

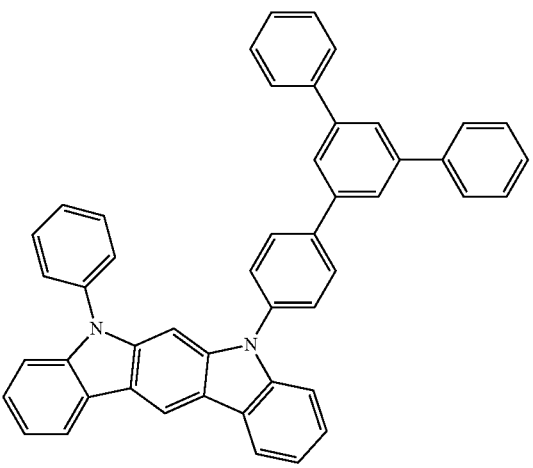

[E-5]

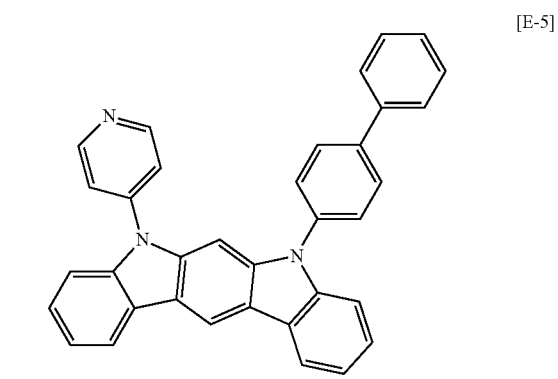

[E-6]

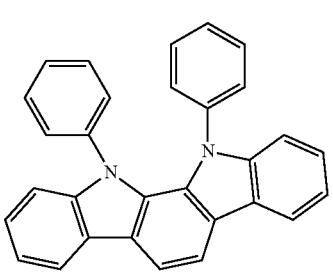

[E-7]
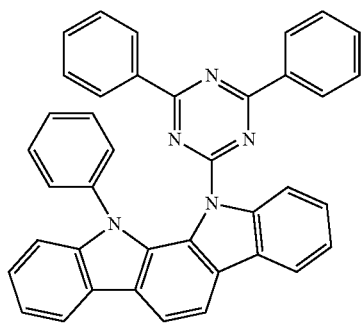
[E-8]
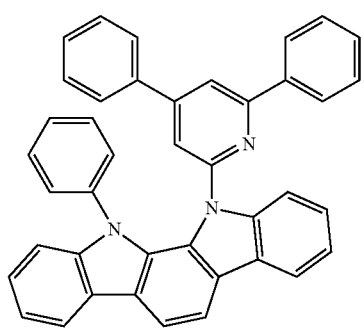
[E-9]
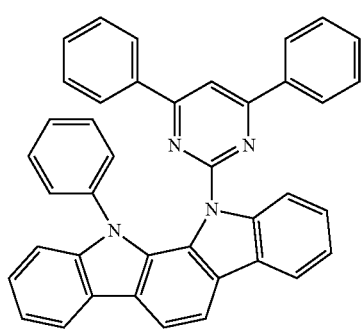
[E-10]
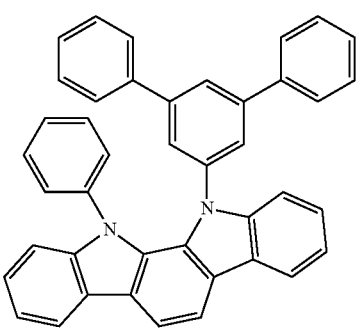
[E-11]
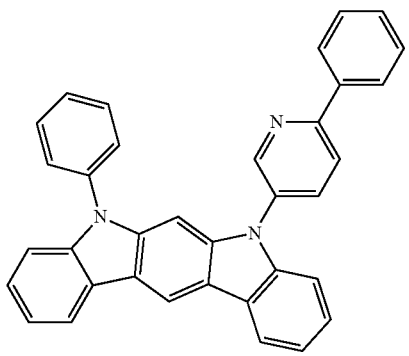
[E-12]
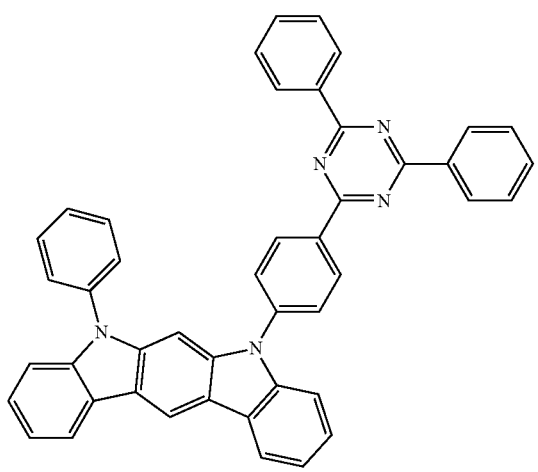
[E-13]
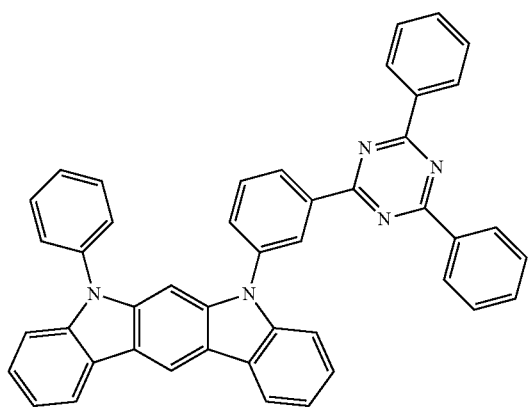
[E-14]
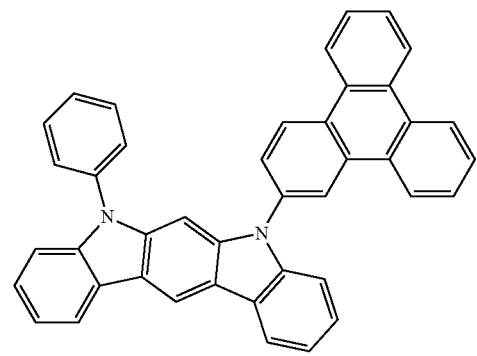

[E-15]
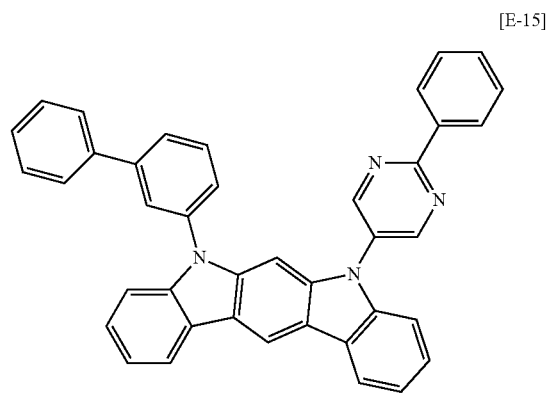
[E-19]
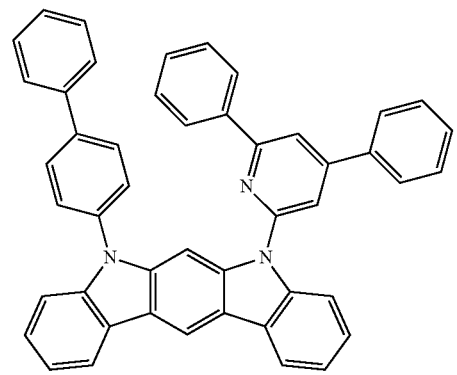
[E-16]
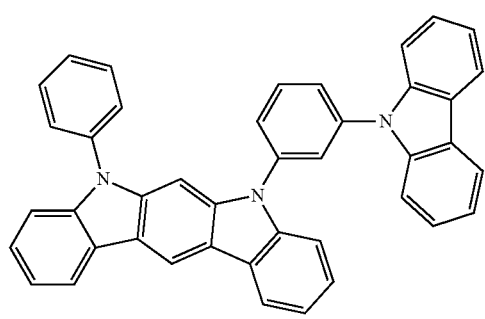
[E-20]
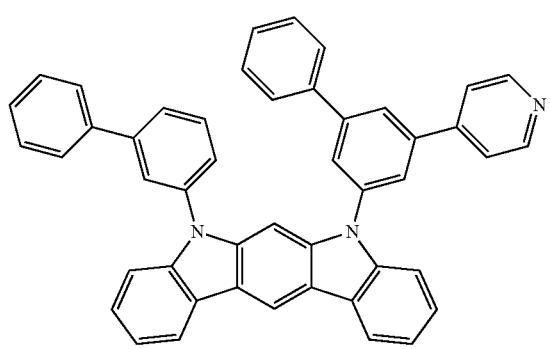
[E-17]
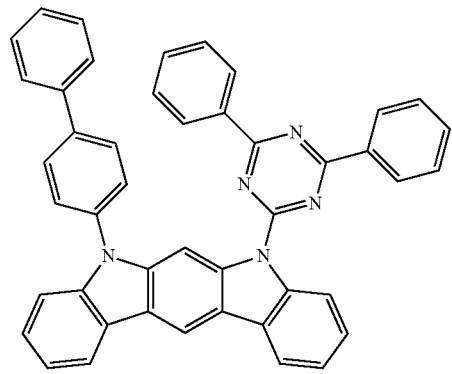
[E-21]
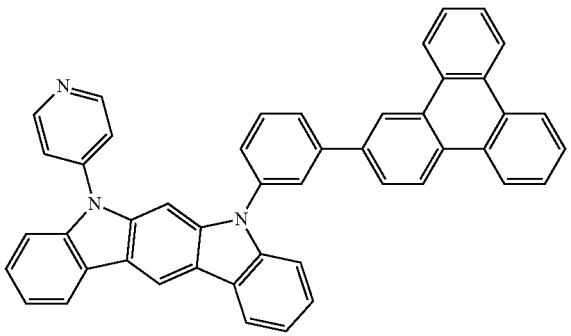
[E-18]
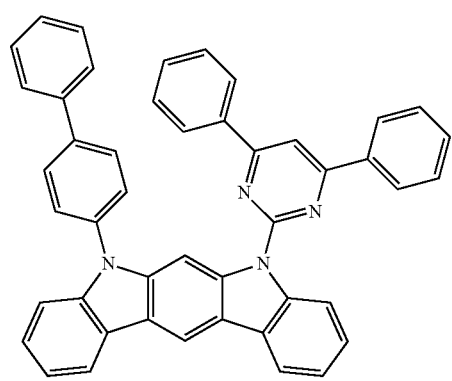
[E-22]
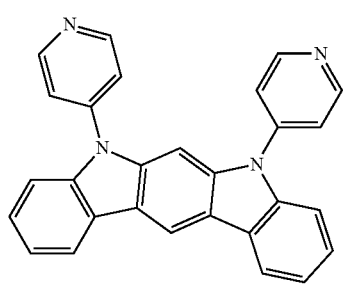
[E-23]
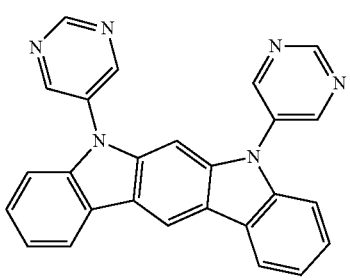

[E-24]
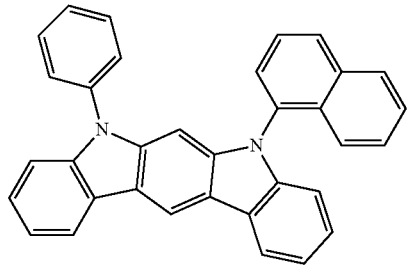
[E-25]
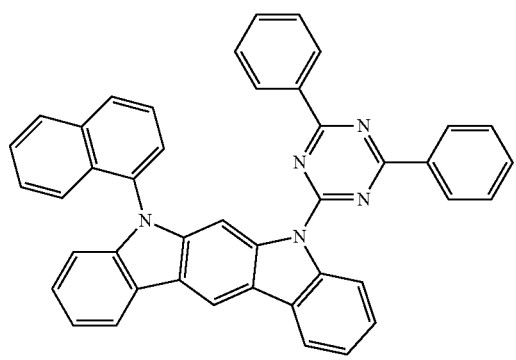
[E-26]
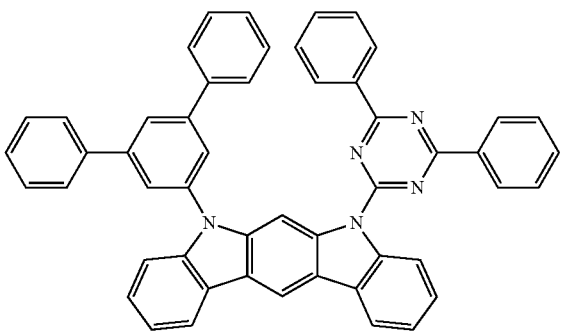
[E-27]
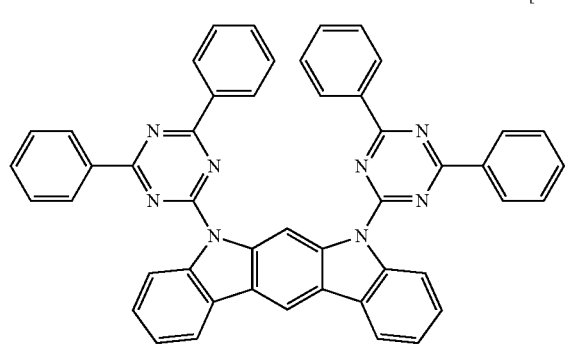
[E-28]
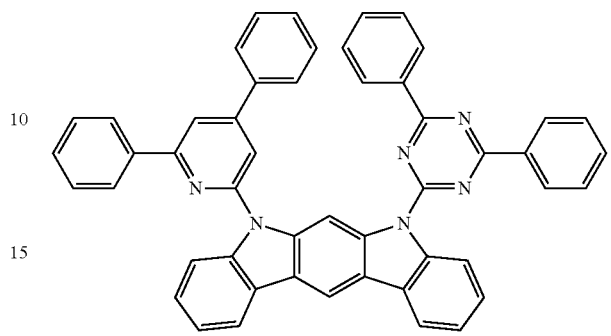
[E-29]
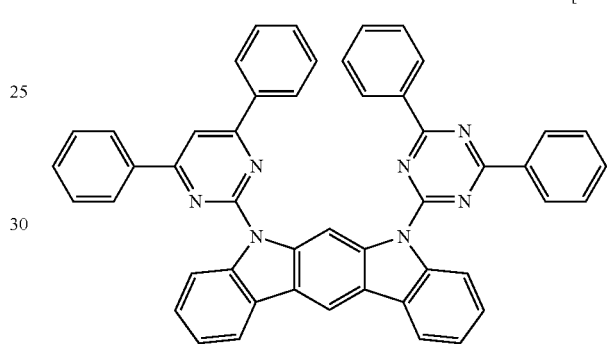
[E-30]
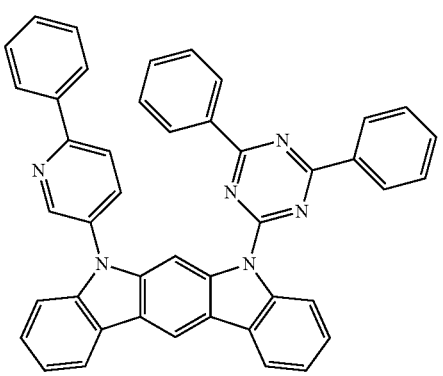
[E-31]
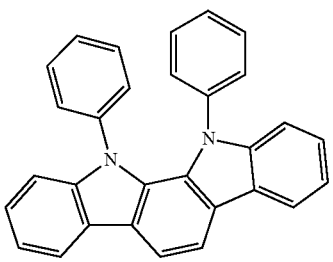

[E-32]
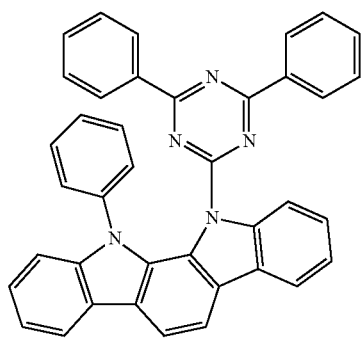
[E-33]
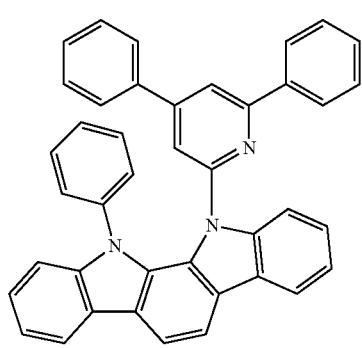
[E-34]
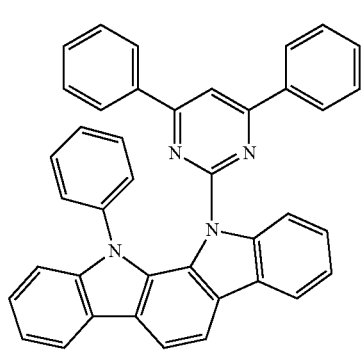
[E-35]
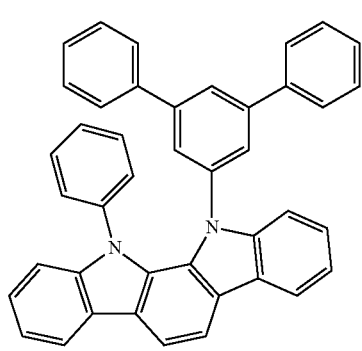
[E-36]
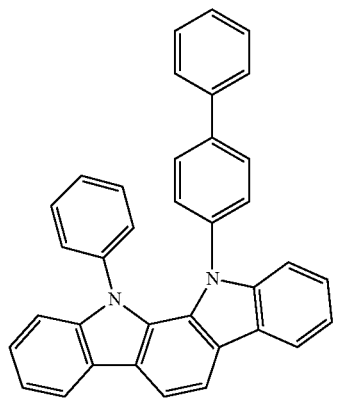
[E-37]
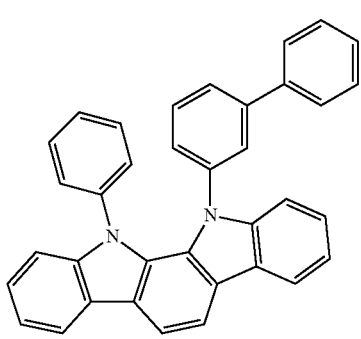
[E-38]
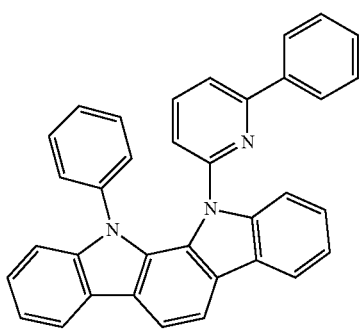
[E-39]
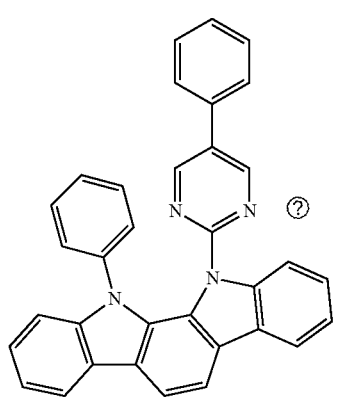

[E-40]

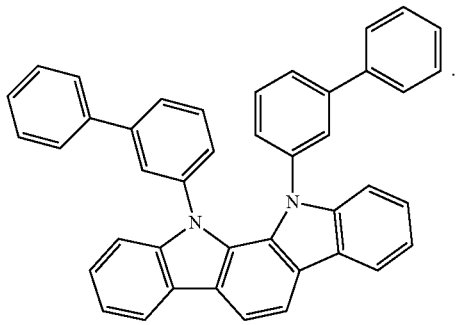

The compound has relatively strong hole characteristics and thus may increase charge mobility and stability and remarkably improve luminance efficiency and life-span characteristics, when used with the compound represented by Chemical Formula I for a emission layer. In addition, the charge mobility may be adjusted by controlling a ratio between the compound having hole characteristics and the compound represented by Chemical Formula I.

The compound may have hole characteristics relatively determined through relationship with the compound represented by Chemical Formula I, and include a substituent having weak electron characteristics such as a substituted or unsubstituted pyridinyl group in one of $R^{11}$ to $R^{14}$ and $Ar^1$ of Chemical Formula II.

The aforementioned first and second hosts may be used in various ratios to prepare various compositions. For example, the first host and the second host may be used in a weight ratio ranging from 1:99 to 99:1, for example, 10:90 to 90:10. For example, the weight ratio may be 2:8 to 8:2, 3:7 to 7:3, 4:6 to 6:4, and 5:5. When the first and second hosts satisfy the weight ratio range, electron transport characteristics by the first host and hole transport characteristics by the second host may be balanced and thus improve luminance efficiency and life-span of an organic light emitting diode.

For example, the composition may be used as a light-emitting material for an organic optoelectric device. Herein, the light-emitting material may be the organic compound as a host, and may further include at least one dopant. The dopant may be a red, green, or blue dopant.

In addition, the electron transport auxiliary layer on the blue emission layer may include the compound for an organic optoelectric device represented by Chemical Formula I.

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The dopant may be a phosphorescent dopant, and examples of the phosphorescent dopant may be an organic metal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

L$_2$MX                                   [Chemical Formula Z]

In Chemical Formula Z, M is a metal, and L and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or a combination thereof, and the L and X may be, for example a bidendate ligand.

A thickness of the emission layer may be about 100 Å to about 1000 Å, for example about 200 Å to about 600 Å. When the thickness of the emission layer is within these ranges, the emission layer may have improved emission characteristics without a substantial increase in a driving voltage.

Next, an electron transport region is disposed on the emission layer.

The electron transport region may include at least one of a hole blocking layer, an electron transport layer, and an electron injection layer.

For example, the electron transport region may have a structure of a hole blocking layer/electron transport layer/electron injection layer or electron transport layer/electron injection layer, but is not limited thereto. For example, an organic light emitting diode according to an embodiment of the present invention includes at least two electron transport layers in the electron transport region, and in this case, an electron transport layer contacting the emission layer is defined as an electron transport auxiliary layer 35.

The electron transport layer may have a monolayer or multi-layer structure including two or more different materials.

The electron transport region may include the compound for an organic optoelectric device represented by Chemical Formula I. For example, the electron transport region may include an electron transport layer, and the electron transport layer may include the compound for an organic optoelectric device represented by Chemical Formula I. More specifically, the electron transport auxiliary layer may include the compound for an organic optoelectric device represented by Chemical Formula I.

The formation conditions of the hole blocking layer, electron transport layer, and electron injection layer of the electron transport region refers to the formation condition of the hole injection layer.

When the electron transport region includes the hole blocking layer, the hole blocking layer may include at least one of BCP, Bphen, and BAlq, but is not limited thereto.

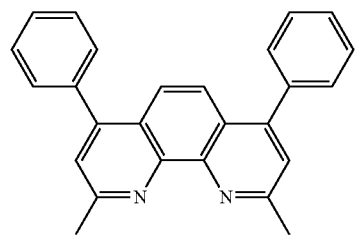

BCP

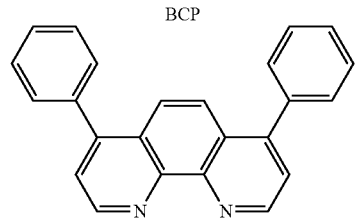

Bphen

The thickness of the hole blocking layer may be from about 20 Å to about 1000 Å, for example about 30 Å to about 300 Å. When the thickness of the hole blocking layer is within these ranges, the hole blocking layer may have improved hole blocking ability without a substantial increase in driving voltage.

The electron transport layer may further include at least one of the BCP, Bphen and the following Alq₃, Balq, TAZ and NTAZ.

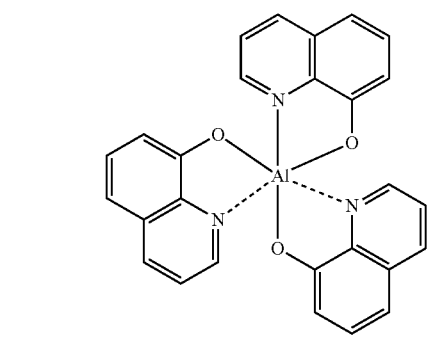

Alq₃

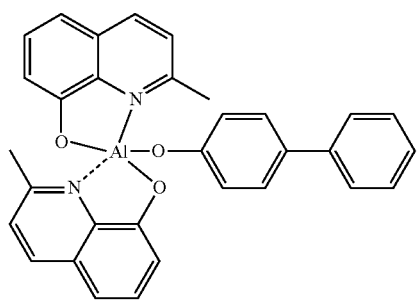

Balq

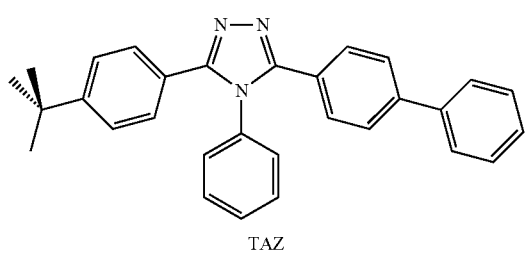

TAZ

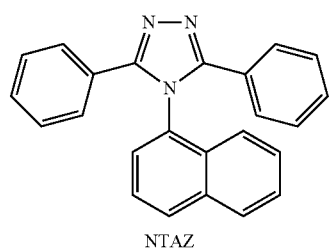

NTAZ

Or, the electron transport layer may include at least one of the following compounds ET1 and ET2, but is not limited thereto.

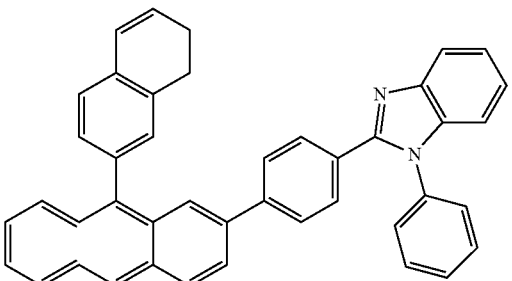

ET1

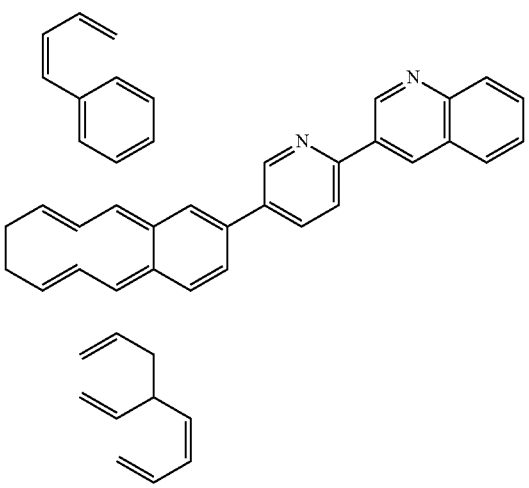

ET2

A thickness of the electron transport layer may be about 100 Å to about 1000 Å, for example about 150 Å to about 500 Å. When the thickness of the electron transport layer is within these ranges, the electron transport layer may have satisfactory electron transporting ability without a substantial increase in driving voltage.

The electron transport layer may further include a metal-containing material, in addition to the above-described materials.

The metal-containing material may include a lithium (Li) complex. The Li complex may include, for example, the following compound ET-D1 (lithium quinolate, LiQ) or ET-D2.

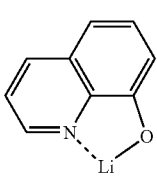

ET-D1

ET-D2

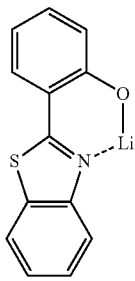

In addition, the electron transport region may include an electron injection layer (EIL) that may facilitate injection of electrons from the cathode 110.

The electron injection layer 36 is disposed on an electron transport layer and may play a role of facilitating an electron injection from a cathode and ultimately improving power efficiency and be formed by using any material used in a related art without a particular limit, for example, LiF, Liq, NaCl, CsF, Li$_2$O, BaO, and the like.

The electron injection layer may include at least one selected from LiF, NaCl, CsF, Li$_2$O, and BaO.

A thickness of the EIL may be from about 1 Å to about 100 Å, or about 3 Å to about 90 Å. When the thickness of the electron injection layer is within these ranges, the electron injection layer may have satisfactory electron injection ability without a substantial increase in driving voltage.

The cathode 110 is disposed on the organic layer 105. A material for the cathode 110 may be a metal, an alloy, or an electrically conductive compound that have a low work function, or a combination thereof. Specific examples of the material for the cathode 110 may be lithium (Li), magnesium (Mg), aluminum (Al), aluminum-lithium (Al—Li), calcium (Ca), magnesium-indium (Mg—In), magnesium-silver (Mg—Ag), etc. In order to manufacture a top-emission light-emitting device, the cathode 110 may be formed as a transmissive electrode from, for example, indium tin oxide (ITO) or indium zinc oxide (IZO).

[Mode for Invention]

Hereinafter, the embodiments are illustrated in more detail with reference to examples. However, the present disclosure is not limited to the following examples.

Synthesis of Compound for Organic Optoelectric Device

Hereinafter, a compound and an organic light emitting device according to an embodiment of the present invention are specifically illustrated referring to Synthesis Examples and Examples, but the present invention is not limited to the following Synthesis Examples and Examples. In the following Synthesis Examples, when "'B' is used instead of 'A'", the amounts of 'A' and 'B' are the same as based on a mole equivalent.

Hereinafter, a starting material and a reaction material used in Examples and Synthesis Examples may commercially be available from Sigma-Aldrich Co. Ltd. TCI Inc. or AAA Chemistry or may be synthesized referring to reference (J. Org. Chem. 40, 3514-3518 1975) unless there is particularly mentioned.

As specific examples of the compound for an organic optoelectric device of the present invention, the compound of Chemical Formula I is synthesized by the following reaction schemes.

(First Host)

Synthesis Example 1: Synthesis of Compound 1

[Reaction Scheme 1]

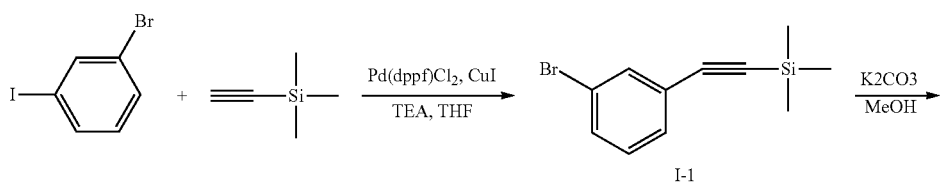

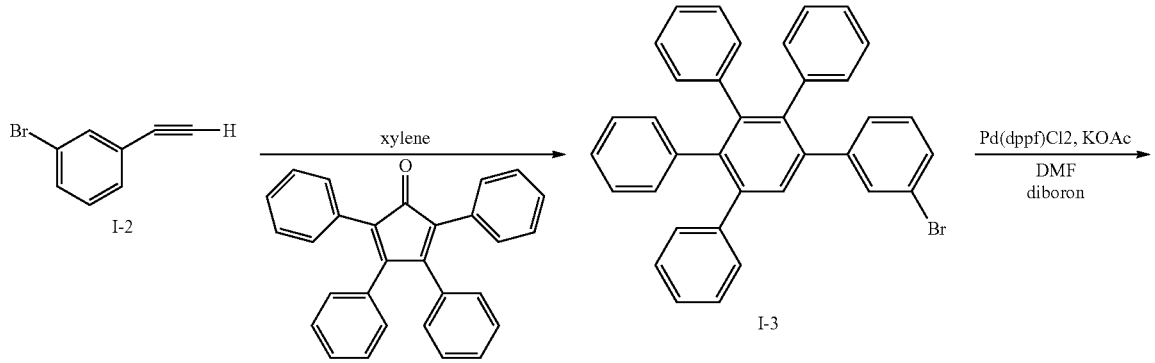

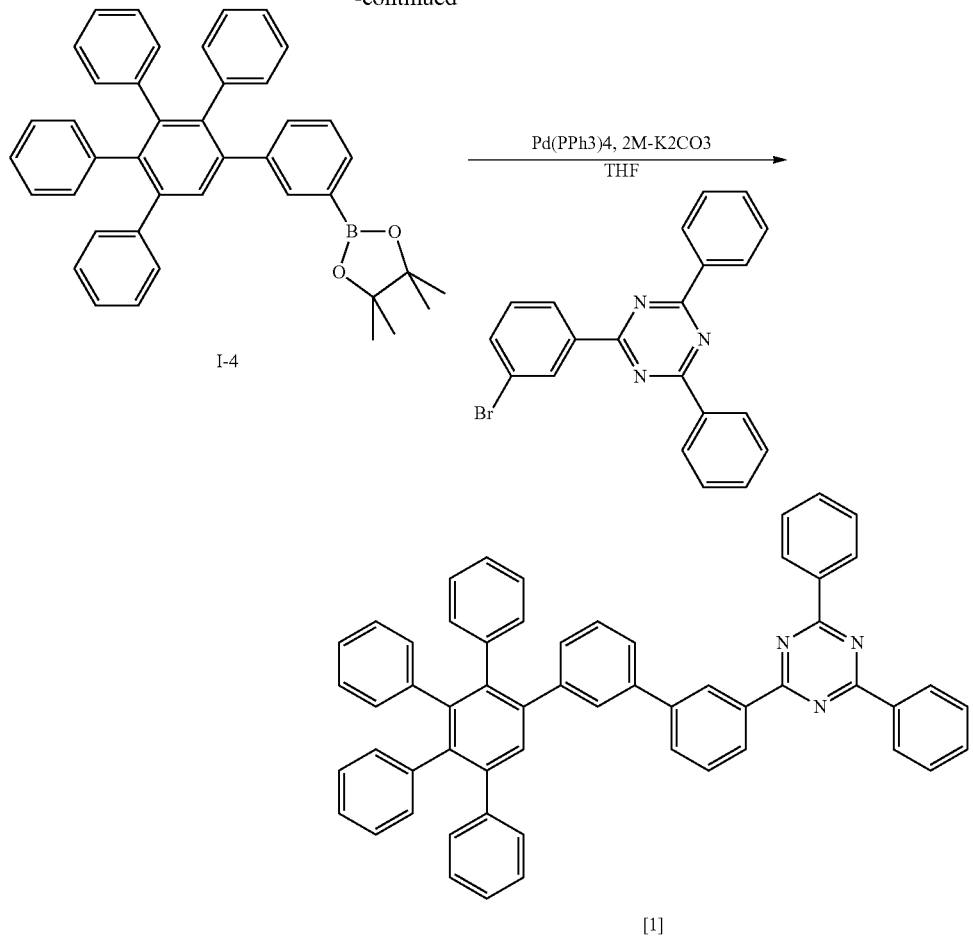

First Step: Synthesis of Intermediate I-1

1-bromo-3-iodobenzene (60.7 g, 214.5 mmol), (1,1'-bis(diphenylphosphine)ferrocene)dichloropalladium (II) (7.8 g, 10.7 mmol), copper iodide (1.22 g, 6.43 mmol), triethylamine (86.8 g, 858 mmol), and tetrahydrofuran (800 mL) were put in a 2 L round-bottomed flask under a nitrogen environment. Trimethyl silylacetylene (23.6 g, 40.2 mmol) is added thereto in a dropwise fashion, and the mixture is stirred at room temperature for 3 hours. The reactant is filtered, and a solvent is removed therefrom. Then, a compound therein is purified through column chromatography, obtaining 52 g of an intermediate I-1 (96%).

Second Step: Synthesis of Intermediate I-2

The intermediate I-1 (52 g, 205.36 mmol) is added to and dissolved in methanol (400 mL) in a reactor, and potassium carbonate (28.4 g, 205.36 mmol) is slowly added in a dropwise fashion. The mixture is stirred for 30 minutes and filtered. The solvent is completely removed therefrom, the reactant is dissolved in ethylacetate, and the solution is two to three times washed with distilled water. The solvent is removed, obtaining 37 g of an intermediate I-2 (100%).

Third Step: Synthesis of Intermediate I-3

The intermediate I-2 (20 g, 114.44 mmol) and tetraphenylcyclopentadione (40 g, 104.04 mmol) were dissolved in 100 mL of xylene, and the solution was heated and refluxed for 3 hours. The reactant was poured into methanol (500 mL), completing a reaction. Then, a solid therein was filtered, obtaining 40 g of an intermediate I-3 (72%).

Fourth Step: Synthesis of Intermediate I-4

The intermediate I-3 (32.5 g, 60.47 mmol) was dissolved in 300 ml of dimethyl formamide (DMF) under a nitrogen environment, bis(pinacolato)diboron (18.4 g, 72.56 mmol), (1,1'-bis(diphenylphosphine)ferrocene)dichloropalladium (II) (2.96 g, 3.63 mmol), and potassium acetate (17.8 g, 181.4 mmol) were added thereto, and the mixture was heated and refluxed at 150° C. for 48 hours. When the reaction was complete, water was added to the reaction, and the mixture was filtered and dried in a vacuum oven. The obtained residue was separated and purified through column chromatography, obtaining 15 g of an intermediate I-4 (42%).

Fifth Step: Synthesis of Compound 1

The intermediate I-4 (27 g, 46.43 mmol) and 2-(3-bromophenyl)-4,6-diphenyl-1,3,5-triazine (17.56 g, 45.07 mmol) were dissolved in 250 mL of tetrahydrofuran under a nitrogen environment, tetrakis(triphenylphosphine)palladium (2.6 g, 2.25 mmol) was added thereto, and the mixture was stirred. Then, potassium carbonate saturated in water (15.57 g, 112.68 mmol) was added thereto, and the mixture was heated and refluxed at 80° C. for 24 hours. When the reaction was complete, water was added to the reaction solution, dichloromethane was used to perform an extraction, an anhydrous $MgSO_4$ was used to remove moisture therefrom, and a resultant therefrom was filtered and concentrated under a reduced pressure. This obtained residue was separated and purified through column chromatography, obtaining 25 g of the compound 1 (72%).

LC Mass (theoretical value: 765.94 g/mol, measured value: M+H⁺=766.91 g/mol)
Synthesis Example 2: Synthesis of Compound 3
First Step: Synthesis of Intermediate I-5
13 g of an intermediate I-5 (61%) was obtained in the same synthesis method as the synthesis method of the compound 1 by using the intermediate I-4 (20.4 g, 34.92
[Reaction Scheme 2]
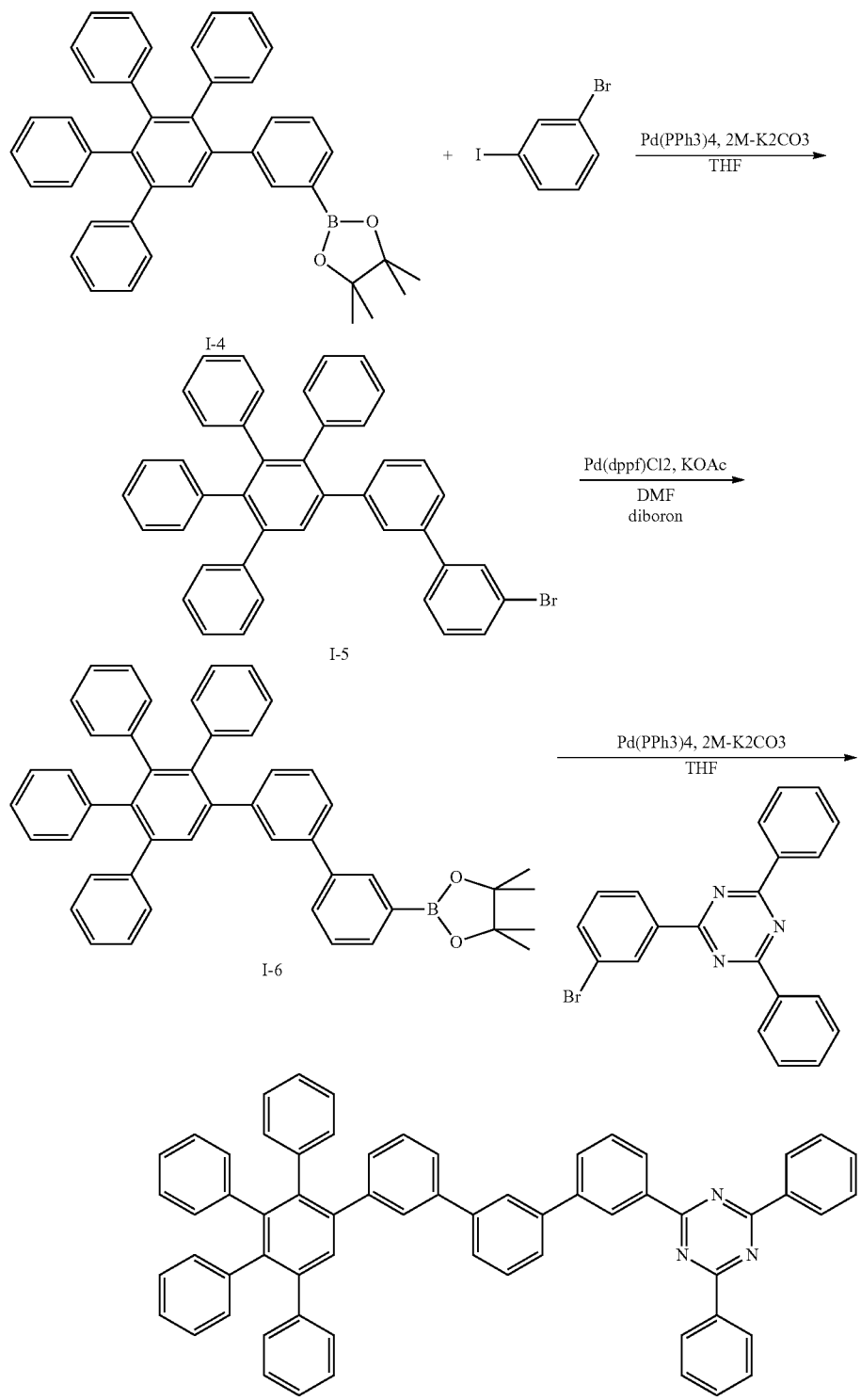

mmol) and 1-bromo-3-iodobenzene (16.5 g, 52.39 mmol) under a nitrogen environment.

Second Step: Synthesis of Intermediate I-6

10 g of an intermediate I-6 (74%) was obtained in the same synthesis method as the synthesis method of the intermediate I-4 by using the intermediate I-5 (12.6 g, 20.54 mmol) under a nitrogen environment.

Third Step: Synthesis of Compound 3

8.7 g of a compound 3 (68%) was obtained in the same synthesis method as the synthesis method of the compound 1 by using the intermediate I-6 (10 g, 15.2 mmol) and 2-(3-bromophenyl)-4,6-diphenyl-1,3,5-triazine (7.9 g, 18.32 mmol) under a nitrogen environment.

LC Mass (theoretical value: 842.04 g/mol, measured value: M+H$^+$=843.03 g/mol)

Synthesis Example 3: Synthesis of Compound 2

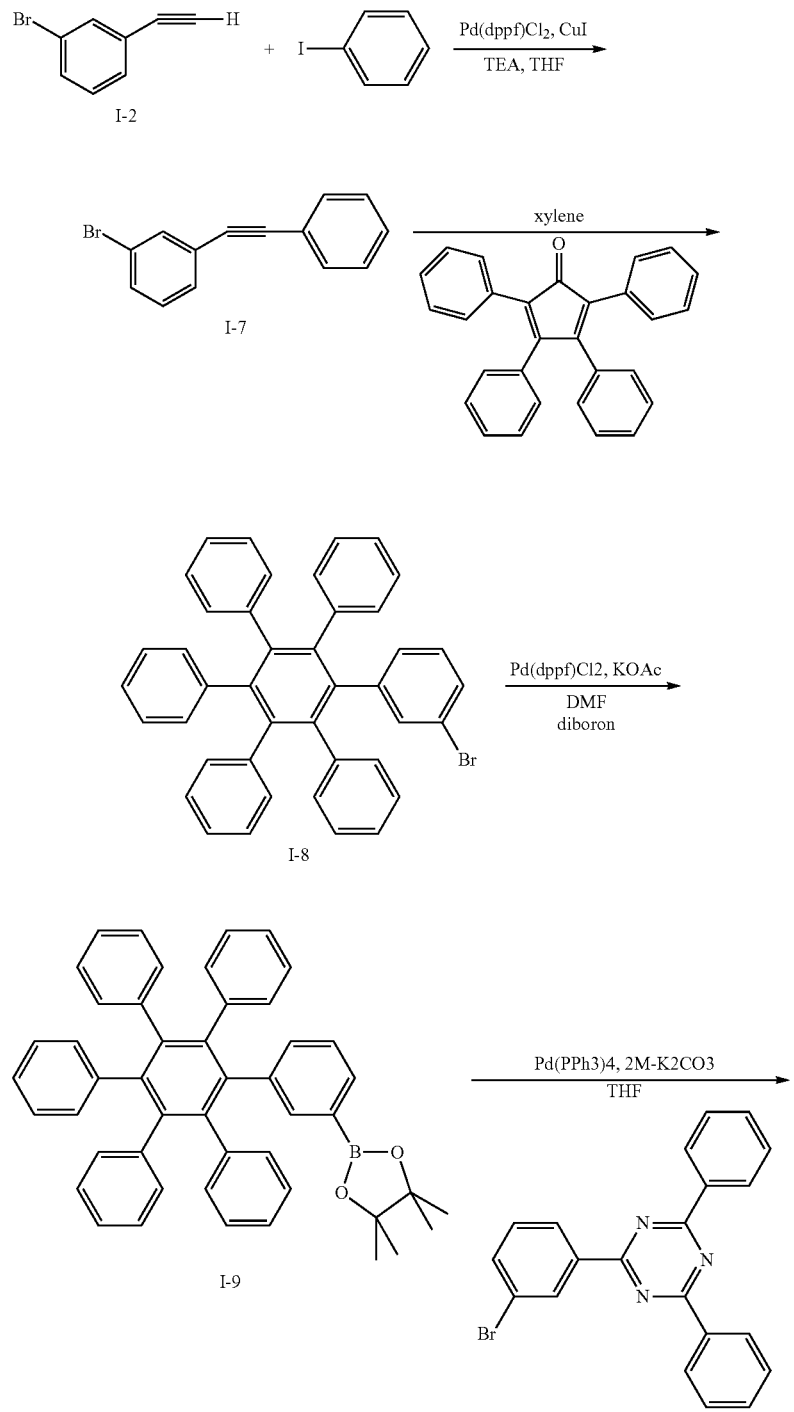

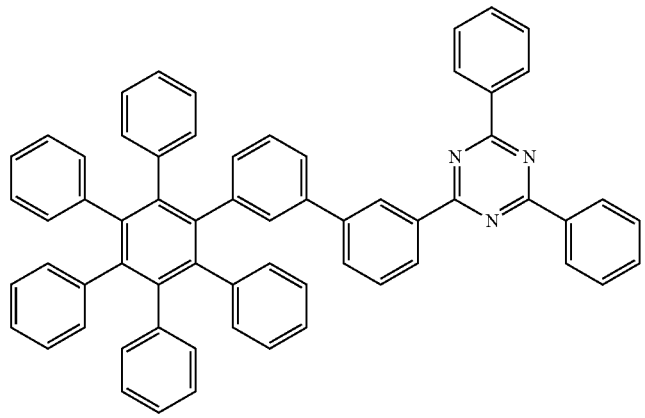

[2]

First Step: Synthesis of Intermediate I-7

20 g of an intermediate I-7 (79%) was obtained in the same synthesis method as the synthesis method of the intermediate I-1 by using the intermediate I-2 (20 g, 109.8 mmol) and iodobenzene (20 g, 98.03 mmol) under a nitrogen environment.

Second Step: Synthesis of Intermediate I-8

31 g of an intermediate I-8 (74%) was obtained in the same synthesis method as the synthesis method of the intermediate I-3 by using the intermediate I-7 (15.5 g, 85.83 mmol) and tetraphenylcyclopentadione (30 g, 78.03 mmol) under a nitrogen environment.

Third Step: Synthesis of Intermediate I-9

16 g of an intermediate I-9 (75%) was obtained in the same synthesis method as the synthesis method of the intermediate I-4 by using the intermediate I-8 (19.9 g, 32.44 mmol) under a nitrogen environment.

Fourth Step: Synthesis of Compound 2

14 g of a compound 2 (75%) was obtained in the same synthesis method as the synthesis method of the compound 1 by using the intermediate I-9 (14.6 g, 22.06 mmol) and 2-(3-bromophenyl)-4,6-diphenyl-1,3,5-triazine (11.4 g, 26.47 mmol) under a nitrogen environment.

LC Mass (theoretical value: 842.04 g/mol, measured value: M+H$^+$=843.02 g/mol)

Synthesis Example 4: Synthesis of Compound 7

[Reaction Scheme 4]

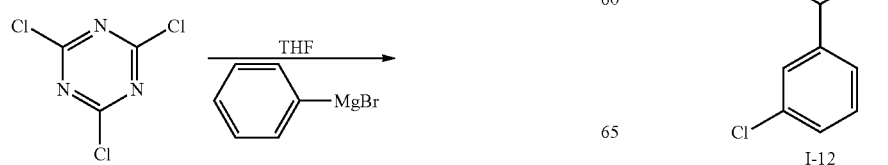

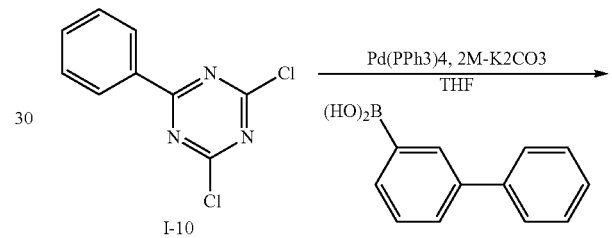

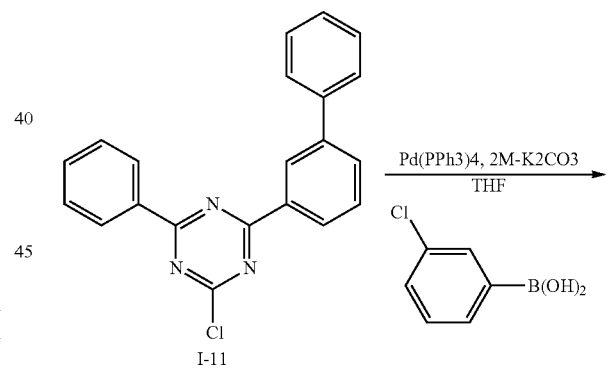

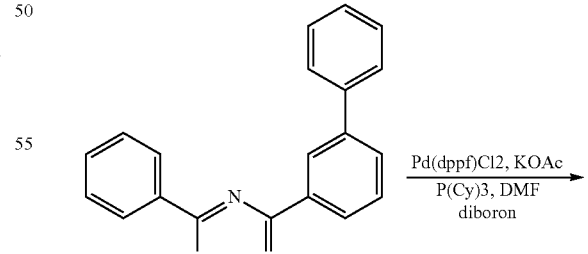

-continued

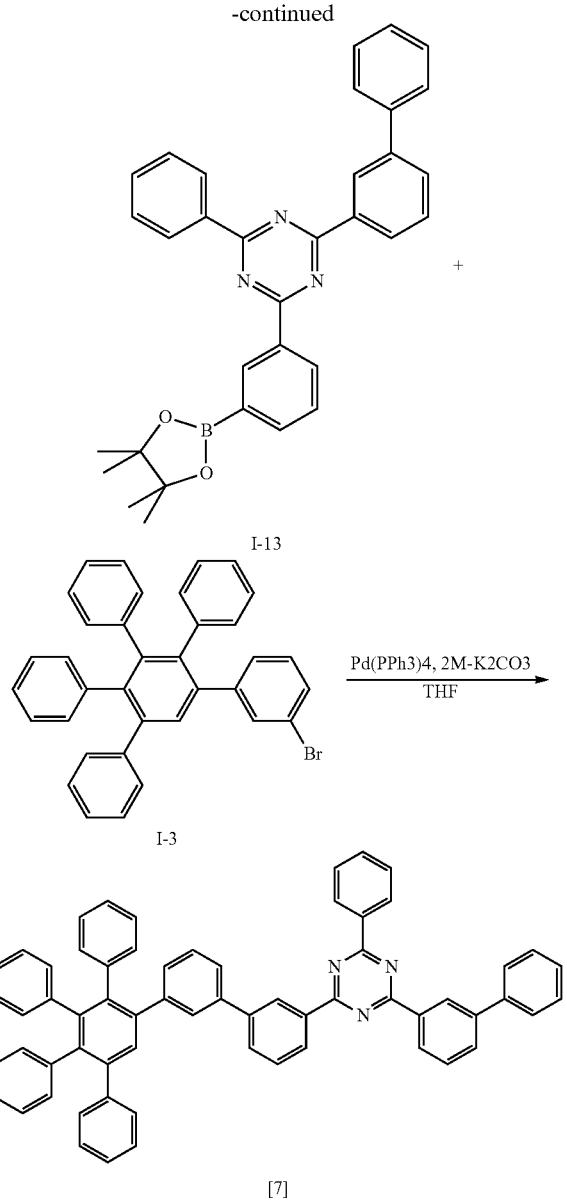

First Step: Synthesis of Intermediate I-10

Cyanuric chloride (35 g, 189.58 mmol) was dissolved in anhydrous tetrahydrofuran (750 mL) under a nitrogen environment, and then, the reaction temperature was decreased down to less than or equal to −60° C. by using dry ice and acetone. Then, a phenyl magnesium bromide (a 1M solution in THF) (199 mL, 199.06 mmol) solution was slowly added thereto in a dropwise fashion. The reaction temperature was increased up to room temperature, and the reactant was stirred for 5 hours. The reactant was poured into water to complete the reaction, and the resultant was recrystallized by using dichloromethane and hexane after removing a solvent therefrom, obtaining 33 g of an intermediate I-10 (77%).

Second Step: Synthesis of Intermediate I-11

25 g of an intermediate I-11 (58%) was obtained according to the same method as the synthesis method of the compound 1 by using the intermediate I-10 (28.2 g, 124.65 mmol) and 3-biphenylboronic acid (30.2 g, 137.12 mmol) under a nitrogen environment.

Third Step: Synthesis of Intermediate I-12

25 g of an intermediate I-12 (88%) was obtained according to the same method as the synthesis method of the compound 1 by using the intermediate I-11 (23.4 g, 68.04 mmol) and 3-chlorophenylboronic acid (13 g, 74.85 mmol) under a nitrogen environment.

Fourth Step: Synthesis of Intermediate I-13

21 g of an intermediate I-13 (74%) was obtained according to the same method as the synthesis method of the intermediate I-4 by using the intermediate I-12 (23.5 g, 55.87 mmol) under a nitrogen environment.

Fifth Step: Synthesis of Compound 7

16 g of a compound 7 (75%) was obtained according to the same method as the synthesis method of the compound 1 by using the intermediate I-13 (13 g, 25.45 mmol) and the intermediate I-3 (16.7 g, 27.99 mmol) under a nitrogen environment.

LC Mass (theoretical value: 842.04 g/mol, measured value: M+H$^+$=843.03 g/mol)

Synthesis Example 5: Synthesis of Compound 13

[Reaction Scheme 5]

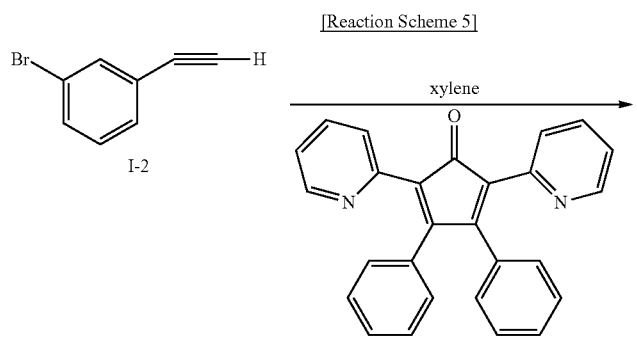

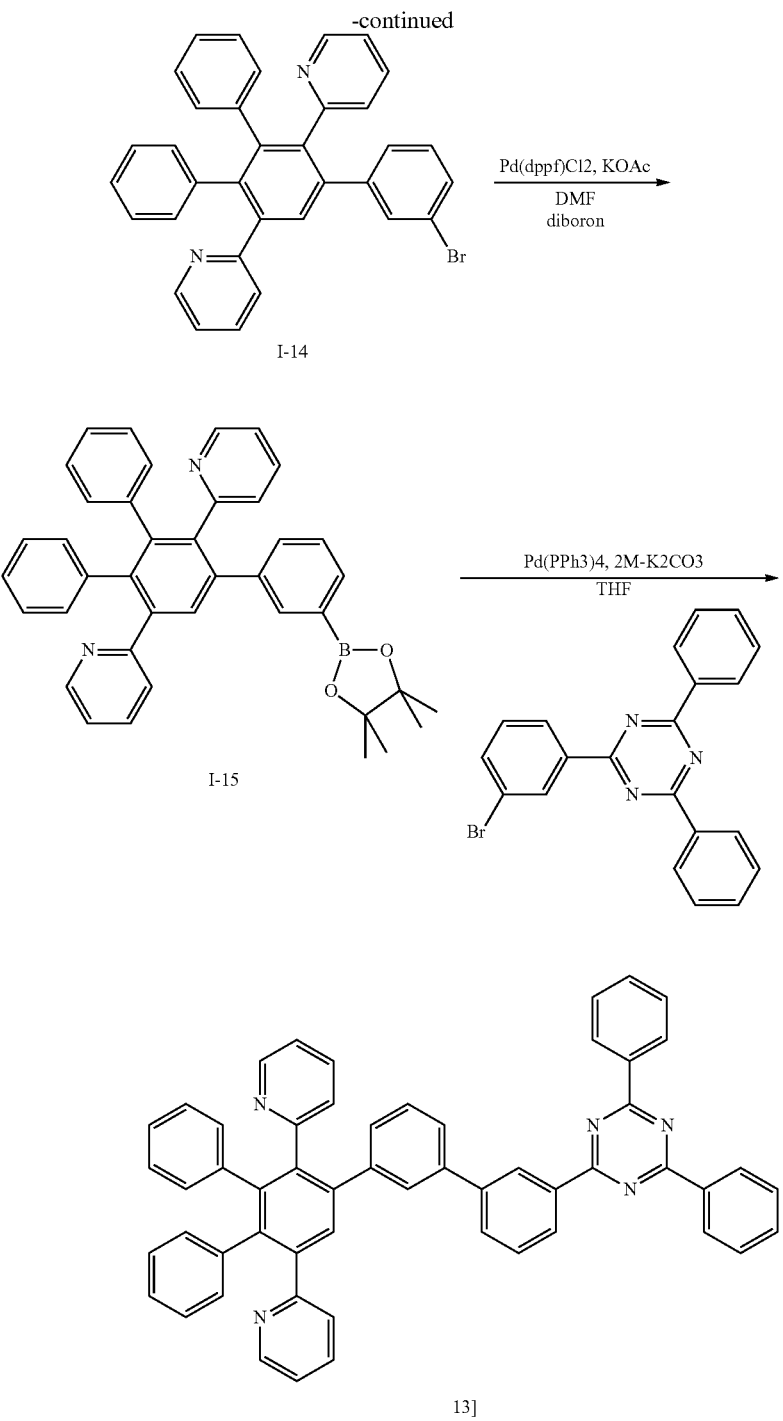

First Step: Synthesis of Intermediate I-14

16 g of an intermediate I-14 (57%) was obtained according to the same method as the synthesis method of the intermediate I-3 by using the intermediate I-2 (10.3 g, 56.93 mmol) and 3,4-diphenyl-2,5-(2-pyridyl)cyclopentadione (J. Org. Chem. 40, 3514-3518, 1975) (20 g, 51.75 mmol) under a nitrogen environment.

Second Step: Synthesis of Intermediate I-15

12.5 g of an intermediate I-15 (73%) was obtained according to the same method as the synthesis method of the intermediate I-4 by using the intermediate I-14 (15.8 g, 29.23 mmol) under a nitrogen environment.

Third Step: Synthesis of Compound 13

10 g of a compound 13 (64%) was obtained according to the same method as the synthesis method of the compound 1 by using the intermediate I-15 (12 g, 20.46 mmol) and 2-(3-bromophenyl)-4,6-diphenyl-1,3,5-triazine (9.7 g, 22.51 mmol) under a nitrogen environment.

LC Mass (theoretical value: 767.92 g/mol, measured value: M+H$^+$=768.91 g/mol)

Synthesis Example 6: Synthesis of Compound 31

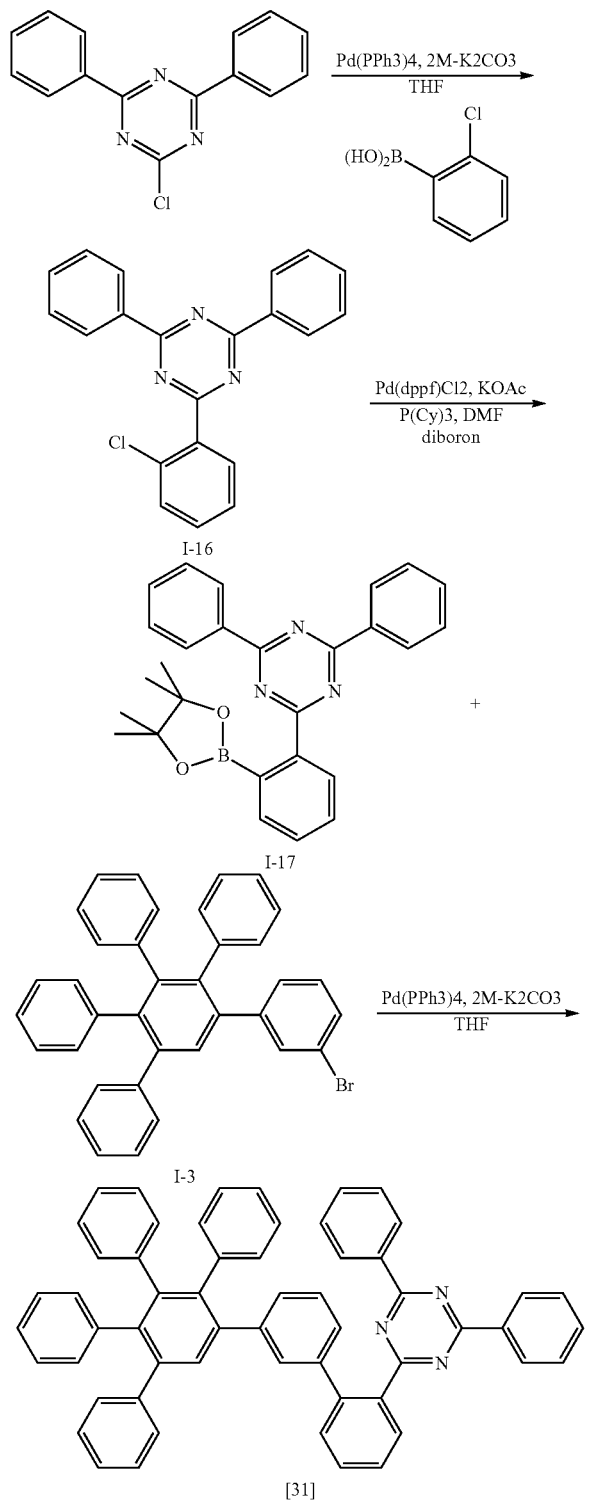

First Step: Synthesis of Intermediate I-16

33 g of an intermediate I-16 (77%) was obtained according to the same method as the synthesis method of the compound 1 by using 2-chloro 4,6-diphenyl-1,3,5-triazine (33.4 g, 124.65 mmol) and 2-chlorophenylboronic acid (26 g, 149.58 mmol) under a nitrogen environment.

Second Step: Synthesis of Intermediate I-17

25 g of an intermediate I-17 (63%) was obtained according to the same method as the synthesis method of the intermediate I-4 by using the intermediate I-16 (31.6 g, 91.88 mmol) and additionally, tricyclohexylphosphine (2.58 g, 9.19 mmol) under a nitrogen environment.

Third Step: Synthesis of Compound 31

13 g of a compound 31 (61%) was obtained according to the same method as the synthesis method of the compound 1 by using the intermediate I-17 (12.2 g, 27.98 mmol) and intermediate I-3 (18.4 g, 30.77 mmol) under a nitrogen environment.

LC Mass (theoretical value: 765.94 g/mol, measured value: M+H$^+$=766.92 g/mol)

Synthesis Example 7: Synthesis of Compound 55

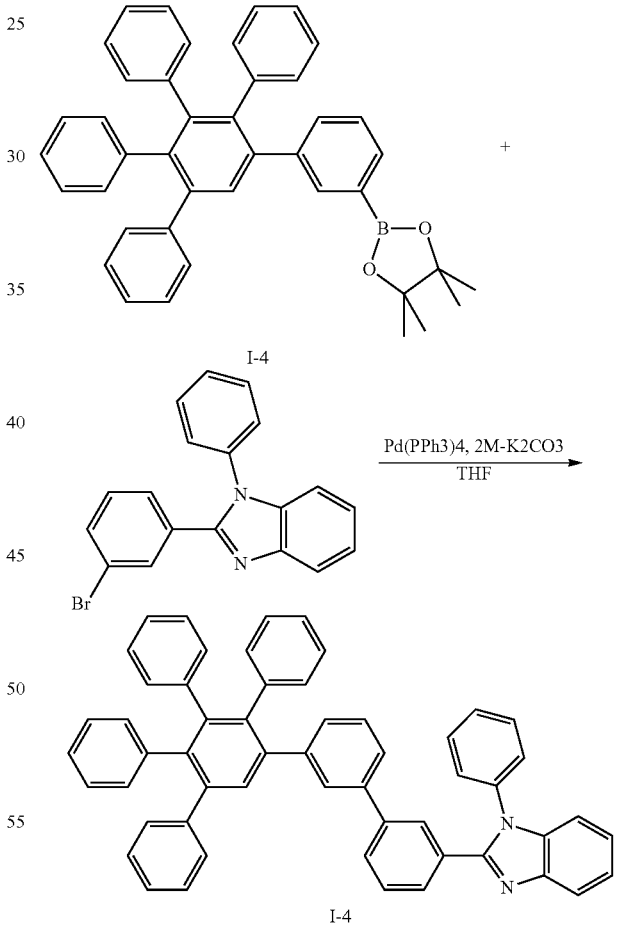

16 g of a compound 55 (75%) was obtained according to the same method as the synthesis method of the compound 1 by using the intermediate I-4 (17.3 g, 29.48 mmol) and 2-(3-bromophenyl)-1-phenyl-1H-benzimidazole (12.6 g, 32.43 mmol) under a nitrogen environment.

LC Mass (theoretical value: 726.90 g/mol, measured value: M+H$^+$=727.88 g/mol)

(Second Host)

Synthesis Example 8: Synthesis of Compound C-1

[Reaction Scheme 8]

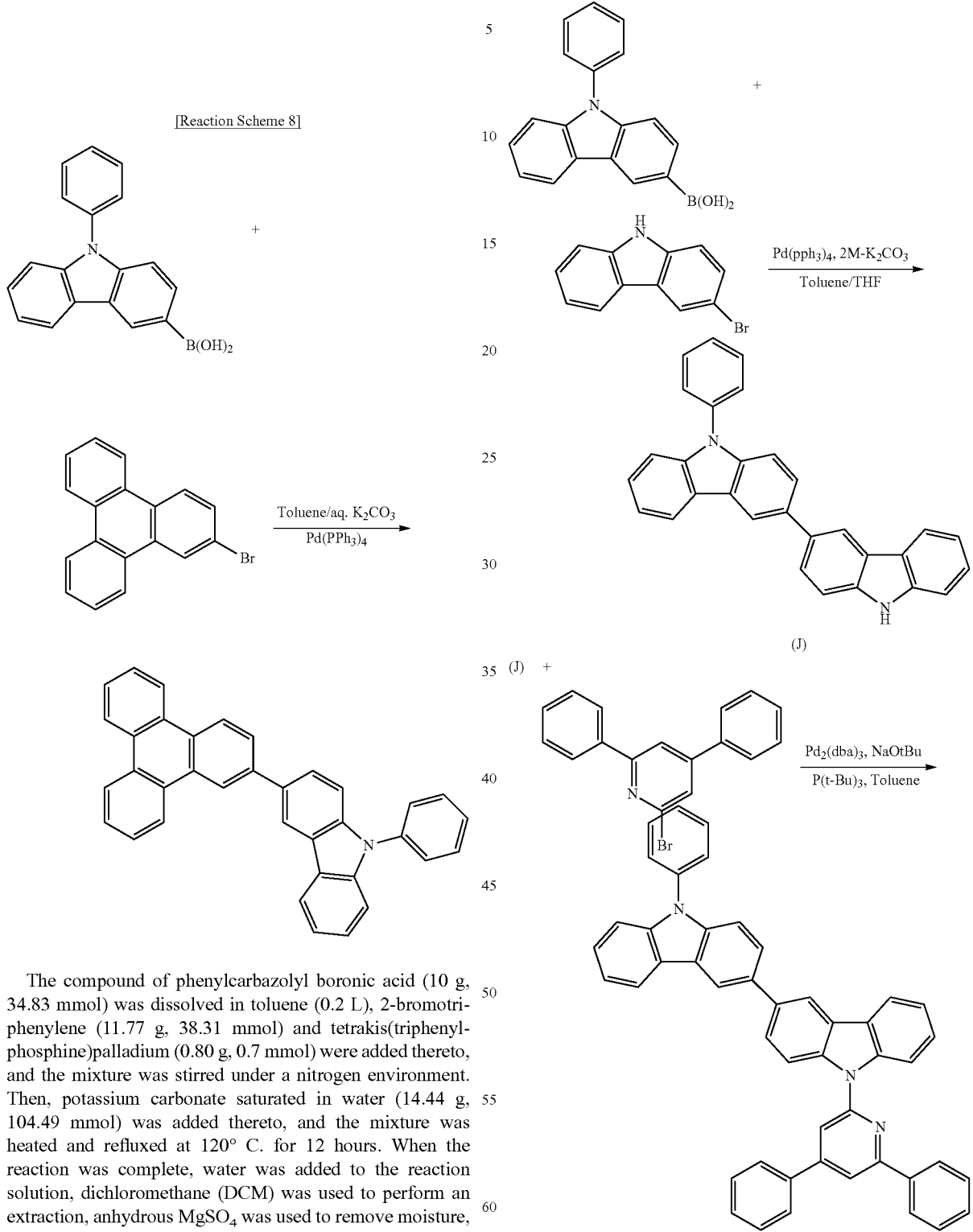

The compound of phenylcarbazolyl boronic acid (10 g, 34.83 mmol) was dissolved in toluene (0.2 L), 2-bromotriphenylene (11.77 g, 38.31 mmol) and tetrakis(triphenylphosphine)palladium (0.80 g, 0.7 mmol) were added thereto, and the mixture was stirred under a nitrogen environment. Then, potassium carbonate saturated in water (14.44 g, 104.49 mmol) was added thereto, and the mixture was heated and refluxed at 120° C. for 12 hours. When the reaction was complete, water was added to the reaction solution, dichloromethane (DCM) was used to perform an extraction, anhydrous $MgSO_4$ was used to remove moisture, and a resultant therefrom was filtered and concentrated under a reduced pressure. The obtained residue was separated and purified through flash column chromatography, obtaining the compound C-1 (14.4 g, 88%).

LC Mass (theoretical value: 469.57 g/mol, measured value: $M+H^+$=470.55 g/mol)

Synthesis Example 9: Synthesis of Compound B-1

[Reaction Scheme 9]

First Step: Synthesis of Compound J 10 g (34.83 mmol) of 9-phenyl-9H-carbazole-3-yl boronic acid (-TCI), 11.77 g (38.31 mmol) of 3-bromocarbazole (Aldrich), 14.44 g (104.49 mmol) of potassium carbonate, and 0.80 g (0.7 mmol) of tetrakis-(triphenylphosphine)palladium (0) were suspended in 140 ml of toluene and 50 ml of distilled water and then, refluxed and stirred for 12 hours. Subsequently, dichloromethane and distilled water were used for an extraction, and an organic layer therein was silica gel-filtered. When the reaction was complete, a solid produced by pouring the reactant into methanol was filtered and dissolved again in chlorobenzene, activated carbon and anhydrous magnesium sulfate were added thereto, and the mixture was stirred. The solution was filtered, and a product obtained therefrom was recrystallized with chlorobenzene and methanol, obtaining a compound J (22.6 g, 68%).

Second Step: Synthesis of Compound B-1

22.42 g (54.88 mmol) of the compound J, 20.43 g (65.85 mmol) of 2-bromo-4,6-diphenylpyridine (the compound B), and 7.92 g (82.32 mmol) of tertiarybutoxysodium were dissolved in 400 ml of toluene, and 1.65 g (1.65 mmol) of palladium dibenzylideneamine and 1.78 g (4.39 mmol) of tertiarybutyl phosphorus were added thereto in a dropwise fashion. The reaction solution was heated and stirred under a nitrogen stream for 12 hours at 110° C. When the reaction was complete, a solid produced by pouring methanol into the reactant was filtered and dissolved in chlorobenzene again, activated carbon and anhydrous magnesium sulfate were added thereto, and the mixture was stirred. The solution was filtered, and chlorobenzene and methanol were used for recrystallization, obtaining a compound B-1 (28.10 g, 80%).

LC Mass (theoretical value: 637.77 g/mol, measured value: M+H⁺638.75 g/mol)

Synthesis Example 10: Synthesis of Compound B-31

[Reaction Scheme 10]

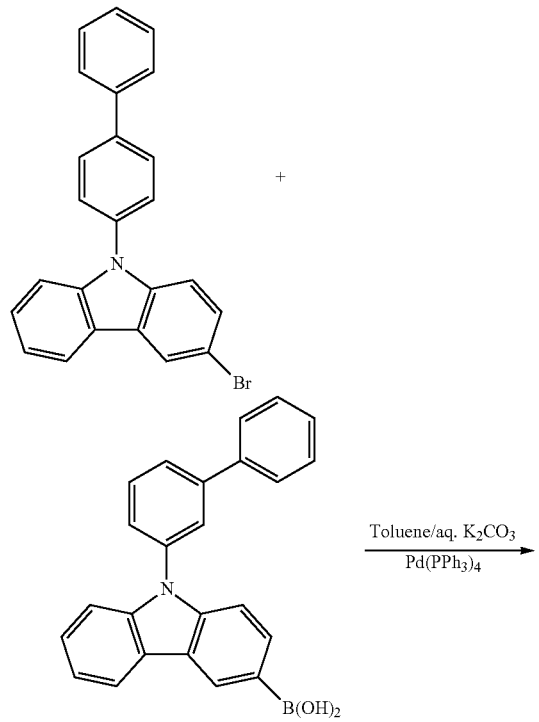

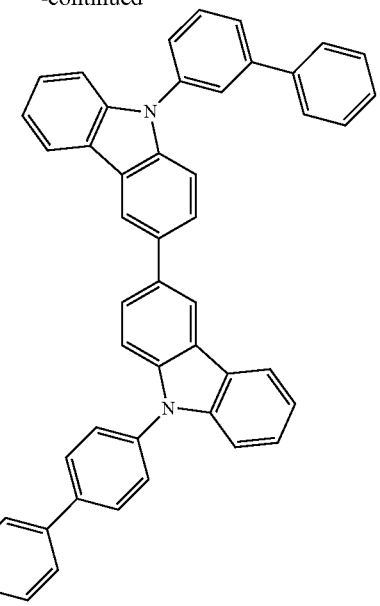

17.88 g (44.9 mmol) of 4-biphenylcarbazolyl bromide, 13 g (49.4 mmol) of 3-biphenylcarbazolyl boronic acid, 18.6 g (134.61 mmol) of potassium carbonate, and 1.55 g (1.35 mmol) of tetrakis-(triphenylphosphine)palladium (0) were suspended in 180 ml of toluene and 70 ml of distilled water and then, refluxed and stirred for 12 hours. Subsequently, dichloromethane and distilled water were used for an extraction, and an organic layer produced therein was silica gel-filtered. Subsequently, an organic solution was removed, and a solid product was recrystallized with dichloromethane and n-hexane, obtaining 21.3 g of a compound B-31 (a yield: 75%).

LC Mass (theoretical value: 636.78 g/mol, measured value: M+H⁺=637.77 g/mol)

Synthesis Example 11: Synthesis of Compound B-166

[Reaction Scheme 11]

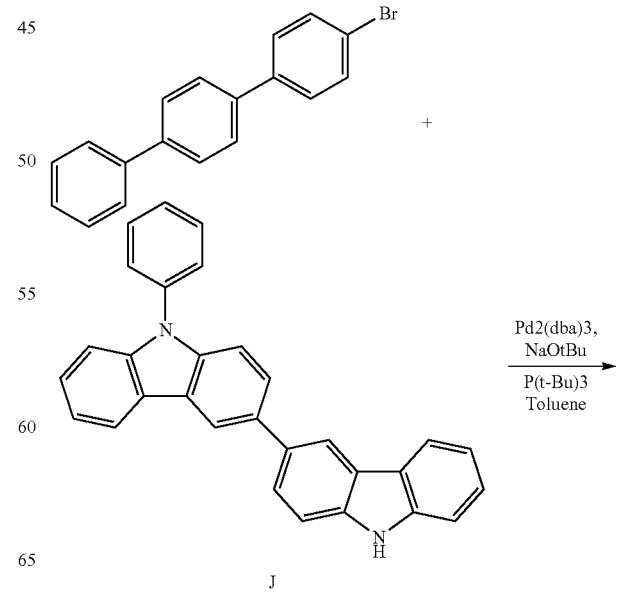

-continued
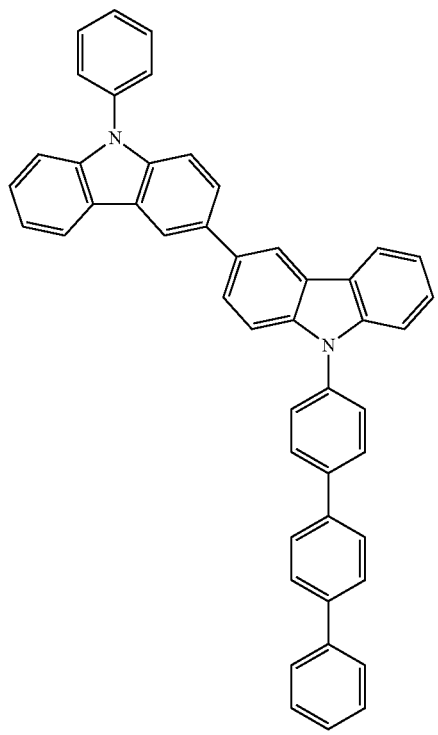
B-166
21.3 g of a compound B-166 (75%) was synthesized according to the same method as the synthesis method of the compound B-1 by using 15.26 g (49.36 mmol) of 4-bromo-1,1':4',1'-terphenyl and 18.3 g (44.87 mmol) of the intermediate (J) under a nitrogen environment.
LC Mass (theoretical value: 636.78 g/mol, measured value: M+H$^+$=637.76 g/mol)
Synthesis Example 12: Synthesis of Compound B-154
[Reaction Scheme 12]
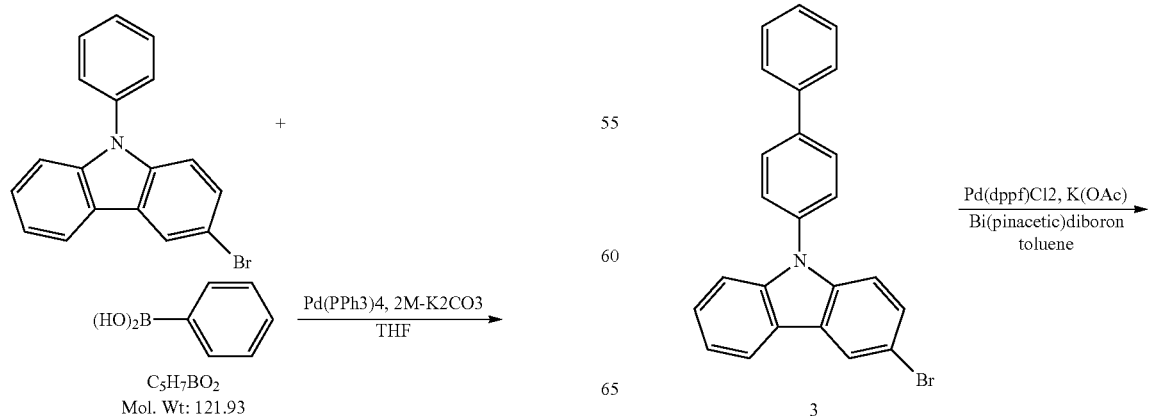
-continued
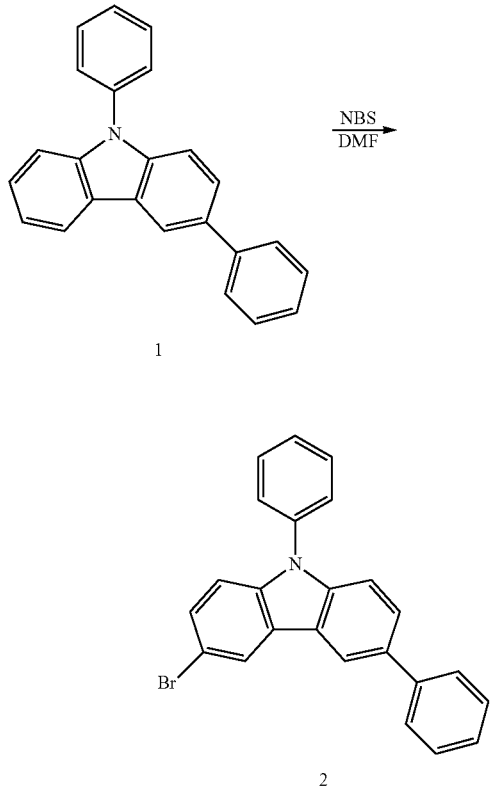

-continued

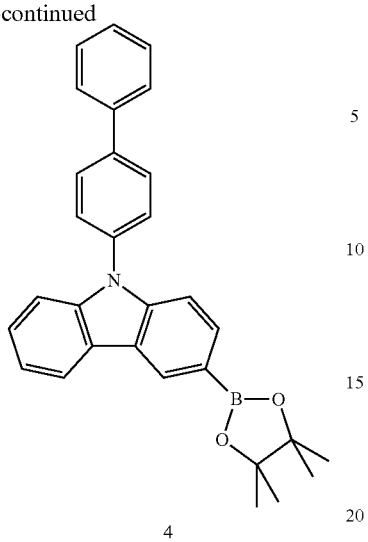
4

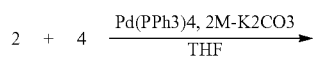

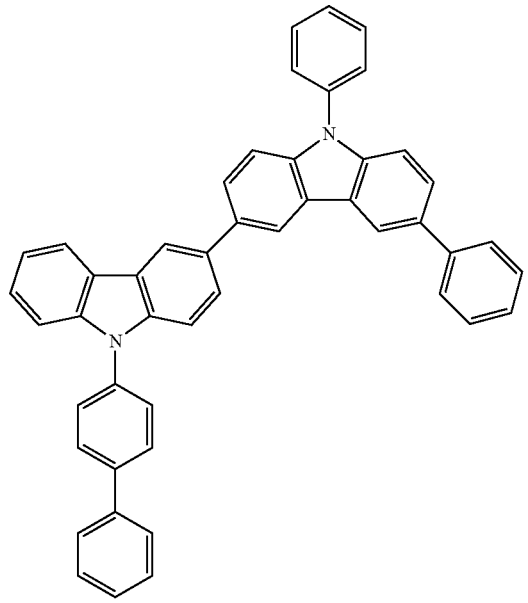
B-154

First Step: Synthesis of Intermediate 1

32 g of an intermediate 1 (75%) was synthesized according to the same method as the synthesis method of the intermediate J by using 43.2 g (134.2 mmol) of 3-bromo-N-phenyl carbazole and 18 g (147.6 mmol) of phenylboronic acid.

Second Step: Synthesis of Intermediate 2

35 g of an intermediate 2 (82%) was synthesized by dissolving 34.4 g (107.6 mmol) of the intermediate 1 in 500 mL of dichloromethane, adding 19.2 g (107.6 mmol) of N-bromosuccinimide thereto, and stirring the mixture at room temperature for 8 hours.

Third Step: Synthesis of Intermediate 3

15 g of an intermediate 3 (53%) was synthesized according to the same method as the synthesis method of the compound B-1 by using 17.65 g (71.74 mmol) of 3-bromo-carbazole and 22 g (78.91 mmol) of 4-Iodobiphenyl.

Fourth Step: Synthesis of Intermediate 4

20 g of an intermediate 4 (89%) was synthesized according to the same method as the synthesis method of the intermediate 1-4 by using 20.1 g (50.5 mmol) of the intermediate 3 and 19.2 g (75.8 mmol) of bis(pinacolato)diboron.

Fifth Step: Synthesis of Compound B-154

18 g of a compound B-154 (84%) was synthesized according to the same method as the synthesis method of the intermediate J by using 13 g (33.1 mmol) of the intermediate 2 and 16.2 g (36.4 mmol) of the intermediate 4.

LC Mass (theoretical value: 636.78 g/mol, measured value: M+H$^+$=637.77 g/mol)

Synthesis Example 13: Synthesis of Compound B-156

[Reaction Scheme 13]

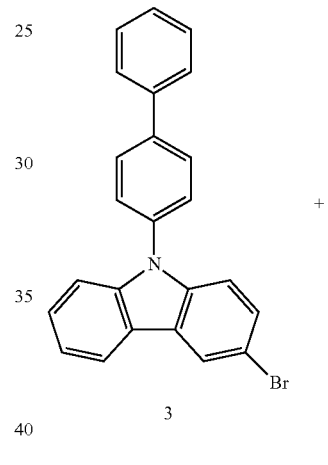
3

C$_5$H$_7$BO$_2$
Mol. Wt: 121.93

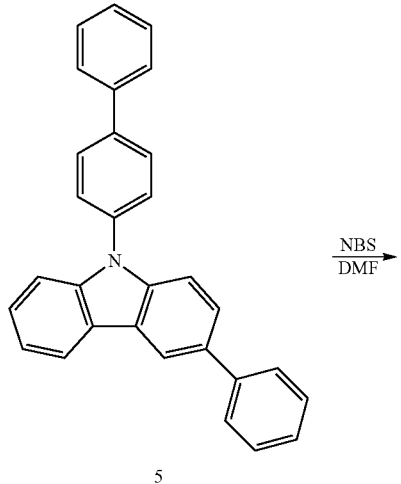
5

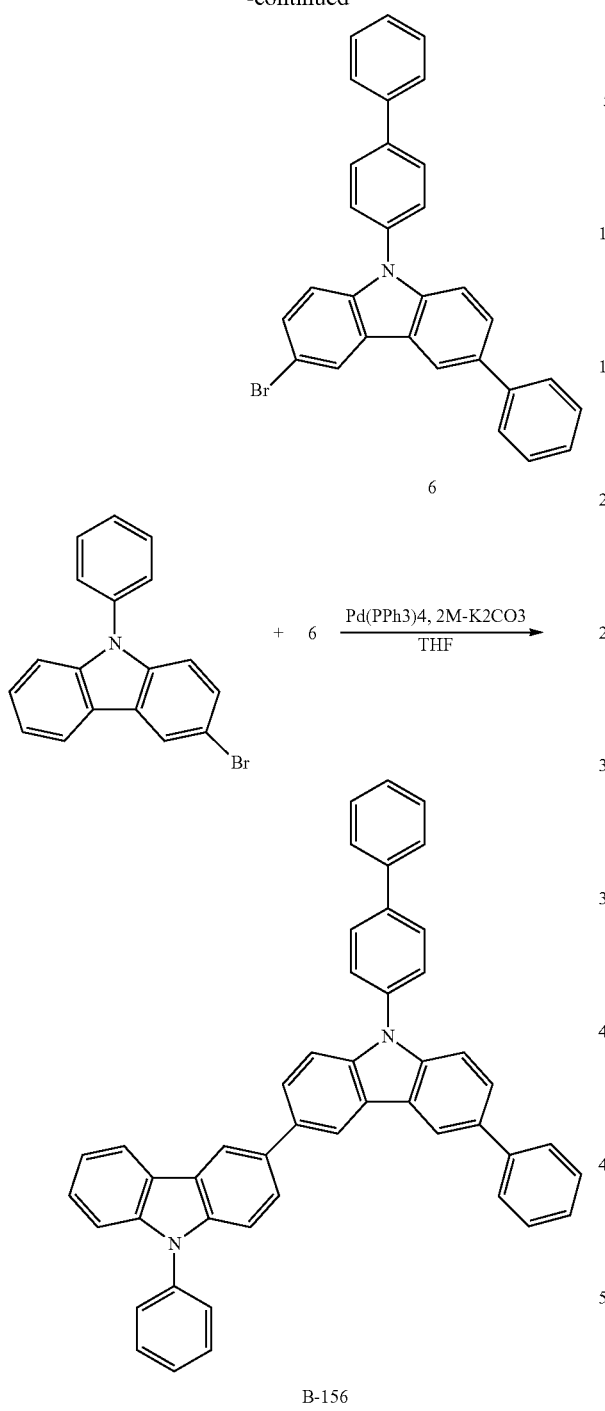

B-156

First Step: Synthesis of Intermediate 5

33 g of an intermediate 5 (77%) was synthesized according to the same method as the synthesis method of the intermediate J by using 43.2 g (108.4 mmol) of the intermediate 3 and 14.5 g (119 mmol) of phenylboronic acid.

Second Step: Synthesis of Intermediate 6

29 g of an intermediate 6 (81%) was synthesized according to the same method as the synthesis method of the intermediate 2 by using 29.8 g (75.28 mmol) of the intermediate 5 and 14 g (75.28 mmol) of N-bromosuccinimide.

Third Step: Synthesis of Compound B-156

17 g of a compound B-156 (79%) was synthesized according to the same method as the synthesis method of the intermediate J by using 9.7 g (33.65 mmol) of N-phenyl-carbazole-3-yl-boronic acid and 16 g (33.65 mmol) of the intermediate 6.

LC Mass (theoretical value: 636.78 g/mol, measured value: M+H$^+$=637.77 g/mol)

Synthesis Example 14: Synthesis of Compound E-1

[Reaction Scheme 14]

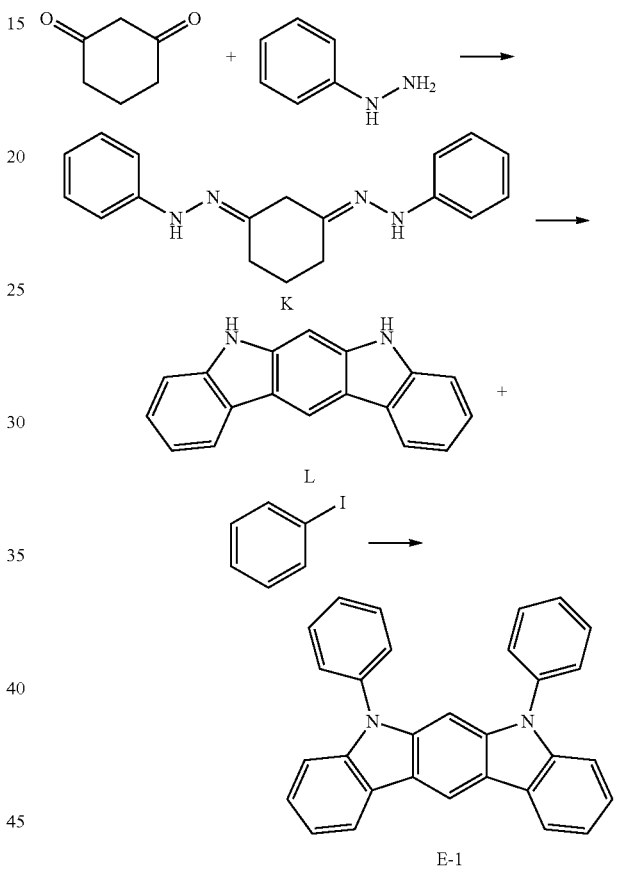

E-1

First Step: Synthesis of Compound K

Phenylhydrazine hydrochloride was dissolved in distilled water, and a 2 M NaOH aqueous solution was added thereto. Then, a solid produced therein was filtered, obtaining phenylhydrazine. The compound of cyclohexane-1,3-dione (30 g, 267.5 mmol) was dissolved in 1000 ml of ethanol under a nitrogen environment, phenylhydrazine was slowly added thereto, and the mixture was reacted for 20 minutes. When the reaction was complete, ice water was added thereto. Then, a solid produced therein was washed with ethanol and filtered. The solid was dried under a reduced pressure, obtaining a compound K (46.2 g, 38%).

Second Step: Synthesis of Compound L

The compound K (46.2 g, 102.6 mmol) was slowly added to 140 ml of a mixed solution of acetic acid and sulfuric acid in a ratio of 1:4 under a nitrogen environment at 0° C. The mixture was stirred for 5 minutes and heated rapidly up to 50° C. and then, slowly up to 110° C. After 20 minutes, the resultant was cooled down to room temperature and stirred for 12 hours. Then, ethanol was added thereto, and a solid produced one hour later was filtered under a reduced pressure and neutralized. The solid was dried under a reduced pressure, obtaining the compound L (21.7 g, 51%).

Third Step: Synthesis of Compound E-1

The compound L (10 g, 39.0 mmol), iodobenzene (10.4 ml, 93.6 mmol), 18-crown-6 (4.2 g, 15.6 mmol), copper (3 g, 46.8 mmol), and potassium carbonate (48.6 g, 351 mmol) were put under a nitrogen environment, heated at 180° C. for 20 hours, and heated and refluxed. When the reaction was complete, water was added to the reaction solution, ethyl acetate (e.a) was used for extraction, anhydrous $MgSO_4$ was used to remove moisture, and a resultant therefrom was filtered and concentrated under a reduced pressure. This obtained residue was separated and purified through flash column chromatography, obtaining the compound E-1 (6.7 g, 17.3%).

LC Mass (theoretical value: 408.49 g/mol, measured value: $M+H^+$=409.45 g/mol)

(Manufacture of Organic Light Emitting Diode: Emission Layer Device 1)

Example 1

An organic light emitting diode was manufactured by using the compound 1 according to Synthesis Example 1 as a host and $Ir(PPy)_3$ as a dopant.

A 1000 Å-thick ITO was used as an anode, and a 1000 Å-thick aluminum (Al) as a cathode. Specifically, the organic light emitting diode was manufactured in a method of cutting an ITO glass substrate having sheet resistance of 15 Ω/cm² into a size of 50 mm×50 mm×0.7 mm, ultrasonic wave-cleaning it in acetone, isopropylalcohol, and pure water respectively for 15 minutes and UV ozone-cleaning it for 30 minutes.

On the substrate, an 800 Å-thick hole transport layer was formed by depositing N4,N4'-di(naphthalen-1-yl)-N4,N4'-diphenylbiphenyl-4,4'-diamine (NPB) (80 nm) under a vacuum degree of 650×10-7 Pa at a deposit speed of 0.1 to 0.3 nm/s. Subsequently, a 300 Å-thick film as an emission layer was formed by using the compound 1 according to Synthesis Example 1 under the same vacuum deposit condition as above, and herein, $Ir(PPy)_3$ as a phosphorescent dopant was simultaneously deposited. Herein, the phosphorescent dopant was deposited in an amount of 10 wt % based on 100 wt % of the entire amount of the emission layer by adjusting a deposit speed.

On the emission layer, a 50 Å-thick film as a hole blocking layer as formed by depositing bis(2-methyl-8-quinolinolate)-4-(phenylphenolato)aluminium (BAlq) under the same vacuum deposit condition as above. Subsequently, a 200 Å-thick film as an electron transport layer was formed by depositing Alq3 under the same vacuum deposit condition as above. On the electron transport layer, LiF and Al were sequentially deposited as a cathode, manufacturing the organic photoelectric device.

The organic photoelectric device had a structure of ITO/NPB (80 nm)/EML (compound 1 (90 wt %)+$Ir(PPy)_3$ (10 wt %), 30 nm)/BAlq (5 nm)/Alq3 (20 nm)/LiF (1 nm)/Al (100 nm).

Example 2

An organic light emitting diode was manufactured according to the same method as Example 1 by using the compound 3 according to Synthesis Example 2 instead of the compound 1 according to Synthesis Example 1.

Example 3

An organic light emitting diode was manufactured according to the same method as Example 1 by using the compound 2 according to Synthesis Example 3 instead of the compound 1 according to Synthesis Example 1.

Example 4

An organic light emitting diode was manufactured according to the same method as Example 1 by using the compound 7 according to Synthesis Example 4 instead of the compound 1 according to Synthesis Example 1.

Example 5

An organic light emitting diode was manufactured according to the same method as Example 1 by using the compound 13 according to Synthesis Example 5 instead of the compound 1 according to Synthesis Example 1.

Example 6

An organic light emitting diode was manufactured according to the same method as Example 1 by using the compound 31 according to Synthesis Example 6 instead of the compound 1 according to Synthesis Example 1.

Example 7

An organic light emitting diode was manufactured according to the same method as Example 1 by using the compound 55 according to Synthesis Example 7 instead of the compound 1 according to Synthesis Example 1.

Comparative Example 1

An organic light emitting diode was manufactured according to the same method as Example 1 by using CBP having the following structure instead of the compound 1 according to Synthesis Example 1.

NPB, BAlq, CBP and Ir(PPy)3 used to manufacture the organic light emitting diode respectively have the following structures.

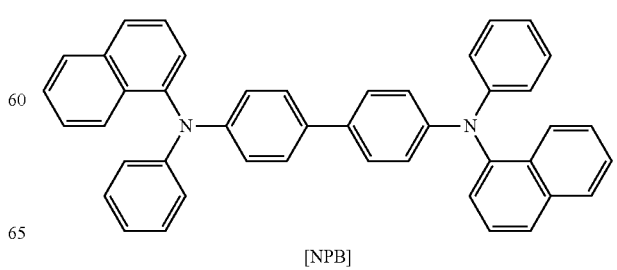

[NPB]

-continued

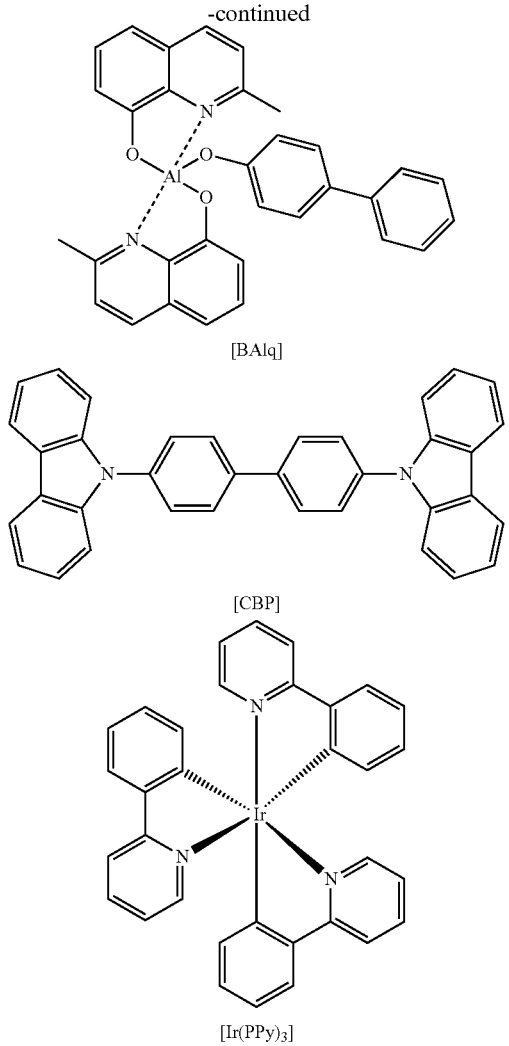

[BAlq]

[CBP]

[Ir(PPy)₃]

Evaluation

Current density change, luminance change, and luminous efficiency of each organic light emitting diode according to Examples 1 to 7 and Comparative Example 1 were measured.

Specific measurement methods are as follows, and the results are shown in the following Table 1.
(1) Measurement of Current Density Change Depending on Voltage Change The obtained organic light emitting diodes were measured regarding a current value flowing in the unit device, while increasing the voltage from 0 V to 10 V using a current-voltage meter (Keithley 2400), and the measured current value was divided by area to provide the result.
(2) Measurement of Luminance Change Depending on Voltage Change Luminance was measured by using a luminance meter (Minolta Cs-1000A), while the voltage of the organic light emitting diodes was increased from 0 V to 10 V.
(3) Measurement of Luminous Efficiency Current efficiency (cd/A) at the same current density (10 mA/cm$^2$) were calculated by using the luminance, current density, and voltages (V) from the items (1) and (2).
(4) Measurement of Life-Span A life span was obtained by measuring a time when current efficiency (cd/A) was decreased down to 90%, while Luminance (cd/m$^2$) was maintained to be 5000 cd/m$^2$.

TABLE 1

| Nos. | Compounds | Driving voltage (V) | EL color | Efficiency (cd/A) | 90% life-span (h) (@5000 cd/m$^2$) |
|---|---|---|---|---|---|
| Example 1 | compound 1 | 3.81 | Green | 36.2 | 50 |
| Example 2 | compound 3 | 4.09 | Green | 34.6 | 45 |
| Example 3 | compound 2 | 4.10 | Green | 44.7 | 55 |
| Example 4 | compound 7 | 3.78 | Green | 37.1 | 52 |
| Example 5 | compound 13 | 3.99 | Green | 37.3 | 35 |
| Example 6 | compound 31 | 3.75 | Green | 35.5 | 38 |
| Example 7 | compound 55 | 4.13 | Green | 38.6 | 41 |
| Comparative Example 1 | CBP | 4.25 | Green | 31.7 | 25 |

Referring to Table 1, the organic light emitting diodes according to Examples 1 to 7 exhibited excellent driving voltage and efficiency and improved life-span characteristics compared with the organic light emitting diode according to Comparative Example 1. As described above, stacking a relatively plane heterocyclic moiety by a bulky substituent facilitates injection and transport of electrons and resultantly, decreases a driving voltage, and herein, the organic light emitting diode having a biphenyl substituent relatively advantageous for stacking molecules according to Example 4 exhibited a lower driving voltage than that of Example 1. On the other hand, the organic light emitting diode according to Example 6 had a kink molecular structure due to an ortho bond and thus exhibited a lower driving voltage than that of Example 1, since the kink molecular structure promoted stacking a heterocyclic moiety as an ET characteristic substituent.

(Manufacture of Organic Light Emitting Diode: Emission Layer Device 2)

Example 8

A glass substrate coated with ITO (indium tin oxide) as a 1500 Å-thick thin film was ultrasonic wave-washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, a 700 Å-thick hole injection layer was formed on the ITO substrate by vacuum depositing the compound A, and a hole transport layer was formed on the injection layer by depositing the compound B to be 50 Å thick and the compound C to be 1020 Å thick. On the hole transport layer, a 400 Å-thick emission layer was formed by vacuum-depositing both the compound 1 according to Synthesis Example 1 and the compound B-1 according to Synthesis Example 9 as a second host compound simultaneously as a host and tris(2-phenylpyridine)iridium (III) [Ir(ppy)₃] as a dopant in a doping amount of 10 wt %. Herein, the compound 1 and the compound B-1 were used in a ratio of 1:1.

Subsequently, on the emission layer, a 300 Å-thick electron transport layer was formed by simultaneously vacuum-depositing the compound D and Liq in a ratio of 1:1, and on the electron transport layer, Liq and Al were sequentially vacuum-deposited to be 15 Å thick and 1200 Å thick, manufacturing an organic light emitting diode.

The organic light emitting diode had a structure of 5-layered organic thin films specifically as follows.

ITO/Compound A 700 Å/Compound B 50 Å/Compound C 1020 Å/EML [Compound 1:B-1:Ir(ppy)$_3$=45 wt %:45 wt %:10 wt %] 400 Å/Compound D:Liq 300 Å/Liq 15 Å/Al 1200 Å.

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline

Example 9

An organic light emitting diode was manufactured according to the same method as Example 8 except for using the compound 1 and the compound B-31 in a weight ratio of 1:1.

Example 10

An organic light emitting diode was manufactured according to the same method as Example 8 except for using the compound 1 and the compound B-154 in a weight ratio of 1:1.

Example 11

An organic light emitting diode was manufactured according to the same method as Example 8 except for using the compound 2 and the compound B-31 in a weight ratio of 1:1.

Example 12

An organic light emitting diode was manufactured according to the same method as Example 8 except for using the compound 2 and the compound B-166 in a weight ratio of 1:1.

Example 13

An organic light emitting diode was manufactured according to the same method as Example 8 except for using the compound 3 and the compound B-156 in a weight ratio of 1:1.

Example 14

An organic light emitting diode was manufactured according to the same method as Example 8 except for using the compound 7 and the compound C-1 in a weight ratio of 1:1.

Example 15

An organic light emitting diode was manufactured according to the same method as Example 8 except for using the compound 7 and the compound B-31 in a weight ratio of 1:1.

Example 16

An organic light emitting diode was manufactured according to the same method as Example 8 except for using the compound 31 and the compound E-1 in a weight ratio of 1:1.

Comparative Example 2

An organic light emitting diode was manufactured according to the same method as Example 8 except for using CBP as a solo host.

Comparative Example 3

An organic light emitting diode was manufactured according to the same method as Example 8 except for using the compound B-1 as a solo host.

Comparative Example 4

An organic light emitting diode was manufactured according to the same method as Example 8 except for using the compound B-31 as a solo host.

Evaluation

Luminous efficiency and life-span characteristics of the organic light emitting diodes according to Examples 8 to 16 and Comparative Examples 2 to 4 were measured.

Specific measurement methods are as follows, and the results are shown in Table 2.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the result.

(2) Measurement of Luminance Change Depending on Voltage Change

Luminance was measured by using luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) was calculated by using the luminance, current density, and voltages (V) from the items (1) and (2).

(4) Measurement of Life-Span

Life-span was obtained by measuring time taken until current efficiency (cd/A) was decreased down to 97%, while the organic light emitting diodes were set to maintain luminance (cd/m$^2$) of 6000 cd/m$^2$.

TABLE 2

| | First host | Second host | First host:Second host | (cd/A) | Life-span T97 (h) |
|---|---|---|---|---|---|
| Example 8 | compound 1 | B-1 | 1:1 | 45.5 | 58 |
| Example 9 | compound 1 | B-31 | 1:1 | 48.1 | 68 |
| Example 10 | compound 1 | B-154 | 1:1 | 47.8 | 60 |
| Example 11 | compound 2 | B-31 | 1:1 | 51.3 | 66 |
| Example 12 | compound 2 | B-166 | 1:1 | 45.5 | 62 |
| Example 13 | compound 3 | B-156 | 1:1 | 44.2 | 50 |
| Example 14 | compound 7 | C-1 | 1:1 | 46.5 | 56 |
| Example 15 | compound 7 | B-31 | 1:1 | 50.0 | 70 |
| Example 16 | compound 31 | E-1 | 1:1 | 40.4 | 49 |

TABLE 2-continued

| | First host | Second host | First host:Second host | (cd/A) | Life-span T97 (h) |
|---|---|---|---|---|---|
| Comparative Example 2 | | CBP | — | 27.1 | 10 |
| Comparative Example 3 | | B-1 | — | 38.5 | 40 |
| Comparative Example 4 | | B-30 | — | 10.2 | 5 |

Referring to Table 2, the organic light emitting diodes according to Examples 8 to 16 exhibited improved luminance efficiency and life-span characteristics compared with the organic light emitting diodes according to Comparative Examples 2 to 4.

(Manufacture of Organic Light Emitting Diode: Electron Transport Auxiliary Layer Device)

Example 17

A glass substrate coated with ITO (indium tin oxide) as a 1500 Å-thick thin film was washed with a distilled water. After the washing with distilled water, the glass substrate was ultrasonic wave-washed with a solvent such as isopropyl alcohol, acetone, methanol, and the like and dried, moved to a plasma cleaner, cleaned with oxygen plasma for 10 minutes, and moved to a vacuum depositor. This obtained ITO transparent electrode was used as an anode, a 700 Å-thick hole injection layer was formed on the ITO substrate by vacuum-depositing the compound A, and a hole transport layer was formed on the injection layer by depositing the compound B to be 50 Å thick and the compound C to be 1020 Å thick. Then, a 200 Å-thick emission layer was formed thereon by vacuum-depositing BH113 and BD370 (dealer: SFC Inc.) as a blue fluorescent luminescent host and a dopant in a dopant concentration of 5 wt %. On the emission layer, the compound 1 was vacuum-deposited to form a 50 Å-thick electron transport auxiliary layer. The electron transport auxiliary layer may be formed by using a material represented by Chemical Formula I alone or mixing the material with the compound B, C, and D. On the electron transport auxiliary layer, a 300 Å-thick electron transport layer was formed by vacuum-depositing the compound D and Liq simultaneously in a weight ratio of 1:1, and on the electron transport layer, a cathode was formed by sequentially vacuum-depositing Liq to be 15 Å thick and Al to be 1200 Å thick, manufacturing an organic light emitting diode. The organic light emitting diode had a structure of 5 organic thin film layers and specifically, ITO/Compound A 700 Å/Compound B 50 Å/Compound C (1020 Å)/EML[BH113:BD370=95:5 (wt:wt)] 200 Å/Compound 1 50 Å/Compound D:Liq 300 Å=1:1/Liq 15 Å/Al 1200 Å.

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline Example 18

An organic light emitting diode was manufactured according to the same method as Example 17 except for using the compound 3.

Example 19

An organic light emitting diode was manufactured according to the same method as Example 17 except for using the compound 2.

Example 20

An organic light emitting diode was manufactured according to the same method as Example 17 except for using the compound 7.

Comparative Example 5

An organic light emitting diode was manufactured according to the same method as Example 17 except for using no electron transport auxiliary layer.

Evaluation

Current density change, luminance change, and luminous efficiency of each organic light emitting diode according to Examples 17 to 20 and Comparative Example 5 were measured.

Specific measurement methods are as follows, and the results are shown in Table 3.

(1) Measurement of Current Density Change Depending on Voltage Change

The obtained organic light emitting diodes were measured regarding current value flowing in the unit device while increasing the voltage from 0 V to 10 V using a current-voltage meter (Keithley 2400), and the measured current value was divided by area to provide the result.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(5) Measurement of Life-Span

T97 life-spans of the organic light emitting diodes according to Examples 17 to 20 and Comparative Example 5 were measured as a time when their luminance decreased down to 97% relative to the initial luminance (cd/m$^2$) after emitting light with 750 cd/m$^2$ as the initial luminance (cd/m$^2$) and measuring their luminance decrease depending on a time with a Polanonix life-span measurement system.

TABLE 3

| Devices | Electron transport auxiliary layer (weight ratio) | Luminance efficiency (cd/A) | Color coordinate (x, y) | T97 (h) @750 nit |
|---|---|---|---|---|
| Example17 | compound 1 | 8.2 | (0.132, 0.149) | 63 |
| Example18 | compound 3 | 6.3 | (0.133, 0.148) | 40 |
| Example19 | compound 2 | 7.5 | (0.132, 0.149) | 60 |
| Example20 | compound 7 | 6.8 | (0.132, 0.150) | 61 |
| Comparative Example 5 | Not used | 5.8 | (0.135, 0.147) | 25 |

Referring to Table 3, the organic light emitting diodes according to Examples 17 to 20 exhibited improved luminance efficiency and life-span characteristics simultaneously compared with the organic light emitting diode according to Comparative Example 5.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A compound for an organic optoelectric device represented by Chemical Formula I:

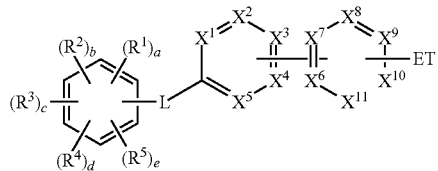

wherein, in Chemical Formula I, $X^1$ to $X^{11}$ are independently, N, C, or $CR^a$, $R^a$ is independently, hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heterocyclic group, a substituted or unsubstituted C6 to C30 arylamine group, a substituted or unsubstituted C1 to C30 alkoxy group, a substituted or unsubstituted C3 to C40 silyl group, a substituted or unsubstituted C3 to C40 silyloxy group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof, $R^1$ to $R^5$ are independently a substituted or unsubstituted C6 to C30 aryl group, a to e are independently an integer of 0 or 1, $4 \leq a+b+c+d+e \leq 5$, L is a single bond, a substituted or unsubstituted C6 to C30 arylene group, a substituted or unsubstituted C2 to C30 heteroarylene group, or a combination thereof, and ET is a substituted or unsubstituted heteroaryl group including at least one N, provided that ET is not a carbazolyl group and is not a substituted or unsubstituted pyridinyl group, wherein "substituted" refers to that at least one hydrogen is replaced by deuterium, a halogen, a hydroxy group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

2. The compound for an organic optoelectric device of claim 1, which is represented by one of Chemical Formulae I-1 to I-3:

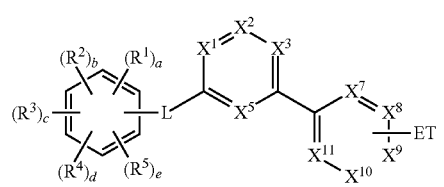

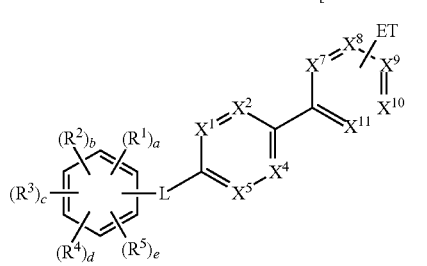

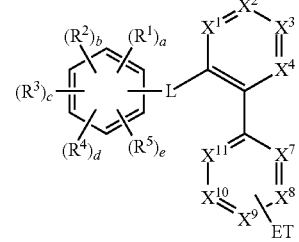
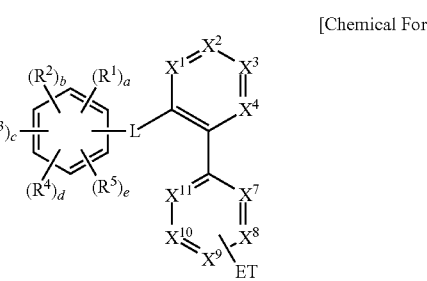

wherein, in Chemical Formulae I-1 to I-3, $X^1$ to $X^5$, $X^7$ to $X^{11}$, $R^1$ to $R^5$, a to e, L, and ET are the same as defined in claim 1.

3. The compound for an organic optoelectric device of claim 2, wherein the compound represented by Chemical Formula I-1 is represented by one of Chemical Formulae I-1a to I-1f:

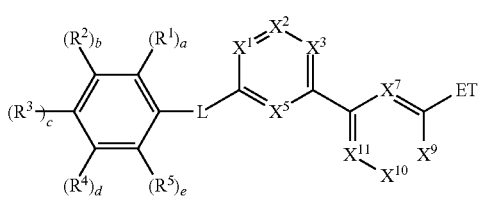

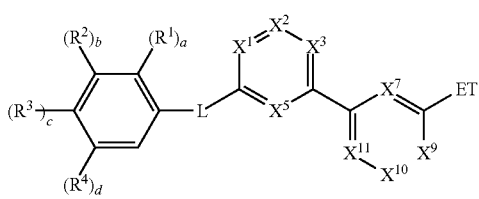

-continued

[Chemical Formula I-1c]

[Chemical Formula I-1d]

[Chemical Formula I-1e]

[Chemical Formula I-1f]

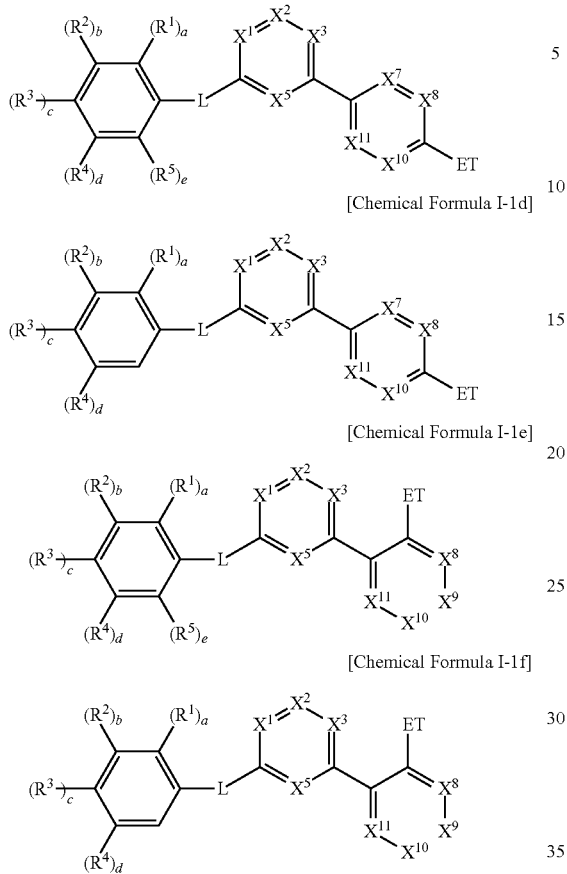

wherein, in Chemical Formulae I-1a to I-1f, $X^1$, $X^2$, $X^3$, $X^5$ and $X^7$ to $X^{11}$ are independently N, C, or $CR^a$, $R^1$ to $R^5$ are independently a substituted or unsubstituted phenyl group, or a substituted or unsubstituted naphthyl group, a to e are an integer of 1, and $R^a$, L and ET are the same as defined in claim 1.

4. The compound for an organic optoelectric device of claim 2, wherein the compound represented by Chemical Formula I-2 is represented by one of Chemical Formulae I-2a to I-2f:

[Chemical Formula I-2a]

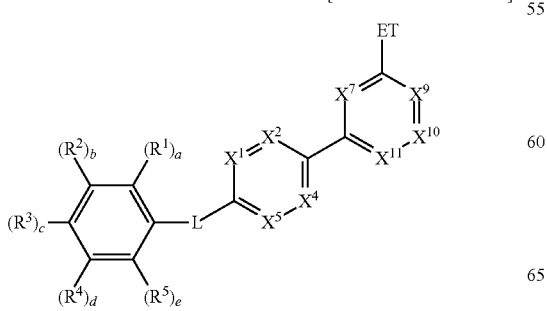

-continued

[Chemical Formula I-2b]

[Chemical Formula I-2c]

[Chemical Formula I-2d]

[Chemical Formula I-2e]

[Chemical Formula I-2f]

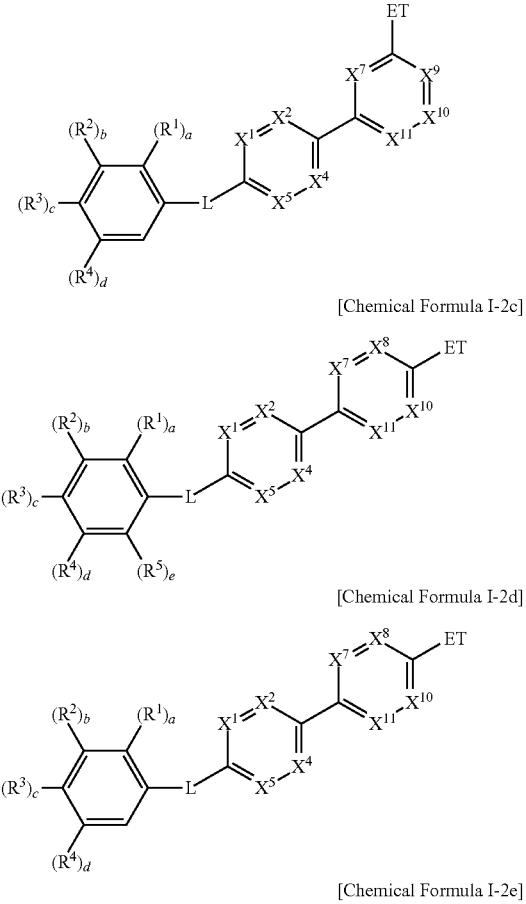

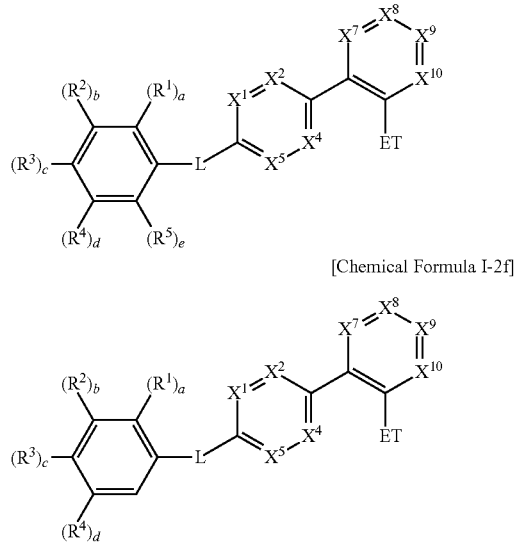

wherein, in Chemical Formulae I-2a to I-2f, $X^1$, $X^2$, $X^5$, $X^6$ and $X^7$ to $X^{11}$ are independently, N, C, or $CR^a$, $R^1$ to $R^5$ are independently a substituted or unsubstituted phenyl group, or a substituted or unsubstituted naphthyl group, a to e are an integer of 1, and $R^a$, L and ET are the same as defined in claim 1.

5. The compound for an organic optoelectric device of claim 2, wherein the compound represented by Chemical Formula I-3 is represented by one of Chemical Formulae I-3a to I-3f:

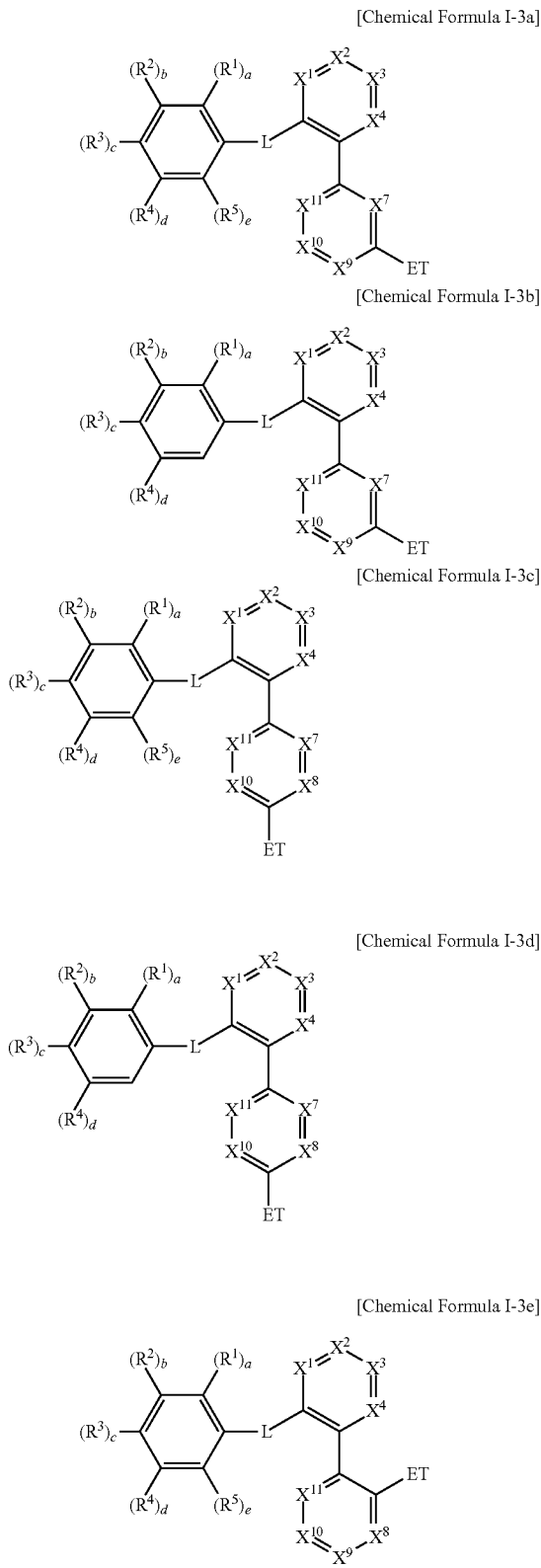

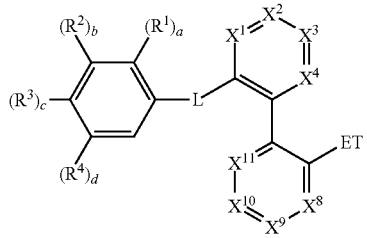

wherein, in Chemical Formulae I-3a to I-3f, $X^1$, $X^2$, $X^3$, $X^6$ and $X^7$ to $X^{11}$ are independently N, C, or $CR^a$, $R^1$ to $R^5$ are independently a substituted or unsubstituted phenyl group, or a substituted or unsubstituted naphthyl group, a to e are an integer of 1, and $R^a$, L and ET are the same as defined in claim 1.

6. The compound for an organic optoelectric device of claim 1, wherein the ET is a substituted or unsubstituted imidazolyl group, a substituted or unsubstituted pyrazolyl group, a substituted or unsubstituted thiazolyl group, a substituted or unsubstituted isothiazolyl group, a substituted or unsubstituted oxazolyl group, a substituted or unsubstituted isoxazolyl group, a substituted or unsubstituted pyrazinyl group, a substituted or unsubstituted pyrimidinyl group, a substituted or unsubstituted pyridazinyl group, a substituted or unsubstituted triazinyl group, a substituted or unsubstituted indazolyl group, a substituted or unsubstituted purinyl group, a substituted or unsubstituted quinolinyl group, a substituted or unsubstituted isoquinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzimidazolyl group, a substituted or unsubstituted isobenzothiazolyl group, a substituted or unsubstituted benzoxazolyl group, a substituted or unsubstituted benzothiazolyl group, a substituted or unsubstituted benzoquinazolinyl group, a substituted or unsubstituted isobenzooxazolyl group, a substituted or unsubstituted triazolyl group, a substituted or unsubstituted tetrazolyl group, a substituted or unsubstituted oxadiazolyl group, a substituted or unsubstituted thiadiazolyl group, a substituted or unsubstituted imidazopyridinyl group, a substituted or unsubstituted imidazopyrimidinyl group, or a combination thereof.

7. The compound for an organic optoelectric device of claim 6, wherein the ET is a substituted or unsubstituted groups of Group I:

[Group I]

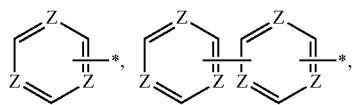

-continued

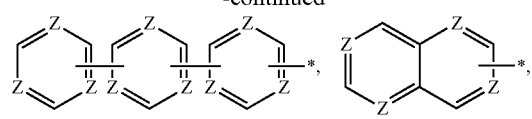

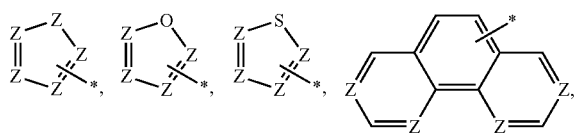

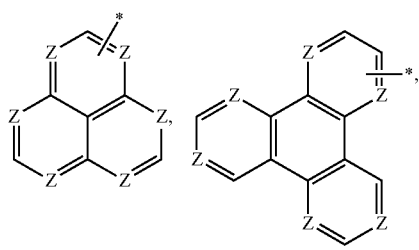

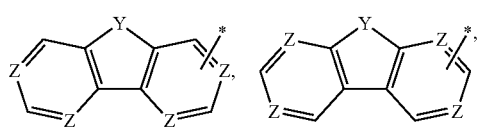

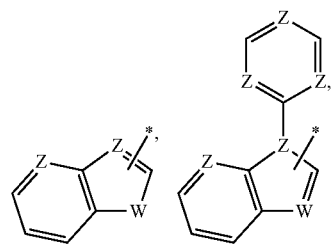

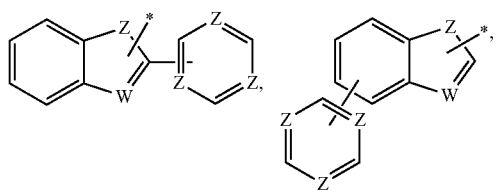

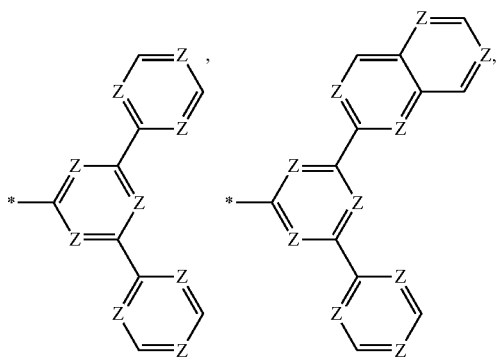

-continued

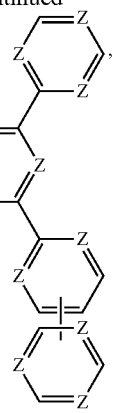

wherein, in Group I,
Z is independently N or CR$^b$, wherein at least one of Z is N, and
W and Y are independently N, O, S, SO, SO$_2$, CR$^c$, CR$^d$R$^e$, SiR$^f$, or SiR$^g$R$^h$,
wherein R$^b$ to R$^h$ are independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C2 to C30 heteroaryl group, or a combination thereof, and
* indicates bonding sites with neighboring atoms, and is positioned at one of element of the functional group, and
provided that ET is not a carbazolyl group and is not a substituted or unsubstituted pyridinyl group.

8. The compound for an organic optoelectric device of claim 1, wherein the L is a single bond, a phenylene group, a biphenylene group, a terphenylene group, a quarterphenylene group, a pentalenylene group, an indenylene group, a naphthylene group, a phenalenylene group, a phenanthrenylene group, an anthracenylene group, a fluoranthrenylene group, a triphenylenylene group, a pyrenylene group, a chrysenylene group, a pyrrolylene group, an imidazolylene group, a pyrazolylene group, a pyridinylene group, a pyrazinylene group, a pyrimidinylene group, a triazinylene group, a pyridazinylene group, a quinolinylene group, an isoquinolinylene group, an oxazolylene group, a triazolylene group a tetrazolylene group, an oxadiazolylene group, or a combination thereof.

9. The compound for an organic optoelectric device of claim 8, wherein the L is a single bond or selected from substituted or unsubstituted groups of Group II:

[Group II]

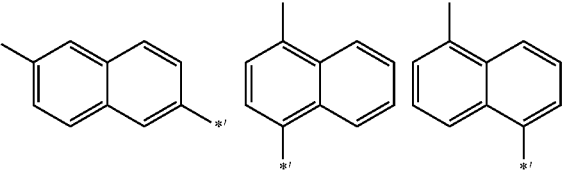

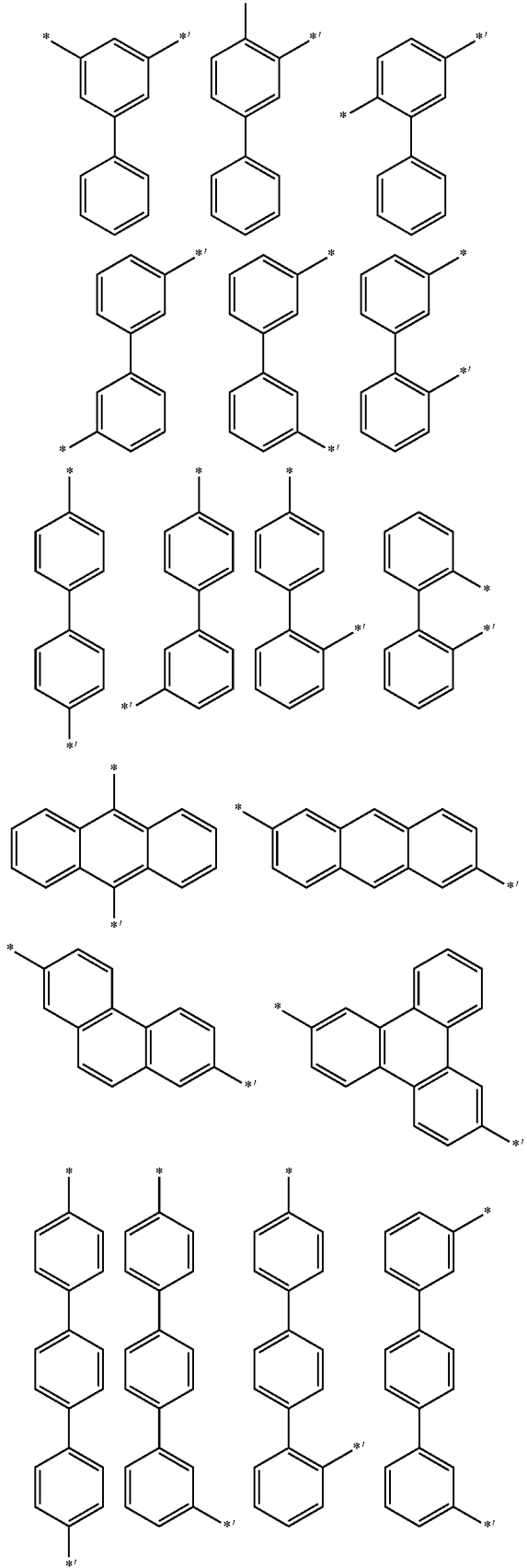
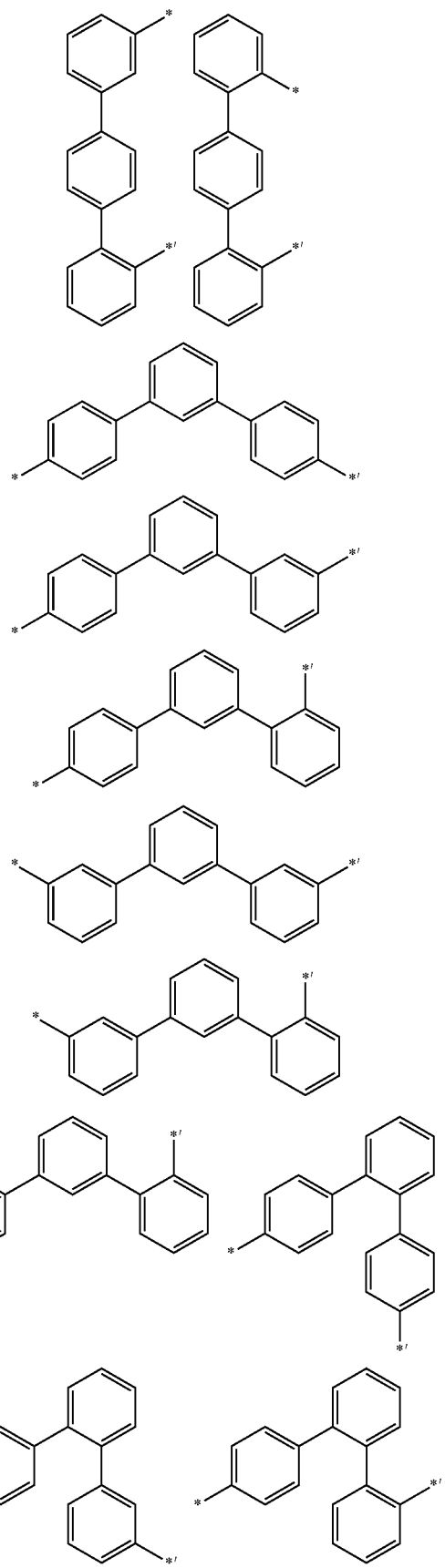

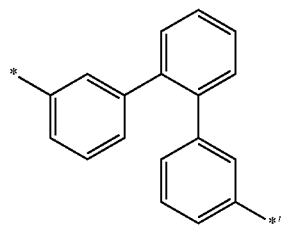
* and *' indicate bonding sites with neighboring atoms.
10. The compound for an organic optoelectric device of claim 1, which is one of compounds of Group 1:
[Group 1]
[1]
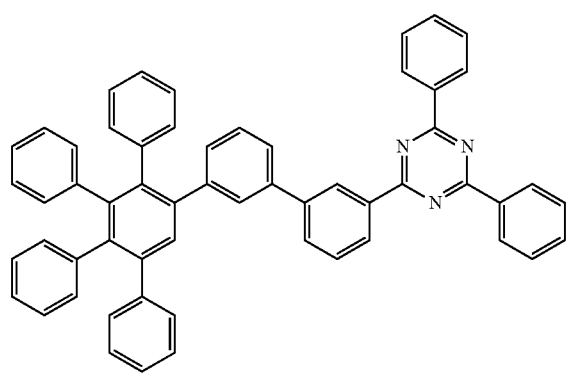
[2]
[3]
[4]
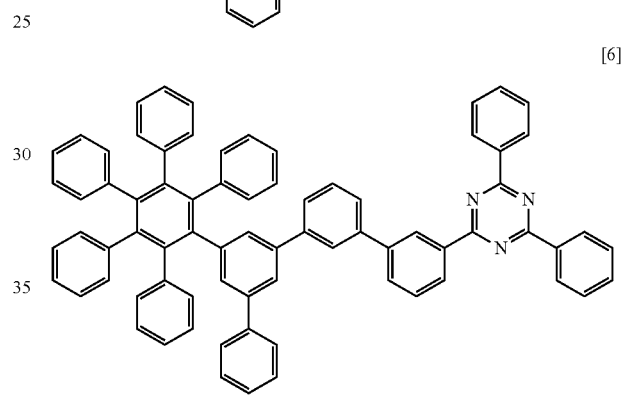
[5]
[6]
[7]
[8]

[9]
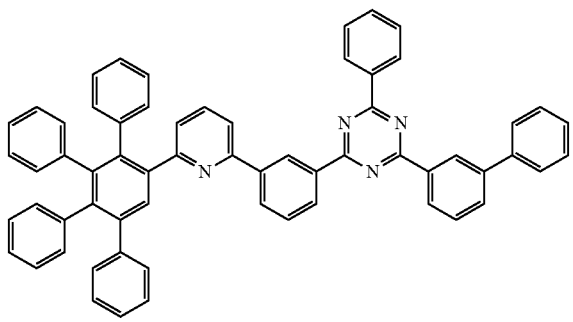
[10]
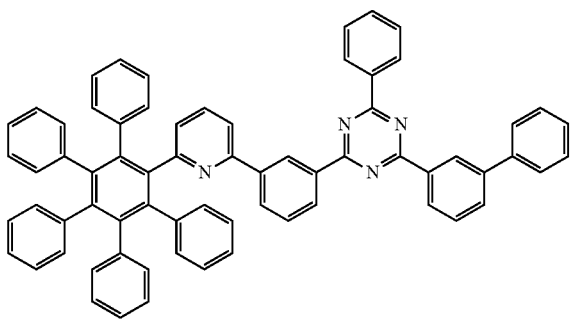
[11]
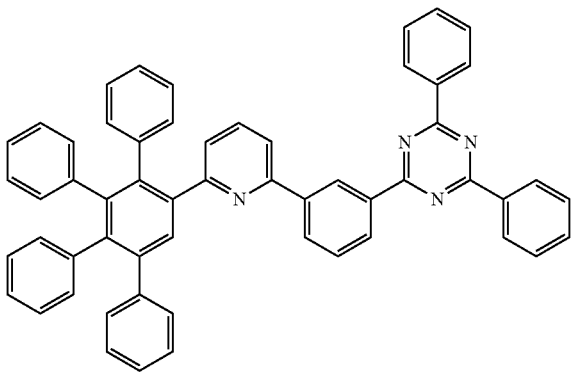
[12]
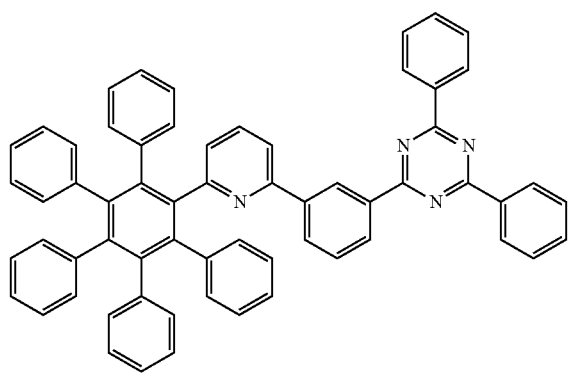
[13]
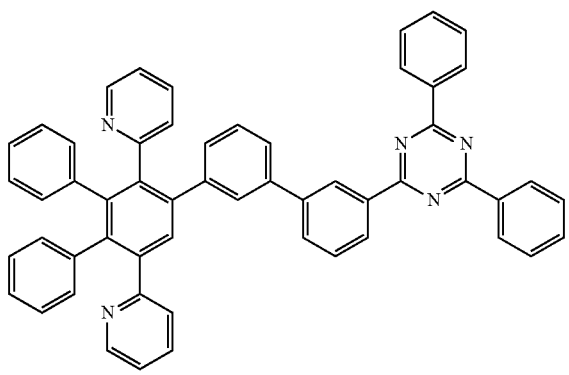
[14]
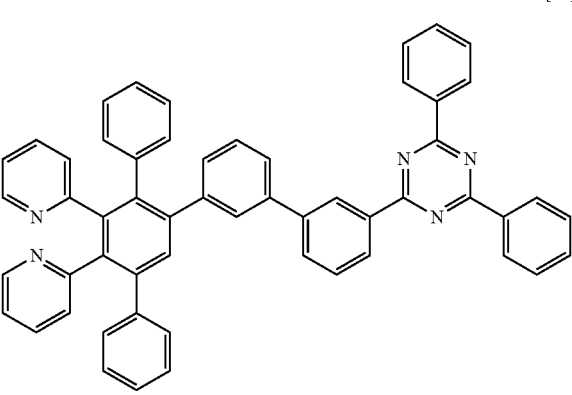
[15]
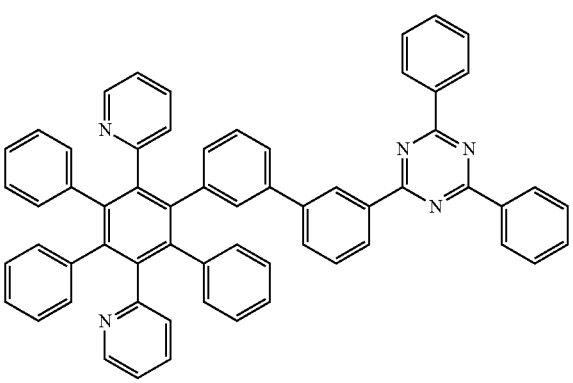
[16]
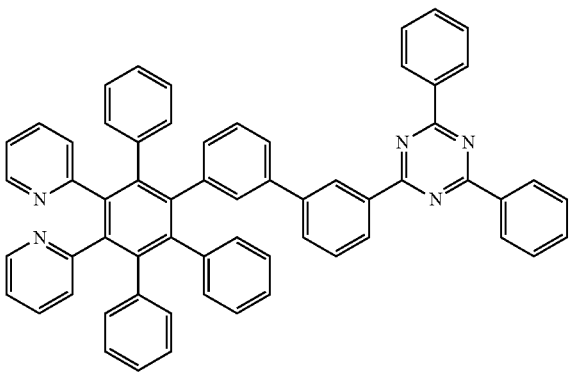

[17]
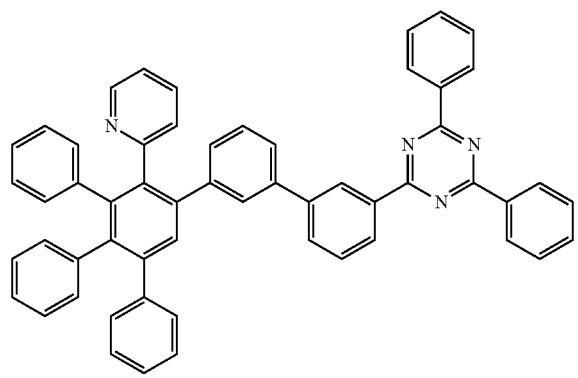
[22]
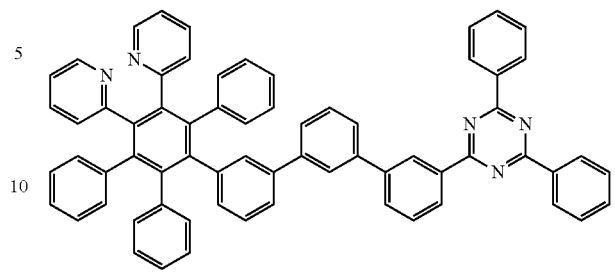
[18]
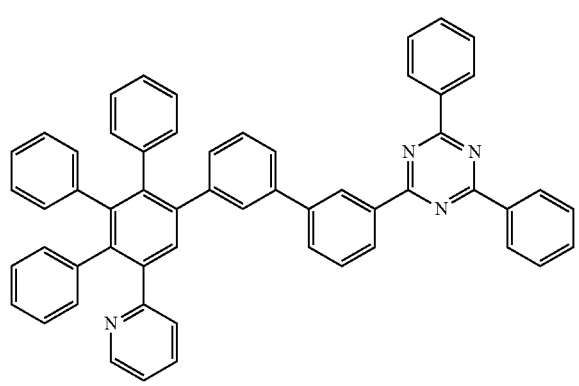
[23]
[19]
[24]
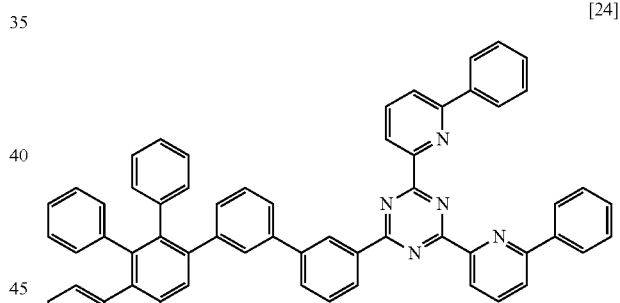
[20]
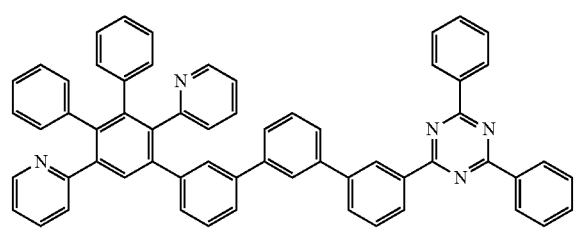
[25]
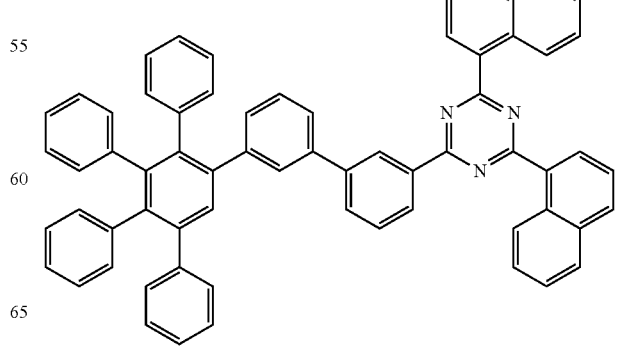
[21]

[26]
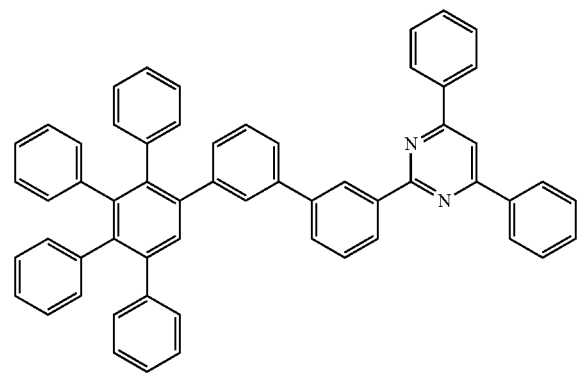
[27]
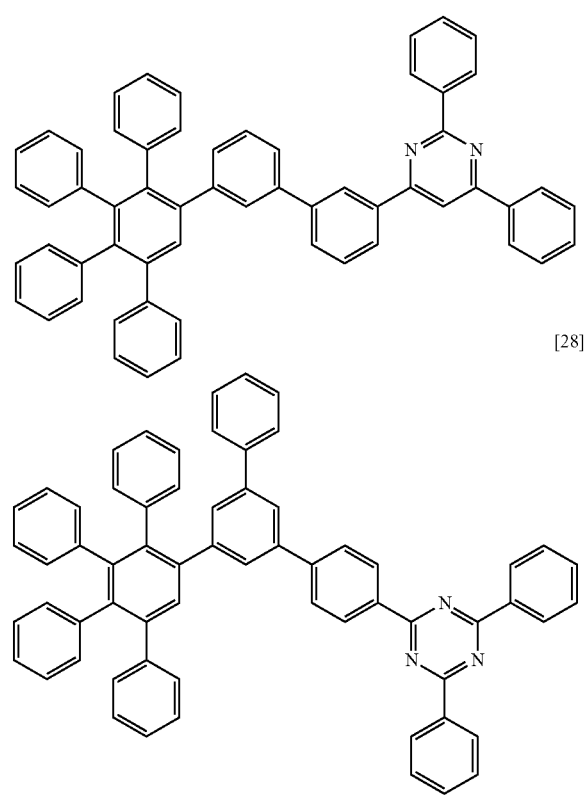
[28]
[29]
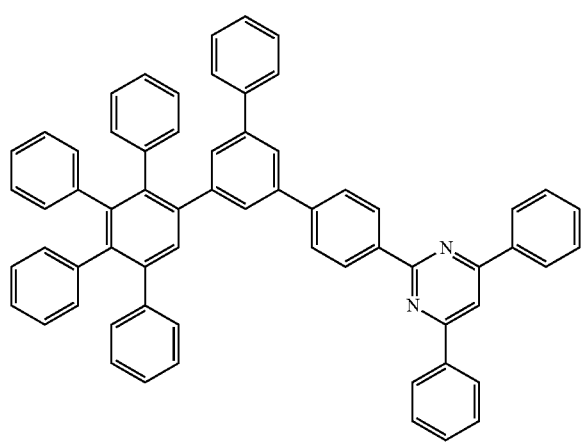
[30]
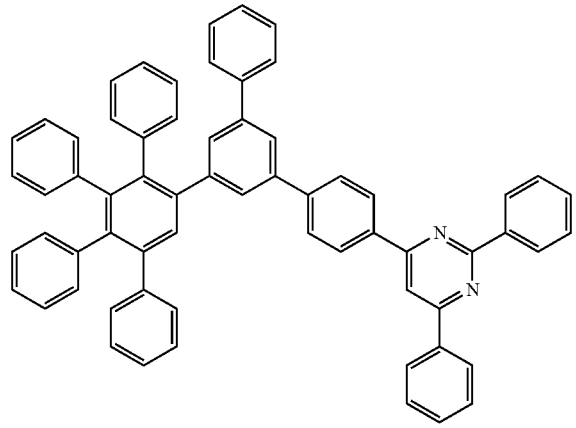
[31]
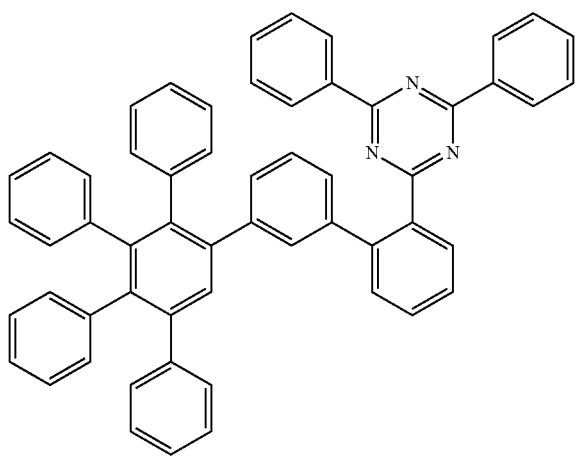
[32]
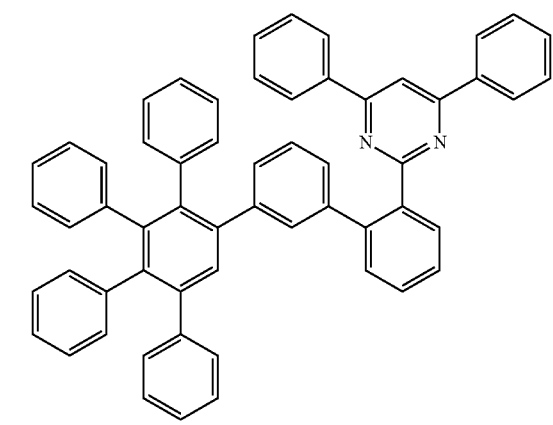

-continued
[33]
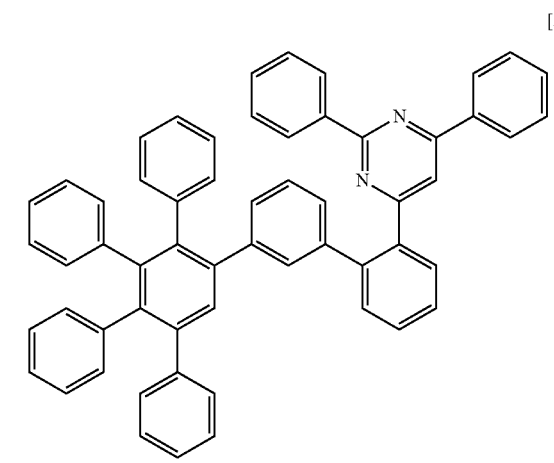
[34]
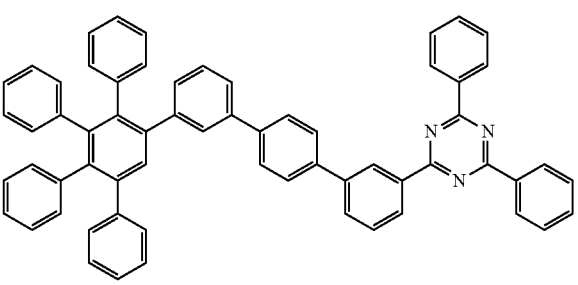
[35]
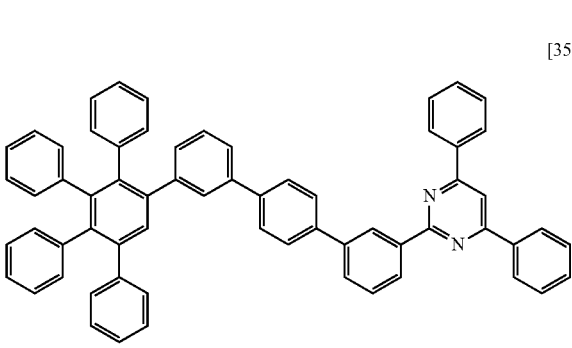
[36]
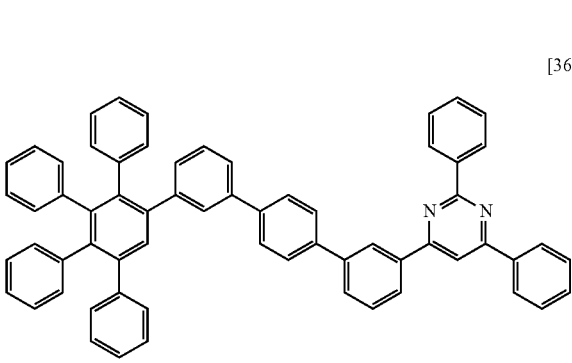
-continued
[37]
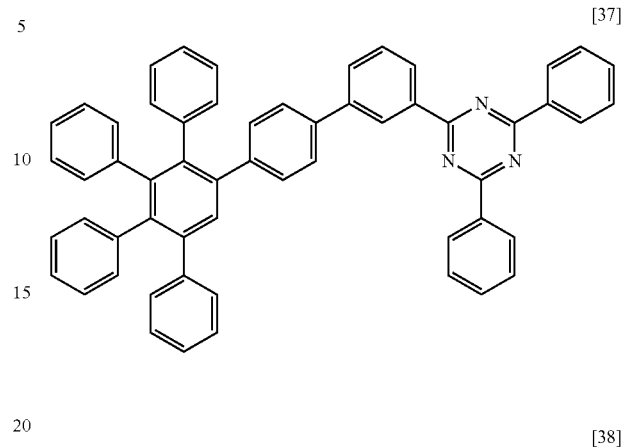
[38]
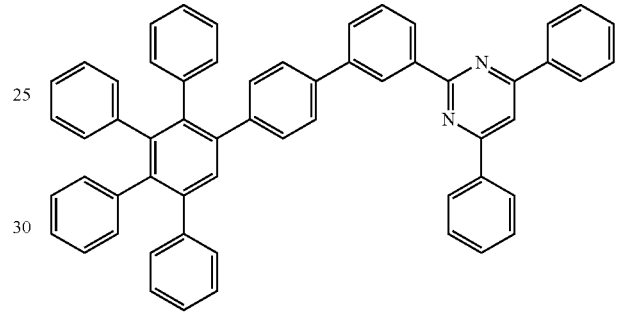
[39]
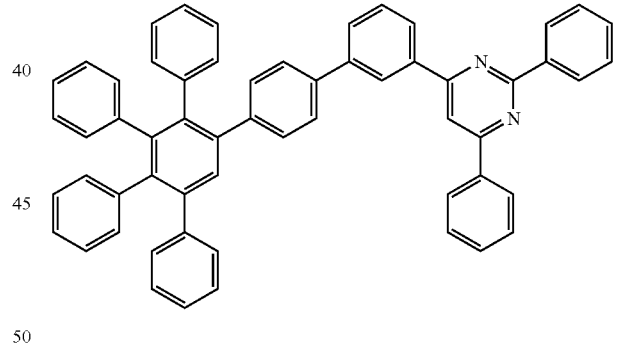
[40]
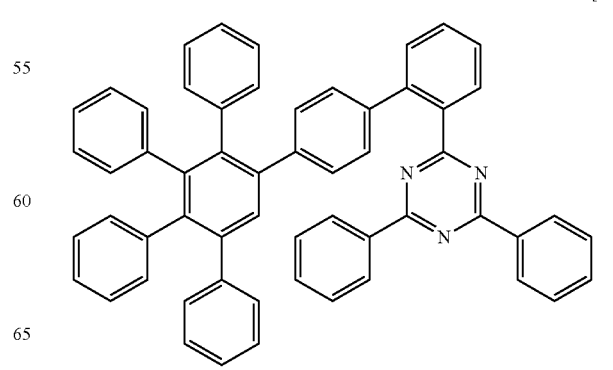

[41]
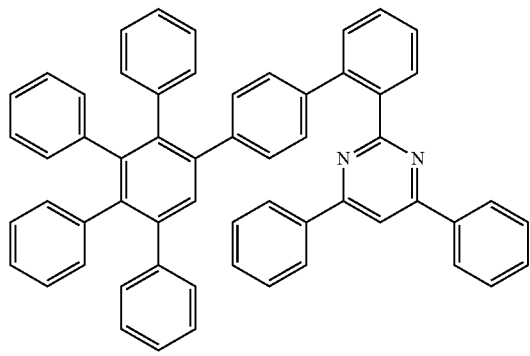
[42]
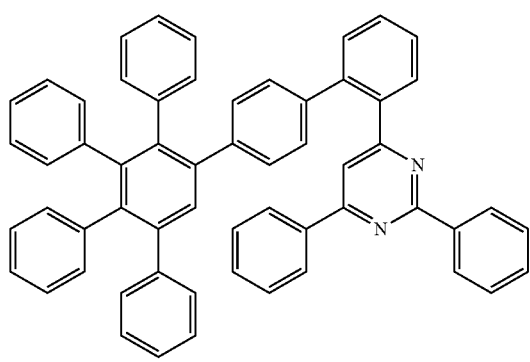
[43]
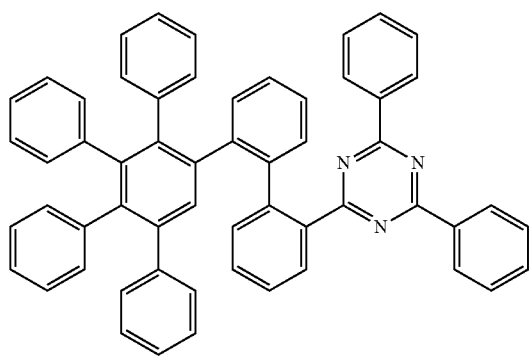
[44]
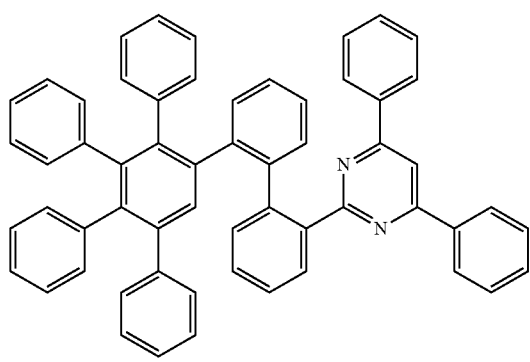
[45]
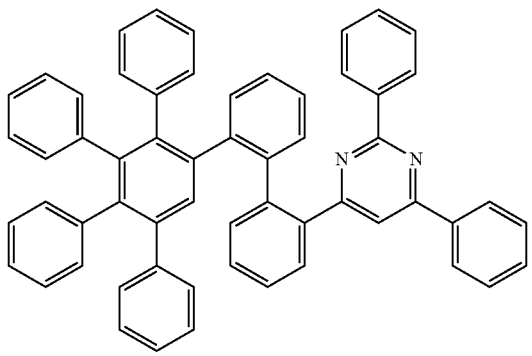
[46]
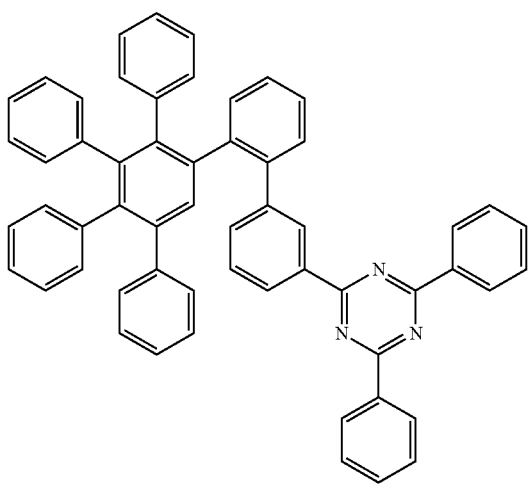
[47]
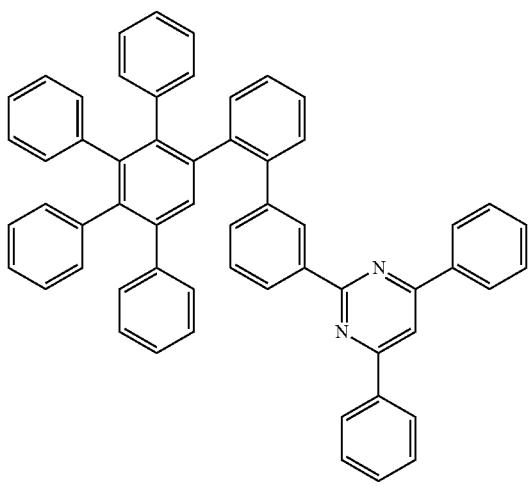

[48]
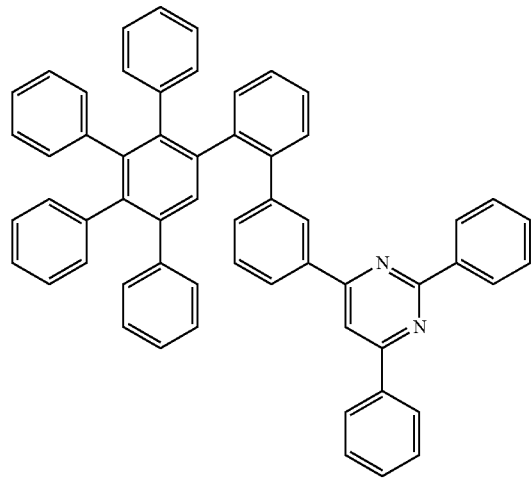
[49]
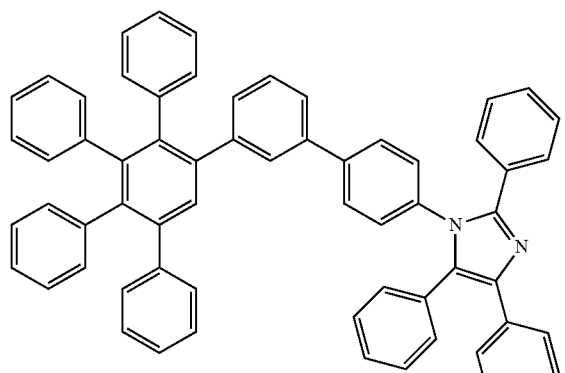
[50]
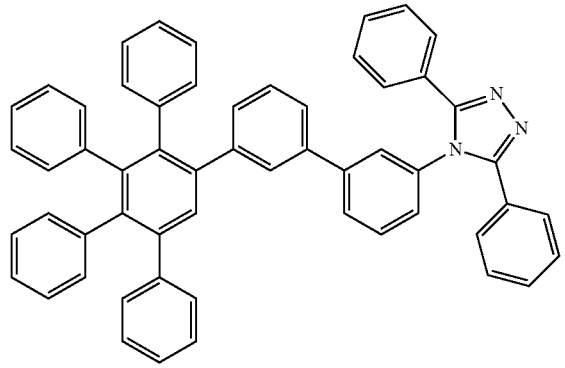
[51]
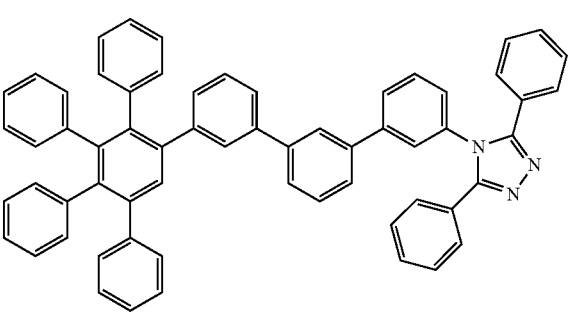
[52]
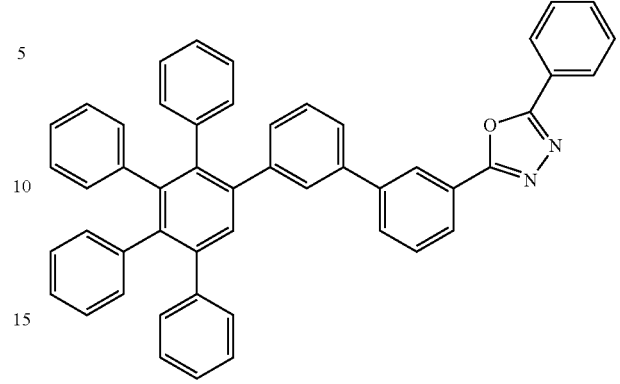
[53]
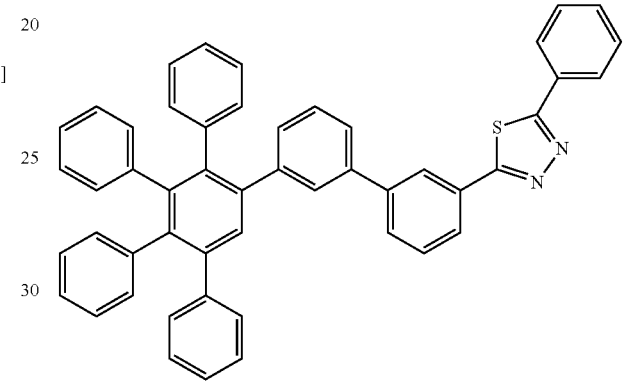
[54]
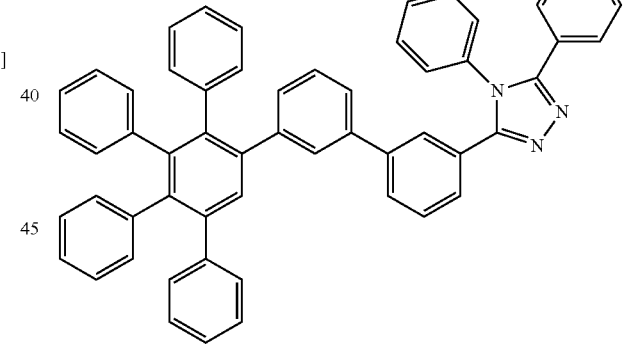
[55]
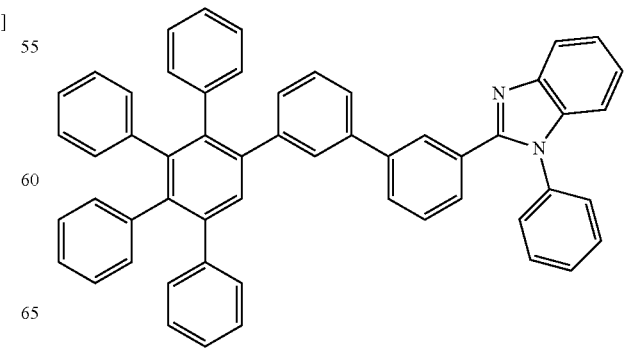

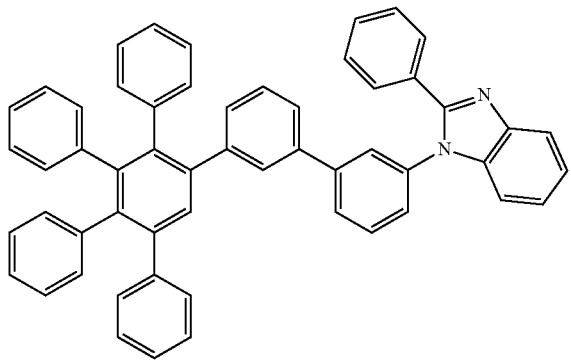

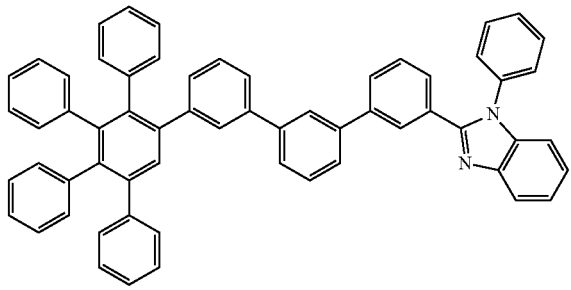

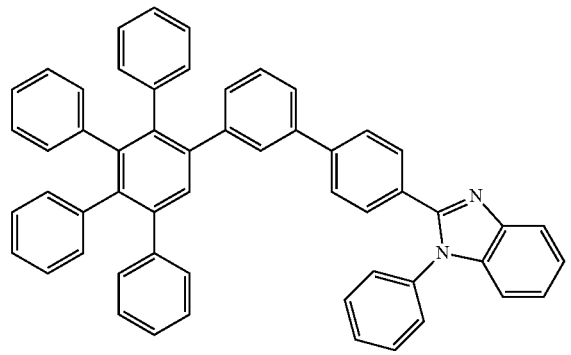

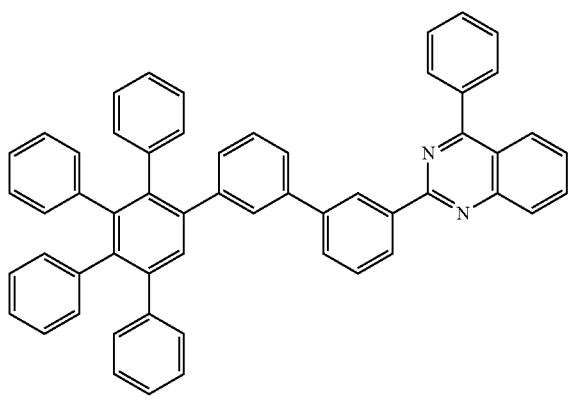

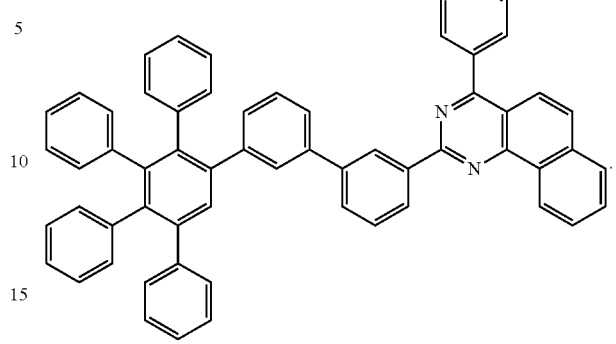

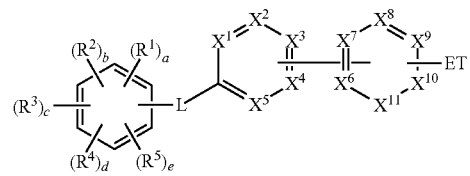

11. A compound for an organic optoelectric device represented by Chemical Formula I:

[Chemical Formula I]

wherein, in Chemical Formula I,
$X^1$ to $X^{11}$ are independently, N, C, or $CR^a$,
$R^a$ is independently, hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heterocyclic group, a substituted or unsubstituted C6 to C30 arylamine group, a substituted or unsubstituted C1 to C30 alkoxy group, a substituted or unsubstituted C3 to C40 silyl group, a substituted or unsubstituted C3 to C40 silyloxy group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof,
$R^1$ to $R^5$ are independently a substituted or unsubstituted C6 to C30 aryl group,
a to e are independently an integer of 0 or 1,
$4 \le a+b+c+d+e \le 5$,
L is a single bond, a substituted or unsubstituted C6 to C30 arylene group, a substituted or unsubstituted C2 to C30 heteroarylene group, or a combination thereof, and
ET is a substituted or unsubstituted heteroaryl group including at least one N except a carbazolyl group,
wherein "substituted" refers to that at least one hydrogen is replaced by deuterium, a halogen, a hydroxy group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group, wherein ET is one of substituted or unsubstituted functional groups of Group I-1:
[Group I-1]
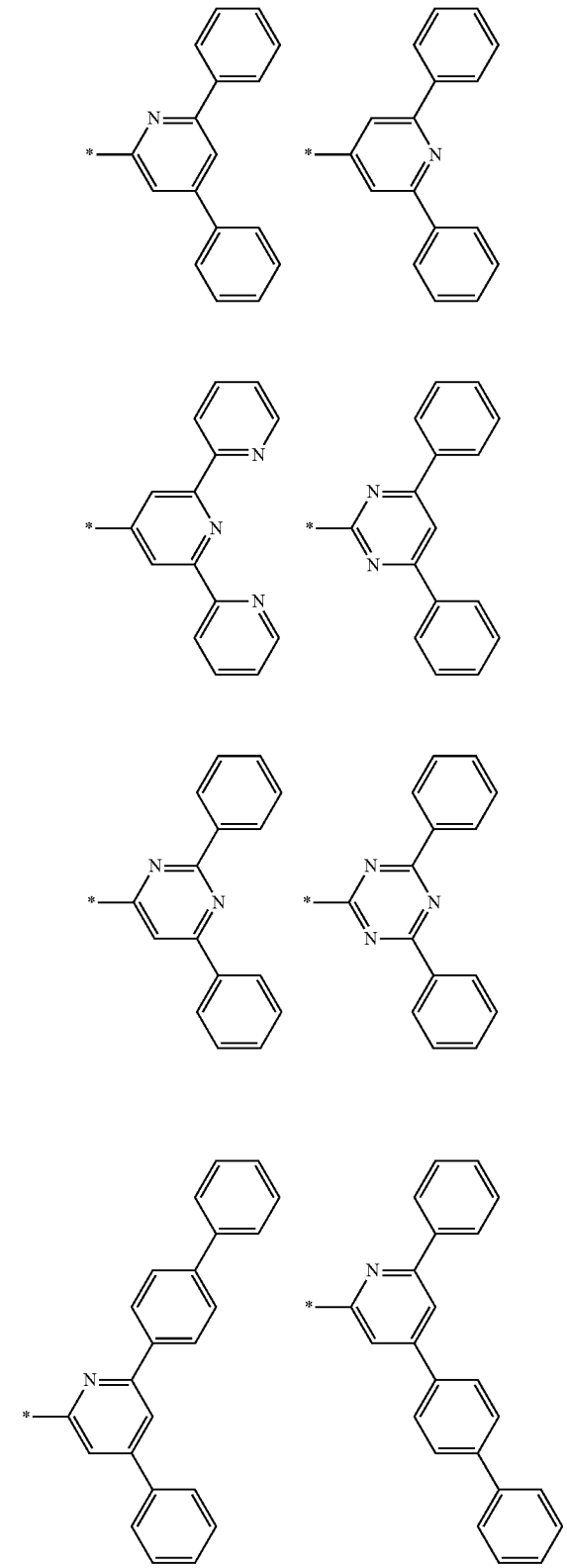
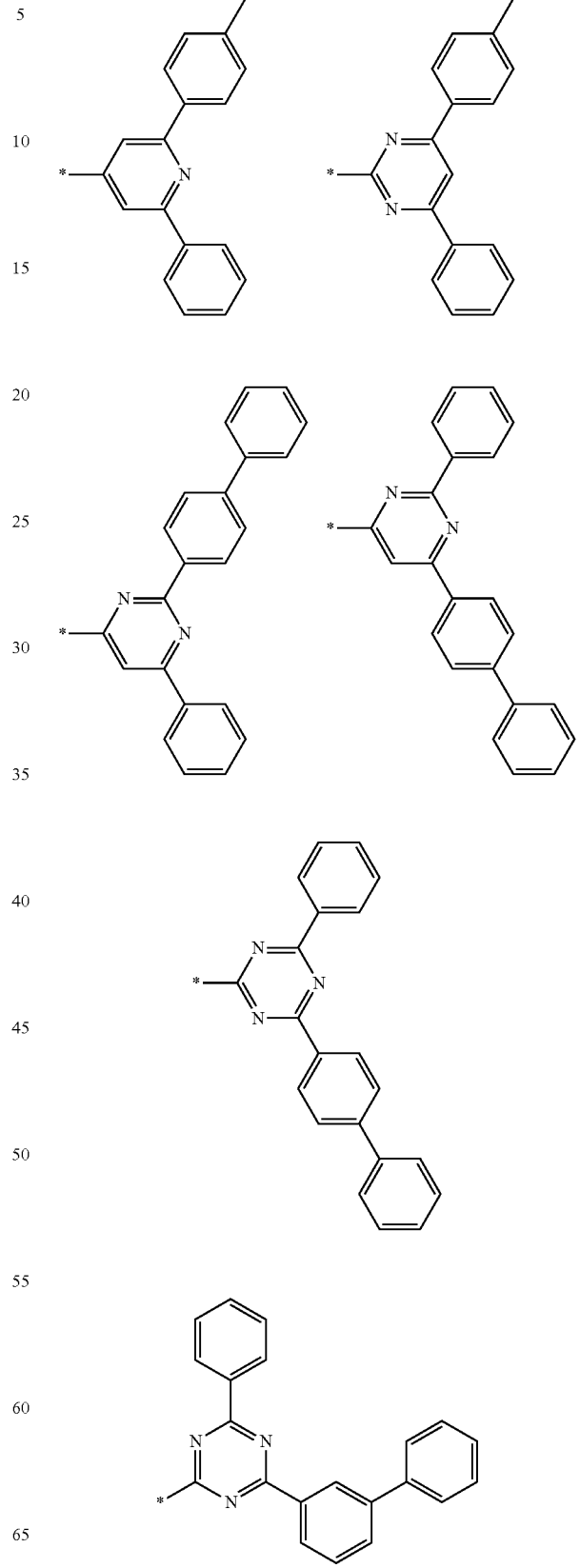

201
-continued

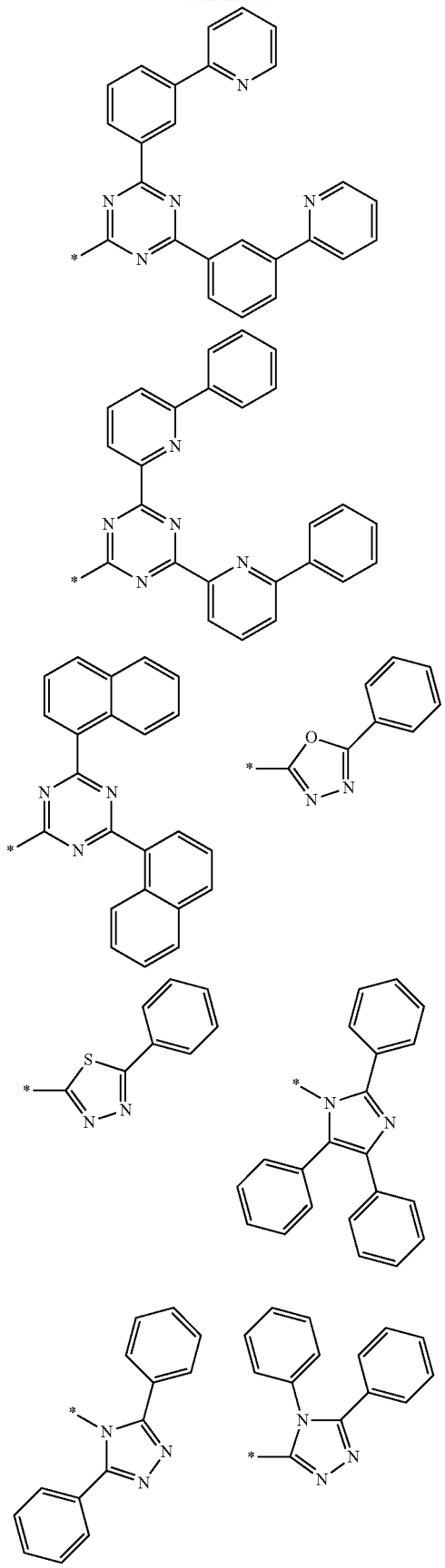

202
-continued

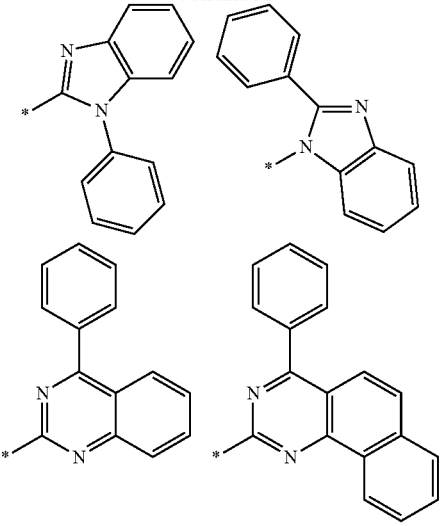

wherein, in Group I-1,
* indicates bonding sites with neighboring atoms.

12. An organic optoelectric device, comprising
an anode and a cathode facing each other and
at least one organic layer between the anode and the cathode
wherein the organic layer includes a compound for an organic optoelectric device represented by Chemical Formula I:

[Chemical Formula I]

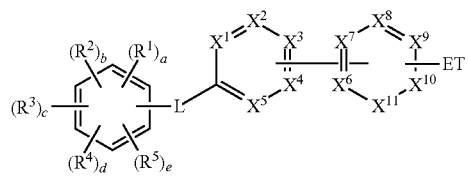

wherein, in Chemical Formula I,
$X^1$ to $X^{11}$ are independently, N, C, or $CR^a$,
$R^a$ is independently, hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heterocyclic group, a substituted or unsubstituted C6 to C30 arylamine group, a substituted or unsubstituted C1 to C30 alkoxy group, a substituted or unsubstituted C3 to C40 silyl group, a substituted or unsubstituted C3 to C40 silyloxy group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof,
$R^1$ to $R^5$ are independently a substituted or unsubstituted C6 to C30 aryl group,
a to e are independently an integer of 0 or 1,
$4 \leq a+b+c+d+e \leq 5$,
L is a single bond, a substituted or unsubstituted C6 to C30 arylene group, a substituted or unsubstituted C2 to C30 heteroarylene group, or a combination thereof, and ET is a substituted or unsubstituted heteroaryl group including at least one N except a carbazolyl group,
wherein "substituted" refers to that at least one hydrogen is replaced by deuterium, a halogen, a hydroxy group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

13. The organic optoelectric device of claim 12, wherein the compound for an organic optoelectric device is included as a host of an emission layer of the organic layer, or in an electron transport auxiliary layer of the organic layer.

14. The organic optoelectric device of claim 13, wherein the host of the emission layer further comprises at least one of a compound represented by Chemical Formula II and a compound consisting of a combination of a moiety represented by Chemical Formula III and a moiety represented by Chemical Formula IV:

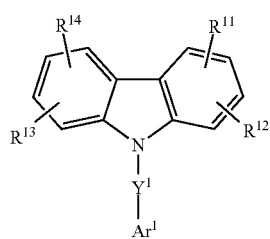

[Chemical Formula II]

wherein, in Chemical Formula II,
$Y^1$ is a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof,
$Ar^1$ is a substituted or unsubstituted C6 to C30 aryl group, a substituted or unsubstituted C2 to C30 heterocyclic group, or a combination thereof,
$R^{11}$ to $R^{14}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, and
at least one of $R^{11}$ to $R^{14}$ and $Ar^1$ includes a substituted or unsubstituted triphenylene group or a substituted or unsubstituted carbazole group,

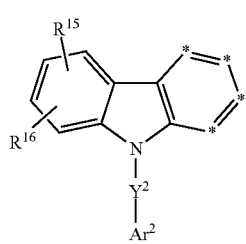

[Chemical Formula III]

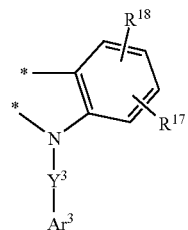

[Chemical Formula IV]

wherein, in Chemical Formulae III and IV,
$Y^2$ and $Y^3$ are independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof,
$Ar^2$ and $Ar^3$ are independently a substituted or unsubstituted C6 to C30 aryl group, a substituted or unsubstituted C2 to C30 heterocyclic group, or a combination thereof,
$R^{15}$ to $R^{18}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof,
adjacent two *'s of Chemical Formula III are combined with two *'s of Chemical Formula IV to form a fused ring and * that does not form the fused ring of Chemical Formula III is independently $CR^i$, and
$R^i$ is hydrogen, deuterium, a substituted or unsubstituted C1 to C10 alkyl group, a substituted or unsubstituted C6 to C12 aryl group, a substituted or unsubstituted C2 to C12 heterocyclic group or a combination thereof.

15. The organic optoelectric device of claim 14, wherein the compound represented by Chemical Formula II is represented by at least one of Chemical Formulae II-1 to II-3:

[Chemical Formula II-1]

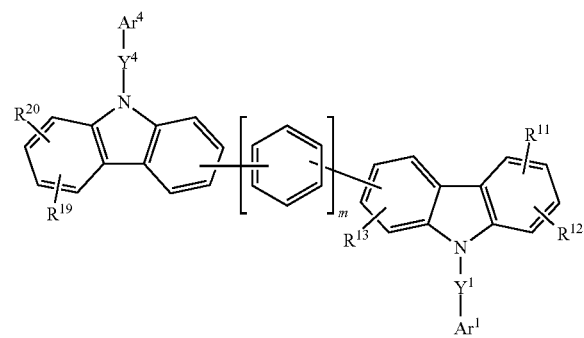

lp;-2p

[Chemical Formula II-2]

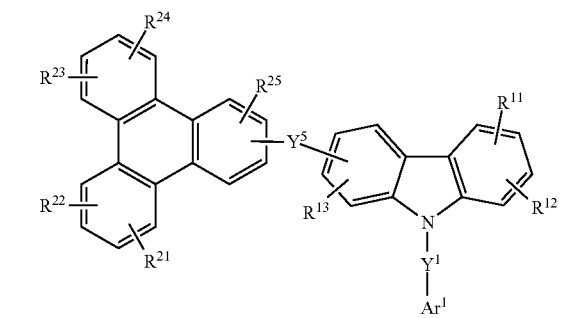

[Chemical Formula II-3]

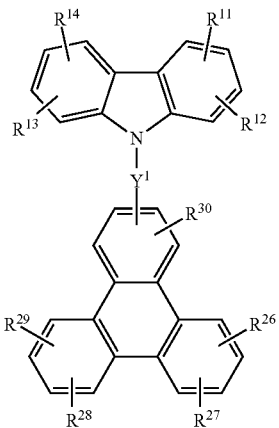

[Chemical Formula III-1]

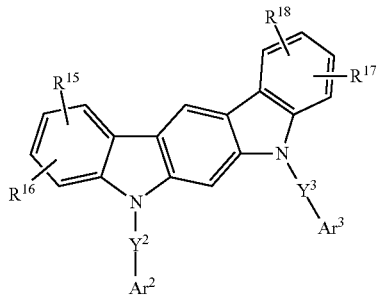

[Chemical Formula III-2]

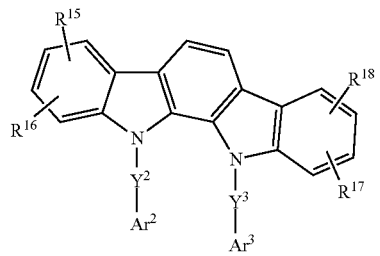

[Chemical Formula III-3]

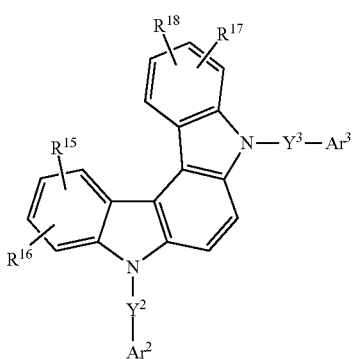

[Chemical Formula III-4]

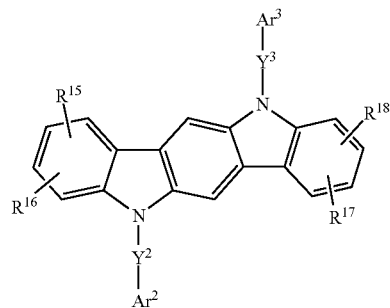

[Chemical Formula III-5]

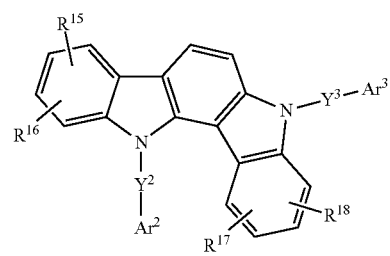

wherein, in Chemical Formulae II-1 to II-3, $Y^1$, $Y^4$ and $Y^5$ are independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, $Ar^1$ and $Ar^4$ are independently a substituted or unsubstituted C6 to C30 aryl group, a substituted or unsubstituted C2 to C30 heterocyclic group, or a combination thereof, $R^{11}$ to $R^{14}$ and $R^{19}$ to $R^{30}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, and m is one of integers of 0 to 4, wherein, "substituted" refers to that at least one hydrogen is replaced by deuterium, a halogen, a hydroxy group, an amino group, a C1 to C30 amine group, a nitro group, a C1 to C40 silyl group, a C1 to C30 alkyl group, a C3 to C30 cycloalkyl group, a C2 to C30 heterocycloalkyl group, a C6 to C30 aryl group, a C2 to C30 heterocyclic group, a C1 to C20 alkoxy group, a fluoro group, C1 to C10 trifluoroalkyl group, or a cyano group.

16. The organic optoelectric device of claim 15, wherein $Ar^1$ and $Ar^4$ of Chemical Formulae II-1 to II-3 are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted carbazolyl group, a substituted or unsubstituted benzofuranyl group, a substituted or unsubstituted benzothiophenyl group, a substituted or unsubstituted fluorenyl group, a substituted or unsubstituted dibenzofuranyl group, a substituted or unsubstituted dibenzothiophenyl group, a substituted or unsubstituted pyridinyl group, or a combination thereof.

17. The organic optoelectric device of claim 14, wherein the compound consisting of a combination of the moiety represented by Chemical Formula III and the moiety represented by Chemical Formula IV is represented by at least one of Chemical Formulae III-1 to III-5:

wherein, in Chemical Formulae III-1 to III-5, $Y^2$ and $Y^3$ are independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, $Ar^2$ and $Ar^3$ are independently a substituted or unsubstituted C6 to C30 aryl group, a substituted or unsubstituted C2 to C30 heterocyclic group, or a combination thereof, $R^{15}$ to $R^{18}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, and wherein, "substituted" refers to that at least one hydrogen is replaced by deuterium, a halogen, a hydroxy group, an amino group, a C1 to C30 amine group, a nitro group, a C1 to C40 silyl group, a C1 to C30 alkyl group, a C3 to C30 cycloalkyl group, a C2 to C30 heterocycloalkyl group, a C6 to C30 aryl group, a C2 to C30 heterocyclic group, a C1 to C20 alkoxy group, a fluoro group, C1 to C10 trifluoroalkyl group, or a cyano group.

18. A display device comprising the organic optoelectric device of claim 12.

* * * * *